US009844775B2

(12) United States Patent
Miyake et al.

(10) Patent No.: US 9,844,775 B2
(45) Date of Patent: Dec. 19, 2017

(54) ALKYL TIN COMPOUND

(71) Applicant: Asahi Kasei Chemicals Corporation, Tokyo (JP)

(72) Inventors: Nobuhisa Miyake, Tokyo (JP); Masaaki Shinohata, Tokyo (JP); Budianto Nishiyama, Tokyo (JP); Atsushi Okubo, Tokyo (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/024,449

(22) PCT Filed: Sep. 22, 2014

(86) PCT No.: PCT/JP2014/075128
§ 371 (c)(1),
(2) Date: Mar. 24, 2016

(87) PCT Pub. No.: WO2015/046167
PCT Pub. Date: Apr. 2, 2015

(65) Prior Publication Data
US 2016/0228863 A1    Aug. 11, 2016

(30) Foreign Application Priority Data

Sep. 26, 2013 (JP) ................. 2013-199871
Sep. 26, 2013 (JP) ................. 2013-199873

(51) Int. Cl.
*C07F 7/22* (2006.01)
*C07C 68/04* (2006.01)
*B01J 31/12* (2006.01)

(52) U.S. Cl.
CPC ............ *B01J 31/12* (2013.01); *B01J 31/122* (2013.01); *C07C 68/04* (2013.01); *C07F 7/2224* (2013.01); *C07F 7/2252* (2013.01); *C07F 7/2256* (2013.01); *B01J 2231/648* (2013.01)

(58) Field of Classification Search
CPC ...... B01J 31/12; B01J 2231/648; C07F 7/256; C07F 7/2224; C07C 69/96
USPC ................. 556/83, 89; 558/260; 502/152
See application file for complete search history.

(56) References Cited

U.S. PATENT DOCUMENTS

| 3,773,694 A | 11/1973 | Nakata et al. |
| 3,790,611 A | 2/1974 | Gitlitz et al. |
| 4,108,990 A | 8/1978 | Plum et al. |
| 4,191,698 A | 3/1980 | Gitlitz et al. |
| 4,547,320 A | 10/1985 | Bulten et al. |
| 5,545,600 A | 8/1996 | Knudsen et al. |
| 2005/0080274 A1 | 4/2005 | Miyake et al. |
| 2005/0240045 A1 | 10/2005 | Miyake et al. |
| 2007/0055042 A1 | 3/2007 | Miyake et al. |
| 2008/0275262 A1 | 11/2008 | Miyake et al. |
| 2009/0169461 A1 | 7/2009 | Miyake et al. |
| 2010/0041908 A1 | 2/2010 | Shinohata et al. |
| 2010/0160662 A1 | 6/2010 | Bijanto et al. |
| 2010/0292496 A1 | 11/2010 | Shinohata et al. |

FOREIGN PATENT DOCUMENTS

| BE | 889026 A2 | 12/1981 |
| CA | 1092127 A | 12/1980 |
| CN | 1431190 A | 7/2003 |
| CN | 1608045 A | 4/2005 |
| CN | 101389404 A | 3/2009 |
| CN | 1997654 B | 5/2011 |
| DE | 2424891 A1 | 12/1975 |
| EP | 0214842 A2 | 3/1998 |
| EP | 1460056 A1 | 9/2004 |
| EP | 1535896 A1 | 6/2005 |
| EP | 1760085 A1 | 3/2007 |
| FR | 2362149 A1 | 3/1978 |
| JP | S49-134630 A | 12/1974 |
| JP | S51-040920 B | 11/1976 |
| JP | S52-007983 A | 1/1977 |
| JP | 2005-298433 A | 10/2005 |
| JP | 2011-042593 A | 3/2011 |
| TW | 201008953 A1 | 3/2010 |
| WO | 03/055840 A1 | 7/2003 |
| WO | 2004/014840 A1 | 2/2004 |
| WO | 2005/000783 A1 | 1/2005 |
| WO | 2005/111049 A1 | 11/2005 |
| WO | 2007/097388 A1 | 8/2007 |
| WO | 2007/114130 A1 | 10/2007 |
| WO | 2008/044575 A1 | 4/2008 |
| WO | 2010/016297 A1 | 2/2010 |

OTHER PUBLICATIONS

Martins et al., J.Am. Chem. Soc., vol. 121, No. 14, pp. 3284-3291 (1999).*
Pommier et al., Journal of Organometallic Chem., 74 (1974) 405-416.*
International Preliminary Report on Patentability and Written Opinion issued in counterpart International Patent Application No. PCT/JP2014/075128 dated Apr. 7, 2016.
International Search Report issued in corresponding International Patent Application No. PCT/JP2014/075128 dated Dec. 16, 2014.
Davies et al., "Organotin Chemistry. Part XI. The Preparation of Organotin Alkoxides," Journal of the Chemical Society, 23: 3972-3976 (1971).

(Continued)

*Primary Examiner* — Fereydoun G Sajjadi
*Assistant Examiner* — Kofi Adzamli
(74) *Attorney, Agent, or Firm* — Morgan, Lewis & Bockius LLP

(57) ABSTRACT

An alkyl tin compound having an alkyl group bonded to a tin atom, wherein the alkyl group is a branched alkyl or cyclic group-substituted alkyl group, the branched alkyl group being an alkyl group branched at at least one carbon atom of the first to third carbon atoms counting from the tin atom, and the cyclic group-substituted alkyl group being an alkyl group having a cyclic group bonded at at least one carbon atom of the first to third carbon atoms counting from the tin atom.

36 Claims, 5 Drawing Sheets

(56) References Cited

OTHER PUBLICATIONS

Mori et al., "Reaction between dialkyl tin oxide and acetic acid ester or higher alcohol and pyrolysis of dialkyl tin dialkoxide," Kogyo Kagaku Zasshi, 72: 1543-1549 (1969).
Choi et al., "Reaction of Dialkyltin Methoxide with Carbon Dioxide Relevant to the Mechanism of Catalytic Carbonate Synthesis," Journal of the American Chemical Society, 121: 3793-3794 (1999).
Ballivet-Tkatchenko et al., "Reactivity of ditert-butyldimethoxystannane with carbon dioxide and methanol: X-ray structure of the resulting complex," Journal of Organometallic Chemistry, 691: 1498-1504 (2006).
Neumann et al., "Organotin compounds. X. Hydrostannation of aldehydes and ketones," Justus Liebigs Annalen der Chemie, 683: 11-23 (1965).
Pommier et al., "Etude de la reaction d'oxydation d'alcools par voie organostannique," Journal of Organometallic Chemistry, 74: 405-416 (1974) (see English abstract).
Maire et al., "Etude des spectres infrarouges de divers dialcoyl-dimethoxy-stannanes," Helvetica Chimica Acta, 51: 1150-1154 (1968).
Cummins et al., "The infrared spectra of some alkyltin methoxides," Spectrochimica Acta, 21: 1016-1018 (1965).
European Search Report issued in counterpart European Patent Application No. 14847310.1 dated Aug. 24, 2016.
"Stannane, bis(2-ethylhexyl)dimethoxy-" Registry, CAS No. 15322-74-4 (1984).

* cited by examiner

ALKYL TIN COMPOUND

TECHNICAL FIELD

The present invention relates to alkyl tin compounds. In particular, it relates to branched alkyl tin compounds and cyclic group-substituted alkyl tin compounds with excellent thermostability.

The invention is an advancement from 2010 Innovation and Development: "Project for Fostering of Practical Development of Industrial Technologies" by the New Energy and Industrial Technology Development Organization (NEDO).

BACKGROUND ART

Alkyl tin compounds are widely used as a variety of organic synthesis catalysts. The subset of dialkyl tin dialkoxides are highly useful as catalysts such as ester synthesis catalysts, carbonic acid ester synthesis catalysts, transesterification reaction catalysts and silicone polymer or urethane curing catalysts. Carbonic acid esters are used as additives, such as gasoline additives for the purpose of increasing octane value, and diesel fuel additives to reduce particles in exhaust gas, while they are also useful compounds as alkylating agents, carbonylating agents, solvents and the like for synthesis of organic compounds such as polycarbonates and urethanes, drugs and agricultural chemicals, or as lithium battery electrolytes, lubricant oil starting materials or starting materials for deoxidizers for rust prevention of boiler pipes, and the aforementioned dialkyl tin dialkoxides are of particular interest as catalysts for their synthesis.

In PTL 1 there is disclosed a method for producing carbonic acid esters by thermal decomposition of an addition product formed by reacting an organometallic compound comprising a dialkyl tin dialkoxide with carbon dioxide.

In the prior art there have been known methods for producing dialkyl tin dialkoxides by dehydrating reaction of dialkyl tin oxides and alcohols, and removal of the generated low boiling point components including the generated water from the reaction mixture (see PTLs 2 to 4 and NPLs 1 to 2, for example). Methods for producing dialkyl tin dialkoxides by dehydrating reaction between dialkyl tin oxides and alcohols are assumed to be equilibrium reactions occurring with dehydration, represented by chemical equation (5).

[Chemical Formula 1]

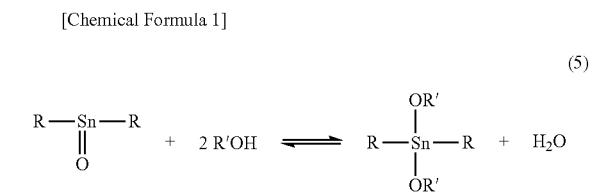

[In the equation, R and R' represent alkyl groups.]

The equilibrium reaction is overwhelmingly unbalanced toward the left, and is presumably often accompanied by successive dehydrating reaction via a tetraalkyldialkoxydistannoxane, as represented by chemical equations (6) and (7).

[Chemical Formula 2]

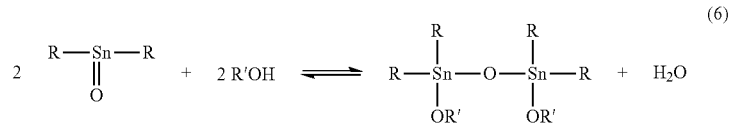

[In the equation, R and R' represent alkyl groups.]

[Chemical Formula 3]

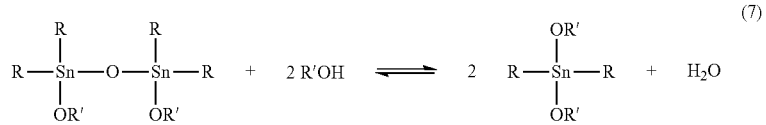

[In the equation, R and R' represent alkyl groups.]

In order to obtain a dialkyl tin dialkoxide at high yield, production is carried out while removing the water generated by the dehydrating reaction out of the system, but since this reaction is disadvantageous in terms of energy, the reaction must be carried out for a long period at high temperature (for example, 180° C.). Even when dialkyl tin dialkoxides are used as catalysts for other esterification reactions and urethanation reactions, they are often used at high temperatures exceeding 100° C.

On the other hand, it is known that heating dialkyl tin alkoxide compounds (such as dialkyl tin dialkoxides) to about 180° C., for example, generate modified forms such as trialkyl tin alkoxides having three alkyl groups on one tin atom (see NPL 2, for example). While it is not clear by what reaction the trialkyl tin alkoxides are generated, it is believed that alkyl groups are transferred within the molecule. For example, when the alkyl tin alkoxide is a tetraalkyldialkoxydistannoxane, formation of modified compounds (trialkyl tin alkoxides and high boiling point tin components) by the disproportionation reaction represented by chemical equation (8) has been confirmed, and when the dialkyl tin alkoxide is a dialkyl tin dialkoxide, formation of modified compounds (trialkyl tin alkoxides and high boiling point tin components) by the disproportionation reaction represented by chemical equation (9) has been confirmed, while production of trialkyl tin alkoxides has also been confirmed with the passage of time during synthesis of dialkyl tin dialkoxides from dialkyl tin oxides and alcohols and during synthesis of dialkyl tin dialkoxides from tetraalkyldialkoxydistannoxanes and alcohols. Throughout the present specification, "tin component" refers to a compound containing all of the tin atoms contained in a reaction mixture or composition.

[Chemical Formula 4]

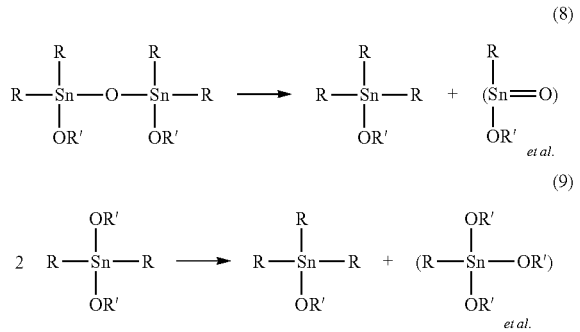

From Chemical Equation (8) it is inferred that a trialkyl tin alkoxide and a monoalkyl tin compound having one alkyl group on one tin atom are generated as modified forms of a tetraalkyldialkoxydistannoxane. The present inventors have in fact confirmed that trialkyl tin alkoxides and high-boiling-point tin components are present among the modified forms of tetraalkyldialkoxydistannoxanes, and it is conjectured that the high-boiling-point tin components correspond to monoalkyl tin compounds.

However, the structures of the high-boiling-point tin components presumed to correspond to monoalkyl tin compounds have not yet been elucidated. Modified compounds presumed to be trialkyl tin alkoxides and monoalkyl tin alkoxides are produced from dialkyl tin dialkoxides as well, but the structures of the modified compounds presumed to be monoalkyl tin alkoxides have not yet been elucidated.

Generation of such modified compounds has also been confirmed in the course of production of the dialkyl tin dialkoxides mentioned above, and in the course of production of carbonic acid esters by thermal decomposition of addition products formed by reacting carbon dioxide with organometallic compounds containing dialkyl tin dialkoxides.

Trialkyl tin alkoxides are known to have very low ability to produce carbonic acid esters, in production of carbonic acid esters by reaction of carbon dioxide with tin compounds (see NPL 3, for example). High-boiling-point tin components, which are present among the aforementioned modified compounds and whose structures cannot be identified, also have very low ability to produce carbonic acid esters in production of carbonic acid esters by reaction between carbon dioxide and tin compounds (see PTL 4, for example).

Thus, since modified compounds do not exhibit high reactivity in production of carbonic acid esters by reaction between carbon dioxide and tin compounds, when such modified compounds are generated during production of such carbonic acid esters, repeated use of the alkyl tin alkoxide compounds will result in accumulation of modified forms of dialkyl tin alkoxide compounds with low activity and decrease in the proportion of active dialkyl tin alkoxide compounds, often lowering the reaction rate and reducing carbonic acid ester yields. In such cases, small amounts of fresh dialkyl tin alkoxide compound are added in order to maintain a constant reaction rate or yield for most reactions, but if fresh dialkyl tin alkoxide compounds are simply added and the modified compounds are left to remain, this results in the problem of accumulation of large amounts of degradation products with low activity (modified compounds) in the reaction system. Even when some mixtures of alkyl tin alkoxide compounds containing modified products of dialkyl tin alkoxide compounds are extracted from the reaction system while fresh dialkyl tin alkoxide compounds are added to maintain a constant concentration of dialkyl tin alkoxide compounds in the reaction system, the modified dialkyl tin alkoxide compounds that have been extracted not only constitute waste, but active dialkyl tin alkoxide compounds are also extracted at the same time as waste, and this results in major problems in terms of cost and disposal.

Several solutions have been presented to counter this problem (see PTLs 5 to 6, for example). Specifically, PTL 5 discloses a method in which, during production of carbonic acid esters using dialkyl tin alkoxide compounds containing modified forms of dialkyl tin alkoxide compounds, the trialkyl tin compound component is separated by distillation from the dialkyl tin alkoxide compounds that include the modified compounds, thereby preventing their accumulation in the reaction system. However, high-boiling-point tin components whose structures cannot be identified, and which are present among the modified forms of dialkyl tin alkoxide compounds, cannot be removed from the reaction system and therefore it is not possible to completely prevent accumulation of modified dialkyl tin alkoxide compounds by this method.

The present inventors have previously disclosed a method for separating and recovering products derived from dialkyl tin alkoxide compounds as dialkyl tin dialkoxides, by reacting alcohols and/or carbonic acid esters with the mixtures of dialkyl tin alkoxide compounds and modified forms of dialkyl tin alkoxide compounds that have been extracted from the reaction system (see PTL 6). This method solved the problem in which the active dialkyl tin alkoxide compounds are disposed with the modified compounds, allowing selective disposal of only the modified forms of the dialkyl tin alkoxide compounds. However, since modified dialkyl tin alkoxide compounds cannot be reused, the problems of cost and waste have remained.

The present inventors have further disclosed a method of highly efficient regeneration of dialkyl tin dialkoxides, by subjecting tin compounds obtained from disproportionation reaction, to redistribution reaction (see PTL 7). We have further disclosed a method of producing carbonic acid esters over long periods without loss of productivity, by incorporating the aforementioned redistribution reaction step as a step in carbonic acid ester synthesis processes (see PTL 8).

However, it has not been possible to prevent the inactivation of the dialkyl tin dialkoxide compounds themselves, and there is a need for development of dialkyl tin alkoxide compounds that are resistant to disproportionation reaction when used for ester synthesis, urethanation reaction and the like and alkyl tin catalysts with high carbonic acid ester productivity, with minimal disproportionation inactivation particularly during production of carbonic acid esters that have high practical industrial value, and a solution yet remains to be found.

CITATION LIST

Patent Literature

Patent Literature 1: International Patent Publication No. WO2003/055840
Patent Literature 2: U.S. Pat. No. 5,545,600
Patent Literature 3: International Patent Publication No. WO2005/111049
Patent Literature 4: Japanese Unexamined Patent Application Publication No. 2005-298433
Patent Literature 5: International Patent Publication No. WO2004/014840
Patent Literature 6: International Patent Publication No. WO2007/097388
Patent Literature 7: International Patent Publication No. WO2008/044575
Patent Literature 8: International Patent Publication No. WO2010/016297

Non Patent Literature

Non Patent Literature 1: Journal of Chemical Society, 23(1971), 3972
Non Patent Literature 2: Kogaku Kagaku Zasshi Vol. 72, No. 7, 1543-1549(1969)
Non Patent Literature 3: Journal of the American Chemical Society, 121(1999), 3793

SUMMARY OF INVENTION

Technical Problem

It is an object of the invention to provide alkyl tin compounds that have minimal production of modified compounds (inactivated forms) even when used repeatedly at high temperatures.

Solution to Problem

As a result of diligent research directed toward this object, the present inventors have found that the problems described above can be overcome by alkyl tin compounds having specific branched alkyl or cyclic group-substituted alkyl groups, and the present invention has thus been completed. Specifically, the invention provides the following.

[1] An alkyl tin compound having an alkyl group bonded to a tin atom, wherein the alkyl group is a branched alkyl or cyclic group-substituted alkyl group, the branched alkyl group being an alkyl group branched at at least one carbon atom of the first to third carbon atoms counting from the tin atom, and the cyclic group-substituted alkyl group being an alkyl group having a cyclic group bonded at at least one carbon atom of the first to third carbon atoms counting from the tin atom.

[2] An alkyl tin compound according to [1], which has one to three branched alkyl groups bonded to one tin atom, the valency of the tin atom being tetravalent.

[3] An alkyl tin compound according to [2], wherein the branched alkyl group is a C4-18 branched alkyl group, and a C1-8 alkoxy group is further bonded to the tin atom.

[4] An alkyl tin compound according to [2] or [3], which is a dialkyl tin alkoxide or a tetraalkyldialkoxydistannoxane.

[5] An alkyl tin compound according to [4], which is a compound represented by the following formula (1) or a compound represented by formula (2).

[Chemical Formula 5]

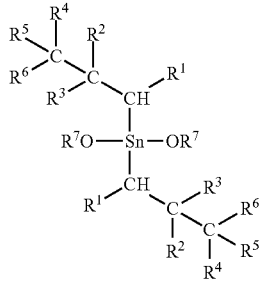

(1)

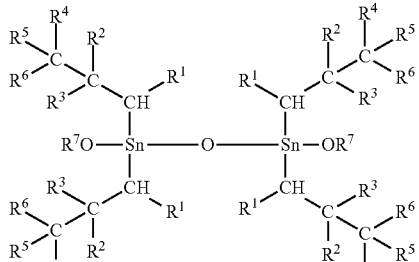

(2)

[$R^1$, $R^2$, $R^3$, $R^4$, $R^5$ and $R^6$ each independently represent hydrogen or a C1-15 alkyl group, and $R^7$ represents a C1-8 alkyl group. This is with the proviso that $R^1$, $R^2$, $R^3$, $R^4$, $R^5$ and $R^6$ are not all hydrogen, at least one of $R^1$, $R^2$ and $R^3$ is an alkyl group, or all of $R^1$, $R^2$ and $R^3$ are hydrogen, and at least two of $R^4$, $R^5$ and $R^6$ are alkyl groups, the total number of carbon atoms of $R^1$, $R^2$, $R^3$, $R^4$, $R^5$ and $R^6$ being 2 to 15].

[6] An alkyl tin compound according to [2] or [3], which is a trialkyl tin compound.

[7] An alkyl tin compound according to [6], which is a compound represented by formula (3).

[Chemical Formula 6]

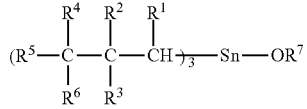

(3)

[$R^1$, $R^2$, $R^3$, $R^4$, $R^5$ and $R^6$ each independently represent hydrogen or a C1-15 alkyl group, and $R^7$ represents a C1-8 alkyl group. This is with the proviso that $R^1$, $R^2$, $R^3$, $R^4$, $R^5$ and $R^6$ are not all hydrogen, at least one of $R^1$, $R^2$ and $R^3$ is an alkyl group, or all of $R^1$, $R^2$ and $R^3$ are hydrogen, and at least two of $R^4$, $R^5$ and $R^6$ are alkyl groups, the total number of carbon atoms of $R^1$, $R^2$, $R^3$, $R^4$, $R^5$ and $R^6$ being 2 to 15.]

[8] An alkyl tin compound according to [3], wherein the alkoxy group is an alkoxy group selected from among n-butyloxy, isobutyloxy, sec-butyloxy and C5-8 alkoxy groups.

[9] An alkyl tin compound according to [3] or [8], wherein the alkoxy group is a branched alkoxy group.

[10] An alkyl tin compound according to any one of [3], [8] and [9], which is an alkyl tin alkoxide obtained from an alkyl tin carboxylate, alkyl tin oxide, alkyl tin oxide polymer or alkyl tin halide.

[11] An alkyl tin compound according to [2], which is an alkyl tin alkoxide having a C5-18 branched alkyl group and a C4-8 branched alkoxy group, and which is a compound represented by formula (1) or a compound represented by formula (2).

[Chemical Formula 7]

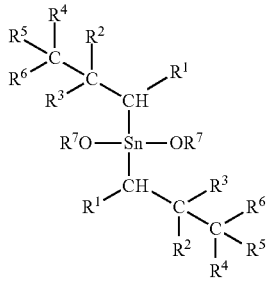
(1)

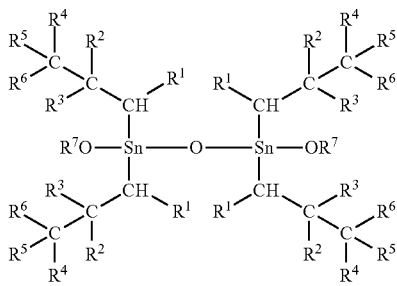
(2)

[$R^1$, $R^2$, $R^3$, $R^4$, $R^5$ and $R^6$ each independently represent hydrogen or a C1-15 alkyl group, and $R^7$ represents a C4-8 branched alkyl group. This is with the proviso that $R^1$, $R^2$, $R^3$, $R^4$, $R^5$ and $R^6$ are not all hydrogen, at least one of $R^1$, $R^2$ and $R^3$ is an alkyl group, or all of $R^1$, $R^2$ and $R^3$ are hydrogen, and at least two of $R^4$, $R^5$ and $R^6$ are alkyl groups, the total number of carbon atoms of $R^1$, $R^2$, $R^3$, $R^4$, $R^5$ and $R^6$ being 2 to 15.]

[12] A composition comprising an alkyl tin compound according to any one of [1] to [11].

[13] A composition according to [12], comprising an alkyl tin compound according to [4] or [5] and an alkyl tin compound according to [6] or [7].

[14] An alkyl tin compound according to [1], which is an alkyl tin compound having a cyclic group-substituted alkyl group bonded to a tin atom, the cyclic group-substituted alkyl group being an alkyl group having a cyclic group selected from among alicyclic hydrocarbon groups and aromatic hydrocarbon groups bonded to at least one carbon atom among the first to third carbon atoms counting from the tin atom, and the valency of the tin atom being tetravalent.

[15] An alkyl tin compound according to [14], wherein the alkyl tin compound further has a C1-8 alkoxy group, and the cyclic group is a C4-18 cyclic group.

[16] An alkyl tin compound according to [14] or [15], which is a di(cyclic group-substituted alkyl) tin dialkoxide or a tetra(cyclic group-substituted alkyl)dialkoxydistannoxane.

[17] An alkyl tin compound according to [16], which is a compound represented by the following formula (1) or a compound represented by formula (2).

[Chemical Formula 8]

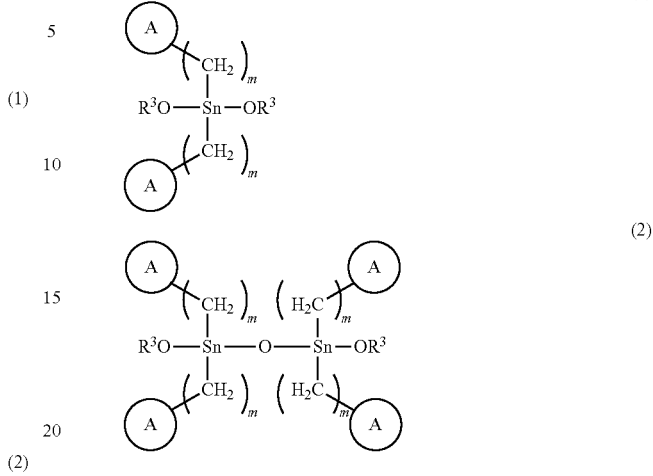

[Ring A represents a C3-16 alicyclic hydrocarbon group or a C6-16 aromatic hydrocarbon group, m is an integer of 1 to 3, and $R^3$ represents a C1-8 alkyl group.]

[18] An alkyl tin compound according to [14] or [15], which is a tri(cyclic group-substituted alkyl) tin compound.

[19] An alkyl tin compound according to [18], which is a compound represented by formula (3).

[Chemical Formula 9]

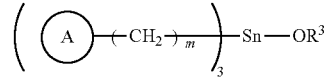
(3)

[Ring A represents a C3-16 alicyclic hydrocarbon group or a C6-16 aromatic hydrocarbon group, m is an integer of 1 to 3, and $R^3$ represents a C1-8 alkyl group.]

[20] An alkyl tin compound according to [15], wherein the alkoxy group is a C4-8 alkoxy group, and the alcohol corresponding to the alkoxy group is an alcohol having a boiling point of 100° C. or higher at ordinary pressure.

[21] An alkyl tin compound according to [20], wherein the alcohol forms an azeotropic mixture with water.

[22] An alkyl tin compound according to any one of [15], [20] and [21], wherein the alkoxy group is a branched alkoxy group.

[23] An alkyl tin compound according to any one of [15], [20], [21] and [22], which is an alkyl tin alkoxide obtained from a cyclic group-substituted alkyl tin carboxylate, a cyclic group-substituted alkyl tin oxide, a cyclic group-substituted alkyl tin oxide polymer or a halogenated (cyclic group-substituted alkyl) tin compound.

[24] A composition comprising an alkyl tin compound according to any one of [14] to [23].

[25] A composition according to [24], comprising an alkyl tin compound according to [16] or [17] and an alkyl tin compound according to [18] or [19].

[25] A catalyst for a process for producing a carbonic acid ester from carbon dioxide and an alcohol, the catalyst comprising an alkyl tin compound according to any one of [1] to [11] and [14] to [23].

[26] A method for producing a carbonic acid ester using an alkyl tin compound according to any one of [1] to [11] and [14] to [23], the method comprising the following steps (1) to (3).

Step (1): A step of reacting the alkyl tin compound with carbon dioxide to obtain a reaction mixture containing a carbonic acid ester.
Step (2): A step of separating the carbonic acid ester from the reaction mixture to obtain a residual solution.
Step (3): A step of reacting the residual solution with an alcohol and removing the water produced by the reaction, to obtain an alkyl tin alkoxide, and recycling it to step (1).

[28] The method according to [27], wherein the alkyl tin compound includes either or both a compound represented by formula (1) and/or a compound represented by formula (2).

[Chemical Formula 10]

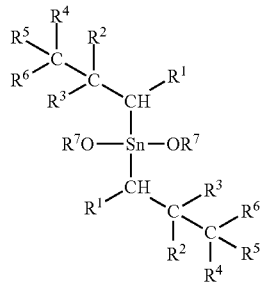

(1)

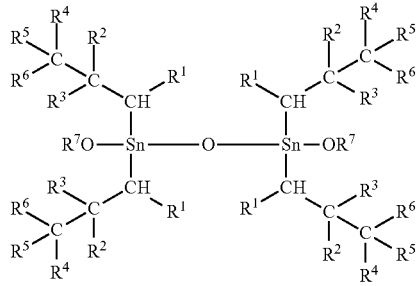

(2)

[$R^1$, $R^2$, $R^3$, $R^4$, $R^5$ and $R^6$ each independently represent hydrogen or a C1-15 alkyl group, and $R^7$ represents a C1-8 alkyl group. This is with the proviso that $R^1$, $R^2$, $R^3$, $R^4$, $R^5$ and $R^6$ are not all hydrogen, at least one of $R^1$, $R^2$ and $R^3$ is an alkyl group, or all of $R^1$, $R^2$ and $R^3$ are hydrogen, and at least two of $R^4$, $R^5$ and $R^6$ are alkyl groups, the total number of carbon atoms of $R^1$, $R^2$, $R^3$, $R^4$, $R^5$ and $R^6$ being 2 to 15.]

[29] The method according to [28], wherein the alkyl tin compound further includes a compound represented by formula (3).

[Chemical Formula 11]

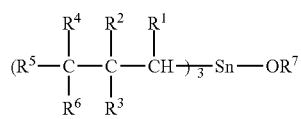

(3)

[$R^1$, $R^2$, $R^3$, $R^4$, $R^5$ and $R^6$ each independently represent hydrogen or a C1-15 alkyl group, and $R^7$ represents a C1-8 alkyl group. This is with the proviso that $R^1$, $R^2$, $R^3$, $R^4$, $R^5$ and $R^6$ are not all hydrogen, at least one of $R^1$, $R^2$ and $R^3$ is an alkyl group, or all of $R^1$, $R^2$ and $R^3$ are hydrogen, and at least two of $R^4$, $R^5$ and $R^6$ are alkyl groups, the total number of carbon atoms of $R^1$, $R^2$, $R^3$, $R^4$, $R^5$ and $R^6$ being 2 to 15.]

[30] The method according to [28] or [29], wherein the alkoxy group of the alkyl tin compound is selected from among n-butyloxy, isobutyloxy, sec-butyloxy and C5-8 alkoxy groups.

[31] The method according to any one of [28] to [30], wherein the alcohol is an alcohol selected from among n-butyl alcohol, isobutyl alcohol, sec-butyl alcohol and C5-8 alkyl alcohols.

[32] The method according to any one of [28] to [31], wherein the alkoxy group of the alkyl tin compound is a branched alkoxy group, and the alcohol is the branched alcohol corresponding to the branched alkoxy group.

[33] The method according to [27], wherein the alkyl tin compound includes either or both a compound represented by formula (1) and/or a compound represented by formula (2).

[Chemical Formula 12]

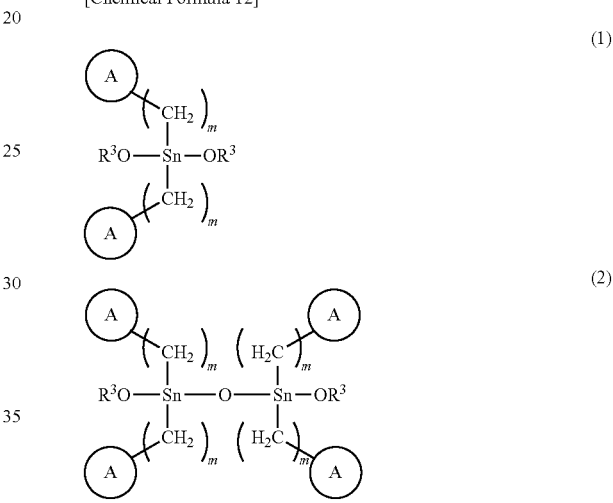

[Ring A represents a C3-16 alicyclic hydrocarbon group or a C6-16 aromatic hydrocarbon group, m is an integer of 1 to 3, and $R^3$ represents a C1-8 alkyl group.]

[34] The method according to [33], wherein the alkyl tin compound further includes a compound represented by formula (3).

[Chemical Formula 13]

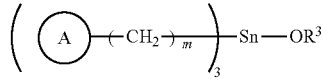

(3)

[Ring A represents a C3-16 alicyclic hydrocarbon group or a C6-16 aromatic hydrocarbon group, m is an integer of 1 to 3, and $R^3$ represents a C1-8 alkyl group.]

[35] The method according to [33] or [34], wherein the alkoxy groups of the compound represented by formula (1) and the compound represented by formula (2) are C4-8 alkoxy groups, the alcohols corresponding to the alkoxy groups are alcohols with boiling points of 100° C. or higher at ordinary pressure, and the alcohol used in step (3) is the alcohol corresponding to the alkoxy group.

[36] The method according to [33] or [34], wherein the alcohol is a C4-8 alcohol with a boiling point of 100° C. or higher at ordinary pressure.

[37] The method according to any one of [33] to [36], wherein the alcohol is an alcohol selected from among n-butyl alcohol, isobutyl alcohol, sec-butyl alcohol and C5-8 alkyl alcohols.

[38] The method according to any one of [33] to [37], wherein the alkoxy group of the alkyl tin compound is a branched alkoxy group, and the alcohol is a branched alcohol.

Advantageous Effects of Invention

According to the invention there are provided alkyl tin compounds that have minimal production of modified compounds (inactivated forms) even when used repeatedly at high temperatures. Since the alkyl tin compounds of the invention can minimize generation of inactivated forms even when used at high temperatures, and allow repeated and continuous production of esters in a stable manner, they are highly useful in industrial fields for synthesis of esters.

DESCRIPTION OF EMBODIMENTS

Figure 1:
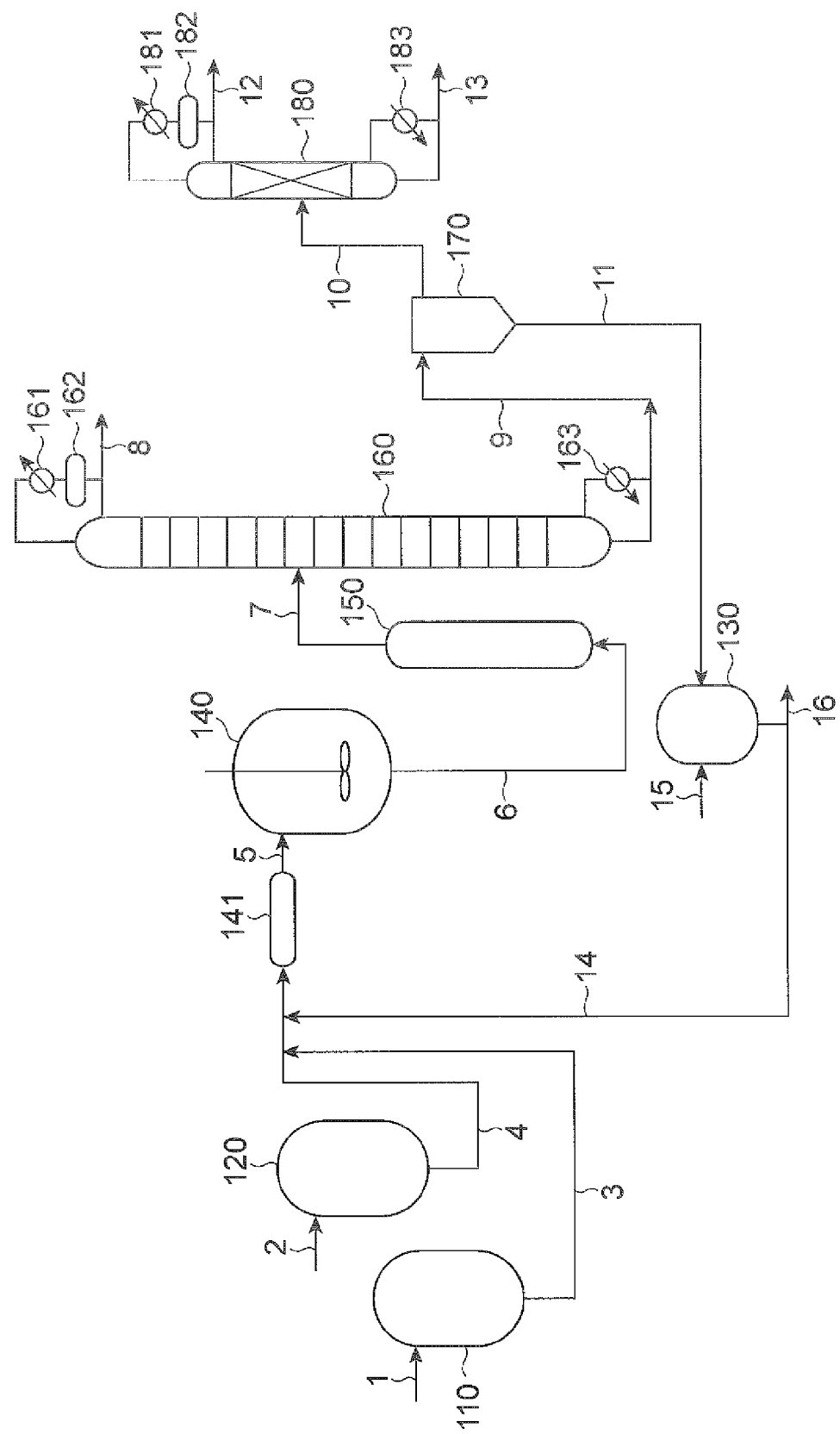
FIG. 1 is a schematic diagram of a continuous circulating reactor in which an ester compound is produced by transesterification reaction using an alkyl tin compound according to one embodiment.

Preferred modes for carrying out the invention (hereunder, "embodiments") will now be described in detail. The invention is not limited to the described embodiments, and may be carried out with various modifications such as are within the scope of the gist thereof.

According to one aspect, the invention relates to alkyl tin compounds having an alkyl group bonded to a tin atom. In the alkyl tin compound, the alkyl group is a branched alkyl or cyclic group-substituted alkyl group, the branched alkyl group being an alkyl group branched at at least one carbon atom of the first to third carbon atoms counting from the tin atom, and the cyclic group-substituted alkyl group being an alkyl group having a cyclic group bonded at at least one carbon atom of the first to third carbon atoms counting from the tin atom.

According to one embodiment, the alkyl tin compound may be an alkyl tin compound having one to three branched alkyl groups bonded to one tin atom. The valency of the tin atom may be tetravalent.

According to one embodiment, the branched alkyl groups may be C4-18 branched alkyl groups. The tin atom may also have a C1-8 alkoxy group bonded to it.

According to one embodiment, the alkyl tin compound may be a dialkyl tin alkoxide or a tetraalkyldialkoxydistannoxane.

According to one embodiment, the alkyl tin compound may be a compound represented by formula (1) or a compound represented by formula (2).

[Chemical Formula 14]

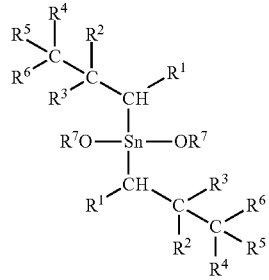

(1)

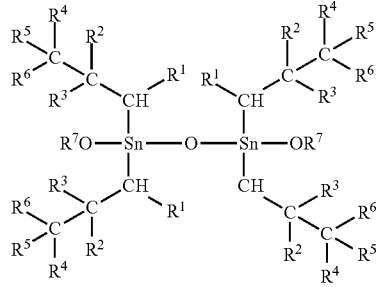

(2)

[$R^1$, $R^2$, $R^3$, $R^4$, $R^5$ and $R^6$ each independently represent hydrogen or a C1-15 alkyl group, and $R^7$ represents a C1-8 alkyl group. This is with the proviso that $R^1$, $R^2$, $R^3$, $R^4$, $R^5$ and $R^6$ are not all hydrogen, at least one of $R^1$, $R^2$ and $R^3$ is an alkyl group, or all of $R^1$, $R^2$ and $R^3$ are hydrogen, and at least two of $R^4$, $R^5$ and $R^6$ are alkyl groups, the total number of carbon atoms of $R^1$, $R^2$, $R^3$, $R^4$, $R^5$ and $R^6$ being 2 to 15.]

According to one embodiment, the alkyl tin compound may be a trialkyl tin compound.

According to one embodiment, the alkyl tin compound may be a compound represented by formula (3).

[Chemical Formula 15]

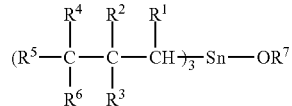

(3)

[$R^1$, $R^2$, $R^3$, $R^4$, $R^5$ and $R^6$ each independently represent hydrogen or a C1-15 alkyl group, and $R^7$ represents a C1-8 alkyl group. This is with the proviso that $R^1$, $R^2$, $R^3$, $R^4$, $R^5$ and $R^6$ are not all hydrogen, at least one of $R^1$, $R^2$ and $R^3$ is an alkyl group, or all of $R^1$, $R^2$ and $R^3$ are hydrogen, and at least two of $R^4$, $R^5$ and $R^6$ are alkyl groups, the total number of carbon atoms of $R^1$, $R^2$, $R^3$, $R^4$, $R^5$ and $R^6$ being 2 to 15.]

According to one embodiment, the tin atom may also have a C1-8 alkoxy group bonded to it. In that case, the alkoxy group may be an alkoxy group selected from among n-butyloxy, isobutyloxy, sec-butyloxy and C5-8 alkoxy groups. The alkoxy group may also be a branched alkoxy group.

According to one embodiment, the alkyl tin compound may be an alkyl tin alkoxide obtained from an alkyl tin carboxylate, alkyl tin oxide, alkyl tin oxide polymer or alkyl tin halide.

According to one embodiment, the alkyl tin compound may be an alkyl tin alkoxide having a C5-18 branched alkyl group and a C4-8 branched alkoxy group, and it may be a compound represented by formula (1) or a compound represented by formula (2).

[Chemical Formula 16]

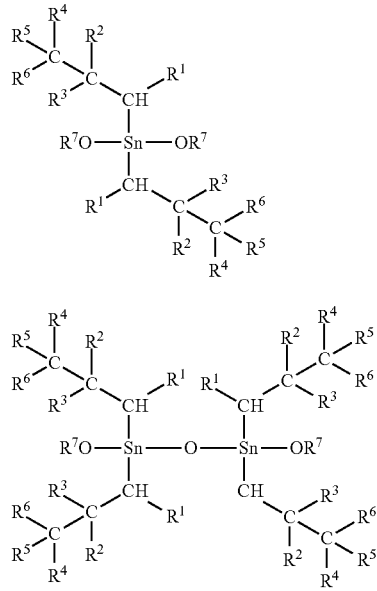

[$R^1$, $R^2$, $R^3$, $R^4$, $R^5$ and $R^6$ each independently represent hydrogen or a C1-15 alkyl group, and $R^7$ represents a C4-8 branched alkyl group. This is with the proviso that $R^1$, $R^2$, $R^3$, $R^4$, $R^5$ and $R^6$ are not all hydrogen, at least one of $R^1$, $R^2$ and $R^3$ is an alkyl group, or all of $R^1$, $R^2$ and $R^3$ are hydrogen, and at least two of $R^4$, $R^5$ and $R^6$ are alkyl groups, the total number of carbon atoms of $R^1$, $R^2$, $R^3$, $R^4$, $R^5$ and $R^6$ being 2 to 15.]

According to one embodiment, the alkyl tin compound may be an alkyl tin compound having a cyclic group-substituted alkyl group bonded to a tin atom, the cyclic group-substituted alkyl group being an alkyl group having a cyclic group selected from among alicyclic hydrocarbon groups and aromatic hydrocarbon groups bonded to at least one carbon atom among the first to third carbon atoms counting from the tin atom, and the valency of the tin atom being tetravalent.

According to one embodiment, the alkyl tin compound may also have a C1-8 alkoxy group.

According to one embodiment, the cyclic group may be a C4-18 cyclic group.

According to one embodiment, the alkyl tin compound may be a di(cyclic group-substituted alkyl) tin dialkoxide or a tetra(cyclic group-substituted alkyl)dialkoxydistannoxane.

According to one embodiment, the alkyl tin compound may be a compound represented by formula (1) or a compound represented by formula (2).

[Chemical Formula 17]

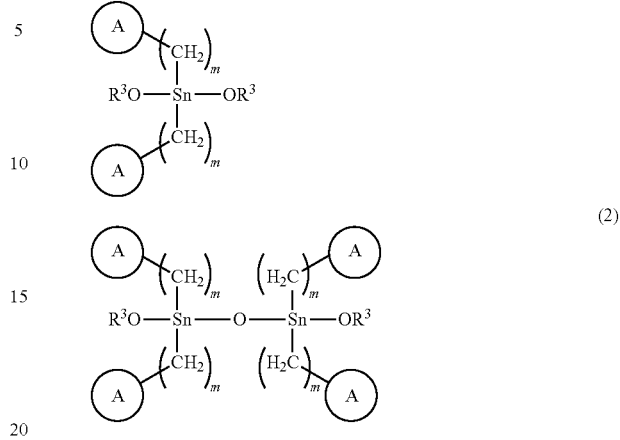

[Ring A represents a C3-16 alicyclic hydrocarbon group or a C6-16 aromatic hydrocarbon group, m is an integer of 1 to 3, and $R^3$ represents a C1-8 alkyl group.]

According to one embodiment, the alkyl tin compound may be a tri(cyclic group-substituted alkyl) tin compound.

According to one embodiment, the alkyl tin compound may be a compound represented by formula (3).

[Chemical Formula 18]

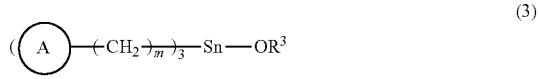

[Ring A represents a C3-16 alicyclic hydrocarbon group or a C6-16 aromatic hydrocarbon group, m is an integer of 1 to 3, and $R^3$ represents a C1-8 alkyl group.]

According to one embodiment, the alkyl tin compound may also have a C1-8 alkoxy group bonded to the tin atom. The alkoxy group may be a C4-8 alkoxy group. The alcohol corresponding to the alkoxy group is preferably an alcohol with a boiling point of 100° C. or higher at ordinary pressure.

According to one embodiment, the alcohol is preferably one that forms an azeotropic mixture with water.

According to one embodiment, the alkoxy group may be a branched alkoxy group.

According to one embodiment, the alkyl tin compound may be an alkyl tin alkoxide obtained from a cyclic group-substituted alkyl tin carboxylate, a cyclic group-substituted alkyl tin oxide, a cyclic group-substituted alkyl tin oxide polymer or a halogenated (cyclic group-substituted alkyl) tin compound.

According to another aspect, the invention relates to a composition comprising the alkyl tin compound.

According to one embodiment, the composition may be a composition comprising one or more of the aforementioned alkyl tin compounds.

According to one embodiment, the composition may be one comprising at least one type of first alkyl tin compound selected from among dialkyl tin alkoxides and tetraalkyl-dialkoxydistannoxanes, and at least one type of second alkyl tin compound selected from among trialkyl tin compounds.

According to one embodiment, the first alkyl tin compound may be a compound represented by formula (1) or a compound represented by formula (2).

[Chemical Formula 19]

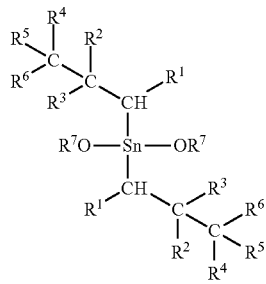
(1)

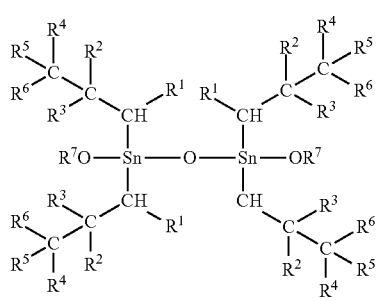
(2)

[$R^1$, $R^2$, $R^3$, $R^4$, $R^5$ and $R^6$ each independently represent hydrogen or a C1-15 alkyl group, and $R^7$ represents a C1-8 alkyl group. This is with the proviso that $R^1$, $R^2$, $R^3$, $R^4$, $R^5$ and $R^6$ are not all hydrogen, at least one of $R^1$, $R^2$ and $R^3$ is an alkyl group, or all of $R^1$, $R^2$ and $R^3$ are hydrogen, and at least two of $R^4$, $R^5$ and $R^6$ are alkyl groups, the total number of carbon atoms of $R^1$, $R^2$, $R^3$, $R^4$, $R^5$ and $R^6$ being 2 to 15.]

According to one embodiment, the second alkyl tin compound may be a compound represented by formula (3).

[Chemical Formula 20]

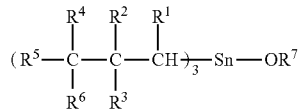
(3)

[$R^1$, $R^2$, $R^3$, $R^4$, $R^5$ and $R^6$ each independently represent hydrogen or a C1-15 alkyl group, and $R^7$ represents a C1-8 alkyl group. This is with the proviso that $R^1$, $R^2$, $R^3$, $R^4$, $R^5$ and $R^6$ are not all hydrogen, at least one of $R^1$, $R^2$ and $R^3$ is an alkyl group, or all of $R^1$, $R^2$ and $R^3$ are hydrogen, and at least two of $R^4$, $R^5$ and $R^6$ are alkyl groups, the total number of carbon atoms of $R^1$, $R^2$, $R^3$, $R^4$, $R^5$ and $R^6$ being 2 to 15.]

According to one embodiment, the composition may comprise at least one type of third alkyl tin compound selected from among di(cyclic group-substituted alkyl) tin dialkoxides and tetra (cyclic group-substituted alkyl)dialkoxydistannoxanes, and at least one type of fourth alkyl tin compound selected from among tri(cyclic group-substituted alkyl) tin compounds.

According to one embodiment, the third alkyl tin compound may be a compound represented by formula (1) or a compound represented by formula (2).

[Chemical Formula 21]

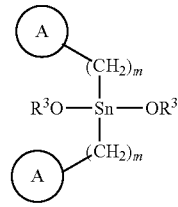
(1)

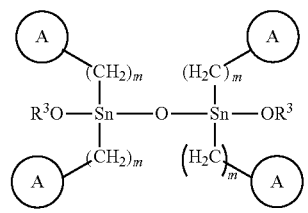
(2)

[Ring A represents a C3-16 alicyclic hydrocarbon group or a C6-16 aromatic hydrocarbon group, m is an integer of 1 to 3, and $R^3$ represents a C1-8 alkyl group.]

According to one embodiment, the fourth alkyl tin compound may be a compound represented by formula (3).

[Chemical Formula 22]

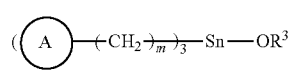
(3)

[Ring A represents a C3-16 alicyclic hydrocarbon group or a C6-16 aromatic hydrocarbon group, m is an integer of 1 to 3, and $R^3$ represents a C1-8 alkyl group.]

According to yet another aspect, the invention relates to a catalyst for a process for producing a carbonic acid ester from a carbon dioxide and an alcohol. The catalyst comprises the aforementioned alkyl tin compound.

According to yet another aspect, the invention relates to a method for producing a carbonic acid ester using the alkyl tin compound. The production method has the following steps (1) to (3).

Step (1): A step of reacting the alkyl tin compound with carbon dioxide to obtain a reaction mixture containing a carbonic acid ester.

Step (2): A step of separating the carbonic acid ester from the reaction mixture to obtain a residual solution.

Step (3): A step of reacting the residual solution with an alcohol and removing the water produced by the reaction, to obtain an alkyl tin alkoxide, and recycling it to step (1).

According to one embodiment, the alkyl tin compound in the production method may include either or both a compound represented by formula (1) and/or a compound represented by formula (2).

[Chemical Formula 23]

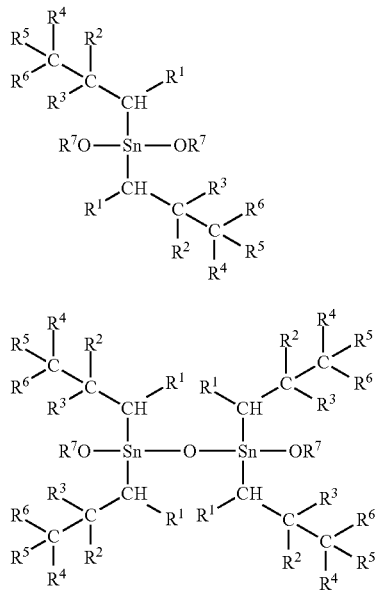

(1)

(2)

[$R^1$, $R^2$, $R^3$, $R^4$, $R^5$ and $R^6$ each independently represent hydrogen or a C1-15 alkyl group, and $R^7$ represents a C1-8 alkyl group. This is with the proviso that $R^1$, $R^2$, $R^3$, $R^4$, $R^5$ and $R^6$ are not all hydrogen, at least one of $R^1$, $R^2$ and $R^3$ is an alkyl group, or all of $R^1$, $R^2$ and $R^3$ are hydrogen, and at least two of $R^4$, $R^5$ and $R^6$ are alkyl groups, the total number of carbon atoms of $R^1$, $R^2$, $R^3$, $R^4$, $R^5$ and $R^6$ being 2 to 15.]

The alkyl tin compound used in the production method may further comprise a compound represented by formula (3).

[Chemical Formula 24]

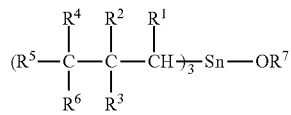

(3)

[$R^1$, $R^2$, $R^3$, $R^4$, $R^5$ and $R^6$ each independently represent hydrogen or a C1-15 alkyl group, and $R^7$ represents a C1-8 alkyl group. This is with the proviso that $R^1$, $R^2$, $R^3$, $R^4$, $R^5$ and $R^6$ are not all hydrogen, at least one of $R^1$, $R^2$ and $R^3$ is an alkyl group, or all of $R^1$, $R^2$ and $R^3$ are hydrogen, and at least two of $R^4$, $R^5$ and $R^6$ are alkyl groups, the total number of carbon atoms of $R^1$, $R^2$, $R^3$, $R^4$, $R^5$ and $R^6$ being 2 to 15.]

According to this embodiment, the alkoxy group of the alkyl tin compound used in the production method may be selected from among n-butyloxy, isobutyloxy, sec-butyloxy and C5-8 alkoxy groups.

According to one embodiment, the alcohol used in the production method may be an alcohol selected from among n-butyl alcohol, isobutyl alcohol, sec-butyl alcohol and C5-8 alkyl alcohols.

According to one embodiment, the alkoxy group of the alkyl tin compound used in the production method may be a branched alkoxy group, in which case the alcohol may be a branched alcohol corresponding to the branched alkoxy group.

According to one embodiment, the alkyl tin compound used in the production method may include either or both a compound represented by formula (1) and/or a compound represented by formula (2).

[Chemical Formula 25]

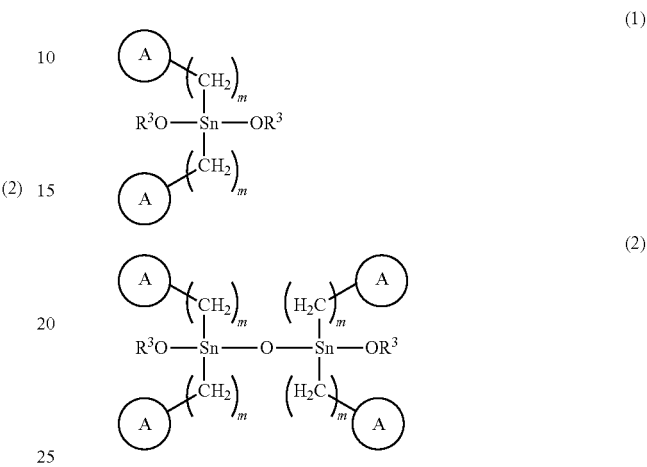

(1)

(2)

[Ring A represents a C3-16 alicyclic hydrocarbon group or a C6-16 aromatic hydrocarbon group, m is an integer of 1 to 3, and $R^3$ represents a C1-8 alkyl group.]

The alkyl tin compound used in the production method may further comprise a compound represented by formula (3).

[Chemical Formula 26]

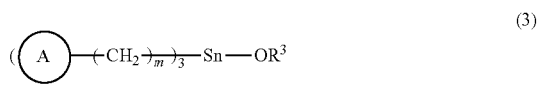

(3)

[Ring A represents a C3-16 alicyclic hydrocarbon group or a C6-16 aromatic hydrocarbon group, m is an integer of 1 to 3, and $R^3$ represents a C1-8 alkyl group.]

In the production method described above, the alkoxy groups of the compounds represented by formula (1) and the compounds represented by formula (2) may be C4-8 alkoxy groups, and the alcohols corresponding to the alkoxy groups may be alcohols with boiling points of 100° C. or higher at ordinary pressure, while the alcohol used in step (3) may be the alcohol corresponding to the alkoxy group.

Also, the alcohol in the production method is a C4-8 alcohol with a boiling point of 100° C. or higher at ordinary pressure.

In this production method, the alcohol may be an alcohol selected from among n-butyl alcohol, isobutyl alcohol, sec-butyl alcohol and C5-8 alkyl alcohols.

Furthermore, the alkoxy group of the alkyl tin compound used in the production method may be a branched alkoxy group, and the alcohol may be a branched alcohol.

(First Embodiment)

A first embodiment of the invention, as a preferred embodiment, will now be described.

The alkyl tin compound of this embodiment is an alkyl tin compound for ester synthesis, and specifically an alkyl tin compound having one to three branched alkyl groups bonded to a tin atom, the branched alkyl groups being alkyl groups branched at at least one carbon atom among the first to third carbon atoms counting from the tin atom, and the valency of the tin atom being tetravalent. Furthermore, the alkyl tin compound is an alkyl tin compound that functions as a catalyst during ester synthesis.

Synthesis reactions generally employ catalysts. They are used to more rapidly promote specific reactions. The catalysts themselves are unaltered before and after the reaction, or even if consumed they can be regenerated for repeated use in the reaction. Ideally, therefore, the catalyst is added initially and used perpetually and repeatedly in the reaction to produce a chemical product.

However, catalyst degradation and inactivation is an often encountered phenomenon, and in order to maintain the reaction rate, procedures are necessary for addition and replacement of fresh catalyst. With continued addition of catalyst, inactivated catalyst accumulates within the reaction system and replacement also results in removal and disposal of catalyst that still maintains its activity, together with the inactivated catalyst. The productivity is also impaired by carrying out the aforementioned procedure.

Inactivation of catalyst differs depending on the reaction and on the type (homogeneous system or non-homogeneous system) and structure of the catalyst, and therefore the method for dealing with it cannot be defined for all cases.

Among such synthesis reactions, the alkyl tin compound of this embodiment is a homogeneous catalyst for ester synthesis, the tin atom of the alkyl tin compound being tetravalent, and it is highly useful for industry. For the purpose of this embodiment, "ester synthesis reaction" refers to transesterification reaction, esterification reaction, carbonic acid ester synthesis reaction or carbamic acid ester synthesis reaction, and it is synthesis of a neutral ester of a carboxylic acid or carbamic acid, or transesterification reaction.

While very few examples exist of detailed research into inactivating reactions of the catalyst performance of alkyl tin compounds, the results of our research have shown that the alkyl group disproportionation reactions represented by chemical equations (8) and (9) occur very readily.

[Chemical Formula 27]

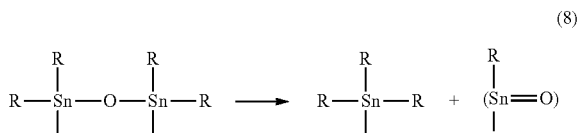

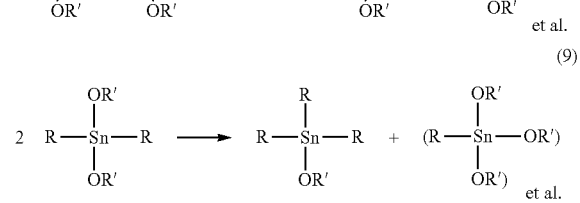

It was found that in these inactivation reactions, the number of alkyl groups bonding to the tin atom in the alkyl tin compound changes, such that the initial catalytic activity can no longer be obtained. While the reason for the reduction in catalytic activity occurring with inactivation reaction is not clearly understood, it is possible that, for example, the distannoxane-type alkyl tin compound represented in chemical equation (8) is structurally stabilized by adopting the ladder structure shown in formula (10) (or as has also been reported, forming a cyclic structure of two or more molecules when existing as a monomer), and the alkyl tin compound in equation (9) exhibits its catalytic action by forming a structure containing an aggregate such as the core structure shown in formula (11). It is presumed that when this disproportionation reaction takes place, such structures are difficult to form, or that the catalytic activity is altered by electronic effects due to changes in the number of alkyl groups bonding to tin or by mutual effects between them.

[Chemical Formula 28]

The present invention has been completed in light of this situation, by specific alkyl tin compounds that inhibit these disproportionation reactions and function as homogeneous catalysts in ester synthesis.

The compounds to be used for this embodiment will now be described.

The compound names used herein are in most cases names based on the rules of convention of Nomenclature (IUPAC Nomenclature of Organic Chemistry) as established by the IUPAC (The International Union of Pure and Applied Chemistry). The term "organic" refers to the group of compounds that are the subject matter of the Nomenclature according to the aforementioned rules of convention. This subject matter may be the subject matter described in the recommendations of 1993. However, "organic" compounds that are the subject matter of the aforementioned Nomenclature include organometallic compounds and metal complexes. For the embodiments described herein, "organic", "organic group" and/or "substituent", as well as other compounds used for the embodiments, are composed of atoms that do not include metal atoms and/or metalloids, unless otherwise specified. More preferably, "organic compound", "organic group" or "substituent" as used for the embodiments are composed of atoms selected from among H (hydrogen), C (carbon), N (nitrogen), O (oxygen), S (sulfur), Cl (chlorine), Br (bromine) and I (iodine).

The terms "aliphatic" and "aromatic" are also frequently used throughout the following explanation. According to IUPAC rules, organic compounds are classified as aliphatic compounds and aromatic compounds. Aliphatic compounds are defined as aliphatic compounds based on the IUPAC recommendations of 1995. The recommendations define aliphatic compounds as "acyclic or cyclic, saturated or unsaturated carbon compounds, excluding aromatic compounds". Also, the term "aliphatic compounds" used for the embodiments includes saturated aliphatic compounds and unsaturated aliphatic compounds, as well as straight-chain aliphatic compounds and cyclic aliphatic compounds, and it refers to "organic compounds", "organic groups" or "substituents" that are composed of atoms selected from among H (hydrogen), C (carbon), N (nitrogen), O (oxygen), S (sulfur), Si (silicon) and halogen atoms such as Cl (chlorine), Br (bromine) and I (iodine).

Also, when an aromatic group is bonded to an aliphatic group, as in an "aralkyl group", this will often be referred to as an "aliphatic group substituted with an aromatic group", an "aromatic aliphatic group" or a "group comprising an aliphatic group to which an aromatic group is bonded". This is based on the reactivity in the embodiments, as the property relating to reaction of groups such as aralkyl groups is very similar to aliphatic reactivity instead of aromaticity. Furthermore, non-aromatic reactive groups that include aralkyl and alkyl groups are often referred to as "aliphatic groups optionally substituted with aromatic groups", "aromatic-substituted aliphatic groups" or "aromatic group-bonded aliphatic groups", and these are also included among "aliphatic groups".

When explaining a general formula for a compound used herein, the definition according to the rules of Nomenclature established by the IUPAC are used, but common names will often be used for the specific group names and exemplary compound names. Moreover, numbers of atoms and numbers of substituents are often mentioned herein, and these are all integers.

When the substituents or compounds mentioned herein have structural isomers, they include the structural isomers unless otherwise specified.

The alkyl tin compounds of the invention will be described first.

The alkyl tin compound of one embodiment is an alkyl tin compound having one to three branched alkyl groups bonded to a tin atom, the branched alkyl groups being alkyl groups branched at at least one carbon atom among the first to third carbon atoms counting from the tin atom, and the valency of the tin atom being tetravalent. While an effect will sometimes be exhibited even if the branched alkyl group includes a heteroatom (for example, oxygen), as with an ether bond, alkenyl tin compounds or alkyl tin compounds are preferred, among which alkyl tin compounds with branched alkyl groups composed of carbon and hydrogen are more preferred.

As a result of diligent research on the problems of the prior art, it was found, surprisingly, that the placement of the carbon atom near the tin atom of the alkyl tin compound has a notable effect on formation of the inactivated form. It is unclear whether this effect is an electron effect or a steric effect, but it is presumed to be less than an effect of steric hindrance. Regardless of the manner of the effect, a notable effect is exhibited by alkyl groups with certain specific branching. An effect has been found when using alkyl tin compounds in which the alkyl groups are branched at a carbon atom of the alkyl tin compound that is near tin (within the first to third carbon atoms counting from the tin atom). On the other hand, in a structure wherein an aromatic group is directly substituted on the tin atom, the original catalytic action and reactivity are reduced. In order to obtain an effect of both preventing inactivation and maintaining activity, an alkyl group with specific branching is preferred.

From the viewpoint of activity, in an alkyl group having the aforementioned specific branching, preferably the first carbon atom counting from the tin atom is a secondary or tertiary carbon atom bonded to at least one hydrogen.

A specific example where one branched alkyl group is bonded to a tin atom is shown in formula (13) (where the tin atom is tetravalent, and the other groups are omitted).

[Chemical Formula 29]

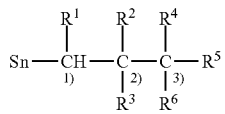

(13)

[$R^1$, $R^2$, $R^3$, $R^4$, $R^5$ and $R^6$ each independently represent hydrogen or a C1-15 alkyl group, and $R^7$ represents a C1-8 alkyl group. This is with the proviso that $R^1$, $R^2$, $R^3$, $R^4$, $R^5$ and $R^6$ are not all hydrogen, at least one of $R^1$, $R^2$ and $R^3$ is an alkyl group, or all of $R^1$, $R^2$ and $R^3$ are hydrogen, and at least two of $R^4$, $R^5$ and $R^6$ are alkyl groups, the total number of carbon atoms of $R^1$, $R^2$, $R^3$, $R^4$, $R^5$ and $R^6$ being 2 to 15. The numerals 1), 2) and 3) represent the ordering of carbon atoms from the tin atom, being the primary, secondary and tertiary carbon atoms, respectively.]

Of these, C4-18 alkyl tin compounds with branched alkyl groups are preferred from the viewpoint of flow properties and solubility in solvents, when used as a homogeneous catalysts.

Examples of such branched alkyl groups include 1-methyl-propyl, 1-methyl-butyl, 1,2-dimethyl-butyl, 1,3-dimethyl-butyl, 1-ethyl-butyl, 1-propyl-butyl, 1,3-dimethyl-pentyl, 1-methyl-2,2-dimethyl-butyl, 1-ethyl-pentyl, 1,2-dimethyl-hexyl, 1-methyl-hexyl, 1-ethyl-hexyl, 1-propyl-hexyl, 1-butyl-hexyl, 1,2-diethyl-hexyl, 1,2-dimethyl-heptyl, 1-ethyl-heptyl, 1-propyl-hexyl, 1-butyl-hexyl, 1,2-dimethyl-octyl, 1-ethyl-octyl, 1-propyl-hexyl, 1-butyl-hexyl, 1,2-dimethyl-nonyl, 1-ethyl-nonyl, 1,2-dimethyl-decyl, 1-ethyl-decyl, 1,2-dimethyl-undecyl, 1-ethyl-undecyl, 1,2-dimethyl-dodecyl, 1-ethyl-dodecyl, 1,2-dimethyl-tridecyl, 1-ethyl-tridecyl, 1,2-dimethyl-tetradecyl, 1-ethyl-tetradecyl, 1,2-dimethyl-pentadecyl, 2-ethyl-pentadecyl, 2-methyl-propyl, 2-methyl-butyl, 3-methyl-butyl, 2,3-dimethyl-butyl, 3,3-dimethyl-butyl, 2-ethyl-butyl, 2-propyl-butyl, 2-methyl-butyl, 2,3-dimethyl-pentyl, 2-methyl-3,3-dimethyl-butyl, 2-ethyl-pentyl, 3-ethyl-pentyl, 2,2-dimethyl-hexyl, 2-methyl-hexyl, 2-ethyl-hexyl, 3-ethyl-hexyl, 2-propyl-hexyl, 2-butyl-hexyl, 2,2-diethyl-hexyl, 2,2-dimethyl-heptyl, 2-ethyl-heptyl, 2-propyl-hexyl, 2-butyl-hexyl, 2,2-dimethyl-octyl, 2-ethyl-octyl, 2-propyl-hexyl, 2-butyl-hexyl, 2,2-dimethyl-nonyl, 2-ethyl-nonyl, 2,2-dimethyl-decyl, 2-ethyl-decyl, 2,2-dimethyl-undecyl, 2-ethyl-undecyl, 2,2-dimethyl-dodecyl, 2-ethyl-dodecyl, 2,2-dimethyl-tridecyl, 2-ethyl-tridecyl, 2,2-dimethyl-tetradecyl, 2-ethyl-tetradecyl, 2,2-dimethyl-pentadecyl and 2-ethyl-pentadecyl. More effective branched alkyl groups that are preferred for maintaining catalytic activity are branched alkyl groups wherein the carbon atom at the first position (adjacent to the tin atom) is a secondary or tertiary carbon atom having at least one hydrogen bonded thereto. More preferably, it is a branched alkyl group in which a C1-4 alkyl group is substituted at the second or third position counting from the tin atom. Examples of such branched alkyl groups include 2,2-dimethyl-butyl, 2,2-dimethyl-hexyl, 2,2-dimethyl-octyl, 2-propyl-butyl, 2-ethyl-butyl, 2-methyl-pentyl, 2-ethyl-pentyl, 2-propyl-pentyl, 2-butyl-pentyl, 2-methyl-hexyl, 2-propyl-hexyl, 2-butyl-hexyl, 2-ethyl-heptyl, 2-ethyl-octyl, 2-ethyl-decyl, 2-ethyl-dodecyl, 2,3-dimethyl-butyl, 2,3-dimethyl-hexyl, 2,3-dimethyl-octyl, 3-propyl-butyl, 3-ethyl-butyl, 3-methyl-pentyl, 3-ethyl-pentyl, 3-propyl-pentyl, 3-butyl-pentyl, 3-methyl-hexyl, 3-propyl-hexyl, 3-butyl-hexyl, 3-ethyl-heptyl, 3-ethyl-octyl, 3-ethyl-decyl and 3-ethyl-dodecyl.

As mentioned above, the degree of inactivation is higher when the alkyl tin compound is an alkyl tin alkoxide. Therefore, the effect of the invention is greater when the alkyl tin compounds in the embodiments are alkyl tin alkoxides. Also, the alkoxy group is more preferably C1-8 in consideration of catalytic action and reactivity.

Examples of preferred alkoxy groups include methyloxy, ethyloxy, propyloxy (all isomers), butyloxy (all isomers), pentyloxy (all isomers), hexyloxy (all isomers), heptyloxy (all isomers), and octyloxy (all isomers).

Although it will depend on the purpose of use of the alkyl tin compound, in consideration of regeneration of the alkyl tin compound, more preferably the number of carbon atoms of the alkoxy group is 4 to 8, and the alcohol corresponding to the alkoxy group is an alcohol with a boiling point of 100° C. or higher at ordinary pressure, when it is to be used as a catalyst for carbonic acid ester synthesis.

Examples of such alkoxy groups include n-butyloxy, isobutyloxy, sec-butyloxy and C5-8 alkoxy groups.

For use at high temperature, branched alkoxy groups are preferred as alkoxy groups with an effect of further inhibiting disproportionation reaction of the alkyl groups. More preferably, it is a group in which a C1-3 alkyl group is substituted at the secondary or tertiary position (the position of the carbon in the alkoxy group, which is the position from the oxygen bonded to the tin atom). Examples of such alkyl groups include 2-methyl-propyloxy, 2-methyl-butyloxy, 2-ethyl-butyloxy, 2-propyl-butyloxy, 2-methyl-pentyloxy, 2-ethyl-pentyloxy, 2-propyl-pentyloxy, 2-methyl-hexyloxy, 2-ethyl-hexyloxy, 3-methyl-butyloxy, 3-ethyl-butyloxy, 3-propyl-butyloxy, 3-methyl-pentyloxy, 3-ethyl-pentyloxy, 3-propyl-pentyloxy, 3-methyl-hexyloxy and 3-ethyl-hexyloxy.

In light of the above, the alkoxy group of the alkyl tin alkoxide is most preferably an alkoxy group selected from the group consisting of isobutyloxy and C5-8 alkoxy groups, and an alkoxy group in which a C1-3 alkyl group is substituted at the secondary or tertiary position (as the position of the carbon in the alkoxy group, which is the position from the oxygen bonded to the tin atom).

Preferred for use as alkyl tin compounds are compositions containing either or both a dialkyl tin dialkoxide and/or tetraalkyldialkoxydistannoxane (hereunder also referred to as "dialkyl tin dialkoxide composition"), which are useful as catalysts. The expression "active component" as used herein refers to, rather than alkyl tin compounds in general, alkyl tin compounds having two alkyl groups bonded to a tin atom, and specifically they include dialkyl tin alkoxides, tetraalkylalkoxydistannoxanes and/or dialkyl tin oxides.

When the composition is used, the molar ratio of tin atoms composing the dialkyl tin dialkoxide and tetraalkyldialkoxydistannoxane in the composition is not particularly restricted but is usually preferred to be in the range of 1:99 to 99:1 (1:49.5 to 99:0.5, represented as the molar ratio of dialkyl tin dialkoxide molecules and tetraalkyldialkoxydistannoxane molecules). When it is to be used at high temperature (for example, 100° C. or higher), a higher proportion of the more stable dialkyl tin dialkoxide is preferred, with introduction into the reactor at a proportion of 99:1 to 50:50 (99:0.5 to 50:25 in terms of the molecular molar ratio).

The dialkyl tin dialkoxide is preferably a compound represented by formula (1). The tetraalkyldialkoxydistannoxane is preferably a compound represented by formula (2).

[Chemical Formula 30]

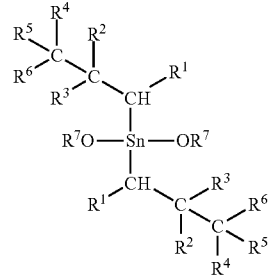

(1)

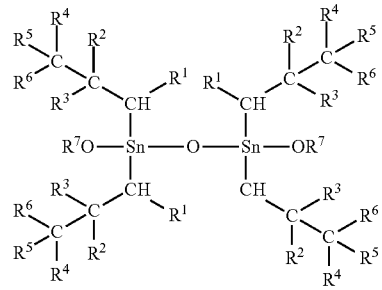

(2)

[$R^1$, $R^2$, $R^3$, $R^4$, $R^5$ and $R^6$ each independently represent hydrogen or a C1-15 alkyl group, and $R^7$ represents a C1-8 alkyl group. This is with the proviso that $R^1$, $R^2$, $R^3$, $R^4$, $R^5$ and $R^6$ are not all hydrogen, at least one of $R^1$, $R^2$ and $R^3$ is an alkyl group, or all of $R^1$, $R^2$ and $R^3$ are hydrogen, and at least two of $R^4$, $R^5$ and $R^6$ are alkyl groups, the total number of carbon atoms of $R^1$, $R^2$, $R^3$, $R^4$, $R^5$ and $R^6$ being 2 to 15.]

As used herein, the tetraalkyldialkoxydistannoxane structure is the structure represented by formula (2) as the canonical structure. However, as with the dialkyl tin oxides described below, it may be present as the hydroxy structure represented by formula (14). Since the presence and content of hydroxy structures cannot be defined by analysis at the current time, the structures represented by formulas (2) and (14) mentioned herein are included among tetraalkyldialkoxydistannoxanes.

[Chemical Formula 31]

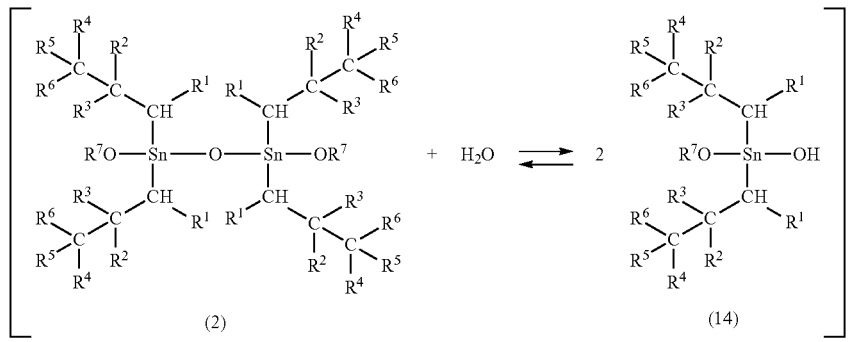

[$R^1$, $R^2$, $R^3$, $R^4$, $R^5$, $R^6$ and $R^7$ have the same definitions as above.]

In order to increase analysis precision for production control, preferably the alkyl groups of the dialkyl tin dialkoxide and tetraalkyldialkoxydistannoxane are the same alkyl groups, and the alkoxy groups are also the same alkoxy groups.

According to one embodiment of the invention, the alkyl tin compound may be a trialkyl tin compound, so that the composition contains a trialkyl tin compound. When the composition containing a dialkyl tin dialkoxide and/or tetraalkyldialkoxydistannoxane further includes a trialkyl tin compound, the number of moles of tin atoms composing the trialkyl tin compound is preferably in the range of 1 to 50 mol % with respect to the number of moles of tin atoms in the entire composition (the total number of moles of tin atoms composing the dialkyl tin dialkoxide, tetraalkyldialkoxydistannoxane and trialkyl tin compound in the composition). The thermostability can sometimes be increased if the trialkyl tin compound is present within this range. While the chemical reason for this is not completely understood, it is conjectured that the disproportionation equilibrium of alkyl groups may be shifted in the desired direction by heating. The catalytic activity and reactivity of the trialkyl tin compound is low compared to the dialkyl tin dialkoxide and tetraalkyldialkoxydistannoxane, and if the trialkyl tin compound content is greater than 50 mol %, it becomes necessary to increase the amount of composition in order to obtain desirable reaction results. The trialkyl tin compound content is more preferably 1 to 30 mol %.

Examples of such trialkyl tin compounds include compounds represented by formula (3).

[Chemical Formula 32]

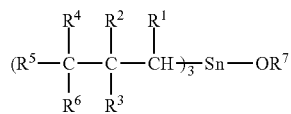

(3)

[$R^1$, $R^2$, $R^3$, $R^4$, $R^5$ and $R^6$ each independently represent hydrogen or a C1-15 alkyl group, and $R^7$ represents a C1-8 alkyl group. This is with the proviso that $R^1$, $R^2$, $R^3$, $R^4$, $R^5$ and $R^6$ are not all hydrogen, at least one of $R^1$, $R^2$ and $R^3$ is an alkyl group, or all of $R^1$, $R^2$ and $R^3$ are hydrogen, and at least two of $R^4$, $R^5$ and $R^6$ are alkyl groups, the total number of carbon atoms of $R^1$, $R^2$, $R^3$, $R^4$, $R^5$ and $R^6$ being 2 to 15.]

The alkyl tin alkoxides (dialkyl tin dialkoxide, tetraalkyldialkoxydistannoxane and/or trialkyl tin alkoxide) may be obtained by known methods. The preferred starting materials are alkyl tin carboxylates, alkyl tin oxides, alkyl tin oxide polymers or alkyl tin halides. Publicly known synthesis methods for these starting materials are preferably employed. The production conditions may modified for optimal performance (for example, Wilhelm P. Neumann et al., Justus Liebigs Annalen der Chemie, Vol. 663, pp 11-21 (1963), Egmond, J. C. van et al., Journal of Applied Chemistry (London), vol. 12, pp 17-27 (1962), Seyferth et al., Journal of Organic Chemistry, vol. 26, p 2934 (1961), Kerk, G. J. van der; Luijten et al., Journal of Applied Chemistry (London), vol. 7, pp 369-374(1957), P. Fostein et al., Journal of Organometallic Chemistry, vol. 114, pp C7-C10 (1976)). Methods for producing alkyl tin alkoxides from starting materials may be any publicly known methods. The composition containing the alkyl tin alkoxide may also include an alkyl tin oxide and/or alkyl tin oxide polymer, but the alkyl tin carboxylate and alkyl tin halide contents are preferably as low as possible. For example, they are preferably used with purification to no greater than 20 mol %, as expressed in mol % of tin atoms. A publicly known method is preferably used for purification. A trialkyl tin alkoxide can also be obtained by heat degradation of a dialkyl tin dialkoxide or tetraalkyldialkoxydistannoxane. The method for producing an alkyl tin oxide or alkyl tin oxide polymer as a starting material is also preferably a known method.

In order to increase analysis precision for production control, preferably the alkyl groups of the dialkyl tin dialkoxide, tetraalkyldialkoxydistannoxane and trialkyl tin alkoxide are the same alkyl groups, and the alkoxy groups are also the same alkoxy groups.

The alkyl tin compound is preferably used as a homogeneous catalyst for ester synthesis, among other synthesis reactions. For the purpose of this disclosure, "ester synthesis reaction" refers to transesterification reaction, esterification reaction, carbonic acid ester synthesis reaction or carbamic acid ester synthesis reaction, and it is synthesis of a neutral ester of a carboxylic acid or carbamic acid, or transesterification reaction.

There are no particular restrictions on the reaction temperature, but the range is preferably 0° C. to 250° C. There are no restrictions on the use of reaction solvents, but preferred examples are hydroxy hydrocarbons such as alcohols and phenols; hydrocarbons; and ethers such as THF, and any solvents that do not notably impair the structure of the alkyl tin compound by oxidation reaction, reduction reaction or alkyl group dissociation reaction may be selected as appropriate. Undesirable secondary reactions often occur with strongly acidic solvents or strong alkali solvents, and preferably the reaction solvent and reaction temperature are selected in consideration of the appropriate secondary reaction rate.

Ester synthesis reaction is preferably conducted with the alkyl tin compound in a dissolved or molten state, and the temperature and solvent are preferably selected as appropriate for this.

An inert gas may be used for the ester synthesis reaction. Examples of inert gases include nitrogen, argon and helium. Carbon dioxide may be used as it has no adverse effects. Oxygen, hydrogen, hydrogen sulfide, carbon monoxide and the like may be included in ranges that do not notably impair the structure of the alkyl tin compound or the reaction results, and they are purified and controlled by known methods so that consistent, desired reaction results are obtained.

A method for producing a carbonic acid ester will now be described as a preferred method for the invention.

According to one embodiment, the alkyl tin compound is a catalyst for a process of producing a carbonic acid ester by reaction with carbon dioxide. The alkyl tin compound is preferably an alkyl tin alkoxide.

The production method for this embodiment is a method for producing a carbonic acid ester using an alkyl tin alkoxide, wherein the alkyl tin alkoxide includes either or both a compound represented by formula (1) and/or a compound represented by formula (2), and the method for producing a carbonic acid ester comprises the following steps (1) to (3).

Step (1): A step of reacting an alkyl tin alkoxide with carbon dioxide to obtain a reaction mixture containing a carbonic acid ester.

Step (2): A step of separating the carbonic acid ester from the reaction mixture to obtain a residual solution.

Step (3): A step of reacting the residual solution with an alcohol and removing the water produced by the reaction, to obtain an alkyl tin alkoxide, and recycling it to step (1).

[Chemical Formula 33]

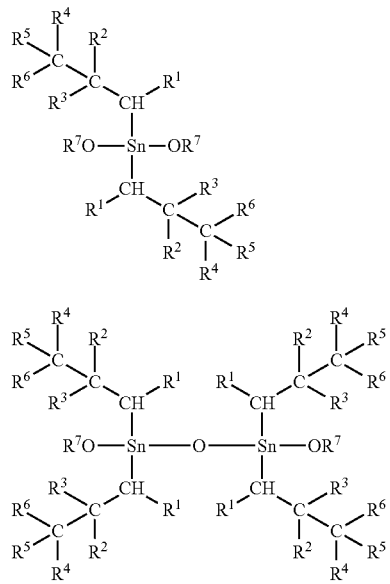

[$R^1$, $R^2$, $R^3$, $R^4$, $R^5$ and $R^6$ each independently represent hydrogen or a C1-15 alkyl group, and $R^7$ represents a C1-8 alkyl group. This is with the proviso that $R^1$, $R^2$, $R^3$, $R^4$, $R^5$ and $R^6$ are not all hydrogen, at least one of $R^1$, $R^2$ and $R^3$ is an alkyl group, or all of $R^1$, $R^2$ and $R^3$ are hydrogen, and at least two of $R^4$, $R^5$ and $R^6$ are alkyl groups, the total number of carbon atoms of $R^1$, $R^2$, $R^3$, $R^4$, $R^5$ and $R^6$ being 2 to 15.]

The dialkyl tin dialkoxide and tetraalkyldialkoxydistannoxane to be used in the method for producing a carbonic acid ester may be the dialkyl tin dialkoxide and tetraalkyldialkoxydistannoxane mentioned above, preferably as a composition comprising either or both the dialkyl tin dialkoxide and/or tetraalkyldialkoxydistannoxane. In the case of a composition, the molar ratio of tin atoms composing the dialkyl tin dialkoxide and tetraalkyldialkoxydistannoxane in the composition is not particularly restricted but is preferred to be in the range of 1:99 to 99:1 (1:49.5 to 99:0.5, represented as the molar ratio of dialkyl tin dialkoxide molecules and tetraalkyldialkoxydistannoxane molecules). When it is to be used at high temperature (for example, 100° C. or higher), a higher proportion of the more stable dialkyl tin dialkoxide is preferred, with introduction into the reactor so that the proportion is 99:1 to 50:50 (99:0.5 to 50:25 in terms of the molecular molar ratio).

In order to carry out step (3) in a desirable manner, in consideration of recycling of the alkyl tin compound, more preferably the alkoxy group of the alkyl tin alkoxide is a C4-8 alkoxy group, and the alcohol corresponding to the alkoxy group has a boiling point of 100° C. or higher at ordinary pressure.

Examples of such alkoxy groups include n-butyloxy, isobutyloxy, sec-butyloxy and C5-8 alkoxy groups.

In order to increase analysis precision for production control, preferably the alkyl groups of the dialkyl tin dialkoxide and tetraalkyldialkoxydistannoxane are the same alkyl groups, and the alkoxy groups are also the same alkoxy groups.

In the production method for this embodiment, the composition preferably includes a trialkyl tin compound as the alkyl tin compound. The thermostability will sometimes be improved if the composition contains a trialkyl tin compound in a range such that the number of moles of tin atoms in the trialkyl tin compound with respect to the number of moles of tin atoms in the composition is 1 to 50 mol %. While the chemical reason for this is not completely understood, it is conjectured that the disproportionation equilibrium of alkyl groups may be shifted in the desired direction by heating. The catalytic action or reactivity of the trialkyl tin compound is low compared to the dialkyl tin dialkoxide or tetraalkyldialkoxydistannoxane. If the trialkyl tin compound content is greater than 50 mol % with respect to the number of moles of tin atoms in the composition, it will be necessary to increase the amount of composition to obtain the desired reaction results, and therefore the composition more preferably contains the trialkyl tin compound in a range of 1 to 30 mol %.

Preferred examples of trialkyl tin compounds include compounds represented by formula (3).

[Chemical Formula 34]

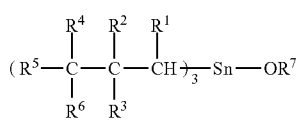

[R$^1$, R$^2$, R$^3$, R$^4$, R$^5$ and R$^6$ each independently represent hydrogen or a C1-15 alkyl group, and R$^7$ represents a C1-8 alkyl group. This is with the proviso that R$^1$, R$^2$, R$^3$, R$^4$, R$^5$ and R$^6$ are not all hydrogen, at least one of R$^1$, R$^2$ and R$^3$ is an alkyl group, or all of R$^1$, R$^2$ and R$^3$ are hydrogen, and at least two of R$^4$, R$^5$ and R$^6$ are alkyl groups, the total number of carbon atoms of R$^1$, R$^2$, R$^3$, R$^4$, R$^5$ and R$^6$ being 2 to 15.]

In order to increase analysis precision for production control, preferably the alkyl groups of the dialkyl tin dialkoxide, tetraalkyldialkoxydistannoxane and trialkyl tin alkoxide are the same alkyl groups, and the alkoxy groups are also the same alkoxy groups.

The alcohol used in step (3) will now be described.

The alcohol to be used in step (3) is preferably a C4-8 alcohol and an alcohol having a boiling point of 100° C. or higher at ordinary pressure, in consideration of recycling of the alkyl tin compound.

Examples of such alcohols include n-butyl alcohol, isobutyl alcohol, sec-butyl alcohol and C5-8 alkyl alcohols.

Through step (3), the alcohol is incorporated as the alkoxy group of the alkyl tin alkoxide. For use at high temperatures, the alcohol used in step (3) is preferably an alcohol having a C1-3 alkyl group substituting on the 2nd or 3rd carbon atom from the hydroxyl group, from the viewpoint of preventing alkyl group disproportionation reaction. Examples of such alcohols include 2-methyl-propyl alcohol, 2-methyl-butyl alcohol, 2-ethyl-butyl alcohol, 2-propyl-butyl alcohol, 2-methyl-pentyl alcohol, 2-ethyl-pentyl alcohol, 2-propyl-pentyl alcohol, 2-methyl-hexyl alcohol, 2-ethyl-hexyl alcohol, 3-methylbutyl alcohol, 3-ethyl-butyl alcohol, 3-propyl-butyl alcohol, 3-methyl-pentyl alcohol, 3-ethyl-pentyl alcohol, 3-propyl-pentyl alcohol, 3-methyl-hexyl alcohol and 3-ethyl-hexyl alcohol.

In order to increase the analysis precision for production control and increase the purity of the carbonic acid ester that is produced, the alkoxy groups of the dialkyl tin dialkoxide, tetraalkyldialkoxydistannoxane and trialkyl tin alkoxide are preferably the same alkoxy groups, and the alcohol used in step (3) is preferably the alcohol corresponding to the alkoxy groups.

(Method for Producing Carbonic Acid Ester)

A method for producing carbonic acid esters using alkyl tin alkoxides will now be explained in detail.

Methods previously disclosed by the present inventors are preferably used (for example, International Patent Publication No. WO03/055840, International Patent Publication No. WO2004/014840, International Patent Publication No. WO2005/000783, International Patent Publication No. WO2005/111049 and International Patent Publication No. WO2007/114130).

(i) Alkyl Tin Alkoxide Synthesis Step (Continuous Operation Start-Up Step)

The alkyl tin alkoxide to be used for this embodiment may be an alkyl tin alkoxide obtained by a known method, as described above. The alkyl tin alkoxide may be obtained, for example, from an alkyl tin carboxylate, alkyl tin oxide, alkyl tin oxide polymer or alkyl tin halide. It is preferred to use the previously disclosed method for producing alkyl tin alkoxides (International Patent Publication No. WO2005/111049 and elsewhere). This process produces an alkyl tin alkoxide from preferably a dialkyl tin oxide and an alcohol. The alcohol used may be any of the aforementioned alcohols.

The alkyl tin oxide used in this process may be a compound represented by formula (15).

[Chemical Formula 35]

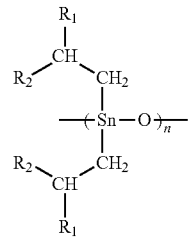

(15)

[Here, R$^1$ and R$^2$ each independently represent hydrogen or a C1-15 alkyl group, and R$^3$ represents a C1-8 alkyl group. This is with the proviso that R$^1$ and R$^2$ are not both hydrogen, and the total number of carbon atoms of R$^1$ and R$^2$ is 2 to 16, with n representing a positive integer.]

The structures of dialkyl tin oxides have not been fully elucidatable by current analysis methods. In this process, the dialkyl tin oxide may be one having the monomer structure represented by formula (16) or the hydroxy structure represented by formula (17), instead of the polymer structure represented by formula (15). The hydroxy structure represented by formula (17) is not usually referred to as a dialkyl tin dioxide, but because it is difficult to confirm its presence and content by current methods of analysis, and the invention may be carried out under the conditions for this process with either structure, for the sake of convenience it will be described herein as having the same definition as a dialkyl tin oxide.

[Chemical Formula 36]

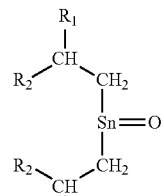

(16)

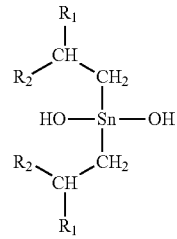

(17)

[Here, R$^1$ and R$^2$ each independently represent hydrogen or a C1-15 alkyl group, and R$^3$ represents a C1-8 alkyl group. This is with the proviso that R$^1$ and R$^2$ are not both hydrogen, and the total number of carbon atoms of R$^1$ and R$^2$ is 2 to 16.]

The alcohol and the dialkyl tin oxide are used for dehydrating reaction to obtain a tetraalkyldialkoxydistannoxane and/or a dialkyl tin dialkoxide, while removing the generated water out of the reaction system. During this time, the alcohol used is converted to an alkoxy group to form the alkyl tin alkoxide. The temperature for carrying out the reaction may be in the range of 80° C. to 180° C., for example, and from the viewpoint of easier distillation removal of the generated water out of the reaction system, it is more preferably in the range of 60° C. to 180° C., although this will depend on the reaction pressure, while from the viewpoint of increasing the reaction rate the reaction temperature is even more preferably a high temperature. On the other hand, since undesirable secondary reactions such as decomposition take place at high temperatures, thus lowering yields, the temperature is more preferably in the range of 80° C. to 160° C. The pressure in the reactor for the reaction is a pressure that allows the generated water to be removed out of the system, and although it will depend on the reaction temperature it may be between 20 and $1 \times 10^6$ Pa. The reaction time is not particularly restricted but will usually be 0.001 hour to 50 hours, preferably 0.01 hour to 10 hours and more preferably 0.1 hour to 2 hours. The reaction may be completed when the desired alkyl tin alkoxide has been obtained. Progress of the reaction can be confirmed by a method of measuring the amount of water removed out of the reaction system or a method of sampling the reaction mixture to measure the $^{119}$Sn-NMR spectrum. For production of an alkyl tin alkoxide in step (1), the reaction is completed upon confirming production of an alkyl tin alkoxide with a molar ratio in the range of 0:100 to 80:20 and preferably 1:99 to 70:30 for the tetraalkyldialkoxydistannoxane and dialkyl tin dialkoxide in the alkyl tin alkoxide obtained by the reaction. The used alcohol may continue to be used while copresent, or in some cases the alcohol may be distilled off and then used. It is preferred to remove the alcohol as much as possible since this will allow the reactor to be reduced in size for the other steps. The method of removal is preferably by a known distillation process, and the distiller used for distillation may be a known distilling apparatus. A thin-film distillation apparatus may be used as a preferred distilling apparatus, since it allows removal within a short period of time. There are no particular restrictions on the form of the reactor used, and a known type of tank or tower reactor may be used. The low-boiling-point reaction mixture containing water is gaseous and can be removed from the reactor by distillation, and the produced alkyl tin alkoxide or the high boiling point reaction mixture containing the alkyl tin alkoxide may be extracted as liquid from the bottom of the reactor. Examples for such a reactor include reactors comprising a stirring tank, a multistage stirring tank, a distillation column, a multistage distillation column, a multitube reactor, a continuous multistage distillation column, a packed tower, a thin-film evaporator, a reactor provided with an interior support, a forced circulation reactor, a falling film evaporator, a falling drop evaporator, a trickle phase reactor or a bubble tower, and known methods may be used that employ systems of these in combination. A method using a tower-type reactor is preferred from the viewpoint of efficiently shifting the equilibrium of the dehydrating reaction toward the alkyl tin alkoxide (product), or a method using a reactor with a large gas-liquid contact area is used so that the formed water rapidly migrates to the gas phase. This step may be carried out by a continuous method using a multitube reactor, multistage distillation column or a filler-packed tower, but when the dialkyl tin oxide used is solid, it is more preferred to use a method of carrying out the reaction in a tank reactor and then increasing the dialkyl tin dialkoxide content with a tower reactor. The materials of the reactor and line may be any publicly known materials that do not adversely affect the reaction, and since SUS304, SUS316, SUS316L and the like are inexpensive they are preferred for use. If necessary, there may be further included measuring devices such as a flowmeter and thermometer, and known processing equipment such as a reboiler, pump, condenser, heating means, cooling means and the like, while the heating means may be a known heating means such as steam or a heater, and the cooling means may be known cooling means such as natural cooling, cooling water or brine.

Step (1): A Step of Reacting an Alkyl Tin Alkoxide with Carbon Dioxide to Obtain a Reaction Mixture Containing a Carbonic Acid Ester.

In this step, the alkyl tin alkoxide is reacted with gaseous carbon dioxide to produce a carbonic acid ester. The step is preferably carried out using a previously disclosed method for producing carbonic acid esters (International Patent Publication No. WO03/055840, International Patent Publication No. WO04/014840 or elsewhere).

The alkyl tin alkoxide supplied to this step will sometimes be supplied from the alkyl tin alkoxide synthesis step during start-up, or it will sometimes be supplied from the alkyl tin alkoxide production step (3) during continuous production.

For this step, first the alkyl tin alkoxide and gaseous carbon dioxide are reacted to obtain a mixture comprising a carbon dioxide conjugate of the alkyl tin alkoxide.

During the chemical reaction, preferably either the alkyl tin alkoxide is heated to melting, or it is mixed with the solvent as a solution for reaction as a liquid. The pressure in the reactor for this reaction will depend on the reaction temperature, but it is preferably in the range from ordinary pressure to 1 MPa, and more preferably in the range from ordinary pressure to 0.6 MPa. The reaction temperature will depend on the pressure of the reaction, but it is preferably −40° C. to 80° C., and in consideration of the flow property during transport, it is more preferably 0° C. to 80° C., and most preferably in the range of ordinary temperature (for example, 20° C.) to 80° C. The term "ordinary temperature" as used herein means the range of 1° C. to 30° C. The reaction time may be in a range from a few seconds to 100 hours, and is preferably from a few seconds to 10 hours in consideration of productivity. The reactor used may be a known tank reactor or tower reactor. Several different reactors may also be used in combination. Since the reaction is between carbon dioxide (gas) and a solution containing alkyl tin alkoxide or alkyl tin alkoxide (liquid), for efficient reaction it is preferred to increase the gas-liquid contact surface area, in order to increase the contact area between the carbon dioxide and the alkyl tin alkoxide. The method for conducting reaction with increased gas-liquid contact surface area may take advantage of known observations, and preferred methods are those that involve increasing the stirring speed in an tank reactor or generating air bubbles in the liquid, or for a tower reactor, utilizing a packed tower or utilizing a tray tower. Examples of such tower reactors include tray tower systems using trays, such as a bubble-cap tray, porous plate tray, valve tray or counterflow tray; and packed tower systems packed with various types of packing agents such as Raschig rings, Lessing rings, pall rings, Berl saddles, Intalox saddles, Dixon packing, McMahon packing, Heli-Pak, Sulzer packing or Mellapak. The materials of the reactor and line may be any publicly known materials that do not adversely affect the reaction, and since SUS304, SUS316, SUS316L and the like are inexpensive they are preferred for use. If necessary, there may be further included measuring devices such as a flowmeter and thermometer, and known processing equipment such as a reboiler, pump, condenser, heating means, cooling means and the like, while the heating means may be a known heating means such as steam or a heater, and the cooling means may be known cooling means such as natural cooling, cooling water or brine. The reaction will usually be an exothermic reaction, and cooling may be accomplished by heat radiation from the reactor, for example. Heating may be performed when production of a carbonic acid ester is to be carried out simultaneously. Cooling or heating of the reactor may employ a publicly known method, such as a method using a jacket, or a method using an internal coil. The carbon dioxide and alkyl tin alkoxide supplied to the reactor may be supplied separately, or they may be combined before being supplied to the reactor. The carbon dioxide and alkyl tin alkoxide may also be supplied to the reactor from several different sections of the reactor. Completion of the reaction can be confirmed by $^{119}$Sn-NMR spectral analysis, for example. A step of obtaining a carbon dioxide conjugate of the alkyl tin alkoxide is not essential, and in some cases, depending on equipment operation and the like, the alkyl tin alkoxide may be transported directly to the subsequent step to obtain a reaction mixture containing a carbonic acid ester.

The following method may be used to obtain a reaction mixture containing a carbonic acid ester from the carbon dioxide conjugate of the alkyl tin alkoxide that is obtained.

The reaction conditions are preferably a high reaction temperature in the range of 40° C. to 200° C. to increase the reaction rate, but since undesirable secondary reactions such as decomposition may take place at high temperatures, potentially lowering the yield, the preferred range is 60° C. to 180° C., for a reaction time of 0.05 hour to 10 hours, and the reaction pressure is preferably in the range of ordinary pressure to 20 MPa and more preferably in the range of 2.0 MPa to 10 MPa. The reaction may be completed after the desired carbonic acid ester has been produced in the reactor. Progress of the reaction can be confirmed by sampling the reaction mixture in the reactor and analyzing the generated carbonic acid ester by $^1$H-NMR spectrum or gas chromatography. For example, the reaction may be completed after production of at least 10 mol % with respect to the number of moles of the carbon dioxide conjugate of the alkyl tin alkoxide and/or alkyl tin alkoxide in the carbon dioxide conjugate of the alkyl tin alkoxide and/or alkyl tin alkoxide, and if a higher carbonic acid ester yield is desired, the reaction may be continued to a reaction yield of 90% or greater and then terminated. The reactor used may be a known type of reactor, and is preferably a tower reactor or a tank reactor. The materials of the reactor and line may be any publicly known materials that do not adversely affect the reaction, and since SUS304, SUS316, SUS316L and the like are inexpensive they are preferred for use. If necessary, there may be further included measuring devices such as a flowmeter and thermometer, and known processing equipment such as a reboiler, pump, condenser, heating means, cooling means and the like, while the heating means may be a known heating means such as steam or a heater, and the cooling means may be known cooling means such as natural cooling, cooling water or brine.

Step (2): A Step of Separating the Carbonic Acid Ester from the Reaction Mixture to Obtain a Residual Solution.

In this step, the carbonic acid ester is separated from the reaction mixture containing the carbonic acid ester obtained in step (1), and a residual solution is obtained. The separation process may employ any known method or apparatus, but is preferably distillation.

The reaction mixture transported from step (1) is subjected to a batch or semi-batch process or continuous distillation, to obtain a carbonic acid ester and a residual solution. The preferred distillation method is one in which the reaction mixture is supplied to a distiller and the carbonic acid ester is separated out of the system from the top of the distiller as a gas phase component, while the residual solution is removed from the bottom of the distiller as a liquid component. The temperature for this step will depend on the boiling point or pressure of the carbonic acid ester, but it may be carried out in a range from ordinary temperature (for example, 20° C.) to 200° C., and since the tin compound in the residual solution is sometimes degraded at high temperature, or the carbonic acid ester may decrease due to reverse reaction, the reaction is preferably carried out in a range from ordinary temperature (for example, 20° C.) to 150° C. The pressure in the reactor for the reaction will depend on the type of carbonic acid ester and the temperature at which it is carried out, but it will usually be conducted from ordinary pressure to reduced pressure conditions, and in consideration of productivity the pressure is preferably in the range of 100 Pa to 80 KPa and more preferably 100 Pa to 50 KPa. The reaction time may be in the range of 0.01 hour to 10 hours, but because the tin component in the reaction mixture may degrade during long periods at high temperature, or the carbonic acid ester may decrease due to reverse reaction, the time is preferably in the range of 0.01 hour to 0.5 hour and more preferably 0.01 hour to 0.3 hour. The distiller used may be a known one, and is preferably a tower distiller or a tank distiller, which may also be used in combination. A thin-film evaporator or thin-film distiller is even more preferred, and a thin-film evaporator or thin-film distiller equipped with a distillation column is most preferred. The materials of the distiller and line may be any publicly known materials that do not adversely affect the reaction, and since SUS304, SUS316, SUS316L and the like are inexpensive they are preferred for use. If necessary, there may be further included measuring devices such as a flowmeter and thermometer, and known processing equipment such as a reboiler, pump, condenser, heating means, cooling means and the like, while the heating means may be a known heating means such as steam or a heater, and the cooling means may be known cooling means such as natural cooling, cooling water or brine. In step (2), when unreacted carbon dioxide is present in the reaction mixture transported from step (1), or when carbon dioxide is incorporated into the alkyl tin alkoxide molecule, preferably the carbonic acid ester is separated after removal of the carbon dioxide from the reaction mixture. The method for removing the carbon dioxide may be according to the method for separating the carbonic acid ester. It is preferably carried out at a lower temperature and at a higher pressure than for separation of the carbonic acid ester. The conditions are selected depending on the physical properties of the carbonic acid ester to be produced, as conditions having a low vapor pressure of the carbonic acid ester and allowing removal of carbon dioxide. The carbon dioxide that is removed is preferably recycled to step (1). For recycling, it is preferably returned after pressurization with a compressor or the like. When a compressor is used, inclusion of the alkyl tin alkoxide can potentially clog the compressor or reactor, so it is therefore preferably separated out beforehand. In this case, separation may be carried out by a known method with a distillation column or the like.

Step (3): A Step of Reacting the Residual Solution with an Alcohol and Removing the Water Produced by the Reaction, to Obtain an Alkyl Tin Alkoxide, and Recycling it to Step (1).

This step is carried out after obtaining the residual solution in step 2, but it is similar to the alkyl tin alkoxide synthesis step described above. This step accomplishes dehydrating reaction of the residual solution and alcohol obtained in step (2) to regenerate the alkyl tin alkoxide. The residual solution also contains the alkyl tin alkoxide, but in this step recycling (regeneration) is conducted to the ratio of the alkyl tin alkoxide for carrying out step (1). Since the carbonic acid ester is generated preferentially from the dialkyl tin alkoxide and the proportion of the tetraalkyl-dialkoxydistannoxane increases in step (2), this step regenerates alkyl tin alkoxide with an increased proportion of dialkyl tin dialkoxide.

The alcohol used may be any of the aforementioned alcohols. The dehydrating reaction conditions are also preferably the same as for the alkyl tin alkoxide synthesis step described above. The reaction may be completed if the desired alkyl tin alkoxide has been obtained. Progress of the reaction can be confirmed by a method of measuring the amount of water removed out of the reaction system or a method of sampling the reaction mixture to measure the $^{119}$Sn-NMR spectrum. For production of the alkyl tin alkoxide of this embodiment in step (1), the reaction is completed upon confirming that the molar ratio of the tetraalkyl-dialkoxydistannoxane and dialkyl tin dialkoxide in the alkyl tin alkoxide obtained by the previous reaction is in the range of 0:100 to 80:20 and more preferably 1:99 to 70:30. The alcohol may be used directly as a copresent component, or depending on the case the alcohol may be used after being distilled off. It is preferred to remove the alcohol as much as possible as this will allow the reactor to be reduced in size for the other steps. The method of removal is preferably by a known distillation process, and the distiller used for distillation may be a known distilling apparatus. A thin-film distillation apparatus may be used as a preferred distilling apparatus, since it allows removal within a short period of time. Because solid dialkyl tin oxide is generally not used in this step, unlike the alkyl tin alkoxide synthesis step, there are no particular restrictions on the form of the reactor used for the dehydrating reaction, and any known tank or tower reactor may be used. The low-boiling-point reaction mixture containing water is gaseous and can be removed from the reactor by distillation, and the high boiling point reaction mixture containing the alkyl tin alkoxide may be extracted as liquid from the bottom of the reactor. Examples of such a reactor include reactors comprising a stirring tank, a multistage stirring tank, a distillation column, a multistage distillation column, a multitube reactor, a continuous multistage distillation column, a packed tower, a thin-film evaporator, a reactor provided with an interior support, a forced circulation reactor, a falling film evaporator, a falling drop evaporator, a trickle phase reactor or a bubble tower, and known methods may be used that employ systems of these in combination. A method using a tower-type reactor is preferred from the viewpoint of efficiently shifting the equilibrium of the dehydrating reaction toward the alkyl tin alkoxide, or a method using a reactor with a large gas-liquid contact area is used so that the formed water rapidly migrates to the gas phase. For this step it is especially preferred to employ a continuous method with a multitube reactor, a multistage distillation column or a packed tower packed with a filler. The materials of the distiller and line may be any publicly known materials that do not adversely affect the reaction, and since SUS304, SUS316, SUS316L and the like are inexpensive they are preferred for use. If necessary, there may be further included measuring devices such as a flowmeter and thermometer, and known processing equipment such as a reboiler, pump, condenser, heating means, cooling means and the like, while the heating means may be a known heating means such as steam or a heater, and the cooling means may be known cooling means such as natural cooling, cooling water or brine.

The above is an example of producing a carbonic acid ester using an alkyl tin alkoxide.

By using an alkyl tin compound for this embodiment, it is possible to notably improve accumulation of the inactivated forms of alkyl tin alkoxides that occurs during carbonic acid ester production processes in the prior art, and to produce carbonic acid esters at very high efficiency.

The carbonic acid ester obtained in this step can be suitably used as a polycarbonate starting material, isocyanate starting material or other chemical product starting material, or as a battery electrolyte for a lithium ion battery. Using this method it is possible to solve the problems of cost and waste in the production of carbonic acid esters. The invention is therefore of extremely high industrial importance.

EXAMPLES

A first embodiment of the invention will now be explained in greater detail through examples and comparative examples, with the understanding that the invention is not limited to the examples.

The analysis methods applied in the examples and comparative examples will be described first.

<Analysis Methods>
1) NMR Spectral Analysis
Apparatus: JNM-A400 FT-NMR System by JEOL Corp.
(1) Preparation of $^1$H-NMR, $^{13}$C-NMR and $^{119}$Sn-NMR Spectral Analysis Samples After weighing out 0.3 g of liquid containing an alkyl tin alkoxide or alkyl tin alkoxide, there were added approximately 0.7 g of heavy chloroform (99.8% purity, Aldrich Co.) and 0.08 g of tetramethyltin (Wako Grade A, Wako Pure Chemical Industries, Ltd.) as an internal standard for $^{119}$Sn-NMR spectroscopy, and the uniformly mixed solution was used as a sample for NMR spectral analysis.

(2) Quantitative Analysis

The alkyl tin alkoxides (dialkyl tin dialkoxides, tetraalkyldialkoxydistannoxanes and/or trialkyl tin alkoxides) were analyzed and a calibration curve was drawn based on the internal standard. Quantitative analysis was conducted for the analysis sample solution based on the resulting calibration curve.

2) Water Analysis
Apparatus: CA-05 Micro Moisture Analyzer, product of Mitsubishi Chemical Corp.

An analysis sample was taken using a syringe and weighed, and then directly injected into the moisture analyzer for quantitation of the moisture. The mass of the syringe was again measured and the difference used to calculate the weight of injected sample, to determine the moisture content in the sample.

3) Gas Chromatographic Analysis of Carbonic Acid Ester Compounds and Ester Compounds
Apparatus: GC-2010 System by Shimadzu Corp.
(1) Preparation of Sample Solution for Analysis After weighing out 0.2 g of reaction mixture, approximately 1.5 g of dehydrated acetone (product of Wako Pure Chemical Industries, water content: ≤50 ppm). After further adding approximately 0.05 g of dehydrated toluene (product of Wako Pure Chemical Industries, water content: ≤50 ppm) or diphenyl ether (special grade, product of Wako Pure Chemical Industries) as an internal standard, the mixture was used as a sample solution for gas chromatographic analysis.

(2) Gas Chromatographic Analysis Conditions
Column: DB-1 (product of J&W Scientific)
Liquid phase: 100% dimethylpolysiloxane
Length: 30 m
Inner diameter: 0.25 mm
Film thickness: 1 μm
Column temperature: After holding at 50° C. for 5 minutes, the temperature was raised to 300° C. at a temperature-elevating rate of 10° C./min
Injection temperature: 300° C.
Detector temperature: 300° C.
Detector: FID (3) Quantitative Analysis The ester compound or carbonic acid ester compound was analyzed and a calibration curve was drawn based on an internal standard. Quantitative analysis was conducted for the analysis sample solution based on the resulting calibration curve.

4) Analysis of Dialkyl Tin Oxide Compounds

Apparatus: Spectrum One/100 FT-IR system (ATR method), product of Perkin Elmer

Placing approximately 5 mg of dialkyl tin oxide on an ATR plate and applying pressure with a pressure arm, the IR spectrum was measured.

<Calculation of Tin Atom Concentration (in Active Component)>

The active component for this embodiment was an alkyl tin alkoxide that effectively functions in the reaction, and specifically a dialkyl tin dialkoxide and/or tetraalkyl-dialkoxydistannoxane. The tin atom concentration (in the active component) will now be defined for expressing the change in amount of active component.

The tin atom concentration (in the active component) for dialkyl tin dialkoxides was calculated by the following equation (1). For example, the tin atom concentration (in the active component) of the dialkyl tin dialkoxide composition obtained by Synthesis Example 1 below was calculated by the following mathematical formula (1).

[Mathematical Formula 1]

$$\text{(Tin atom concentration (in active component))} = C_1 \quad (1)$$

[In the formula, "tin atom concentration (in active component)" represents the concentration [mol/kg] of tin atoms in the dialkyl tin dialkoxide in the dialkyl tin dialkoxide composition, and $C_1$ represents the concentration [mol/kg] of the dialkyl tin dialkoxide in the dialkyl tin dialkoxide composition. $C_1$ can be determined by $^{119}$Sn-NMR spectral analysis of the composition.]

The tin atom concentration (in the active component) for tetraalkyldialkoxydistannoxane compositions was calculated by mathematical formula (2). For example, the tin atom concentration (in the active component) of the tetraalkyldialkoxydistannoxane composition obtained by Synthesis Example 2 below was calculated by mathematical formula (2).

[Mathematical Formula 2]

$$\text{Tin atom concentration (in active component)} = 2 \cdot C_2 \quad (2)$$

[In the formula, "tin atom concentration (in active component)" represents the concentration [mol/kg] of tin atoms in the tetraalkyldialkoxydistannoxane in the tetraalkyldialkoxydistannoxane composition, and $C_2$ represents the concentration [mol/kg] of the tetraalkyldialkoxydistannoxane in the tetraalkyldialkoxydistannoxane composition. $C_2$ can be determined by $^{119}$Sn-NMR spectral analysis of the tetraalkyldialkoxydistannoxane composition.]

The concentration of tin atoms (in the active component) in compositions comprising a dialkyl tin dialkoxide and/or tetraalkyldialkoxydistannoxane or compositions further containing a trialkyl tin alkoxide was calculated by formula (3).

[Mathematical Formula 3]

$$\text{Tin atom concentration (in active component)} = C_1 + 2 \cdot C_2 \quad (3)$$

[In the formula, "tin atom concentration (in active component)" represents the concentration [mol/kg] of tin atoms composing the dialkyl tin dialkoxide and/or tetraalkyldialkoxydistannoxane in the composition, $C_1$ represents the concentration [mol/kg] of the dialkyl tin dialkoxide in the composition, and $C_2$ represents the concentration [mol/kg] of the tetraalkyldialkoxydistannoxane in the composition. $C_1$ and $C_2$ can be determined by $^{119}$Sn-NMR spectral analysis of the composition.]

[Synthesis Example 1] Synthesis of bis(3-methylbutyl)diethoxytin composition

Synthesis of bis(3-methylbutyl)dichlorotin

After placing 26.52 g (0.1 mol) of tetrachlorotin (99.995% purity, product of Aldrich) and 150 mL of cyclopentyl methyl ether (dehydration grade, product of Aldrich) in a 500 mL-volume four-necked round bottom flask connected to a thermometer, a three-way cock and a Dimroth condenser, in a nitrogen box under a nitrogen atmosphere, a stirring bar was added and a magnetic stirrer was used for stirring at room temperature to form a homogeneous solution. Next, after placing 200 mL of a 2M diethyl ether solution of isopentylmagnesium bromide (product of Aldrich) in a 300 mL dropping funnel, the dropping funnel was connected to the four-necked flask. The flask was removed from the nitrogen box and immersed in an ice bath while under a nitrogen atmosphere, and stirring was commenced. Dropping of the solution from the dropping funnel was then commenced, adjusting the dropping rate so that the temperature of the liquid mixture in the flask did not exceed 30° C. A white solid formed in the flask as dropping proceeded. Upon completion of the dropping, stirring of the mixture in the flask was continued for approximately 3 hours. The flask was then transferred to the nitrogen box, and a suction filter was used to filter the white solid under a nitrogen atmosphere. Distilling separation of diethyl ether and cyclopentyl methyl ether was performed from the collected filtrate. Following distilling separation, further distillation of the high boiling point components was performed, and 38.7 g of tetrakis(3-methylbutyl)-tin was obtained from the collected fraction. Next, the tetrakis(3-methylbutyl)tin was placed in a 100 mL-volume three-necked round bottom flask equipped with a thermometer, three-way cock and branch pipe connecting tube (the branch pipe connecting tube being connected to an apparatus having a Liebig condenser, reduced pressure connecting tube and two distillate collecting vessels linked together), and 25.19 g (0.095 mol) of tetrachlorotin (99.995% purity, product of Aldrich) was added. The flask was immersed in an oil bath, and stirring and heating of the liquid mixture was initiated. The temperature of the oil bath was adjusted so that the temperature of the liquid mixture was 120° C., and after stirring and heating continuously for about 2 hours, the temperature of the oil bath was adjusted so that the temperature of the liquid mixture was 200° C., and stirring and heating were continued for about 4 hours. Next, the flask was gradually reduced in pressure and the low-boiling-point components were distilled off, and upon reducing the pressure of the flask for distilling separation of bis(3-methylbutyl)dichlorotin, 56.4 g of bis(3-methylbutyl)dichlorotin was recovered.

Synthesis of bis(3-methylbutyl)diethoxytin composition

After placing 53.1 g (0.16 mol) of bis(3-methylbutyl) dichlorotin and 50 mL of cyclopentyl methyl ether (dehydration grade, product of Aldrich) in a 500 mL-volume four-necked round bottom flask connected to a thermometer, a three-way cock and a Dimroth condenser, under a nitrogen atmosphere, a stirring bar was added and a magnetic stirrer was used for stirring at room temperature to form a homogeneous solution. Next, 160 mL of a 2M ethanol solution of sodium ethoxide (prepared from an ethanol solution with 21 mass % sodium ethoxide, product of Aldrich) was placed in a 200 mL dropping funnel, and the dropping funnel was connected to the four-necked flask. The flask was removed from the nitrogen box and immersed in an ice bath while under a nitrogen atmosphere, and stirring was commenced. Dropping of the solution from the dropping funnel was then commenced, adjusting the dropping rate so that the temperature of the liquid mixture in the flask did not exceed 40° C. A white solid formed in the flask as dropping proceeded. Upon completion of the dropping, stirring of the mixture in the flask was continued for about 3 hours, and the flask was transferred to the nitrogen box. A suction filter was used to filter the white solid under a nitrogen atmosphere. The collected filtrate was subjected to vacuum distillation, and after distillation 54.1 g of the high boiling point component (composition) containing bis(3-methylbutyl)diethoxytin was collected. The amount of bis(3-methylbutyl)diethoxytin in the composition was determined by $^{119}$Sn-NMR spectral analysis to be 53.3 g. In other words, the bis(3-methylbutyl)diethoxytin concentration in the composition was 2.81 mol/kg, and the tin atom concentration (in the active component) of the composition was 2.81 mol/kg.

[Synthesis Example 2] Synthesis of 1,1,3,3-tetrakis (3-methylbutyl)-1,3-diethoxy-distannoxane Composition After placing 17.5 g (0.05 mol) of the bis(3-methylbutyl) diethoxytin obtained in Synthesis Example 1 in a 300 mL-volume four-necked round bottom flask equipped with a thermometer, three-way cock, dropping funnel and branch pipe connecting tube (the branch pipe connecting tube being connected to an apparatus having a Liebig condenser, reduced pressure connecting tube and two distillate collecting vessels linked together), 80 g of ethanol (dehydration grade, product of Wako Pure Chemical Industries) was added. Next, 85 g of ethanol and 0.45 g (0.025 mol) of ion-exchanged water were mixed in a 200 mL beaker, and upon forming a homogeneous solution it was placed in a dropping funnel. The flask was immersed in an oil bath, and stirring and heating was initiated. Dropping was initiated after adjusting the temperature of the oil bath so that the temperature of the liquid mixture was approximately 40° C. Upon completion of the dropping, the liquid mixture was kept at 40° C. and stirring was continued for 2 hours. The flask was then gradually reduced in pressure and the ethanol was distilled off, after which 15.9 g of the high boiling point component (composition) containing 1,1,3,3-tetrakis(3-methylbutyl)-1,3-diethoxy-distannoxane was collected. The amount of 1,1,3,3-tetrakis(3-methylbutyl)-1,3-diethoxy-distannoxane in the composition was determined by $^{119}$Sn-NMR spectral analysis to be 15.6 g. In other words, the 1,1,3,3-tetrakis(3-methylbutyl)-1,3-diethoxy-distannoxane concentration in the composition was 1.56 mol/kg, and the tin atom concentration (in the active component) of the composition was 3.12 mol/kg.

[Synthesis Example 3] Synthesis of Trialkyl Tin Alkoxide-Containing Composition

After placing 15 g of 1,1,3,3-tetrakis(3-methylbutyl)-1,3-diethoxydistannoxane produced by the method of Synthesis Example 2 in a 50 mL-volume three-necked flask equipped with a three-way cock-connected Dimroth condenser, a silicon cap and a thermometer, using a gas-tight syringe (1050TLL by Hamilton), 10 g of bis(3-methylbutyl)diethoxytin produced by the method of Synthesis Example 1 was subsequently added in the same manner, to prepare a composition comprising 1,1,3,3-tetrakis(3-methylbutyl)-1, 3-diethoxydistannoxane and bis(3-methylbutyl)diethoxytin. The flask was immersed in an oil bath that had been heated to 186° C. After stirring and heating for about 15 minutes, the temperature of the composition in the flask reached 180° C. Stirring and heating were continued while periodically sampling, and $^{119}$Sn-NMR spectral analysis was performed, and upon confirming production of 0.0053 mol of tris(3-methylbutyl)ethoxytin in the composition, the heating was suspended. The post-heating component ratio was expressed as follows in terms of tin atoms. The tin atom concentration (in the active component) of the composition comprising bis(3-methylbutyl)diethoxytin and 1,1,3,3-tetrakis(3-methylbutyl)-1,3-diethoxydistannoxane before heating was calculated by mathematical formula (3) to be 3.05 mol/kg, while the tin atom concentration derived from the starting materials in the composition after heating (the tin atom concentrations determined from the bis(3-methylbutyl)diethoxytin and 1,1,3,3-tetrakis(3-methylbutyl)-1,3-diethoxydistannoxane contents) changed to 2.62 mol/kg (reduced by about 14% compared to before heating), and the tin atom concentration derived from tris(3-methylbutyl)ethoxytin was 0.21 mol/kg. In other words, a trialkyl tin alkoxide-containing composition was obtained, of which approximately 7% had been converted to tris(3-methylbutyl)ethoxytin, with respect to the tin atom concentration (in the active component) of the composition before heating.

[Synthesis Example 4] Synthesis of bis(3-methylbutyl)-bis(3-methylbutoxy)tin composition After placing 48.0 g (0.13 mol) of bis(3-methylbutyl) dichlorotin obtained by the method of Synthesis Example 1 and 50 mL of cyclopentyl methyl ether (dehydration grade, product of Aldrich) in a 500 mL-volume four-necked round bottom flask connected to a thermometer, a three-way cock and a Dimroth condenser, in a nitrogen box, a stirring bar was added and a magnetic stirrer was used for stirring at room temperature to form a homogeneous solution. Next, 130 mL of a 2M ethanol solution of potassium hydroxide (product of Wako Pure Chemical Industries) was placed in a 200 mL dropping funnel, and the dropping funnel was connected to the four-necked flask. The flask was removed from the nitrogen box and immersed in an ice bath while under a nitrogen atmosphere, and stirring was commenced.

Dropping of the solution from the dropping funnel was then commenced, adjusting the dropping rate so that the temperature of the liquid mixture in the flask did not exceed 40° C. A white solid formed in the flask as dropping proceeded. Upon completion of the dropping, stirring of the mixture in the flask was continued for about 3 hours, and a suction filter was used in a nitrogen box for filtration of the white solid. The collected solid was rinsed 3 times with ion-exchanged water and two times with acetone, and then vacuum dried. Upon drying, 32.5 g of a solid was collected. Measurement of the IR spectrum of the solid revealed a bis(3-methylbutyl) tin oxide content of approximately 99% in the solid.

Synthesis of bis(3-methylbutyl)-bis(3-methylbutoxy)tin composition

In a 1 L-volume round bottom flask there were placed 30.5 g (0.1 mol) of bis(3-methylbutyl)tin oxide and 881.5 g (10 mol) of 3-methyl-1-butyl alcohol (product of Aldrich). The flask containing the white slurry-like mixture was mounted on an evaporator connected to an oil bath with a temperature regulator, and a vacuum pump and vacuum controller. The oil bath temperature was set to 140° C., the flask was immersed in the oil bath, and rotation of the evaporator was commenced. After rotated stirring and heating for about 20 minutes at ordinary pressure with the purge valve of the evaporator left open, a distillate containing mainly 3-methyl-1-butyl alcohol began to be collected. This state was maintained for 5 hours, and then the flask was raised out of the oil bath. The reaction mixture at this time was a transparent liquid. The total amount of the obtained distillate was 620.5 g, and analysis of the distillate with a micro moisture analyzer revealed a moisture content of 1.8 g (0.1 mol). The temperature of the oil bath was then set to 120° C., the flask was again immersed in an oil bath and stirred while rotating for about 20 minutes at ordinary pressure, and then in order to remove the excess 3-methyl-1-butyl alcohol, the purge valve of the evaporator was closed and the vacuum pump and vacuum controller were used to gradually reduce the pressure in the reactor to 1.8 to 2.5 kPa. This state was maintained for 3 hours, and then the flask was raised out of the oil bath, the purge valve was slowly opened and dry nitrogen gas was introduced into the reactor interior to restore it to ordinary pressure.

After distillation, 46.5 g of the high boiling point component (composition) containing bis(3-methylbutyl)-bis(3-methylbutoxy)tin was collected. As a result of $^{119}$Sn-NMR spectral analysis of the composition, it was found to have a bis(3-methylbutyl)-bis(3-methylbutoxy)tin content of 45.8 g. In other words, the bis(3-methylbutyl)-bis(3-methylbutoxy)tin concentration in the composition was 2.26 mol/kg, and the tin atom concentration (in the active component) of the composition was 2.26 mol/kg.

[Synthesis Example 5] Synthesis of 1,1,3,3-tetrakis (3-methylbutyl)-1,3-bis(3-methylbutoxy)distannoxane composition After placing 21.8 g (0.05 mol) of the bis(3-methylbutyl) bis(3-methylbutoxy)tin obtained in Synthesis Example 4 in a 300 mL-volume four-necked round bottom flask equipped with a thermometer, three-way cock, dropping funnel and branch pipe connecting tube (the branch pipe connecting tube being connected to an apparatus having a Liebig condenser, reduced pressure connecting tube and two distillate collecting vessels linked together), 80 g of 3-methyl-1-butyl alcohol (product of Wako Pure Chemical Industries) was added. Next, 85 g of 3-methyl-1-butyl alcohol and 0.45 g (0.025 mol) of ion-exchanged water were mixed in a 200 mL beaker, and upon forming a homogeneous solution it was placed in a dropping funnel. The flask was immersed in an oil bath, and stirring and heating was initiated. Dropping was initiated after adjusting the temperature of the oil bath so that the temperature of the liquid mixture was approximately 60° C. Upon completion of the dropping, the liquid mixture was kept at 60° C. and stirring was continued for 2 hours. The flask was then gradually reduced in pressure, and distilling separation of the 3-methyl-1-butyl alcohol was performed. After distillation, 17.9 g of the high boiling point component (composition) containing 1,1,3,3-tetrakis(3-methylbutyl)-1,3-bis(3-methylbutoxy)distannoxane was collected. As a result of $^{119}$Sn-NMR analysis of the composition, the 1,1,3,3-tetrakis(3-methylbutyl)-1,3-bis(3-methylbutoxy)distannoxane content of the composition was found to be 17.6 g. In other words, the 1,1,3,3-tetrakis(3-methylbutyl)-1,3-bis(3-methylbutoxy)distannoxane concentration in the composition was 1.38 mol/kg, and the tin atom concentration (in the active component) of the composition was 2.76 mol/kg.

[Synthesis Example 6] Synthesis of Trialkyl Tin Alkoxide-Containing Composition

After placing 15 g of 1,1,3,3-tetrakis(3-methylbutyl)-1,3-bis(3-methylbutoxy)distannoxane produced by the method of Synthesis Example 5 in a 50 mL-volume three-necked flask equipped with a three-way cock-connected Dimroth condenser, a silicon cap and a thermometer, using a gas-tight syringe (1050TLL by Hamilton), 10 g of bis(3-methylbutyl)-bis(3-methylbutoxy)tin produced by the method of Synthesis Example 4 was subsequently added in the same manner, to prepare a composition comprising 1,1,3,3-tetrakis(3-methylbutyl)-1,3-bis(3-methylbutoxy)distannoxane and bis (3-methylbutyl)-bis(3-methylbutoxy)tin. The flask was immersed in an oil bath that had been heated to 186° C. After stirring and heating for about 15 minutes, the temperature of the composition in the flask reached 180° C. Stirring and heating were continued while periodically sampling, $^{119}$Sn-NMR analysis was performed, and upon confirming production of 0.0023 mol of tris(3-methylbutyl)-(3-methylbutoxy)tin in the composition, the heating was suspended.

The post-heating component ratio was expressed as follows in terms of tin atoms. The tin atom concentration (in the active component) of the composition comprising bis(3-methylbutyl)-bis(3-methylbutoxy)tin and 1,1,3,3-tetrakis(3-methylbutyl)-1,3-bis(3-methylbutoxy)distannoxane before heating was calculated by mathematical formula (3) to be 2.60 mol/kg, while the tin atom concentration derived from the starting materials in the composition after heating (the tin atom concentrations calculated from the bis(3-methyl-butyl)-bis(3-methylbutoxy)tin and 1,1,3,3-tetrakis(3-methylbutyl)-1,3-bis(3-methylbutoxy)distannoxane contents using mathematical formula (7)) changed to 2.24 mol/kg (reduced by about 14% compared to before heating), and the tin atom concentration derived from tris(3-methylbutyl)(3-methylbutoxy)tin was 0.18 mol/kg. In other words, a trialkyl tin alkoxide-containing composition was obtained, of which approximately 7% had been converted to tris(3-methylbutyl) (3-methylbutoxy)tin, with respect to the tin atom concentration (in the active component) of the alkyl tin alkoxide composition before heating.

[Synthesis Example 7] Synthesis of diisopropyl-bis(2-ethylbutoxy)tin composition Synthesis of diisopropyldiiodotin After placing 17.81 g (0.15 mol) of metal tin powder (99.9% purity, product of Wako Pure Chemical Industries), 51.0 g (0.3 mol) of 2-iodopropane (product of Aldrich) and 0.75 g of magnesium iodide (product of Wako Pure Chemical Industries) in a 200 mL-volume three-necked round bottom flask equipped with a thermometer, three-way cock and branch pipe connecting tube (the branch pipe connecting tube being connected to an apparatus having a Liebig condenser, reduced pressure connecting tube and two distillate collecting vessels linked together), a stirring bar was added and a magnetic stirrer was used for stirring. The flask was immersed in an oil bath, and stirring and heating of the reaction mixture was initiated. The temperature of the oil bath was adjusted so that the temperature of the reaction mixture was 140° C., and after continuing stirring and heating for about 3 hours, the reaction mixture changed to a homogeneous solution. The flask was then gradually reduced in pressure, and distillation purification of the diisopropyldiiodotin product was performed. The amount of collected diisopropyldiiodotin was 31.3 g.

Synthesis of diisopropyltin oxide

After placing 45.9 g (0.1 mol) of the diisopropyldiiodotin and 50 mL of cyclopentyl methyl ether (dehydration grade, product of Aldrich) in a 500 mL-volume four-necked round bottom flask connected to a thermometer, a three-way cock and a Dimroth condenser, in a nitrogen box, a stirring bar was added and a magnetic stirrer was used for stirring at room temperature to form a homogeneous solution. Next, 130 mL of a 2M ethanol solution of potassium hydroxide (product of Wako Pure Chemical Industries) was placed in a 200 mL dropping funnel, and the dropping funnel was connected to the four-necked flask. The flask was removed from the nitrogen box and immersed in an ice bath while under a nitrogen atmosphere, and stirring was commenced. Dropping of the solution from the dropping funnel was then commenced, adjusting the dropping rate so that the temperature of the liquid mixture in the flask did not exceed 40° C. A white solid formed in the flask as dropping proceeded. Upon completion of the dropping, stirring of the mixture in the flask was continued for about 3 hours, and a suction filter was used in a nitrogen box for filtration of the white solid. The collected solid was rinsed 3 times with ion-exchanged water and two times with acetone, and then vacuum dried. Upon drying, 19.5 g of a solid was collected. As a result of IR spectrum measurement of the solid, the diisopropyltin oxide content of the solid was found to be approximately 99%.

Synthesis of diisopropyl-bis(2-ethylbutoxy)tin composition

After placing 17.7 g (0.08 mol) of diisopropyltin oxide in a 1 L-volume three-necked round bottom flask equipped with a thermometer, three-way cock, and branch pipe connecting tube (the branch pipe connecting tube being connected to an apparatus having a Liebig condenser, reduced pressure connecting tube and two distillate collecting vessels linked together), 552.8 g (2.4 mol) of bis(2-ethylbutyl) carbonate (product of Tosco) was added. The flask was immersed in an oil bath, and stirring and heating of the liquid mixture was initiated. The temperature of the oil bath was adjusted so that the temperature of the liquid mixture was approximately 130° C., and stirring and heating were continued for about 3 hours. The flask was then gradually reduced in pressure, and distilling separation of the excess bis(2-ethylbutyl) carbonate was performed. After distillation, 14.0 g of the high boiling point component (composition) containing the diisopropyl-bis(2-ethylbutoxy)tin was collected. As a result of $^{119}$Sn-NMR spectral analysis of the composition, the diisopropyl-bis(2-ethylbutoxy)tin content was found to be 13.5 g. In other words, the diisopropyl-bis(2-ethylbutoxy)tin concentration of the composition was 2.37 mol/kg, and the tin atom concentration (in the active component) of the composition was 2.37 mol/kg.

[Synthesis Example 8] Synthesis of 1,1,3,3-tetraisopropyl-1,3-bis(2-ethylbutoxy)distannoxane composition After placing 32.6 g (0.08 mol) of the diisopropyl-bis(2-ethylbutoxy)tin obtained in Synthesis Example 7 in a 300 mL-volume four-necked round bottom flask equipped with a thermometer, three-way cock, dropping funnel and branch pipe connecting tube (the branch pipe connecting tube being connected to an apparatus having a Liebig condenser, reduced pressure connecting tube and two distillate collecting vessels linked together), 100 g of 2-ethyl-1-butyl alcohol (product of Aldrich) that had been purified by distillation was added. Next, 100 g of 2-ethyl-1-butyl alcohol and 0.72 g (0.04 mol) of ion-exchanged water were mixed in a 200 mL beaker, and upon forming a homogeneous solution it was placed in a dropping funnel. The flask was immersed in an oil bath, and stirring and heating was initiated. Dropping was initiated after adjusting the temperature of the oil bath so that the temperature of the liquid mixture was approximately 45° C. Upon completion of the dropping, the liquid mixture was kept at 45° C. and stirring was continued for 2 hours. The flask was then gradually reduced in pressure, and distilling separation of the 2-ethyl-1-butyl alcohol was performed. After distillation, 23.5 g of the high boiling point component (composition) containing 1,1,3,3-tetraisopropyl-1,3-bis(2-ethylbutoxy)-distannoxane was collected. As a result of $^{119}$Sn-NMR spectral analysis of the composition, the 1,1,3,3-tetraisopropyl-1,3-bis(2-ethylbutoxy)distannoxane content was found to be 22.9 g. In other words, the 1,1,3,3-tetraisopropyl-1,3-bis(2-ethylbutoxy)distannoxane concentration in the composition was 1.55 mol/kg, and the tin atom concentration (in the active component) of the composition was 3.10 mol/kg.

[Synthesis Example 9] Synthesis of 1,1,3,3-tetrabutyl-1,3-bis(2-ethylbutyloxy)distannoxane composition In a 2 L-volume three-necked flask equipped with a thermometer, a three-way cock, and a water measuring receptacle connected to a Dimroth condenser there were placed 199.8 g (0.80 mol) of dibutyltin oxide (product of Aldrich), 1045 g (8.0 mol) of 2-ethyl-1-butyl alcohol (product of Aldrich) and 500 g of toluene (for organic synthesis, product of Wako Pure Chemical Industries). The flask containing the white slurry-like mixture was immersed in an oil bath set to 130° C. After stirring and heating for about 30 minutes, the mixture began to boil and thus water and toluene began to be collected in the water measuring receptacle.

After maintaining this state for about 3 hours, approximately 7.2 mL of water was collected in the water measuring receptacle. The temperature of the oil bath was then lowered to 90° C., and once the mixture temperature fell, the water measuring receptacle was removed and the flask was connected to a branch pipe connecting tube, Liebig condenser, reduced pressure connecting tube and two distillate collecting vessels. The reactor interior was reduced to a pressure of 29 kPa and toluene was distilled from the flask, after which the reactor interior was reduced in pressure to distill off the excess 2-ethyl-1-butyl alcohol. After distillation, 300 g of the high boiling point component (composition) was collected from the flask. As a result of $^{119}$Sn-NMR spectral analysis of the composition, the composition was found to contain 295 g of 1,1,3,3-tetrabutyl-1,3-bis(2-ethylbutyloxy)distannoxane.

[Synthesis Example 10] Synthesis of dibutyl-bis(2-ethylbutoxy)tin composition

In a 1 L-volume round bottom flask there were placed 20.1 g (0.081 mol) of dibutyltin oxide (product of Aldrich) and 835 g (8.2 mol) of 2-ethyl-1-butyl alcohol (product of Aldrich). The flask containing the white slurry-like mixture was mounted on an evaporator connected to an oil bath with a temperature regulator, and a vacuum pump and vacuum controller. The oil bath temperature was set to 150° C., the flask was immersed in the oil bath, and rotation of the evaporator was commenced. After rotated stirring and heating for about 20 minutes at ordinary pressure with the purge valve of the evaporator left open, the evaporator purge valve was closed and the reactor interior was gradually reduced in pressure using a vacuum pump and vacuum controller to 54 to 75 kPa. This state was maintained for 1.5 hours, and then the flask was raised out of the oil bath. The reaction mixture at this time was a transparent liquid. The purge valve was gradually opened to introduce dry nitrogen gas into the reactor, restoring the pressure in the reactor to ordinary pressure. The distilled liquid amount was 99.2 g, and it was transparent and separated into 2 layers. Analysis of the distilled liquid with a micro moisture analyzer revealed a moisture content of 1.5 g (0.083 mol). The temperature of the oil bath was then lowered to 100° C., the flask was again immersed in an oil bath and stirred while rotating and stirred normally, for about 20 minutes at ordinary pressure, and then in order to remove the excess 2-ethyl-1-butyl alcohol, the purge valve of the evaporator was closed and the vacuum pump and vacuum controller were used to gradually reduce the pressure in the reactor to 1.8 to 2.5 kPa. This state was maintained for 3 hours, and then the flask was raised out of the oil bath, and the purge valve was slowly opened to restore the reactor interior to ordinary pressure. After distillation, 36 g of the high boiling point component (composition) was collected from the flask. As a result of $^{119}$Sn-NMR spectral analysis of the composition, the dibutyl-bis (2-ethylbutoxy)tin content of the composition was found to be 35.5 g.

Example 1

FIG. 1 shows a continuous circulating reactor comprising a tank reactor, tube reactor and tower reactor for transesterification reaction. The tetraalkyldialkoxydistannoxane composition was introduced into the continuous circulating reactor and circulated for test operation. Approximately 50 kg of a 1,1,3,3-tetrakis(3-methylbutyl)-1,3-bis(3-methylbutoxy)distannoxane composition produced by the method of Synthesis Example 5 (tin atom concentration (in the active component) of the composition: 2.76 mol/kg) was introduced into a SUS316 catalyst tank 130, equipped with a heating jacket and a liquid conveyance pump, through a supply line 15. The composition was circulated in the catalyst tank 130 for about 10 hours. Next, using a chemical gear pump, the composition was conveyed from the catalyst tank 130 to a tank reactor 140 at 12 kg/hr, via a transport line 14, an inline mixer 141 equipped with a heating jacket, and a transport line 5. The tank reactor 140 was a 15 L-volume reactor, comprising a stirrer, heating jacket and liquid conveyance pump, and the heating jacket was heated with steam at about 155° C. A tube reactor 150 with an outer diameter of 200 mm and a length of 1000 mm also comprised a heating jacket, and the heating jacket was heated with steam at about 160° C. A SUS316 tower reactor 160 with an inner diameter of 75 mm and an effective length of 4500 mm, equipped with 30 sieve trays, was heated and thermally insulated with a heater around the entire tower reactor to prevent radiated heat loss, the heater being set to about 150° C. A liquid conveyance pump and reboiler 163 were provided at the bottom of the tower reactor 160, and the reboiler 163 was heated with steam at about 160° C. A thin-film vaporizer 170 with a heat transfer area of 0.1 m$^2$ was equipped with a heating jacket and a chemical gear pump for liquid conveyance of the high boiling point component, the heating jacket being heated with steam at 160° C. and the pressure of the thin-film vaporizer 170 being set to 115 kPaA. The tank and pipes were steam traced to maintain the flow property. The composition conveyed to the tank reactor 140 was then conveyed to the tube reactor 150 through a transport line 6, subsequently conveyed to the tower reactor 160 through a transport line 7, and then conveyed to the thin-film vaporizer 170 through a transport line 9, after which it was conveyed to the catalyst tank 130 through a transport line 11. The composition was thus continuously circulated through the tank reactor 140, tube reactor 150, tower reactor 160, thin-film vaporizer 170 and catalyst tank 130 via the transport line 14, inline mixer 141, transport line 5, transport line 6, transport line 7, transport line 9 and transport line 11, and this was continued for about 5 days. Next, the solution in the catalyst tank 130 was sampled from an extraction line 16, and as a result of $^{119}$Sn-NMR spectral analysis it was confirmed that 1,1,3,3-tetrakis(3-methylbutyl)-1,3-bis(3-methylbutoxy)distannoxane and tris(3-methylbutyl)(3-methylbutoxy)tin were present after the test operation. Upon calculating the tin atom concentration (in the active component) from the 1,1,3,3-tetrakis(3-methylbutyl)-1,3-bis(3-methylbutoxy)distannoxane concentration of the composition in the catalyst tank 130 after test operation based on the analysis results, it was found to be 2.55 mol/kg, which was a reduction of 7.6% compared to before start of the test operation. On the other hand, tris(3-methylbutyl)(3-methylbutoxy)tin was produced at 5.1 mol, which was 3.7% of the number of moles of tin atoms (in the active component) of the composition introduced into the catalyst tank before starting the test operation.

Example 2

Figure 2:
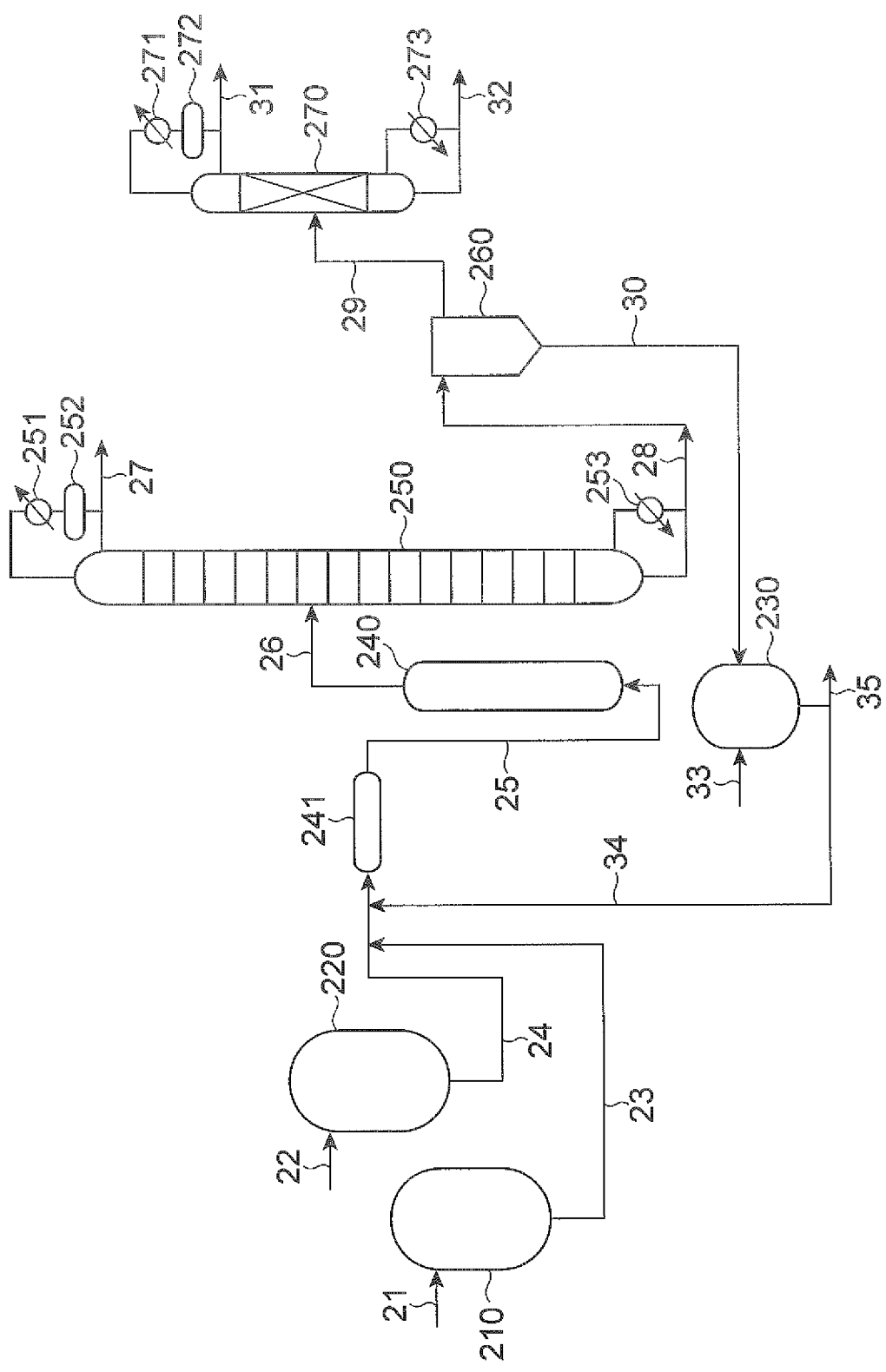
FIG. 2 is a schematic diagram of a continuous circulating reactor in which an ester compound is produced by transesterification reaction using an alkyl tin compound according to one embodiment.

FIG. 2 shows a continuous circulating reactor comprising a tube reactor and tower reactor for transesterification reaction. The dialkyl tin dialkoxide composition was introduced into the continuous circulating reactor and circulated for test operation. After placing approximately 45 kg of a bis(3-methylbutyl)-bis(3-methylbutoxy)tin composition produced by the method of Synthesis Example 4 (tin atom concentration (in the active component) of composition: 2.26 mol/kg) in a SUS316 catalyst tank 230 equipped with a heating jacket and a liquid conveyance pump, via a supply line 33, the composition was circulated in the catalyst tank 230 for about 10 hours. Next, using a chemical gear pump, the composition was conveyed from the catalyst tank 230 to a tube reactor 240 at 8 kg/hr, via a transport line 34, an inline mixer 241 equipped with a heating jacket, and a transport line 25. The tube reactor 240 with an outer diameter of 250 mm and a length of 1500 mm also comprised a heating jacket, which was heated with steam at about 140° C. A SUS316 tower reactor 250 with an inner diameter of 75 mm and an effective length of 4500 mm, equipped with 30 sieve trays, was heated and thermally insulated with a heater around the entire tower reactor to prevent radiated heat loss, the heater being set to about 150° C. A liquid conveyance pump and reboiler 253 were provided at the bottom of the tower reactor 250, and the reboiler 253 was heated with steam at about 160° C. Also, a thin-film vaporizer 260 (heat transfer area: 0.1 m$^2$), equipped with a heating jacket and a chemical gear pump for liquid conveyance of the high boiling point component, was heated to 170° C., and the pressure was set to 115 kPaA. The tank and pipes were steam traced to maintain the flow property. The composition conveyed to the tube reactor 240 was then conveyed to the tower reactor 250 through a transport line 26, subsequently conveyed to the thin-film vaporizer 260 through a transport line 28, and then conveyed to the catalyst tank 230 through a transport line 30. The composition was thus continuously circulated through the tube reactor 240, tower reactor 250, thin-film vaporizer 260 and catalyst tank 230 via the transport line 34, inline mixer 241, transport line 25, transport line 26, transport line 28 and transport line 30, and this was continued for about 6 days. Next, the liquid in the catalyst tank 230 was sampled from an extraction line 35, and as a result of $^{119}$Sn-NMR spectral analysis it was confirmed that bis(3-methylbutyl)-bis(3-methylbutoxy)tin and tris(3-methylbutyl)(3-methylbutoxy)tin were present after the test operation. Upon calculating the concentration of tin atoms from the bis(3-methylbutyl)-bis(3-methylbutoxy)tin concentration of the composition in the catalyst tank 230 after test operation, as determined by the analysis results, it was found to be 2.11 mol/kg, which was a reduction of 6.6% compared to before start of the test operation. On the other hand, tris(3-methylbutyl)(3-methylbutoxy)tin was produced at 3.3 mol, which was 3.2% of the number of moles of tin atoms (in the active component) of the composition introduced into the catalyst tank before starting the test operation.

Example 3

Figure 3:
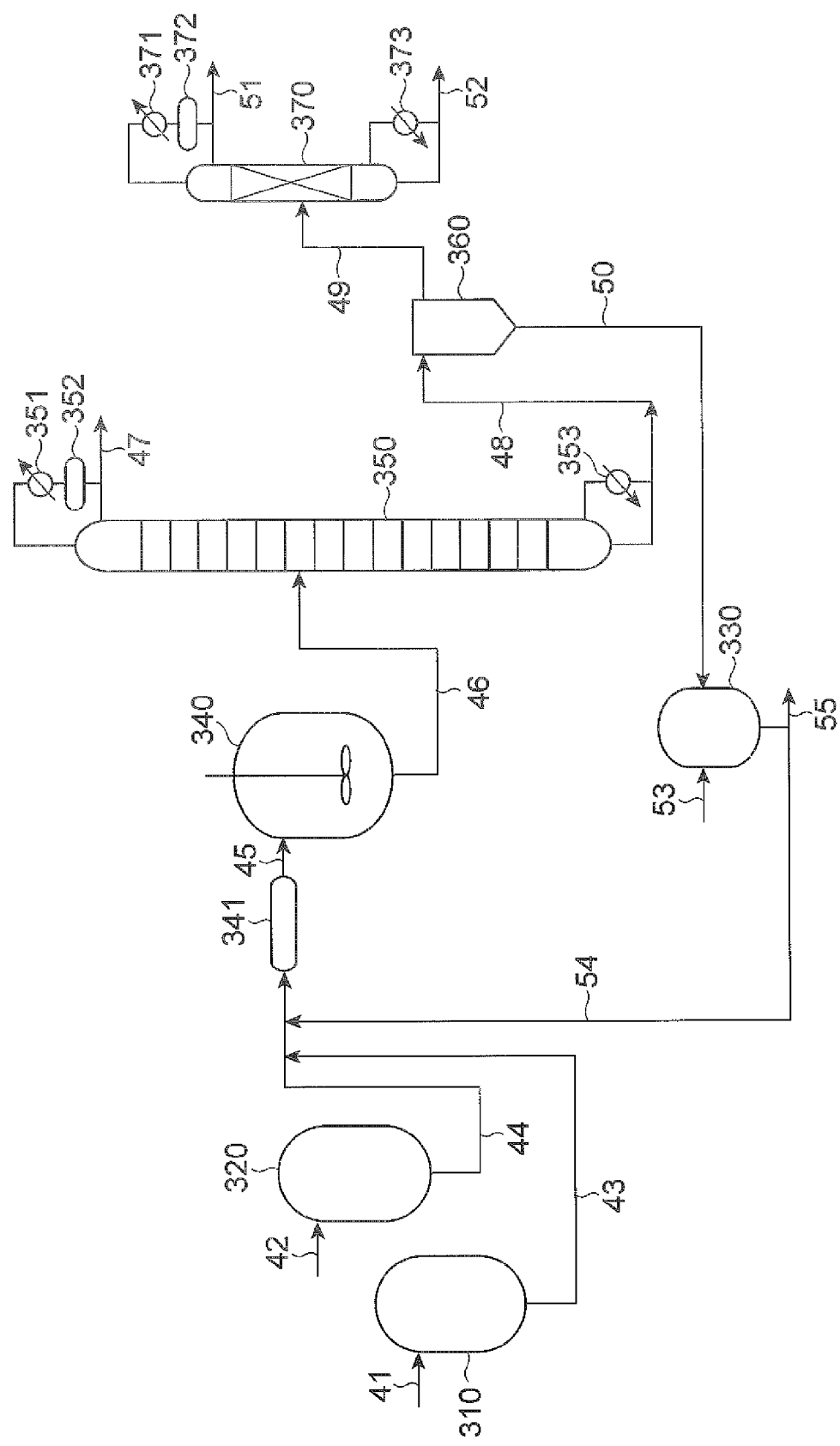
FIG. 3 is a schematic diagram of a continuous circulating reactor in which an ester compound is produced by transesterification reaction using an alkyl tin compound according to one embodiment.

FIG. 3 shows a continuous circulating reactor comprising a tank reactor and tower reactor for transesterification reaction. The alkyl tin alkoxide composition was introduced into the continuous circulating reactor and circulated for test operation. A composition was prepared by mixing bis(3-methylbutyl)-bis(3-methylbutoxy)tin and 1,1,3,3-tetrakis(3-methylbutyl)-1,3-bis(3-methylbutoxy)distannoxane produced by the methods of Synthesis Example 4 and Synthesis Example 5. The mixture was prepared so that the molar ratio of the tin atoms of the bis(3-methylbutyl)-bis(3-methylbutoxy)tin and 1,1,3,3-tetrakis(3-methylbutyl)-1,3-bis(3-methylbutoxy)distannoxane with respect to the number of moles of tin atoms in the composition was 65:35. The tin atom concentration (in the active component) of the alkyl tin alkoxide composition calculated by mathematical formula (3) was 2.44 mol/kg. Approximately 60 kg of the composition was introduced into a SUS316 catalyst tank 330 equipped with a heating jacket and liquid conveyance pump, through a supply line 53. The composition was first circulated in the catalyst tank 330 for about 10 hours. Next, using a chemical gear pump, the composition was conveyed from the catalyst tank 330 to a tank reactor 340 at 10 kg/hr, via a transport line 54, an inline mixer 341 and a transport line 45. The tank reactor 340 was a 15 L-volume reactor, comprising a stirrer, heating jacket and liquid conveyance pump, and the heating jacket was heated with steam at about 150° C. A SUS316 tower reactor 350 with an inner diameter of 76 mm and an effective length of 3500 mm, equipped with 25 sieve trays, was heated and thermally insulated with a heater around the entire tower reactor to prevent radiated heat loss, the heater being set to about 150° C. A liquid conveyance pump and reboiler 353 were provided at the bottom of the tower reactor 350, and the reboiler 353 was heated with steam at about 160° C. Also, a thin-film vaporizer 360 (heat transfer area: 0.1 m$^2$), equipped with a heating jacket and a liquid conveyance pump for conveyance of the high boiling point component, was heated to 165° C., and the pressure was set to 115 kPaA. The tank and pipes were steam traced to maintain the flow property. The composition conveyed to the tank reactor 340 was then conveyed to the tower reactor 350 through a transport line 46, subsequently conveyed to the thin-film vaporizer 360 through a transport line 48, and then conveyed to the catalyst tank 330 through a transport line 50. The alkyl tin alkoxide composition was thus continuously circulated through the tank reactor 340, tower reactor 350, thin-film vaporizer 360 and catalyst tank 330 via the transport line 54, inline mixer 341, transport line 45, transport line 46, transport line 48 and transport line 50, and this was continued for about 5 days. Next, the solution in the catalyst tank 330 was sampled from an extraction line 55, and as a result of $^{119}$Sn-NMR spectral analysis it was confirmed that bis(3-methylbutyl)-bis(3-methylbutoxy)tin, 1,1,3,3-tetrakis(3-methylbutyl)-1,3-bis(3-methylbutoxy)distannoxane and tris(3-methylbutyl)(3-methylbutoxy)tin were present after the test operation. Upon determining the bis (3-methylbutyl)-bis(3-methylbutoxy)tin concentration and 1,1,3,3-tetrakis(3-methylbutyl)-1,3-bis(3-methylbutoxy)distannoxane concentration in the catalyst tank 330 after test operation based on the analysis results, and calculating the tin atom concentration of the composition, it was found to be 2.29 mol/kg, which was a reduction of 6.1% compared to before start of the test operation. On the other hand, tris(3-methylbutyl)(3-methylbutoxy)tin was produced at 4.4 mol, which was 3.0% of the number of moles of tin atoms (in the active component) of the alkyl tin alkoxide composition before starting the test operation.

Example 4

Figure 4:
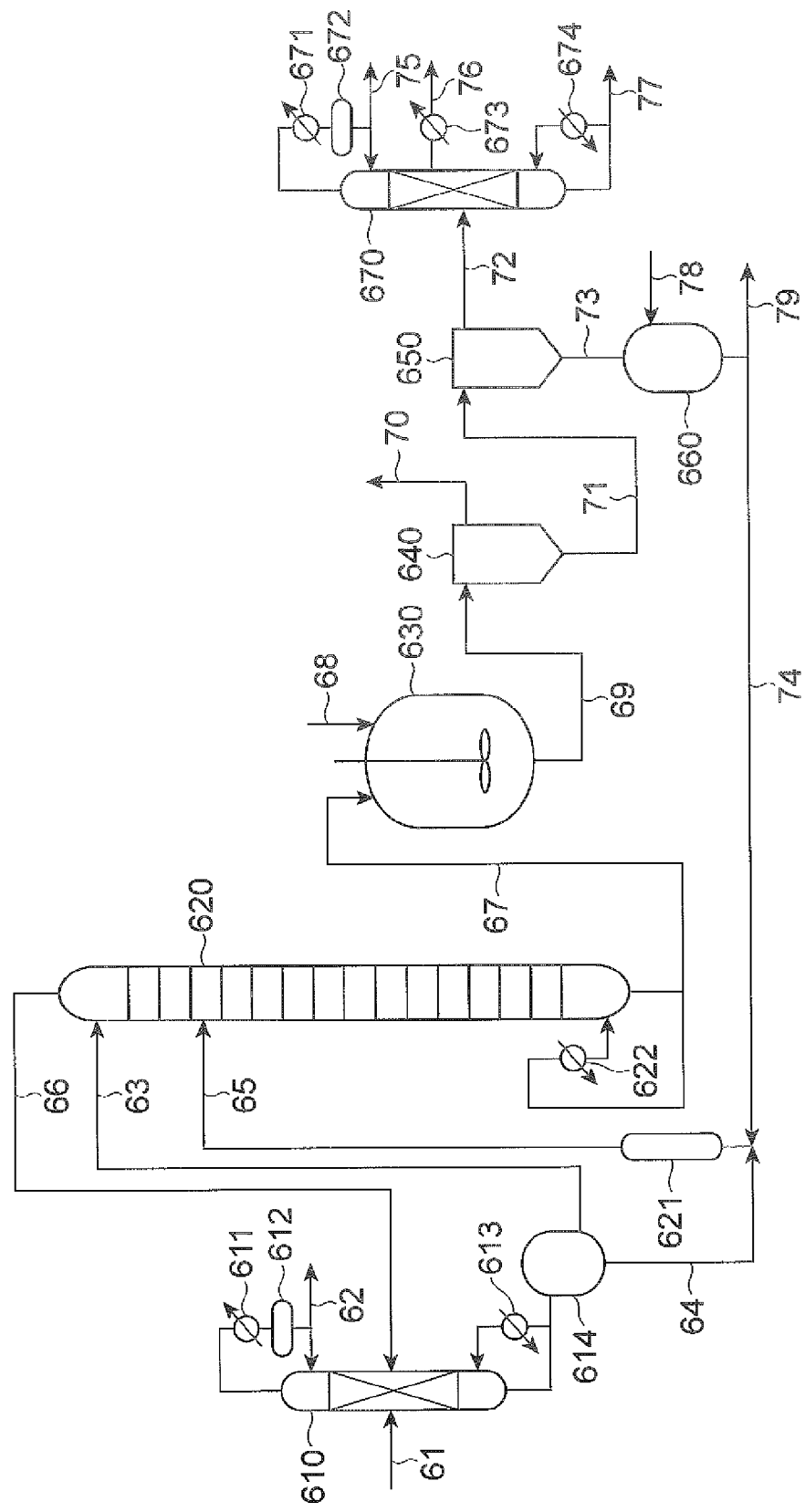
FIG. 4 is a schematic diagram of a continuous circulating reactor in which a carbonic acid ester is produced using an alkyl tin compound according to one embodiment.

FIG. 4 shows a continuous circulating reactor for carbonic acid ester synthesis using an alkyl tin alkoxide composition. The alkyl tin alkoxide composition was introduced into the continuous circulating reactor and circulated for test operation. A composition containing a trialkyl tin alkoxide (an alkyl tin alkoxide composition comprising 1,1,3,3-tetrakis (3-methylbutyl)-1,3-bis(3-methylbutoxy)distannoxane, bis (3-methylbutyl)bis(3-methylbutoxy)tin and tris(3-methylbutyl)(3-methylbutoxy)tin) was produced by the method of Synthesis Example 6. Upon calculating the tin atom concentration (in the active component) in the composition from the 1,1,3,3-tetrakis(3-methylbutyl)-1,3-bis(3-methylbutoxy)distannoxane concentration and bis(3-methylbutyl)bis(3-methylbutoxy)tin concentration determined from the analysis results, it was found to be 2.24 mol/kg. The tris(3-methylbutyl)(3-methylbutoxy)tin concentration was 0.17 mol/kg. Approximately 60 kg of the composition was introduced into a SUS316 catalyst tank 660 equipped with a heating jacket and liquid conveyance pump, through a supply line 78. The composition was first circulated in the catalyst tank 660 for about 12 hours. Next, using a chemical gear pump, the composition was conveyed from the catalyst tank 660 to a tower reactor 620 at 10 kg/hr, via a transport line 74, an inline mixer 621 equipped with a heating jacket, and a transport line 65. A SUS316 tower reactor 620 with an inner diameter of 76 mm and an effective length of 4500 mm, equipped with 30 sieve trays, was heated and thermally insulated with a heater around the entire tower reactor to prevent radiated heat loss, the heater temperature being set to about 150° C. A liquid conveyance pump and reboiler 622 were provided at the bottom of the tower reactor 620, and the reboiler 622 was heated with steam at about 155° C. An autoclave 630 was used which was a 15 L-volume reactor, comprising a stirrer, heating jacket and liquid conveyance pump, and the heating jacket was heated with steam at about 150° C. A thin-film vaporizer 640 (heat transfer area: 0.1 m$^2$) and a thin-film vaporizer 650 (heat transfer area: 0.2 m$^2$) set to 115 kPaA pressure were equipped with a heating jacket and a liquid conveyance pump for conveyance of the high boiling point component, and steam at about 160° C. was used for heating. The tank and pipes were steam traced to maintain the flow property. The alkyl tin alkoxide composition that had been conveyed to the tower reactor 620 was conveyed to the autoclave 630 through a transport line 67, and then conveyed to the thin-film vaporizer 640 through a transport line 69 and further conveyed to the thin-film vaporizer 650 through a transport line 71, after which it was conveyed to the catalyst tank 660 through a transport line 73. The alkyl tin alkoxide composition was thus continuously circulated through the tower reactor 620, autoclave 630, thin-film vaporizer 640, thin-film vaporizer 650 and catalyst tank 660 via the transport line 74, inline mixer 621, transport line 65, transport line 67, transport line 69, transport line 71 and transport line 73, and this was continued for about 5 days. Next, the liquid in the catalyst tank 660 was sampled from an extraction line 79 and $^{119}$Sn-NMR spectral analysis was performed. Upon calculating the concentration of tin atoms in the composition from the 1,1,3,3-tetrakis(3-methylbutyl)-1,3-bis(3-methylbutoxy)distannoxane concentration and bis(3-methylbutyl)-bis(3-methylbutoxy)tin concentration in the catalyst tank 660 after test operation based on the analysis results, it was found to be 2.11 mol/kg, which was a reduction of 5.8% compared to before start of the test operation. On the other hand, tris(3-methylbutyl)-(3-methylbutoxy)tin was produced at 3.8 mol, which was 2.8% with respect to the number of moles of tin atoms (in the active component), as calculated from the amount added to the catalyst tank before the start of test operation and from the 1,1,3,3-tetrakis(3-methylbutyl)-1,3-bis(3-methylbutoxy)distannoxane concentration and bis(3-methylbutyl)bis(3-methylbutoxy)tin concentration in the composition.

Example 5

Figure 5:
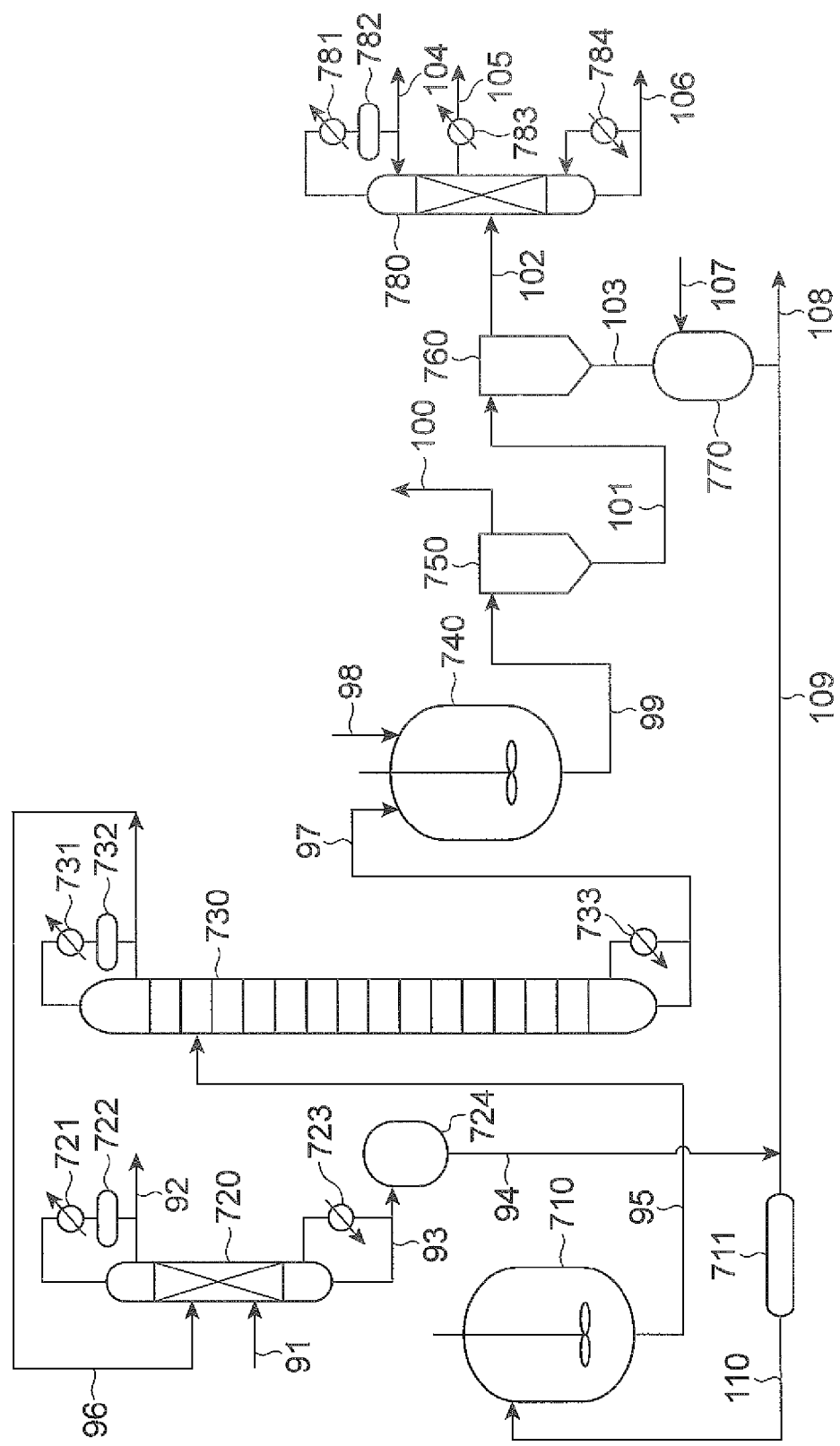
FIG. 5 is a schematic diagram of a continuous circulating reactor in which a carbonic acid ester is produced using an alkyl tin compound according to one embodiment.

FIG. 5 shows a continuous circulating reactor for carbonic acid ester synthesis using an alkyl tin alkoxide composition. The dialkyl tin dialkoxide composition was introduced into the continuous circulating reactor and circulated for test operation. Approximately 60 kg of a bis(3-methylbutyl) dibutoxytin composition obtained by the same method as Synthesis Example 1 (tin atom concentration (in the active component) of the composition: 2.42 mol/kg) was introduced into a SUS316 catalyst tank 770 equipped with a heating jacket and liquid conveyance pump, via a supply line 107. The composition was first circulated in the catalyst tank 770 for about 12 hours. Next, the composition was conveyed from the catalyst tank 770 to a tank reactor 710 at 10 kg/hr, via a transport line 109, an inline mixer 711 equipped with a heating jacket, and a transport line 110. The tank reactor 710 was a 10 L-volume reactor, comprising a stirrer, heating jacket and liquid conveyance pump, and the heating jacket was heated with steam at about 150° C. A SUS316 tower reactor 730 with an inner diameter of 76 mm and an effective length of 3500 mm, equipped with 25 sieve trays, was heated and thermally insulated with a heater around the entire tower reactor to prevent radiated heat loss, the heater being set to about 150° C. A liquid conveyance pump and reboiler 733 were provided at the bottom of the tower reactor 730, and the reboiler 733 was heated with steam at about 160° C. An autoclave 740 was used which was a 15 L-volume reactor, comprising a stirrer, heating jacket and liquid conveyance pump, and the heating jacket was heated with steam at about 140° C. A thin-film vaporizer 750 (heat transfer area: 0.1 m$^2$) and a thin-film vaporizer 760 (heat transfer area: 0.2 m$^2$) set to 85 kPaA pressure were equipped with a heating jacket and a liquid conveyance pump for conveyance of the high boiling point component, and steam at 160° C. was used for heating. The composition conveyed to the tank reactor 710 was then conveyed to the tower reactor 730 through a transport line 95, subsequently conveyed to the autoclave 740 through a transport line 97, then conveyed to the thin-film vaporizer 750 through a transport line 99 and further conveyed to the thin-film vaporizer 760 through a transport line 101, after which it was conveyed to the catalyst tank 770 through a transport line 103. The composition was thus continuously circulated through the tank reactor 710, tower reactor 730, autoclave 740, thin-film vaporizer 750, thin-film vaporizer 760 and catalyst tank 770 via the transport line 109, inline mixer 711, transport line 110, transport line 95, transport line 97, transport line 99, transport line 101 and transport line 103, and this was continued for about 5 days. Next, the liquid in the catalyst tank 770 was sampled from an extraction line 108, and as a result of $^{119}$Sn-NMR spectral analysis it was confirmed that bis(3-methylbutyl)dibutoxytin and tris(3-methylbutyl)butoxytin were present after the test operation. Upon calculating the concentration of tin atoms in the composition from the bis(3-methylbutyl)dibutoxytin concentration of the composition in the catalyst tank after test operation, as determined by the analysis results, it was found to be 2.23 mol/kg, which was a reduction of 7.8% compared to before start of the test operation. On the other hand, tris(3-methylbutyl) butoxytin was produced at 5.7 mol, which was 3.9% of the number of moles of tin atoms (in the active component) of the composition before starting the test operation.

Examples 6 to 80

The tetraalkyldialkoxydistannoxanes listed in Tables 1 and 2 were produced by the same methods as in Synthesis Examples 2, 5 and 8, and test operation of the continuous circulating reactor was conducted by the same method as Example 1, confirming modification reaction during heated circulation. Of these tetraalkyldialkoxydistannoxanes, some have a low flow property at the environmental temperature at the start of the reaction (about 15° C. to 35° C.), and in these cases tetralin (product of Wako Pure Chemical Industries), diphenyl ether (product of Wako Pure Chemical Industries) or undecane (product of Wako Pure Chemical Industries) was added as a diluent to prepare a liquid mixture with a diluent concentration of 10 to 35 mass %, and this was introduced into the catalyst tank before conducting test operation (circulating operation) using a continuous circulating reactor as shown in FIG. 1 in the same manner as atoms (in the active component) of the composition before the start of test operation was calculated. The percentage reductions in the tin atom concentration (in the active component) of the compositions and the trialkyl tin alkoxide production amounts are shown in Tables 1 and 2.

TABLE 1

| | Tetraalkyldialkoxydistannoxane | | Continuous operation time [days] | Percentage reduction in tin atom concentration (in active component) [%] *1) | Trialkyl tin alkoxide production amount [%] *2) |
|---|---|---|---|---|---|
| Example | R' (alkyl group) | OR" (alkoxy group) | | | |
| 6 | Isopentyl | Ethoxy | 5 | 8.2 | 4.3 |
| 7 | Nonan-3-yl | 2-Ethylhexyloxy | 6 | 11.0 | 5.4 |
| 8 | 3-Propylhexyl | N-Octyloxy | 5 | 7.3 | 3.8 |
| 9 | Nonan-3-yl | 2-Methylpropyloxy | 5 | 11.0 | 5.4 |
| 10 | 3-Propylhexyl | 2-Methylpropyloxy | 6 | 7.0 | 3.6 |
| 11 | Pentan-3-yl | N-Pentoxy | 5 | 10.7 | 5.2 |
| 12 | Pentan-3-yl | Methoxy | 6 | 11.2 | 5.8 |
| 13 | 3-Ethylheptyl | 2-Ethylhexyloxy | 6 | 6.7 | 3.5 |
| 14 | Pentan-3-yl | Ethoxy | 5 | 11.4 | 5.6 |
| 15 | Isobutyl | N-Butoxy | 5 | 6.2 | 3.2 |
| 16 | 3-Propylhexyl | Ethoxy | 5 | 7.6 | 3.6 |
| 17 | Pentan-3-yl | 2-Methylpropyloxy | 5 | 11.3 | 5.5 |
| 18 | 2-Butyloctyl | N-Octyloxy | 6 | 5.0 | 2.4 |
| 19 | 3-Ethylheptyl | Methoxy | 6 | 7.6 | 3.8 |
| 20 | 2-Butyloctyl | N-Pentoxy | 5 | 5.1 | 2.5 |
| 21 | 3-Ethylheptyl | N-Pentoxy | 6 | 7.4 | 3.7 |
| 22 | Nonan-3-yl | 3-Methylbutyloxy | 6 | 10.4 | 5.4 |
| 23 | 3-Butylheptyl | N-Pentoxy | 6 | 7.4 | 3.8 |
| 24 | 3-Ethylheptyl | N-Butoxy | 5 | 7.4 | 4.0 |
| 25 | 3-Ethylheptyl | 2-Ethylbutyloxy | 6 | 6.6 | 3.3 |
| 26 | Pentan-3-yl | 3-Methylbutyloxy | 6 | 10.6 | 5.1 |
| 27 | Isobutyl | Ethoxy | 5 | 6.5 | 3.3 |
| 28 | 3-Butylnonyl | 3-Methylbutyloxy | 6 | 7.0 | 3.6 |
| 29 | Nonan-3-yl | Ethoxy | 6 | 11.0 | 5.5 |
| 30 | 3-Propylhexyl | 3-Methylbutyloxy | 5 | 7.0 | 3.7 |
| 31 | Nonan-3-yl | N-Pentoxy | 6 | 10.6 | 5.6 |
| 32 | Isopropyl | 3-Methylbutyloxy | 5 | 11.5 | 5.8 |
| 33 | Isopentyl | N-Octyloxy | 5 | 7.4 | 3.8 |
| 34 | 3-Propylhexyl | 2-Ethylbutyloxy | 5 | 6.5 | 3.3 |
| 35 | Isopentyl | Methoxy | 6 | 8.2 | 4.4 |
| 36 | Isopropyl | N-Butoxy | 6 | 12.2 | 6.1 |
| 37 | 3-Ethylpentyl | 2-Ethylbutyloxy | 6 | 7.2 | 3.5 |
| 38 | Isopentyl | N-Butoxy | 6 | 7.8 | 4.2 |
| 39 | 3-Propylhexyl | N-Pentoxy | 6 | 7.2 | 3.5 |
| 40 | 3-Ethylpentyl | 2-Methylpropyloxy | 5 | 7.9 | 3.8 |
| 41 | Pentan-3-yl | N-Butoxy | 5 | 11.3 | 6.0 |
| 42 | 3-Butylnonyl | N-Pentoxy | 5 | 7.0 | 3.4 |

*1) The percentage reduction in the tin atom concentration (in the active component) of the tetraalkyldialkoxydistannoxane composition was determined by the following mathematical formula (4).
*2) The trialkyl tin alkoxide production amount was determined by mathematical formula (5).

Example 1. The mass of the tetraalkyldialkoxydistannoxane composition introduced into the catalyst tank was about 50 kg, similar to Example 1, whether or not a diluent was used. The tetraalkyldialkoxydistannoxane concentration in the composition was determined by $^{119}$Sn-NMR spectral analysis, and the tin atom concentration (in the active component) of the composition before circulating operation was calculated. A sampling solution was taken from the catalyst tank after circulating operation and subjected to $^{119}$Sn-NMR spectral analysis. The tin atom concentration (in the active component) of the composition was calculated from the tetraalkyldialkoxydistannoxane concentration after test operation as determined from the analysis results, and the percentage reduction from before the start of test operation was calculated. The number of moles of trialkyl tin alkoxide was also determined from the analysis results, and the amount produced with respect to the number of moles of tin

[Mathematical Formula 4]

$$(\text{Percentage reduction in tin atom concentration (in active component)}) = (S_2^0 - S_2^r)/S_2^0 = 100\% \quad (4)$$

[In the formula, "percentage reduction in tin atom concentration (in active component)" is the percentage reduction [%] of the tin atom concentration (in the active component) of the composition after circulating operation, $S_2^0$ is the tin atom concentration (in the active component) [mol/kg] of the composition before circulating operation, and $S_2^r$ is the tin atom concentration (in the active component) [mol/kg] of the composition after circulating operation. $S_2^0$ and $S_2^r$ were calculated from the tetraalkyldialkoxydistannoxane concentration of the composition, as determined by $^{119}$Sn-NMR spectral analysis.]

[Mathematical Formula 5]

Trialkyl tin alkoxide production amount=$(T/W_2^0 \times S_2^0) \times 100\%$ (5)

[In the formula, "trialkyl tin alkoxide production amount" is the amount of trialkyl tin alkoxide produced [%] after circulating operation, T is the number of moles [mol] of trialkyl tin alkoxide produced after circulating operation, $W_2^0$ is the mass [kg] of the composition introduced into the catalyst tank before circulating operation, and $S_2^0$: is the tin atom concentration (in the active component) [mol/kg] of the composition before circulating operation. $S_2^0$ was calculated from the tetraalkyldialkoxydistannoxane concentration of the composition, as determined by $^{119}$Sn-NMR spectral analysis.]

Structural formula of tetraalkyldialkoxydistannoxane

[Chemical Formula 37]

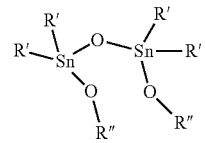

[R' represents a C1-15 alkyl group and R" represents a C1-8 alkyl group.]

TABLE 2

| | Tetraalkyldialkoxydistannoxane | | Continuous operation time [days] | Percentage reduction in tin atom concentration (in active component) [%] *1) | Trialkyl tin alkoxide production amount [%] *2) |
|---|---|---|---|---|---|
| Example | R' (alkyl group) | OR" (alkoxy group) | | | |
| 43 | Nonan-3-yl | N-Octyloxy | 5 | 11.1 | 5.8 |
| 44 | 2-Butyloctyl | 3-Methylbutyloxy | 5 | 4.7 | 2.4 |
| 45 | 3-Propylhexyl | 2-Ethylhexyloxy | 6 | 6.5 | 3.2 |
| 46 | 3-Butylnonyl | N-Octyloxy | 6 | 7.0 | 3.6 |
| 47 | 3-Propylhexyl | N-Butoxy | 5 | 7.3 | 3.9 |
| 48 | 3-Ethylheptyl | Ethoxy | 6 | 7.8 | 4.2 |
| 49 | Pentan-3-yl | N-Octyloxy | 6 | 11.8 | 6.3 |
| 50 | 3-Ethylheptyl | 3-Methylbutyloxy | 5 | 7.1 | 3.8 |
| 51 | 3-Ethylpentyl | Ethoxy | 5 | 8.5 | 4.5 |
| 52 | 3-Ethylpentyl | 3-Methylbutyloxy | 5 | 7.9 | 4.2 |
| 53 | 3-Butylnonyl | 2-Methylpropyloxy | 5 | 6.9 | 3.6 |
| 54 | Isopentyl | 2-Ethylhexyloxy | 5 | 7.0 | 3.6 |
| 55 | Pentan-3-yl | 2-Ethylhexyloxy | 5 | 11.2 | 5.7 |
| 56 | 2-Butyloctyl | 2-Ethylbutyloxy | 5 | 4.4 | 2.3 |
| 57 | Isopentyl | 2-Methylpropyloxy | 5 | 7.5 | 4.0 |
| 58 | 3-Butylnonyl | 2-Ethylbutyloxy | 6 | 6.5 | 3.5 |
| 59 | 3-Butylheptyl | Methoxy | 5 | 8.2 | 4.0 |
| 60 | Isopentyl | 2-Ethylbutyloxy | 5 | 7.0 | 3.6 |
| 61 | 2-Ethylhexyl | 2-Ethylbutyloxy | 6 | 4.3 | 2.2 |
| 62 | Isopropyl | N-Pentoxy | 5 | 11.7 | 6.1 |
| 63 | Nonan-3-yl | N-Butoxy | 6 | 11.0 | 5.5 |
| 64 | 2-Butyloctyl | 2-Ethylhexyloxy | 6 | 4.4 | 2.2 |
| 65 | 3-Butylnonyl | 2-Ethylhexyloxy | 6 | 6.5 | 3.4 |
| 66 | Pentan-3-yl | 2-Ethylbutyloxy | 6 | 11.3 | 6.0 |
| 67 | Nonan-3-yl | 2-Ethylbutyloxy | 6 | 11.0 | 5.9 |
| 68 | 3-Butylheptyl | 3-Methylbutyloxy | 5 | 7.4 | 3.7 |
| 69 | 3-Ethylpentyl | 2-Ethylhexyloxy | 5 | 7.2 | 3.9 |
| 70 | Isopropyl | Ethoxy | 6 | 12.3 | 6.6 |
| 71 | Isobutyl | Methoxy | 6 | 6.3 | 3.3 |
| 72 | 3-Ethylpentyl | N-Octyloxy | 6 | 7.8 | 4.1 |
| 73 | 2-Butyloctyl | N-Butoxy | 6 | 4.9 | 2.4 |
| 74 | 3-Ethylpentyl | N-Butoxy | 5 | 8.2 | 4.3 |
| 75 | 2,2-Dimethylpropyl | Ethoxy | 6 | 5.8 | 2.9 |
| 76 | 3-Ethylheptyl | N-Octyloxy | 6 | 7.6 | 3.8 |
| 77 | Isobutyl | 2-Methylpropyloxy | 6 | 5.9 | 3.1 |
| 78 | Nonan-3-yl | Methoxy | 5 | 11.2 | 5.7 |
| 79 | 3-Ethylpentyl | Methoxy | 5 | 8.6 | 4.4 |
| 80 | 3-Ethylpentyl | N-Pentoxy | 6 | 8.2 | 4.3 |

*1) The percentage reduction in the tin atom concentration (in the active component) of the tetraalkyldialkoxydistannoxane composition was determined by the following mathematical formula (4).
*2) The trialkyl tin alkoxide production amount was determined by mathematical formula (5).

[Mathematical Formula 6]

Percentage reduction in tin atom concentration (in active component)=$(S_2^0-S_2')/S_2^0 \times 100\%$  (4)

[In the formula, "percentage reduction in tin atom concentration (in active component)" is the percentage reduction [%] of the tin atom concentration (in the active component) of the composition after circulating operation, $S_2^0$ is the tin atom concentration (in the active component) [mol/kg] of the composition before circulating operation, and $S_2'$ is the tin atom concentration (in the active component) [mol/kg] of the composition after circulating operation. $S_2^0$ and $S_2'$ were calculated from the tetraalkyldialkoxydistannoxane concentration of the composition, as determined by $^{119}$Sn-NMR spectral analysis.]

[Mathematical Formula 7]

Trialkyl tin alkoxide production amount=$T/(W_2^0 \times S_2^0) \times 100\%$  (5)

[In the formula, "trialkyl tin alkoxide production amount" is the amount of trialkyl tin alkoxide produced [%] after circulating operation, T is the number of moles [mol] of trialkyl tin alkoxide produced after circulating operation, $W_2^0$ is the mass [kg] of the composition introduced into the catalyst tank before circulating operation, and $S_2^0$ is the tin atom concentration (in the active component) [mol/kg] of the composition before circulating operation. $S_2^0$ was calculated from the tetraalkyldialkoxydistannoxane concentration of the composition, as determined by $^{119}$Sn-NMR spectral analysis.]

Structural formula of tetraalkyldialkoxydistannoxane

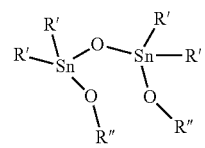

[Chemical Formula 38]

[R' represents a C1-15 alkyl group and R" represents a C1-8 alkyl group.]

Examples 81 to 142

The dialkyl tin dialkoxides listed in Tables 3 and 4 were produced by the same methods as in Synthesis Examples 1, 4 and 7, and test operation of the continuous circulating reactor was conducted by the same method as Example 2, confirming modification reaction during heated circulation. After introducing about 45 kg of the dialkyl tin dialkoxide into a catalyst tank, a continuous circulating reactor as shown in FIG. 2 was used for test operation (circulating operation) in the same manner as Example 2. A sampling solution was taken from the catalyst tank after circulating operation and subjected to $^{119}$Sn-NMR spectral analysis. The tin atom concentration (in the active component) of the composition was calculated from the dialkyl tin dialkoxide concentration after test operation as determined from the analysis results, and the percentage reduction from before the start of test operation was calculated. The number of moles of trialkyl tin alkoxide was also determined from the analysis results, and the amount produced with respect to the number of moles of tin atoms (in the active component) of the composition before the start of test operation was calculated. The percentage reductions in the tin atom concentration (in the active component) of the compositions and the trialkyl tin alkoxide production amounts are shown in Tables 3 and 4.

TABLE 3

| | Dialkyl tin dialkoxide | | Continuous operation time [days] | Percentage reduction in tin atom concentration (in active component) [%] *3) | Trialkyl tin alkoxide production amount [%] *4) |
|---|---|---|---|---|---|
| Example | R' (alkyl group) | OR" (alkoxy group) | | | |
| 81 | 3-Ethylpentyl | 3-Methylbutyloxy | 5 | 6.5 | 3.3 |
| 82 | 3-Ethylheptyl | 3-Methylbutyloxy | 5 | 6.1 | 3.0 |
| 83 | 2-Butyloctyl | Ethoxy | 5 | 4.2 | 2.2 |
| 84 | 3-Propylhexyl | 2-Ethylbutyloxy | 5 | 5.7 | 2.8 |
| 85 | 3-Butylnonyl | Methoxy | 5 | 7.2 | 3.5 |
| 86 | 3-Ethylheptyl | N-Pentoxy | 5 | 6.8 | 3.6 |
| 87 | Pentan-3-yl | 2-Ethylbutyloxy | 6 | 11.1 | 6.0 |
| 88 | 3-Propylhexyl | N-Hexyloxy | 5 | 6.4 | 3.3 |
| 89 | Pentan-3-yl | 3-Methylbutyloxy | 6 | 10.5 | 5.1 |
| 90 | 3-Butylnonyl | N-Pentoxy | 5 | 6.7 | 3.4 |
| 91 | Isopropyl | Ethoxy | 5 | 12.0 | 6.4 |
| 92 | 3-Ethylpentyl | Methoxy | 5 | 7.2 | 3.8 |
| 93 | Isobutyl | N-Butoxy | 5 | 5.0 | 2.6 |
| 94 | 3-Ethylpentyl | Ethoxy | 6 | 7.4 | 3.7 |
| 95 | Pentan-3-yl | N-Butoxy | 6 | 11.0 | 5.8 |
| 96 | 3-Butylnonyl | N-Hexyloxy | 5 | 6.2 | 3.0 |
| 97 | 2-Butyloctyl | N-Pentoxy | 6 | 4.1 | 2.1 |
| 98 | Nonan-3-yl | 2-Ethylbutyloxy | 5 | 11.0 | 5.8 |
| 99 | 2-Hexyldecyl | 2-Ethylhexyloxy | 5 | 3.9 | 2.0 |
| 100 | Nonan-3-yl | 2-Ethylhexyloxy | 6 | 11.0 | 5.8 |
| 101 | 3-Ethylheptyl | Methoxy | 6 | 7.0 | 3.4 |
| 102 | Isobutyl | N-Pentoxy | 5 | 5.1 | 2.5 |
| 103 | 3-Butylnonyl | 2-Ethylhexyloxy | 6 | 6.2 | 3.2 |

TABLE 3-continued

| | Dialkyl tin dialkoxide | | Continuous operation | Percentage reduction in tin atom concentration (in active component) | Trialkyl tin alkoxide production amount |
|---|---|---|---|---|---|
| Example | R' (alkyl group) | OR" (alkoxy group) | time [days] | [%] *3) | [%] *4) |
| 104 | Pentan-3-yl | Methoxy | 6 | 11.2 | 5.4 |
| 105 | Pentan-3-yl | N-Pentoxy | 6 | 11.1 | 5.8 |
| 106 | 3-Ethylheptyl | 2-Ethylhexyloxy | 5 | 6.2 | 3.2 |
| 107 | 2-Hexyldecyl | N-Hexyloxy | 6 | 4.1 | 2.0 |
| 108 | Isopropyl | N-Hexyloxy | 5 | 12.9 | 6.4 |
| 109 | Nonan-3-yl | N-Butoxy | 6 | 10.7 | 5.7 |
| 110 | 2-Butyloctyl | 3-Methylbutyloxy | 5 | 3.7 | 1.9 |
| 111 | Isopentyl | 2-Ethylhexyloxy | 6 | 6.3 | 3.2 |
| 112 | 3-Butylheptyl | N-Butoxy | 5 | 6.7 | 3.5 |

*3) The percentage reduction in the tin atom concentration (in the active component) of the dialkyl tin dialkoxide composition was determined by the following mathematical formula (6).
*4) The trialkyl tin alkoxide production amount was determined by mathematical formula (7).

[Mathematical Formula 8]

Percentage reduction in tin atom concentration (in active component)=$(S_1^0-S_1^t)/S_1^0 \times 100\%$ (6)

[In the formula, "percentage reduction in tin atom concentration (in active component)" is the percentage reduction [%] of the tin atom concentration (in the active component) of the composition after circulating operation, $S_1^0$ is the tin atom concentration (in the active component) [mol/kg] of the composition before circulating operation, and $S_1^t$ is the tin atom concentration (in the active component) [mol/kg] of the composition after circulating operation. $S_1^0$ and $S_1^t$ were calculated from the dialkyl tin dialkoxide concentration of the composition, as determined by $^{119}$Sn-NMR spectral analysis.]

[Mathematical Formula 9]

Trialkyl tin alkoxide production amount=$T/(W_1^0 \times S_1^0) \times 100\%$ (7)

[In the formula, "trialkyl tin alkoxide production amount" is the amount of trialkyl tin alkoxide produced [%] after circulating operation, T is the number of moles [mol] of trialkyl tin alkoxide produced after circulating operation, $W_1^0$ is the mass [kg] of the composition introduced into the catalyst tank before circulating operation, and $S_1^0$ is the tin atom concentration (in the active component) [mol/kg] of the composition before circulating operation. $S_1^0$ was calculated from the dialkyl tin dialkoxide concentration of the composition, as determined by $^{119}$Sn-NMR spectral analysis.]

Structural formula of dialkyl tin dialkoxide

[Chemical Formula 39]

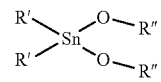

[R' represents a C1-15 alkyl group and R" represents a C1-8 alkyl group.]

TABLE 4

| | Dialkyl tin dialkoxide | | Continuous operation | Percentage reduction in tin atom concentration (in active component) | Trialkyl tin alkoxide production amount |
|---|---|---|---|---|---|
| Example | R' (alkyl group) | OR" (alkoxy group) | time [days] | [%] *3) | [%] *4) |
| 113 | 3-Ethylpentyl | N-Butoxy | 5 | 6.9 | 3.6 |
| 114 | 3-Propylhexyl | N-Butoxy | 5 | 6.5 | 3.4 |
| 115 | 3-Propylhexyl | 2-Ethylhexyloxy | 6 | 6.0 | 2.9 |
| 116 | Pentan-3-yl | Ethoxy | 5 | 11.1 | 6.0 |
| 117 | 3-Propylhexyl | Methoxy | 5 | 6.7 | 3.5 |
| 118 | 3-Ethylheptyl | 2-Ethylbutyloxy | 5 | 5.7 | 2.8 |
| 119 | 3-Butylnonyl | 2-Ethylbutyloxy | 5 | 5.7 | 3.1 |
| 120 | Isopentyl | 2-Ethylbutyloxy | 6 | 6.0 | 3.0 |
| 121 | 2-Hexyldecyl | N-Butoxy | 5 | 4.2 | 2.1 |
| 122 | Nonan-3-yl | 3-Methylbutyloxy | 6 | 10.1 | 5.2 |
| 123 | Isobutyl | 3-Methylbutyloxy | 6 | 4.8 | 2.4 |
| 124 | 3-Propylhexyl | N-Pentoxy | 6 | 6.8 | 3.4 |
| 125 | 3-Propylhexyl | 3-Methylbutyloxy | 5 | 6.1 | 3.2 |
| 126 | 3-Ethylpentyl | N-Pentoxy | 5 | 7.2 | 3.7 |
| 127 | Isopentyl | N-Hexyloxy | 5 | 6.4 | 3.4 |
| 128 | Nonan-3-yl | N-Pentoxy | 5 | 11.0 | 5.4 |
| 129 | 3-Propylhexyl | Ethoxy | 5 | 6.9 | 3.7 |
| 130 | 2-Butyloctyl | Methoxy | 5 | 4.3 | 2.2 |

TABLE 4-continued

| Example | Dialkyl tin dialkoxide R' (alkyl group) | OR" (alkoxy group) | Continuous operation time [days] | Percentage reduction in tin atom concentration (in active component) [%] *3) | Trialkyl tin alkoxide production amount [%] *4) |
|---|---|---|---|---|---|
| 131 | Isopentyl | Ethoxy | 6 | 7.3 | 3.8 |
| 132 | 3-Ethylheptyl | Ethoxy | 5 | 7.0 | 3.6 |
| 133 | Nonan-3-yl | Ethoxy | 6 | 10.8 | 5.6 |
| 134 | Isopropyl | Methoxy | 5 | 12.0 | 6.5 |
| 135 | Nonan-3-yl | N-Hexyloxy | 5 | 11.3 | 5.7 |
| 136 | 3-Ethylheptyl | N-Hexyloxy | 5 | 6.3 | 3.2 |
| 137 | 2-Hexyldecyl | 2-Ethylbutyloxy | 5 | 3.7 | 1.8 |
| 138 | 3-Butylnonyl | N-Butoxy | 6 | 6.6 | 3.3 |
| 139 | 3-Butylnonyl | 3-Methylbutyloxy | 6 | 6.2 | 3.2 |
| 140 | Pentan-3-yl | 2-Ethylhexyloxy | 5 | 11.3 | 5.8 |
| 141 | Isopentyl | Methoxy | 6 | 7.5 | 3.8 |
| 142 | Isopropyl | 2-Ethylbutyloxy | 6 | 12.0 | 6.1 |

*3) The percentage reduction in the tin atom concentration (in the active component) of the dialkyl tin dialkoxide composition was determined by the following mathematical formula (6).
*4) The trialkyl tin alkoxide production amount was determined by mathematical formula (7).

[Mathematical Formula 10]

Percentage reduction in tin atom concentration (in active component)=$(S_1^0-S_1^t)/S_1^0\times 100\%$ (6)

[In the formula, "percentage reduction in tin atom concentration (in active component)" is the percentage reduction [%] of the tin atom concentration (in the active component) of the composition after circulating operation, $S_1^0$ is the tin atom concentration (in the active component) [mol/kg] of the composition before circulating operation, and $S_1^t$ is the tin atom concentration (in the active component) [mol/kg] of the composition after circulating operation. $S_1^0$ and $S_1^t$ were calculated from the dialkyl tin dialkoxide concentration of the composition, as determined by $^{119}$Sn-NMR spectral analysis.]

[Mathematical Formula 11]

Trialkyl tin alkoxide production amount=$T/(W_1^0\times S_1^0)\times 100\%$ (7)

[In the formula, "trialkyl tin alkoxide production amount" is the amount of trialkyl tin alkoxide produced [%] after circulating operation, T is the number of moles [mol] of trialkyl tin alkoxide produced after circulating operation, $W_1^0$ is the mass [kg] of the composition introduced into the catalyst tank before circulating operation, and $S_1^0$ is the tin atom concentration (in the active component) [mol/kg] of the composition before circulating operation. $S_1^0$ was calculated from the dialkyl tin dialkoxide concentration of the composition, as determined by $^{119}$Sn-NMR spectral analysis.]

Structural formula of dialkyl tin dialkoxide

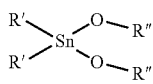

[Chemical Formula 40]

[R' represents a C1-15 alkyl group and R" represents a C1-8 alkyl group.]

Examples 143 to 194

The compositions comprising dialkyl tin dialkoxides and tetraalkyldialkoxydistannoxanes listed in Tables 5 and 6 produced by the same methods as in Synthesis Examples 1, 2, 4, 5, 7 and 8 were prepared, and test operation of the continuous circulating reactor was conducted by the same method as Example 3, confirming modification reaction during heated circulation. They were prepared so that the molar ratios of tin atoms of the dialkyl tin dialkoxide and tetraalkyldialkoxydistannoxane with respect to the number of moles of tin atoms (in the active component) of the compositions comprising the dialkyl tin dialkoxides and tetraalkyldialkoxydistannoxanes having the structures listed in Tables 5 and 6 were 65:35, and approximately 60 kg was introduced into the catalyst tank. The tin atom concentration (in the active component) of each composition was determined by mathematical formula (3). Test operation (circulating operation) of the composition was conducted in the same manner as Example 3, using a continuous circulating reactor as shown in FIG. 3. A sampling solution was taken from the catalyst tank after circulating operation and subjected to $^{119}$Sn-NMR spectral analysis. The tin atom concentration (in the active component) of the composition was calculated from the tetraalkyldialkoxydistannoxane concentration and dialkyl tin dialkoxide concentration of the composition after test operation as determined from the analysis results, and the percentage reduction from before the start of test operation was calculated. The number of moles of trialkyl tin alkoxide produced after test operation was also determined from the analysis results, and the amount produced with respect to the number of moles of tin atoms (in the active component) of the composition before the start of test operation was calculated. The percentage reductions in the tin atom concentration (in the active component) of the compositions and the trialkyl tin alkoxide production amounts are shown in Tables 5 and 6.

TABLE 5

| Example | Alkyl tin alkoxide R' (alkyl group) | Alkyl tin alkoxide OR" (alkoxy group) | Continuous operation time [days] | Percentage reduction in tin atom concentration (in active component) [%] *5) | Trialkyl tin alkoxide production amount [%] *6) |
|---|---|---|---|---|---|
| 143 | 3-Butylnonyl | N-Pentoxy | 6 | 6.4 | 3.3 |
| 144 | Nonan-3-yl | Ethoxy | 6 | 10.4 | 5.5 |
| 145 | Isopropyl | Methoxy | 5 | 11.9 | 6.2 |
| 146 | 3-Ethylpentyl | N-Hexyloxy | 5 | 6.2 | 3.3 |
| 147 | Isopentyl | N-Hexyloxy | 6 | 6.5 | 3.2 |
| 148 | Isopropyl | Ethoxy | 6 | 11.7 | 5.9 |
| 149 | Pentan-3-yl | N-Pentoxy | 5 | 10.5 | 5.1 |
| 150 | 3-Ethylheptyl | Ethoxy | 6 | 6.5 | 3.3 |
| 151 | Pentan-3-yl | 2-Methylpropyloxy | 5 | 10.8 | 5.5 |
| 152 | Isobutyl | 3-Methylbutyloxy | 5 | 4.6 | 2.5 |
| 153 | Isopentyl | Methoxy | 5 | 7.2 | 3.8 |
| 154 | 2-Butyloctyl | 2-Methylpropyloxy | 6 | 3.6 | 1.8 |
| 155 | Isopropyl | 3-Methylbutyloxy | 5 | 11.0 | 5.5 |
| 156 | 3-Ethylpentyl | 2-Ethylbutyloxy | 5 | 5.9 | 3.2 |
| 157 | Isobutyl | N-Pentoxy | 5 | 4.9 | 2.6 |
| 158 | 3-Butylnonyl | 3-Methylbutyloxy | 5 | 6.0 | 3.0 |
| 159 | Nonan-3-yl | 2-Methylpropyloxy | 5 | 10.5 | 5.4 |
| 160 | Pentan-3-yl | 3-Methylbutyloxy | 6 | 10.3 | 5.0 |
| 161 | Nonan-3-yl | 3-Methylbutyloxy | 6 | 10.0 | 5.4 |
| 162 | 3-Ethylpentyl | N-Pentoxy | 6 | 6.8 | 3.7 |
| 163 | Nonan-3-yl | Methoxy | 6 | 10.8 | 5.2 |
| 164 | Isobutyl | Methoxy | 6 | 5.5 | 2.8 |
| 165 | 2-Butyloctyl | 2-Ethylbutyloxy | 6 | 3.3 | 1.7 |
| 166 | 3-Ethylheptyl | 2-Ethylbutyloxy | 5 | 5.6 | 2.9 |
| 167 | Isopentyl | 2-Methylpropyloxy | 5 | 6.2 | 3.3 |
| 168 | Isopropyl | N-Hexyloxy | 5 | 11.9 | 6.2 |
| 169 | Isopropyl | N-Pentoxy | 5 | 11.6 | 6.2 |
| 170 | 3-Butylnonyl | N-Hexyloxy | 5 | 6.1 | 2.9 |

*5) The percentage reduction in the tin atom concentration (in the active component) of each alkyl tin alkoxide composition was determined by mathematical formula (8).
*6) The trialkyl tin alkoxide production amount was determined by mathematical formula (9).

[Mathematical Formula 12]

Percentage reduction in tin atom concentration (in active component)=$S_3^0-S_3^t/S_3^0 \times 100\%$  (8)

[In the formula, "percentage reduction in tin atom concentration (in active component)" is the percentage reduction [%] of the tin atom concentration (in the active component) of the composition after circulating operation, $S_3^0$ is the tin atom concentration (in the active component) [mol/kg] of the composition before circulating operation, and $S_3^t$ is the tin atom concentration (in the active component) [mol/kg] of the composition after circulating operation. $S_3^0$ and $S_3^t$ were calculated from the tetraalkyldialkoxydistannoxane concentration and dialkyl tin dialkoxide concentration of the composition, as determined by $^{119}$Sn-NMR spectral analysis.]

[Mathematical Formula 13]

Trialkyl tin alkoxide production amount=$T/(W_3^0 \times S_3^0) \times 100\%$  (9)

[In the formula, "trialkyl tin alkoxide production amount" is the amount of trialkyl tin alkoxide produced [%] after circulating operation, T is the number of moles [mol] of trialkyl tin alkoxide produced after circulating operation, $W_3^0$ is the mass [kg] of the composition introduced into the catalyst tank before circulating operation, and $S_3^0$ is the tin atom concentration (in the active component) [mol/kg] of the composition before circulating operation. $S_3^0$ was calculated from the tetraalkyldialkoxydistannoxane concentration and dialkyl tin dialkoxide concentration of the composition, as determined by $^{119}$Sn-NMR spectral analysis.]

Structural formulas of tetraalkyldialkoxydistannoxane and dialkyl tin dialkoxide in alkyl tin alkoxide composition

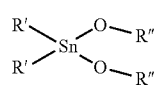

[Chemical Formula 41]

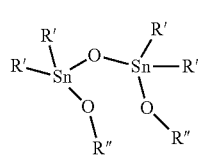

[Chemical Formula 42]

[R' represents a C1-15 alkyl group and R" represents a C1-8 alkyl group.]

TABLE 6

| Example | Alkyl tin alkoxide R' (alkyl group) | Alkyl tin alkoxide OR" (alkoxy group) | Continuous operation time [days] | Percentage reduction in tin atom concentration (in active component) [%] *5) | Trialkyl tin alkoxide production amount [%] *6) |
|---|---|---|---|---|---|
| 171 | Isopropyl | 2-Methylpropyloxy | 6 | 11.7 | 5.6 |
| 172 | Pentan-3-yl | 2-Ethylbutyloxy | 6 | 11.0 | 5.6 |
| 173 | Nonan-3-yl | N-Hexyloxy | 6 | 11.5 | 6.1 |
| 174 | 2-Butyloctyl | 3-Methylbutyloxy | 6 | 3.6 | 1.8 |
| 175 | Isopentyl | Ethoxy | 6 | 6.8 | 3.3 |
| 176 | 3-Butylnonyl | 2-Ethylbutyloxy | 5 | 5.6 | 2.9 |
| 177 | Isopentyl | 2-Ethylbutyloxy | 5 | 5.8 | 2.8 |
| 178 | 3-Butylnonyl | 2-Methylpropyloxy | 6 | 6.0 | 3.0 |
| 179 | Nonan-3-yl | N-Pentoxy | 5 | 10.1 | 5.4 |
| 180 | 3-Ethylpentyl | 3-Methylbutyloxy | 5 | 6.3 | 3.3 |
| 181 | 3-Ethylheptyl | 2-Methylpropyloxy | 6 | 5.9 | 2.8 |
| 182 | 3-Ethylheptyl | Methoxy | 5 | 7.0 | 3.5 |
| 183 | 3-Ethylheptyl | N-Hexyloxy | 6 | 5.9 | 3.1 |
| 184 | Nonan-3-yl | 2-Ethylbutyloxy | 6 | 10.9 | 5.4 |
| 185 | Isobutyl | Ethoxy | 5 | 5.0 | 2.5 |
| 186 | 3-Propylhexyl | N-Pentoxy | 5 | 6.1 | 3.2 |
| 187 | Isopropyl | 2-Ethylbutyloxy | 5 | 11.7 | 5.7 |
| 188 | 2-Butyloctyl | N-Hexyloxy | 5 | 3.6 | 1.9 |
| 189 | 3-Propylhexyl | 2-Ethylbutyloxy | 6 | 5.3 | 2.6 |
| 190 | Isobutyl | 2-Methylpropyloxy | 5 | 4.6 | 2.3 |
| 191 | 3-Ethylpentyl | 2-Methylpropyloxy | 6 | 6.4 | 3.4 |
| 192 | 3-Ethylheptyl | N-Pentoxy | 5 | 6.5 | 3.2 |
| 193 | 3-Ethylheptyl | 3-Methylbutyloxy | 5 | 5.9 | 2.9 |
| 194 | 3-Propylhexyl | 3-Methylbutyloxy | 6 | 5.8 | 2.9 |

*5) The percentage reduction in the tin atom concentration (in the active component) of each alkyl tin alkoxide composition was determined by mathematical formula (8).
*6) The trialkyl tin alkoxide production amount was determined by mathematical formula (9).

[Mathematical Formula 14]

Percentage reduction in tin atom concentration (in active component)=$(S_3^0-S_3^t)/S_3^0 \times 100\%$ (8)

[In the formula, "percentage reduction in tin atom concentration (in active component)" is the percentage reduction [%] of the tin atom concentration (in the active component) of the composition after circulating operation, $S_3^0$ is the tin atom concentration (in the active component) [mol/kg] of the composition before circulating operation, and $S_3^t$ is the tin atom concentration (in the active component) [mol/kg] of the composition after circulating operation. $S_3^0$ and $S_3^t$ were calculated from the tetraalkyldialkoxydistannoxane concentration and dialkyl tin dialkoxide concentration of the composition, as determined by $^{119}$Sn-NMR spectral analysis.]

[Mathematical Formula 15]

Trialkyl tin alkoxide production amount=$T/(W_3^0 \times S_3^0) \times 100\%$ (9)

[In the formula, "trialkyl tin alkoxide production amount" is the amount of trialkyl tin alkoxide produced [%] after circulating operation, T is the number of moles [mol] of trialkyl tin alkoxide produced after circulating operation, $W_3^0$ is the mass [kg] of the composition introduced into the catalyst tank before circulating operation, and $S_3^0$ is the tin atom concentration (in the active component) [mol/kg] of the composition before circulating operation. $S_3^0$ was calculated from the tetraalkyldialkoxydistannoxane concentration and dialkyl tin dialkoxide concentration of the composition, as determined by $^{119}$Sn-NMR spectral analysis.]

Structural formulas of tetraalkyldialkoxydistannoxane and dialkyl tin dialkoxide in alkyl tin alkoxide composition

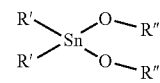

[Chemical Formula 43]

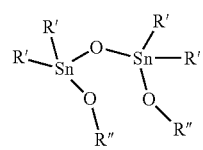

[Chemical Formula 44]

[R' represents a C1-15 alkyl group and R" represents a C1-8 alkyl group.]

Examples 195 to 257

The compositions comprising dialkyl tin dialkoxides, tetraalkyldialkoxydistannoxanes and trialkyl tin alkoxides listed in Tables 7 and 8 produced by the same methods as in Synthesis Examples 3 and 6 were used for test operation (circulating operation) of the continuous circulating reactor as shown in FIG. 4 by the same method as Example 4, confirming modification reaction during heated circulation. Approximately 60 kg of each composition comprising a dialkyl tin dialkoxide, tetraalkyldialkoxydistannoxane and trialkyl tin alkoxide produced by the same methods as Synthesis Examples 3 and 6 was introduced into a catalyst tank, and circulated in the continuous circulating reactor. A sampling solution was taken from the catalyst tank after circulating operation and subjected to $^{119}$Sn-NMR spectral analysis. The tin atom concentration (in the active component) of the composition was calculated from the tetraalkyldialkoxydistannoxane concentration and dialkyl tin dialkoxide concentration of the composition after test operation as determined from the analysis results, and the percentage reduction from before the start of test operation was calculated. The number of moles of trialkyl tin alkoxide was also determined from the analysis results, and the amount produced with respect to the number of moles of tin atoms (in the active component) of the composition before the start of test operation was calculated. The percentage reductions in the tin atom concentration (in the active component) of the compositions and the trialkyl tin alkoxide production amounts are shown in Tables 7 and 8.

atom concentration (in the active component) [mol/kg] of the composition before circulating operation, and $S_3^t$ is the tin atom concentration (in the active component) [mol/kg] of the composition after circulating operation. $S_3^0$ and $S_3^t$ were calculated from the tetraalkyldialkoxydistannoxane concentration and dialkyl tin dialkoxide concentration of the composition, as determined by $^{119}$Sn-NMR spectral analysis.]

[Mathematical Formula 17]

$$\text{Trialkyl tin alkoxide production amount} = T/(W_3^0 \times S_3^0) \times 100\% \quad (9)$$

[In the formula, "trialkyl tin alkoxide production amount" is the amount of trialkyl tin alkoxide produced [%] after circulating operation, T is the number of moles [mol] of trialkyl tin alkoxide produced after circulating operation,

TABLE 7

| Example | Alkyl tin alkoxide R' (alkyl group) | Alkyl tin alkoxide OR'' (alkoxy group) | Trialkyl tin alkoxide concentration [mol %] | Continuous operation time [days] | Percentage reduction in tin atom concentration (in active component) [%] *7) | Trialkyl tin alkoxide production amount [%] *8) |
|---|---|---|---|---|---|---|
| 195 | Isopropyl | 2-Methylpropyloxy | 9 | 6 | 11.5 | 6.1 |
| 196 | 2-Butyloctyl | N-Pentoxy | 8 | 6 | 3.4 | 1.8 |
| 197 | Nonan-3-yl | 2-Ethylhexyloxy | 8 | 6 | 10.7 | 5.7 |
| 198 | 3-Ethylheptyl | Ethoxy | 9 | 5 | 6.0 | 3.0 |
| 199 | 3-Butylnonyl | N-Butoxy | 10 | 5 | 5.7 | 2.9 |
| 200 | Isobutyl | N-Butoxy | 10 | 6 | 4.5 | 2.3 |
| 201 | Nonan-3-yl | N-Hexyloxy | 10 | 6 | 11.1 | 5.7 |
| 202 | 3-Ethylpentyl | 2-Ethylbutyloxy | 7 | 5 | 5.3 | 2.8 |
| 203 | Isopentyl | N-Butoxy | 8 | 5 | 6.0 | 3.0 |
| 204 | 3-Butylheptyl | N-Pentoxy | 7 | 5 | 5.7 | 2.9 |
| 205 | 3-Butylheptyl | 3-Methylbutyloxy | 9 | 5 | 5.5 | 2.9 |
| 206 | Isopropyl | Ethoxy | 7 | 6 | 11.8 | 6.0 |
| 207 | 3-Propylhexyl | 2-Ethylhexyloxy | 10 | 5 | 5.4 | 2.9 |
| 208 | 3-Butylnonyl | N-Hexyloxy | 10 | 5 | 5.6 | 2.8 |
| 209 | 3-Ethylheptyl | 2-Ethylbutyloxy | 8 | 6 | 5.0 | 2.6 |
| 210 | Nonan-3-yl | N-Pentoxy | 9 | 5 | 10.1 | 4.8 |
| 211 | Pentan-3-yl | 3-Methylbutyloxy | 9 | 6 | 10.2 | 5.5 |
| 212 | Pentan-3-yl | Ethoxy | 9 | 5 | 10.8 | 5.6 |
| 213 | Pentan-3-yl | N-Butoxy | 8 | 5 | 10.6 | 5.1 |
| 214 | Pentan-3-yl | 2-Methylpropyloxy | 9 | 5 | 10.7 | 5.4 |
| 215 | 3-Propylhexyl | 2-Methylpropyloxy | 7 | 6 | 5.4 | 2.7 |
| 216 | Pentan-3-yl | 2-Ethylhexyloxy | 9 | 6 | 10.7 | 5.7 |
| 217 | Isopentyl | Ethoxy | 7 | 5 | 6.4 | 3.3 |
| 218 | Isobutyl | 2-Ethylhexyloxy | 7 | 5 | 4.3 | 2.3 |
| 219 | Nonan-3-yl | 2-Methylpropyloxy | 9 | 5 | 10.3 | 5.1 |
| 220 | 3-Butylnonyl | 2-Methylpropyloxy | 9 | 5 | 5.4 | 2.8 |
| 221 | 2-Hexyldecyl | N-Butoxy | 7 | 5 | 3.6 | 1.9 |
| 222 | Isobutyl | Ethoxy | 6 | 5 | 4.7 | 2.3 |
| 223 | Isopentyl | 2-Methylpropyloxy | 9 | 6 | 5.7 | 2.8 |
| 224 | 3-Propylhexyl | 3-Methylbutyloxy | 8 | 5 | 5.3 | 2.8 |
| 225 | 3-Propylhexyl | N-Hexyloxy | 6 | 6 | 5.6 | 2.8 |

*7) The percentage reduction in the tin atom concentration (in the active component) of each alkyl tin alkoxide composition was determined by mathematical formula (8).
*8) The trialkyl tin alkoxide production amount was determined by mathematical formula (9).

[Mathematical Formula 16]

$$\text{Percentage reduction of tin atom concentration (in active component)} = (S_3^0 - S_3^t)/S_3^0 \times 100\% \quad (8)$$

[In the formula, "percentage reduction of tin atom concentration (in active component)" is the percentage reduction [%] in the tin atom concentration (in the active component) of the composition after circulating operation, $S_3^0$ is the tin $W_3^0$ is the mass [kg] of the alkyl tin alkoxide composition introduced into the catalyst tank before circulating operation, and $S_3^0$ is the tin atom concentration (in the active component) [mol/kg] of the composition before circulating operation. $S_3^0$ was calculated from the tetraalkyldialkoxydistannoxane concentration and dialkyl tin dialkoxide concentration of the composition, as determined by $^{119}$Sn-NMR spectral analysis.]

Structural formulas of tetraalkyldialkoxydistannoxane and dialkyl tin dialkoxide in alkyl tin alkoxide composition

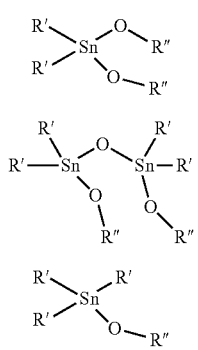

[Chemical Formula 45]

[Chemical Formula 46]

[Chemical Formula 47]

[R' represents a C1-15 alkyl group and R" represents a C1-8 alkyl group.]

[In the formula, "percentage reduction in tin atom concentration (in active component)" is the percentage reduction [%] in the tin atom concentration (in the active component) of the composition after circulating operation, $S_3^0$ is the tin atom concentration (in the active component) [mol/kg] of the composition before circulating operation, and $S_3^t$ is the tin atom concentration (in the active component) [mol/kg] of the composition after circulating operation. $S_3^0$ and $S_3^t$ were calculated from the tetraalkyldialkoxydistannoxane concentration and dialkyl tin dialkoxide concentration of the composition, as determined by $^{119}$Sn-NMR spectral analysis.]

[Mathematical Formula 19]

$$\text{Trialkyl tin alkoxide production amount} = T/(W_3^0 \times S_3^0) \times 100 \quad (9)$$

[In the formula, "trialkyl tin alkoxide production amount" is the amount of trialkyl tin alkoxide produced [%] after circulating operation, T is the number of moles [mol] of trialkyl tin alkoxide produced after circulating operation,

TABLE 8

| Example | Alkyl tin alkoxide R' (alkyl group) | OR" (alkoxy group) | Trialkyl tin alkoxide concentration [mol %] | Continuous operation time [days] | Percentage reduction in tin atom concentration (in active component) [%] *7) | Trialkyl tin alkoxide production amount [%] *8) |
|---|---|---|---|---|---|---|
| 226 | 2-Butyloctyl | 2-Ethylbutyloxy | 7 | 6 | 3.1 | 1.5 |
| 227 | Isopentyl | N-Hexyloxy | 6 | 6 | 5.6 | 2.7 |
| 228 | 3-Ethylheptyl | N-Pentoxy | 9 | 6 | 5.6 | 2.9 |
| 229 | Isopropyl | 3-Methylbutyloxy | 8 | 6 | 11.1 | 5.4 |
| 230 | 2-Butyloctyl | 3-Methylbutyloxy | 9 | 6 | 3.3 | 1.7 |
| 231 | 3-Ethylheptyl | N-Hexyloxy | 9 | 6 | 5.4 | 2.8 |
| 232 | 2-Hexyldecyl | 2-Methylpropyloxy | 9 | 6 | 3.4 | 1.7 |
| 233 | Isopropyl | N-Butoxy | 10 | 6 | 11.3 | 5.9 |
| 234 | 3-Ethylpentyl | N-Hexyloxy | 9 | 6 | 5.8 | 2.9 |
| 235 | 3-Ethylheptyl | N-Butoxy | 8 | 6 | 5.6 | 2.8 |
| 236 | Nonan-3-yl | 2-Ethylbutyloxy | 8 | 5 | 10.7 | 5.4 |
| 237 | 3-Ethylpentyl | 2-Methylpropyloxy | 10 | 6 | 5.6 | 2.7 |
| 238 | 3-Propylhexyl | 2-Ethylbutyloxy | 7 | 6 | 5.0 | 2.4 |
| 239 | 3-Ethylpentyl | N-Butoxy | 8 | 5 | 5.9 | 2.9 |
| 240 | Nonan-3-yl | 3-Methylbutyloxy | 10 | 6 | 9.9 | 4.9 |
| 241 | 3-Butylnonyl | 2-Ethylbutyloxy | 7 | 5 | 5.1 | 2.6 |
| 242 | Isopentyl | 2-Ethylbutyloxy | 10 | 5 | 5.2 | 2.6 |
| 243 | 3-Ethylpentyl | 2-Ethylhexyloxy | 9 | 5 | 5.6 | 2.8 |
| 244 | 3-Ethylpentyl | Ethoxy | 7 | 5 | 6.4 | 3.1 |
| 245 | Nonan-3-yl | N-Butoxy | 7 | 6 | 10.2 | 5.4 |
| 246 | 3-Butylnonyl | 2-Ethylhexyloxy | 9 | 5 | 5.4 | 2.8 |
| 247 | 3-Ethylheptyl | 2-Methylpropyloxy | 7 | 5 | 5.4 | 2.8 |
| 248 | 3-Propylhexyl | N-Pentoxy | 10 | 5 | 5.5 | 2.7 |
| 249 | Pentan-3-yl | N-Hexyloxy | 9 | 5 | 11.4 | 5.6 |
| 250 | 3-Ethylheptyl | 3-Methylbutyloxy | 8 | 6 | 5.4 | 2.8 |
| 251 | Pentan-3-yl | 2-Ethylbutyloxy | 7 | 6 | 10.8 | 5.2 |
| 252 | Isobutyl | 2-Ethylbutyloxy | 8 | 6 | 4.0 | 2.0 |
| 253 | Isopentyl | 2-Ethylhexyloxy | 8 | 6 | 5.5 | 2.9 |
| 254 | 3-Propylhexyl | Ethoxy | 6 | 6 | 5.8 | 2.8 |
| 255 | 3-Propylhexyl | N-Butoxy | 9 | 5 | 5.6 | 2.8 |
| 256 | 2-Butyloctyl | N-Hexyloxy | 10 | 5 | 3.2 | 1.6 |
| 257 | Isopropyl | N-Pentoxy | 9 | 6 | 11.4 | 6.0 |

*7) The percentage reduction in the tin atom concentration (in the active component) of each alkyl tin alkoxide composition was determined by mathematical formula (8).
*8) The trialkyl tin alkoxide production amount was determined by mathematical formula (9).

[Mathematical Formula 18]

$$\text{Percentage reduction in tin atom concentration (in active component)} = (S_3^0 - S_3^t)/S_3^0 \times 100\% \quad (8)$$

$W_3^0$ is the mass [kg] of the alkyl tin alkoxide composition introduced into the catalyst tank before circulating operation, and $S_3^0$ is the tin atom concentration (in the active component) [mol/kg] of the composition before circulating operation. $S_3^0$ was calculated from the tetraalkyldialkoxydistannoxane concentration and dialkyl tin dialkoxide concentration of the composition, as determined by $^{119}$Sn-NMR spectral analysis.]

Structural formulas of tetraalkyldialkoxydistannoxane, dialkyl tin dialkoxide and trialkyl tin alkoxide in alkyl tin alkoxide composition

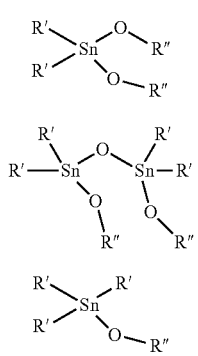

[Chemical Formula 48]

[Chemical Formula 49]

[Chemical Formula 50]

[R' represents a C1-15 alkyl group and R" represents a C1-8 alkyl group.]

moles of tin atoms (in the active component) of the composition were 5:95 to 50:50. The compositions were used by the same method as Example 5 for test operation (circulating operation) in a continuous circulating reactor as shown in FIG. 5, confirming modification reaction during heated circulation. Approximately 60 kg of each prepared composition was introduced into the catalyst tank and circulated in a continuous circulating reactor as shown in FIG. 5 by the same method. The alkyl tin alkoxide composition was sampled from the catalyst tank after circulating operation and subjected to $^{119}$Sn-NMR spectral analysis. The tin atom concentration (in the active component) of the composition was calculated from the tetraalkyldialkoxydistannoxane concentration and dialkyl tin dialkoxide concentration of the composition after test operation as determined from the analysis results, and the percentage reduction from before the start of test operation was calculated. The number of moles of trialkyl tin alkoxide was also determined from the analysis results, and the amount produced with respect to the number of moles of tin atoms (in the active component) of the composition before the start of test operation was calculated. The percentage reductions in the tin atom concentration (in the active component) of the compositions and the trialkyl tin alkoxide production amounts are shown in Table 9.

TABLE 9

| Example | Alkyl tin alkoxide R' (alkyl group) | OR" (alkoxy group) | Molar ratio of tin atoms of dialkyl tin dialkoxide and tetraalkyldialkoxydistannoxane | Continuous operation time [hr] | Percentage reduction in tin atom concentration of alkyl tin alkoxide composition [%] *9) | Trialkyl tin alkoxide production amount [%] *10) |
|---|---|---|---|---|---|---|
| 258 | Isopropyl | 3-Methylbutyloxy | 5:95 | 5 | 13.4 | 6.6 |
| 259 | Isopentyl | 3-Methylbutyloxy | 5:95 | 5 | 7.5 | 3.8 |
| 260 | Isopropyl | 3-Methylbutyloxy | 15:85 | 5 | 12.8 | 6.3 |
| 261 | Isopentyl | 3-Methylbutyloxy | 15:85 | 5 | 7.3 | 3.5 |
| 262 | Isopropyl | 3-Methylbutyloxy | 35:65 | 5 | 12.0 | 5.9 |
| 263 | Isopentyl | 3-Methylbutyloxy | 35:65 | 5 | 7.0 | 3.8 |
| 264 | Isopropyl | 3-Methylbutyloxy | 50:50 | 6 | 11.2 | 5.7 |
| 265 | Isopentyl | 3-Methylbutyloxy | 50:50 | 6 | 6.8 | 3.6 |
| 266 | Isopropyl | N-Butoxy | 5:95 | 5 | 13.5 | 6.7 |
| 267 | Isopentyl | N-Butoxy | 5:95 | 5 | 7.5 | 3.6 |
| 268 | Isopropyl | N-Butoxy | 15:85 | 6 | 13.2 | 6.7 |
| 269 | Isopentyl | N-Butoxy | 15:85 | 6 | 7.4 | 4.0 |
| 270 | Isopropyl | N-Butoxy | 35:65 | 6 | 13.1 | 6.6 |
| 271 | Isopentyl | N-Butoxy | 35:65 | 6 | 7.3 | 3.9 |
| 272 | Isopropyl | N-Butoxy | 50:50 | 6 | 13.0 | 6.6 |
| 273 | Isopentyl | N-Butoxy | 50:50 | 6 | 7.2 | 3.7 |

*9) The percentage reduction in the tin atom concentration (in the active component) of each alkyl tin alkoxide composition was determined by mathematical formula (8).
*10) The trialkyl tin alkoxide production amount was determined by mathematical formula (9).

Examples 258 to 273

Dialkyl tin dialkoxides and tetraalkyl dialkoxydistannoxanes with the structures listed in Table 9 were produced by the same methods as Synthesis Examples 1, 2, 4, 5, 7 and 8, and compositions comprising the dialkyl tin dialkoxides and tetraalkyl dialkoxydistannoxanes were prepared. Compositions comprising dialkyl tin dialkoxides and tetraalkyl dialkoxydistannoxanes were prepared so that the molar ratios of tin atoms of the dialkyl tin dialkoxides and tetraalkyl dialkoxydistannoxanes with respect to the number of

[Mathematical Formula 20]

Percentage reduction in tin atom concentration (in active component)=$(S_3^0-S_3^r)/S_3^0 \times 100\%$ (8)

[In the formula, "percentage reduction in tin atom concentration (in active component)" is the percentage reduction [%] in the tin atom concentration (in the active component) of the composition after circulating operation, $S_3^0$ is the tin atom concentration (in the active component) [mol/kg] of the composition before circulating operation, and $S_3^r$ is the tin atom concentration (in the active component) [mol/kg] of the composition after circulating operation. $S_3^0$ and $S_3^t$ were calculated from the tetraalkyldialkoxydistannoxane concentration and dialkyl tin dialkoxide concentration of the composition, as determined by $^{119}$Sn-NMR spectral analysis.]

[Mathematical Formula 21]

$$\text{Trialkyl tin alkoxide production amount} = T/(W_3^0 \times S_3^0) \times 100\% \quad (9)$$

[In the formula, "trialkyl tin alkoxide production amount" is the amount of trialkyl tin alkoxide produced [%] after circulating operation, T is the number of moles [mol] of trialkyl tin alkoxide produced after circulating operation, $W_3^0$ is the mass [kg] of the alkyl tin alkoxide composition introduced into the catalyst tank before circulating operation, and $S_3^0$ is the tin atom concentration (in the active component) [mol/kg] of the composition before circulating operation. $S_3^0$ was calculated from the tetraalkyldialkoxydistannoxane concentration and dialkyl tin dialkoxide concentration of the composition, as determined by $^{119}$Sn-NMR spectral analysis.]

Structural formulas of tetraalkyldialkoxydistannoxane and dialkyl tin dialkoxide in alkyl tin alkoxide composition

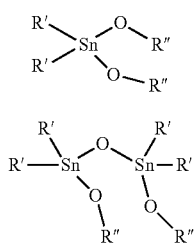

[Chemical Formula 51]

[Chemical Formula 52]

[R' represents a C1-15 alkyl group and R" represents a C1-8 alkyl group.]

Examples 274 to 293

Dialkyl tin dialkoxides and tetraalkyl dialkoxydistannoxanes with the structures listed in Table 10 were produced by the same methods as Synthesis Examples 1, 2, 4, 5, 7 and 8, and first compositions comprising the dialkyl tin dialkoxides and tetraalkyldialkoxydistannoxanes were prepared. The compositions comprising dialkyl tin dialkoxides and tetraalkyldialkoxydistannoxanes were prepared so that the molar ratios of tin atoms of the dialkyl tin dialkoxides and tetraalkyldialkoxydistannoxanes with respect to the number of moles of tin atoms (in the active component) of the composition were 65:35. Next, the trialkyl tin alkoxides having the structures listed in Table 10 were added to the compositions to prepare compositions containing trialkyl tin alkoxides. The compositions were prepared so that the number of moles of tin atoms in the trialkyl tin alkoxides with respect to the number of moles of tin atoms of the compositions containing the trialkyl tin alkoxides were 11 to 13 mol %. The compositions were used by the same method as Example 5 for test operation (circulating operation) in a continuous circulating reactor as shown in FIG. 5, confirming modification reaction during heated circulation. Approximately 60 kg of each prepared composition was introduced into the catalyst tank and circulated in a continuous circulating reactor as shown in FIG. 5 by the same method. Each composition was sampled from the catalyst tank after circulating operation and subjected to $^{119}$Sn-NMR spectral analysis. The tin atom concentration (in the active component) of the composition was calculated from the tetraalkyldialkoxydistannoxane concentration and dialkyl tin dialkoxide concentration of the composition after test operation as determined from the analysis results, and the percentage reduction from before the start of test operation was calculated. The number of moles of trialkyl tin alkoxide was also determined from the analysis results, and the amount produced with respect to the number of moles of tin atoms (in the active component) of the composition before the start of test operation was calculated. The percentage reductions in the tin atom concentration (in the active component) of the compositions and the trialkyl tin alkoxide production amounts are shown in Table 10.

TABLE 10

| | Dialkyl tin alkoxide | | Trialkyl tin alkoxide | | | Percentage reduction in tin atom concentration of alkyl tin alkoxide composition [%] *11) | Trialkyl tin alkoxide production amount [%] *12) |
|---|---|---|---|---|---|---|---|
| Example | R' (alkyl group) | OR" (alkoxy group) | R'" (alkyl group) | Concentration [tin atom mol %] | Continuous operation time [days] | | |
| 274 | Pentan-3-yl | N-Pentoxy | N-Octyl | 11 | 5 | 10.4 | 5.6 |
| 275 | 2-Butyloctyl | N-Pentoxy | N-Octyl | 12 | 5 | 3.4 | 1.7 |
| 276 | 2-Hexyldecyl | N-Pentoxy | N-Octyl | 11 | 6 | 3.5 | 1.7 |
| 277 | 3-Ethylheptyl | N-Pentoxy | N-Octyl | 13 | 5 | 5.6 | 3.0 |
| 278 | 3-Butylheptyl | N-Pentoxy | N-Octyl | 13 | 6 | 5.7 | 2.9 |
| 279 | Pentan-3-yl | N-Pentoxy | Pentan-3-yl | 13 | 6 | 10.4 | 5.6 |
| 280 | 2-Butyloctyl | N-Pentoxy | Pentan-3-yl | 12 | 5 | 3.5 | 1.7 |
| 281 | 2-Hexyldecyl | N-Pentoxy | Pentan-3-yl | 12 | 6 | 3.5 | 1.7 |
| 282 | 3-Ethylheptyl | N-Pentoxy | Pentan-3-yl | 13 | 5 | 5.6 | 2.8 |
| 283 | 3-Butylheptyl | N-Pentoxy | Pentan-3-yl | 12 | 5 | 5.7 | 2.8 |
| 284 | Pentan-3-yl | N-Pentoxy | 2-Butyloctyl | 12 | 5 | 10.4 | 5.2 |
| 285 | 2-Butyloctyl | N-Pentoxy | 2-Butyloctyl | 11 | 6 | 3.4 | 1.7 |
| 286 | 2-Hexyldecyl | N-Pentoxy | 2-Butyloctyl | 12 | 5 | 3.5 | 1.7 |
| 287 | 3-Ethylheptyl | N-Pentoxy | 2-Butyloctyl | 12 | 5 | 5.5 | 2.9 |
| 288 | 3-Butylheptyl | N-Pentoxy | 2-Butyloctyl | 13 | 6 | 5.6 | 2.9 |
| 289 | Pentan-3-yl | N-Pentoxy | 3-Ethylbutyl | 12 | 5 | 10.3 | 5.4 |
| 290 | 2-Butyloctyl | N-Pentoxy | 3-Ethylbutyl | 11 | 6 | 3.5 | 1.8 |

TABLE 10-continued

| | Dialkyl tin alkoxide | | Trialkyl tin alkoxide | | | Percentage reduction in tin atom concentration of alkyl tin alkoxide composition [%] *11) | Trialkyl tin alkoxide production amount [%] *12) |
|---|---|---|---|---|---|---|---|
| Example | R' (alkyl group) | OR" (alkoxy group) | R'" (alkyl group) | Concentration [tin atom mol %] | Continuous operation time [days] | | |
| 291 | 2-Hexyldecyl | N-Pentoxy | 3-Ethylbutyl | 12 | 5 | 3.6 | 1.9 |
| 292 | 3-Ethylheptyl | N-Pentoxy | 3-Ethylbutyl | 12 | 6 | 5.5 | 2.7 |
| 293 | 3-Butylheptyl | N-Pentoxy | 3-Ethylbutyl | 13 | 5 | 5.6 | 3.0 |

*11) The percentage reduction in the tin atom concentration (in the active component) of each alkyl tin alkoxide composition was determined by mathematical formula (8).
*12) The trialkyl tin alkoxide production amount was determined by mathematical formula (9).

[Mathematical Formula 22]

Percentage reduction in tin atom concentration (in active component)=$(S_3^0-S_3^{0'})/S_3^0 \times 100\%$  (8)

[In the formula, "percentage reduction in tin atom concentration (in active component)" is the percentage reduction [%] in the tin atom concentration (in the active component) of the composition after circulating operation, $S_3^0$ is the tin atom concentration (in the active component) [mol/kg] of the composition before circulating operation, and $S_3^{t}$ is the tin atom concentration (in the active component) [mol/kg] of the composition after circulating operation. $S_3^0$ and $S_3^{t}$ were calculated from the tetraalkyldialkoxydistannoxane concentration and dialkyl tin dialkoxide concentration of the composition, as determined by $^{119}$Sn-NMR spectral analysis.]

[Mathematical Formula 23]

Trialkyl tin alkoxide production amount=$T/(W_3^0 \times S_3^0) \times 100\%$  (9)

[In the formula, "trialkyl tin alkoxide production amount" is the amount of trialkyl tin alkoxide produced [%] after circulating operation, T is the number of moles [mol] of trialkyl tin alkoxide produced after circulating operation, $W_3^0$ is the mass [kg] of the alkyl tin alkoxide composition introduced into the catalyst tank before circulating operation, and $S_3^0$ is the tin atom concentration (in the active component) [mol/kg] of the composition before circulating operation. $S_3^0$ was calculated from the tetraalkyldialkoxydistannoxane concentration and dialkyl tin dialkoxide concentration of the composition, as determined by $^{119}$Sn-NMR spectral analysis.]

Structural formulas of tetraalkyldialkoxydistannoxane, dialkyl tin dialkoxide and trialkyl tin alkoxide in alkyl tin alkoxide composition

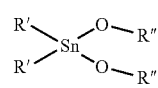

[Chemical Formula 53]

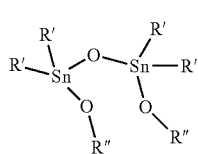

[Chemical Formula 54]

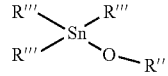

[Chemical Formula 55]

[R' and R'" each represent a C1-15 alkyl group, and R" represents a C1-8 alkyl group.]

Examples 294 to 305

Compositions comprising the dialkyl tin dialkoxides, tetraalkyl dialkoxydistannoxanes and trialkyl tin alkoxides with the structures listed in Table 11 were produced by the same methods as Synthesis Examples 3 and 6. The heating time for production of each composition was adjusted so that the trialkyl tin alkoxide concentration of the composition was as listed in Table 11. Next, the compositions comprising dialkyl tin dialkoxides, tetraalkyl dialkoxydistannoxanes and trialkyl tin alkoxides were used for test operation (circulating operation) of a continuous circulating reactor as shown in FIG. 5 by the same method as Example 5, confirming modification reaction during heated circulation. Approximately 60 kg of the alkyl tin alkoxide composition was introduced into the catalyst tank and circulated in a continuous circulating reactor as shown in FIG. 5 by the same method. Each composition was sampled from the catalyst tank after circulating operation and subjected to $^{119}$Sn-NMR spectral analysis. The tin atom concentration (in the active component) of the composition was calculated from the tetraalkyldialkoxydistannoxane concentration and dialkyl tin dialkoxide concentration of the composition after test operation as determined from the analysis results, and the percentage reduction from before the start of test operation was calculated. The number of moles of trialkyl tin alkoxide was also determined from the analysis results, and the amount produced with respect to the number of moles of tin atoms (in the active component) of the composition before the start of test operation was calculated. The percentage reductions in the tin atom concentration (in the active component) of the compositions and the trialkyl tin alkoxide production amounts are shown in Table 11.

TABLE 11

| | Dialkyl tin alkoxide | | Trialkyl tin alkoxide | | | Percentage reduction in tin atom concentration of alkyl tin alkoxide composition [%] *13) | Trialkyl tin alkoxide production amount [%] *14) |
|---|---|---|---|---|---|---|---|
| Example | R' (alkyl group) | OR" (alkoxy group) | R'" (alkyl group) | Concentration in alkyl tin alkoxide composition [tin atom mol %] | Continuous operation time [days] | | |
| 294 | Pentan-3-yl | N-Butoxy | Pentan-3-yl | 12 | 5 | 10.4 | 5.0 |
| 295 | Isopentyl | N-Butoxy | Isopentyl | 12 | 5 | 5.9 | 2.9 |
| 296 | Pentan-3-yl | N-Butoxy | Pentan-3-yl | 25 | 6 | 10.1 | 5.1 |
| 297 | Isopentyl | N-Butoxy | Isopentyl | 26 | 5 | 5.7 | 3.0 |
| 298 | Pentan-3-yl | N-Butoxy | Pentan-3-yl | 45 | 6 | 10.0 | 5.2 |
| 299 | Isopentyl | N-Butoxy | Isopentyl | 46 | 6 | 5.6 | 2.9 |
| 300 | Pentan-3-yl | 3-Methylbutyloxy | Pentan-3-yl | 12 | 5 | 10.1 | 4.9 |
| 301 | Isopentyl | 3-Methylbutyloxy | Isopentyl | 12 | 5 | 5.6 | 2.9 |
| 302 | Pentan-3-yl | 3-Methylbutyloxy | Pentan-3-yl | 25 | 6 | 10.0 | 5.3 |
| 303 | Isopentyl | 3-Methylbutyloxy | Isopentyl | 26 | 5 | 5.5 | 2.9 |
| 304 | Pentan-3-yl | 3-Methylbutyloxy | Pentan-3-yl | 46 | 6 | 9.7 | 4.8 |
| 305 | Isopentyl | 3-Methylbutyloxy | Isopentyl | 45 | 5 | 5.4 | 2.7 |

*13) The percentage reduction in the tin atom concentration (in the active component) of each alkyl tin alkoxide composition was determined by mathematical formula (8).
*14) The trialkyl tin alkoxide production amount was determined by mathematical formula (9).

[Mathematical Formula 24]

Percentage reduction in tin atom concentration (in active component)=$(S_3^0-S_3^t)/S_3^0 \times 100\%$     (8)

[In the formula, "percentage reduction in tin atom concentration (in active component)" is the percentage reduction [%] in the tin atom concentration (in the active component) of the composition after circulating operation, $S_3^0$ is the tin atom concentration (in the active component) [mol/kg] of the composition before circulating operation, and $S_3^t$ is the tin atom concentration (in the active component) [mol/kg] of the composition after circulating operation. $S_3^0$ and $S_3^t$ were calculated from the tetraalkyldialkoxydistannoxane concentration and dialkyl tin dialkoxide concentration of the composition, as determined by $^{119}$Sn-NMR spectral analysis.]

[Mathematical Formula 25]

Trialkyl tin alkoxide production amount=$T/(W_3^0 \times S_3^0) \times 100\%$     (9)

[In the formula, "trialkyl tin alkoxide production amount" is the amount of trialkyl tin alkoxide produced [%] after circulating operation, T is the number of moles [mol] of trialkyl tin alkoxide produced after circulating operation, $W_3^0$ is the mass [kg] of the alkyl tin alkoxide composition introduced into the catalyst tank before circulating operation, and $S_3^0$ is the tin atom concentration (in the active component) [mol/kg] of the composition before circulating operation. $S_3^0$ was calculated from the tetraalkyldialkoxydistannoxane concentration and dialkyl tin dialkoxide concentration of the composition, as determined by $^{119}$Sn-NMR spectral analysis.]

Structural formulas of tetraalkyldialkoxydistannoxane, dialkyl tin dialkoxide and trialkyl tin alkoxide in alkyl tin alkoxide composition

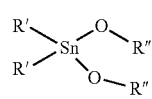

[Chemical Formula 56]

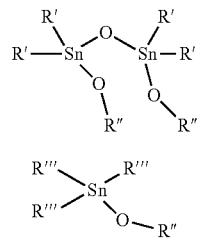

[Chemical Formula 57]

[Chemical Formula 58]

[R' and R'" each represent a C1-15 alkyl group, and R" represents a C1-8 alkyl group.]

Example 306

A continuous circulating reactor comprising a tank reactor, a tube reactor and a tower reactor such as shown in FIG. 1 was used for transesterification reaction. Approximately 20 kg of a bis(3-methylbutyl)-bis(3-methylbutoxy)tin composition produced by the method of Synthesis Example 4 (tin atom concentration (in the active component) of composition: 2.26 mol/kg) was introduced into a SUS316 catalyst tank 130 equipped with a heating jacket and a liquid conveyance pump, via a supply line 15. Next, n-propyl 2-ethylhexanoate ester (product of Wako Pure Chemical Industries) was introduced into a starting material tank 110 via a supply line 1, and 3-methyl-1-butyl alcohol (product of Kuraray Co., Ltd.) was introduced into a starting material tank 120 via a supply line 2. The tank and pipes were steam traced to maintain the flow property. To the tank reactor 140 there were conveyed n-propyl 2-ethylhexanoate ester at a flow rate of about 10 kg/hr via a transport line 3, inline mixer 141 and transport line 5, and 3-methyl-1-butyl alcohol at a flow rate of about 12 kg/hr via a transport line 4, inline mixer 141 and transport line 5. The composition was conveyed from the catalyst tank 130 to the tank reactor 140 at 1.6 kg/hr, via a transport line 14, an inline mixer 141 equipped with a heating jacket, and a transport line 5. At the inline mixer 141, the bis(3-methylbutyl)-bis(3-methylbutoxy)tin composition, n-propyl 2-ethylhexanoate ester and 3-methyl- 1-butyl alcohol were mixed and heated. The concentration of tin atoms in the mixture in the tank reactor was 1.7 mol %. The tank reactor 140 was a 15 L-volume reactor, comprising a stirrer, heating jacket and liquid conveyance pump, and the heating jacked was heated with steam to control the mixture in the reactor to about 160° C. The tube reactor 150 with an outer diameter of 200 mm and a length of 1000 mm also comprised a heating jacket, which was heated with steam at about 160° C. The n-propyl 2-ethylhexanoate ester and 3-methyl-1-butyl alcohol that had been conveyed to the tank reactor 140 were subjected to transesterification reaction using a bis(3-methylbutyl)-bis(3-methylbutoxy)tin composition as the catalyst, and then it was conveyed to a tube reactor 150 via a transport line 6 for reaction and further conveyed to a tower reactor 160 via a transport line 7 for reaction.

A SUS316 tower reactor 160 with an inner diameter of 75 mm and an effective length of 4500 mm, equipped with 30 sieve trays, was heated and thermally insulated with a heater around the entire tower reactor to prevent radiated heat loss, the heater being set to about 160° C. A liquid conveyance pump and reboiler 163 were provided at the bottom of the tower reactor 160, and the reboiler 163 was heated with steam at about 165° C.

As further transesterification reaction proceeded in the tower reactor 160, the n-propyl alcohol and 3-methyl-1-butyl alcohol produced by the reaction were separated off by distillation, and the fraction composed mainly of n-propyl alcohol was collected from a collecting line 8. The mixture containing the 3-methylbutyl 2-ethylhexanoate ester reaction product was conveyed from the tower reactor 160 through a transport line 9 to a thin-film vaporizer 170 set to a temperature of 180° C. and a pressure of about 40 kPaA, and then the low-boiling-point component including 3-methylbutyl 2-ethylhexanoate ester was conveyed through a transport line 10 to a distillation column 180 (column packed with MetalGauze CY filler, inner diameter: 83 mm, effective length: 2800 mm), and purified. Separately, the high boiling point component including the bis(3-methylbutyl)-bis(3-methylbutoxy)tin composition was conveyed to the catalyst tank 130 through a transport line 11, and then circulated to a continuous circulating reactor through the transport line 14, inline mixer 141 and transport line 5. When necessary, supply from the starting material tank and catalyst tank to the tank reactor was reduced or interrupted until the reactor interior reached a steady state. Operation was continued, and after the reactor interior reached a steady state, the mixture was sampled from the bottom of the tower reactor 160 and subjected to quantitative analysis by gas chromatography, and the yield of 3-methylbutyl 2-ethylhexanoate ester was found to be 19.7% based on n-propyl 2-ethylhexanoate ester groups. This state was continued for about 15 days, after which the mixture was again sampled from the bottom of the tower reactor 160 and subjected to quantitative analysis by gas chromatography, and the yield of 3-methylbutyl 2-ethylhexanoate ester was found to be 19.3%. It was possible to stably obtain 3-methylbutyl 2-ethylhexanoate ester at about 2.1 kg/hr from the collecting line 13 during continuous operation. The high boiling point component containing the bis(3-methylbutyl)-bis(3-methylbutoxy)tin composition in the continuous circulating reactor after continuous operation was separated using the thin-film vaporizer 170, and collected in a catalyst tank 130, and the mass was measured. A sample was taken from the catalyst tank 130 through an extraction line 16, and as a result of $^{119}$Sn-NMR spectral analysis it was confirmed that bis(3-methylbutyl)-bis(3-methylbutoxy)tin and tris(3-methylbutyl)(3-methylbutoxy)tin were present after continuous operation. Based on the analysis results, tris(3-methylbutyl)(3-methylbutoxy)tin was produced at approximately 0.27 mol after 15 days of continuous operation, an amount that was approximately 0.6% with respect to the number of moles of tin atoms (in the active component) of the composition introduced into the catalyst tank 130 before the start of continuous operation.

Example 307

A continuous circulating reactor comprising a tank reactor, a tube reactor and a tower reactor such as shown in FIG. 1 was used for transesterification reaction. Approximately 20 kg of a bis(3-methylbutyl)-bis(3-methylbutoxy)tin composition produced by the same method as Synthesis Example 4 (tin atom concentration (in the active component) of composition: 2.26 mol/kg) was introduced into a SUS316 catalyst tank 130 equipped with a heating jacket and a liquid conveyance pump, via a supply line 15. The 3-methylbutyl 2-ethylhexanoate ester obtained from Example 306 was then introduced into a starting material tank 110 through a supply line 1, and ethyl 2-methylpropanoate ester (product of Aldrich) was introduced into a starting material tank 120 through a supply line 2. The tank and pipes were steam traced to maintain the flow property. The 3-methylbutyl 2-ethylhexanoate ester was conveyed at a flow rate of about 12 kg/hr through a transport line 3, inline mixer 141 and transport line 5, and the ethyl 2-methylpropanoate ester was conveyed to a tank reactor 140 at a flow rate of about 10 kg/hr through a transport line 4, inline mixer 141 and transport line 5. Also, the catalyst tank 130 was heated by steam to maintain the flow property of the contents, and the bis(3-methylbutyl)-bis(3-methylbutoxy)tin composition in this state was conveyed at 1.2 kg/hr through a transport line 14, an inline mixer 141 equipped with a heating jacket, and the transport line 5. At the inline mixer 141, the bis(3-methylbutyl)-bis(3-methylbutoxy)tin composition, 3-methylbutyl 2-ethylhexanoate ester and ethyl 2-methylpropanoate ester were mixed and heated. The concentration of tin atoms in the mixture in the tank reactor 140 was 1.9 mol %. The tank reactor 140 was a 15 L-volume reactor, comprising a stirrer, heating jacket and liquid conveyance pump, and the heating jacket was heated with steam to control the mixture in the reactor to about 160° C. The tube reactor 150 also comprised a heating jacket, which was heated with steam at about 160° C. The 3-methylbutyl 2-ethylhexanoate ester and ethyl 2-methylpropanoate ester that had been conveyed to the tank reactor 140 were subjected to transesterification reaction using a bis(3-methylbutyl)-bis(3-methylbutoxy)tin composition as the catalyst, and then it was conveyed to the tube reactor 150 via a transport line 6 for reaction and subsequently conveyed to a tower reactor 160 via a transport line 7 for reaction.

A SUS316 tower reactor 160 with an inner diameter of 75 mm and an effective length of 4500 mm, equipped with 30 sieve trays, was heated and thermally insulated with a heater around the entire tower reactor to prevent radiated heat loss, the heater being set to about 160° C. A liquid conveyance pump and reboiler 163 were provided at the bottom of the tower reactor 160, and the reboiler 163 was heated with steam at about 165° C.

As further transesterification reaction proceeded in the tower reactor 160, the 3-methylbutyl 2-methylpropanoate ester generated by the reaction and the unreacted ethyl 2-methylpropanoate ester were separated out by distillation, and the fraction containing the ethyl 2-methylpropanoate ester and 3-methylbutyl 2-methylpropanoate ester was collected from a collecting line 8.

The mixture containing the ethyl 2-ethylhexanoate ester reaction product and unreacted 3-methylbutyl 2-ethylhexanoate ester was conveyed from the tower reactor 160 through a transport line 9 to a thin-film vaporizer 170 set to a temperature of 180° C. and a pressure of about 30 kPaA, and then the low-boiling-point component including ethyl 2-ethylhexanoate ester and 3-methylbutyl 2-ethylhexanoate ester was conveyed through a transport line 11 to a distillation column 180 (column packed with MetalGauze CY filler, inner diameter: 83 mm, effective length: 2800 mm), and purified. Separately, the high boiling point component including the bis(3-methylbutyl)-bis(3-methylbutoxy)tin composition was conveyed to the catalyst tank 130 through a transport line 11, and then circulated to a continuous circulating reactor through the transport line 14, inline mixer 141 and transport line 5. When necessary, supply from the starting material tank and catalyst tank to the tank reactor was reduced or interrupted until the reactor interior reached a steady state. Operation was continued, and after the reactor interior reached a steady state, the mixture was sampled from the bottom of the tower reactor 160 and subjected to quantitative analysis by gas chromatography, and the yield of ethyl 2-ethylhexanoate ester was found to be 39.2% (based on 3-methylbutyl 2-ethylhexanoate ester groups). This state was continued for about 15 days, after which the mixture was again sampled from the bottom of the tower reactor 160 and subjected to quantitative analysis by gas chromatography, and the yield of ethyl 2-ethylhexanoate ester was found to be 38.5%. It was possible to stably obtain ethyl 2-ethylhexanoate ester in the collected fraction at about 3.5 kg/hr from the collecting line 12 during continuous operation. The high boiling point component containing the bis(3-methylbutyl)-bis(3-methylbutoxy)tin composition in the continuous circulating reactor after continuous operation was separated using the thin-film vaporizer 170, and collected in a catalyst tank 130, and the mass was measured. A sample was taken from the catalyst tank 130 through an extraction line 16, and as a result of $^{119}$Sn-NMR spectral analysis it was confirmed that bis(3-methylbutyl)-bis(3-methylbutoxy)tin, bis(3-methylbutyl)diethoxytin, tris(3-methylbutyl)(3-methylbutoxy)tin and tris(3-methylbutyl)ethoxytin were present. Based on the analysis results, tris(3-methylbutyl)(3-methylbutoxy)tin and tris(3-methylbutyl)ethoxytin were produced at a total of 0.32 mol after 15 days of continuous operation, an amount that was approximately 0.7% with respect to the number of moles of tin atoms (in the active component) of the composition introduced into the catalyst tank 130 before the start of continuous operation.

Example 308

A continuous circulating reactor comprising a tank reactor, a tube reactor and a tower reactor such as shown in FIG. 1 was used for transesterification reaction. Approximately 20 kg of a 1,1,3,3-tetrakis(3-methylbutyl)-1,3-diethoxydistannoxane composition produced by the same method as Synthesis Example 2 (tin atom concentration (in the active component) of the composition: 3.14 mol/kg) was introduced into a SUS316 catalyst tank 130, equipped with a heating jacket and a liquid conveyance pump, through a supply line 15. The 3-methylbutyl 2-ethylhexanoate ester was then introduced into a starting material tank 110 through a supply line 1, and ethyl 2-methylpropanoate ester (product of Aldrich) was introduced into a starting material tank 120 through a supply line 2. The tank and pipes were steam traced to maintain the flow property. The 3-methylbutyl 2-ethylhexanoate ester was conveyed at a flow rate of about 12 kg/hr through a transport line 3, inline mixer 141 and transport line 5, and the ethyl 2-methylpropanoate ester was conveyed to a tank reactor 140 at a flow rate of about 10 kg/hr through a transport line 4, inline mixer 141 and transport line 5. Also, the catalyst tank 130 was heated with steam to maintain the flow property of the contents, and the 1,1,3,3-tetrakis(3-methylbutyl)-1,3-diethoxydistannoxane composition in this state was conveyed at 0.8 kg/hr through a transport line 14, the inline mixer 141 equipped with a heating jacket, and the transport line 5. At the inline mixer 141, the 1,1,3,3-tetrakis(3-methylbutyl)-1,3-diethoxydistannoxane composition, 3-methylbutyl 2-ethylhexanoate ester and ethyl 2-methylpropanoate ester were mixed and heated. The concentration of tin atoms in the mixture in the tank reactor 140 was 1.8 mol %. The tank reactor 140 was a 15 L-volume reactor, comprising a stirrer, heating jacket and liquid conveyance pump, and the heating jacket was heated with steam to control the mixture in the reactor to about 160° C. The tube reactor 150 also comprised a heating jacket, which was heated with steam at about 160° C.

The 3-methylbutyl 2-ethylhexanoate ester and ethyl 2-methylpropanoate ester conveyed to the tank reactor 140 were subjected to transesterification reaction using 1,1,3,3-tetrakis(3-methylbutyl)-1,3-diethoxydistannoxane as the catalyst, and then conveyed to the tube reactor 150 through a transport line 6 for reaction, and further conveyed to a tower reactor 160 through a transport line 7 for reaction. The SUS316 tower reactor 160 with an inner diameter of 75 mm and an effective length of 4500 mm, equipped with 30 sieve trays, was heated and thermally insulated with a heater around the entire tower reactor to prevent radiated heat loss, the heater being set to about 160° C. A liquid conveyance pump and reboiler 163 were provided at the bottom of the tower reactor 160, and the reboiler 163 was heated with steam at about 165° C. As further transesterification reaction proceeded in the tower reactor 160, the 3-methylbutyl 2-methylpropanoate ester generated by the reaction and the unreacted ethyl 2-methylpropanoate ester were separated out by distillation, and the fraction containing the ethyl 2-methylpropanoate ester and 3-methylbutyl 2-methylpropanoate ester was collected from a collecting line 8. The mixture containing the ethyl 2-ethylhexanoate ester reaction product and unreacted 3-methylbutyl 2-ethylhexanoate ester was conveyed from the tower reactor 160 through a transport line 9 to a thin-film vaporizer 170 set to a temperature of 180° C. and a pressure of about 30 kPaA, and then the low-boiling-point component including ethyl 2-ethylhexanoate ester and 3-methylbutyl 2-ethylhexanoate ester was conveyed through a transport line 10 to a distillation column 180 (column packed with MetalGauze CY filler, inner diameter: 83 mm, effective length: 2800 mm), and purified. Separately, the high boiling point component including the 1,1,3,3-tetrakis(3-methylbutyl)-1,3-diethoxydistannoxane composition was conveyed to the catalyst tank 130 through a transport line 11, and then circulated to the continuous circulating reactor through the transport line 14, inline mixer 141 and transport line 5. When necessary, supply from the starting material tank and catalyst tank to the tank reactor was reduced or interrupted until the reactor interior reached a steady state. Operation was continued, and after the reactor interior reached a steady state, the mixture was sampled from the bottom of the tower reactor 160 and subjected to quantitative analysis by gas chromatography, and the yield of ethyl 2-ethylhexanoate ester was found to be 31.5% (based on 3-methylbutyl 2-ethylhexanoate ester groups). This state was continued for about 15 days, after which the mixture was again sampled from the bottom of the tower reactor 160 and subjected to quantitative analysis by gas chromatography, and the yield of ethyl 2-ethylhexanoate ester was found to be 30.9%. It was possible to stably obtain ethyl 2-ethylhexanoate ester in the collected fraction at about 2.8 kg/hr from the collecting line 12 during continuous operation. The high boiling point component including the 1,1,3,3-tetrakis(3-methylbutyl)-1,3-diethoxydistannoxane composition in the continuous circulating reactor after continuous operation was separated using a thin-film vaporizer 170 and collected in the catalyst tank 130, and the mass was measured. A sample was taken from the extraction line 16 of the catalyst tank 130, and as a result of $^{119}$Sn-NMR spectral analysis the catalyst tank 130 was found to contain 1,1,3,3-tetrakis(3-methylbutyl)-1,3-bis(3-methylbutoxy)distannoxane, 1,1,3,3-tetrakis(3-methylbutyl)-1,3-diethoxydistannoxane, tris(3-methylbutyl)(3-methylbutoxy)tin and tris(3-methylbutyl)ethoxytin. Based on the analysis results, tris(3-methylbutyl)(3-methylbutoxy)tin and tris(3-methylbutyl)ethoxytin were produced at a total of approximately 0.57 mol after 15 days of continuous operation, an amount that was approximately 0.9% with respect to the number of moles of tin atoms (in the active component) introduced into the catalyst tank 130 before the start of continuous operation.

Example 309

A continuous circulating reactor comprising a tube reactor and a tower reactor such as shown in FIG. 2 was used for transesterification reaction. Approximately 20 kg of a 1,1,3,3-tetrakis(3-methylbutyl)-1,3-bis(3-methylbutoxy)distannoxane composition produced by the same method as Synthesis Example 5 (tin atom concentration (in the active component) of the composition: 2.76 mol/kg) was placed in a SUS316 catalyst tank 230, equipped with a heating jacket and a liquid conveyance pump, through a supply line 33. The 3-methylbutyl 2-ethylhexanoate ester was then introduced into a starting material tank 210 through a supply line 21, and ethyl 2-methylpropanoate ester was introduced into a starting material tank 220 through a supply line 22. The tank and pipes were steam traced to maintain the flow property. The 3-methylbutyl 2-ethylhexanoate ester was conveyed through a transport line 23, inline mixer 241 and transport line 25 at a flow rate of about 12 kg/hr, and the ethyl 2-methylpropanoate ester was conveyed to a tube reactor 240 equipped with a heating jacket, through a transport line 24, inline mixer 241 and transport line 25 at a flow rate of about 10 kg/hr. Also, the catalyst tank 230 was heated with steam to maintain the flow property of the contents, and the 1,1,3,3-tetrakis(3-methylbutyl)-1,3-bis(3-methylbutoxy)distannoxane composition in this state was conveyed at 0.9 kg/hr through a transport line 34, the inline mixer 241 and the transport line 25. At the inline mixer 241, the 1,1,3,3-tetrakis(3-methylbutyl)-1,3-bis(3-methylbutoxy)distannoxane composition, 3-methylbutyl 2-ethylhexanoate ester and ethyl 2-methylpropanoate ester were mixed and heated. The 3-methylbutyl 2-ethylhexanoate ester and ethyl 2-methylpropanoate ester that had been conveyed to the tube reactor 240 were subjected to transesterification reaction using 1,1,3,3-tetrakis(3-methylbutyl)-1,3-bis(3-methylbutoxy)distannoxane as the catalyst, and were conveyed to the tower reactor 250 through a transport line 26 for further reaction. The SUS316 tower reactor 250 with an inner diameter of 130 mm and an effective length of 4500 mm, equipped with 30 sieve trays, was provided with a heater, reboiler 253 and liquid conveyance pump, and the reactor interior was controlled to approximately 160° C. with the heater and reboiler 253. At the top of the tower reactor 250, the fraction containing the 3-methylbutyl 2-methylpropanoate ester produced by the transesterification reaction and the unreacted ethyl 2-methylpropanoate ester was condensed with a condenser 251, and collected by a collecting line 27 via a condensate tank 252. The mixture containing the ethyl 2-ethylhexanoate ester reaction product and unreacted 3-methylbutyl 2-ethylhexanoate ester was conveyed from the bottom of the tower reactor 250 through a transport line 28 to a thin-film vaporizer 260 set to a temperature of 180° C. and a pressure of about 30 kPaA, and then the low-boiling-point component including ethyl 2-ethylhexanoate ester and the unreacted 3-methylbutyl 2-ethylhexanoate ester was conveyed through a transport line 29 to a distillation column 270 (column packed with MetalGauze CY filler, inner diameter: 83 mm, effective length: 2800 mm), and purified. Separately, the high boiling point component including 1,1,3,3-tetrakis(3-methylbutyl)-1,3-bis(3-methylbutoxy)distannoxane composition was conveyed to the catalyst tank 230 through a transport line 30, and then circulated to the continuous circulating reactor through the transport line 34, inline mixer 241 and transport line 25. When necessary, supply from the starting material tank and catalyst tank to the tube reactor was reduced or interrupted until the reactor interior reached a steady state. Operation was continued, and after the reactor interior reached a steady state, the mixture was sampled from the bottom of the tower reactor 250 and subjected to quantitative analysis by gas chromatography, and the yield of ethyl 2-ethylhexanoate ester was found to be 35.1% (based on 3-methylbutyl 2-ethylhexanoate ester groups). This state was continued for about 15 days, after which the mixture was again sampled from the bottom of the tower reactor 250 and subjected to quantitative analysis by gas chromatography, and the yield of 2-ethyl 2-ethylhexanoate ester was found to be 34.1%.

It was possible to stably obtain ethyl 2-ethylhexanoate ester in the collected fraction at about 3.1 kg/hr from the collecting line 31 during continuous operation. The high boiling point component including the 1,1,3,3-tetrakis(3-methylbutyl)-1,3-bis(3-methylbutoxy)distannoxane composition in the continuous circulating reactor after continuous operation was separated using a thin-film vaporizer 260 and collected in the catalyst tank 230, and the mass was measured. A sample was taken from the extraction line 35 of the catalyst tank 230, and as a result of $^{119}$Sn-NMR spectral analysis the catalyst tank was found to contain 1,1,3,3-tetrakis(3-methylbutyl)-1,3-bis(3-methylbutoxy)distannoxane, 1,1,3,3-tetrakis(3-methylbutyl)-1,3-diethoxydistannoxane, tris(3-methylbutyl)(3-methylbutoxy)tin and tris(3-methylbutyl)ethoxytin. Based on the analysis results, tris(3-methylbutyl)(3-methylbutoxy)tin and tris(3-methylbutyl) ethoxytin were produced at a total of approximately 0.5 mol after 15 days of continuous operation, an amount that was approximately 0.9% with respect to the number of moles of tin atoms (in the active component) introduced into the catalyst tank 230 before the start of continuous operation.

Example 310

A continuous circulating reactor comprising a tank reactor and a tower reactor such as shown in FIG. 3 was used for transesterification reaction. The bis(3-methylbutyl)diethoxytin and 1,1,3,3-tetrakis(3-methylbutyl)-1,3-diethoxydistannoxane produced by the same methods as Synthesis Example 1 and Synthesis Example 2 were mixed to prepare an alkyl tin alkoxide composition. The composition was prepared so that the molar ratio of tin atoms of the bis(3-methylbutyl)diethoxytin and tetrakis(3-methylbutyl)diethoxydistannoxane with respect to the number of moles of tin atoms (in the active component) of the alkyl tin alkoxide composition was 65:35. The tin atom concentration (in the active component) of the alkyl tin alkoxide composition was 2.93 mol/kg as determined from the bis(3-methylbutyl)diethoxytin concentration and 1,1,3,3-tetrakis(3-methylbutyl)-1,3-diethoxydistannoxane concentration in the composition. Approximately 20 kg of the composition was introduced into a SUS316 catalyst tank 330 equipped with a heating jacket and liquid conveyance pump, through a supply line 53. The 3-methylbutyl 2-ethylhexanoate ester was then introduced into a starting material tank 310 through a supply line 41, and ethyl 2-methylpropanoate ester was introduced into a starting material tank 320 through a supply line 42. The tank and pipes were steam traced to maintain the flow property. The 3-methylbutyl 2-ethylhexanoate ester was conveyed at a flow rate of about 12 kg/hr through a transport line 43, inline mixer 341 and transport line 45, and the ethyl 2-methylpropanoate ester was conveyed to a tank reactor 340 at a flow rate of about 10 kg/hr through a transport line 44, inline mixer 341 and transport line 45. Also, the catalyst tank 330 was heated by steam to maintain the flow property of the contents, and the alkyl tin alkoxide composition in this state was conveyed at 0.9 kg/hr through a transport line 54, an inline mixer 341 equipped with a heating jacket, and the transport line 45. At the inline mixer 341, the alkyl tin alkoxide composition, 3-methylbutyl 2-ethylhexanoate ester and ethyl 2-methylpropanoate ester were mixed and heated. The tank reactor 340 was a 15 L-volume reactor, comprising a stirrer, heating jacket and liquid conveyance pump, and the heating jacket was heated with steam to control the mixture in the reactor to about 160° C. The 3-methylbutyl 2-ethylhexanoate ester and ethyl 2-methylpropanoate ester that had been conveyed to the tank reactor 340 were subjected to transesterification reaction using the alkyl tin alkoxide composition as the catalyst, and then it was conveyed to the tower reactor 350 via a transport line 46 for reaction. The SUS316 tower reactor 350 with an inner diameter of 130 mm and an effective length of 4500 mm, equipped with 25 sieve trays, was provided with a heater, reboiler 353 and liquid conveyance pump, and the reactor interior was controlled to approximately 160° C. with the heater and reboiler 353. At the top of the tower reactor 350, the fraction containing the 3-methylbutyl 2-methylpropanoate ester produced by the transesterification reaction and the unreacted ethyl 2-methylpropanoate ester was condensed with a condenser 351, and collected from a collecting line 47 via a condensate tank 352. The mixture containing the ethyl 2-ethylhexanoate ester reaction product and unreacted 3-methylbutyl 2-ethylhexanoate ester was conveyed from the bottom of the tower reactor 350 through a transport line 48 to a thin-film vaporizer 360 set to a temperature of 180° C. and a pressure of about 30 kPaA, and then the low-boiling-point component including ethyl 2-ethylhexanoate ester and 3-methylbutyl 2-ethylhexanoate ester was conveyed through a transport line 49 to a distillation column 370 (column packed with MetalGauze CY filler, inner diameter: 83 mm, effective length: 2800 mm), and purified. Separately, the high boiling point component including the alkyl tin alkoxide composition comprising the bis(3-methylbutyl)diethoxytin and 1,1,3,3-tetrakis(3-methylbutyl)-1,3-diethoxydistannoxane was conveyed to the catalyst tank 330 through a transport line 50, and then circulated to the continuous circulating reactor through the transport line 54, inline mixer 341 and transport line 45. When necessary, supply from the starting material tank and catalyst tank to the tank reactor was reduced or interrupted until the reactor interior reached a steady state. Operation was continued, and after the reactor interior reached a steady state, the mixture was sampled from the bottom of the tower reactor 350 and subjected to quantitative analysis by gas chromatography, and the yield of ethyl 2-ethylhexanoate ester was found to be 36.5% (based on 3-methylbutyl 2-ethylhexanoate ester groups). This state was continued for about 15 days, after which the mixture was again sampled from the bottom of the tower reactor 350 and subjected to quantitative analysis by gas chromatography, and the yield of 2-methylpropyl 2-ethylhexanoate ester was found to be 35.7%.

It was possible to stably obtain ethyl 2-ethylhexanoate ester in the collected fraction at about 3.3 kg/hr from the collecting line 51 during continuous operation. The high boiling point component including the alkyl tin alkoxide composition in the continuous circulating reactor after continuous operation was separated using the thin-film vaporizer 360 and collected in the catalyst tank 330, and the mass was measured. A sample was taken from the extraction line 55 of the catalyst tank 330, and as a result of $^{119}$Sn-NMR spectral analysis the catalyst tank 330 was found to contain bis(3-methylbutyl)-bis(3-methylbutoxy)tin, bis(3-methylbutyl)diethoxytin, 1,1,3,3-tetrakis(3-methylbutyl)-1,3-bis(3-methylbutoxy)distannoxane, 1,1,3,3-tetrakis(3-methylbutyl)-1,3-diethoxydistannoxane, tris(3-methylbutyl)(3-methylbutoxy)tin and tris(3-methylbutyl)ethoxytin. Based on the analysis results, tris(3-methylbutyl)(3-methylbutoxy)tin and tris(3-methylbutyl)ethoxytin were produced at a total of approximately 0.47 mol after 15 days of continuous operation, an amount that was approximately 0.8% with respect to the number of moles of tin atoms (in the active component) of the alkyl tin alkoxide composition introduced into the catalyst tank 330 before the start of continuous operation.

Examples 311 to 332

The dialkyl tin dialkoxide compositions listed in Table 12, obtained by the same methods as Synthesis Examples 1, 4 and 7, were used for transesterification reaction with a continuous circulating reactor by the same method as Example 306. The carboxylic acid esters and alcohols used as starting materials for transesterification reaction, listed in Table 12, were each introduced into a starting material tank and conveyed to a tank reactor, and transesterification reaction was carried out with a dialkyl tin dialkoxide as the catalyst. The flow rate of the dialkyl tin dialkoxide composition conveyed from the catalyst tank was adjusted so that the concentration of tin atoms in the reaction mixture in the tank reactor was 1.5 to 2.5 mol %, and transesterification reaction was carried out at the temperatures listed in Table 12. Table 12 shows the reaction yields (initial yields) immediately after reaching a steady state and the reaction yields and trialkyl tin alkoxide production amounts (production amounts with respect to the number of moles of tin atoms (in the active component) introduced into the catalyst tank before continuous operation), after 15 days of continuous operation.

TABLE 12

| Example | Alkyl tin alkoxide R' (alkyl group) | Alkyl tin alkoxide OR" (alkoxy group) | Starting materials for transesterification reaction Carboxylic acid ester | Starting materials for transesterification reaction Alcohol | Temperature [° C.] | Initial yield [mol %] | Yield [mol %] (after 15 days of continuous operation) | Trialkyl tin alkoxide production amount [mol %] *15) (after 15 days of continuous operation) |
|---|---|---|---|---|---|---|---|---|
| 311 | Pentan-3-yl | Ethoxy | Methyl 2-Ethylhexanoate ester | Ethanol | 150 | 17.2 | 16.1 | 2.9 |
| 312 | Nonan-3-yl | Ethoxy | Methyl 2-Ethylhexanoate ester | Ethanol | 150 | 17.8 | 16.5 | 3.2 |
| 313 | 2-methylbutyl | Ethoxy | Methyl 2-Ethylhexanoate ester | Ethanol | 150 | 30.6 | 29.4 | 1.8 |
| 314 | 3-Ethylpentyl | Ethoxy | Methyl 2-Ethylhexanoate ester | Ethanol | 150 | 39.1 | 37.8 | 1.4 |
| 315 | 3-Butylheptyl | Ethoxy | Methyl 2-Ethylhexanoate ester | Ethanol | 150 | 38.3 | 36.9 | 1.6 |
| 316 | Pentan-3-yl | 2-Methylpropyloxy | Propyl 2-Ethylhexanoate ester | 2-methyl-1-propanol | 170 | 17.6 | 16.4 | 3.0 |
| 317 | Nonan-3-yl | 2-Methylpropyloxy | Propyl 2-Ethylhexanoate ester | 2-methyl-1-propanol | 170 | 18.0 | 16.7 | 3.3 |
| 318 | 2-Butyloctyl | 2-Methylpropyloxy | Propyl 2-Ethylhexanoate ester | 2-methyl-1-propanol | 170 | 38.5 | 37.2 | 1.6 |
| 319 | Isopentyl | 2-Methylpropyloxy | Propyl 2-Ethylhexanoate ester | 2-methyl-1-propanol | 170 | 28.9 | 27.8 | 1.9 |
| 320 | 3-Ethylpentyl | 2-Methylpropyloxy | Propyl 2-Ethylhexanoate ester | 2-methyl-1-propanol | 170 | 43.0 | 41.5 | 1.6 |
| 321 | 3-Butylheptyl | 2-Methylpropyloxy | Propyl 2-Ethylhexanoate ester | 2-methyl-1-propanol | 170 | 41.4 | 40.3 | 1.2 |
| 322 | Pentan-3-yl | 3-Methylbutyloxy | Propyl 2-Ethylhexanoate ester | 3-methyl-1-butanol | 170 | 17.6 | 16.4 | 3.1 |
| 323 | Nonan-3-yl | 3-Methylbutyloxy | Propyl 2-Ethylhexanoate ester | 3-methyl-1-butanol | 170 | 18.0 | 17.0 | 2.4 |
| 324 | 2-Butyloctyl | 3-Methylbutyloxy | Propyl 2-Ethylhexanoate ester | 3-methyl-1-butanol | 170 | 37.2 | 35.5 | 1.9 |
| 325 | 3-Ethylpentyl | 3-Methylbutyloxy | Propyl 2-Ethylhexanoate ester | 3-methyl-1-butanol | 170 | 39.9 | 38.4 | 1.6 |
| 326 | 3-Butylheptyl | 3-Methylbutyloxy | Propyl 2-Ethylhexanoate ester | 3-methyl-1-butanol | 170 | 39.2 | 38.1 | 1.3 |
| 327 | Pentan-3-yl | 2-Ethylbutyloxy | Propyl 2-Ethylhexanoate ester | 2-Ethyl-1-butanol | 170 | 18.8 | 17.7 | 2.6 |
| 328 | Nonan-3-yl | 2-Ethylbutyloxy | Propyl 2-Ethylhexanoate ester | 2-Ethyl-1-butanol | 170 | 18.2 | 17.1 | 2.6 |
| 329 | 2-Butyloctyl | 2-Ethylbutyloxy | Propyl 2-Ethylhexanoate ester | 2-Ethyl-1-butanol | 170 | 35.3 | 33.9 | 1.8 |
| 330 | Isopentyl | 2-Ethylbutyloxy | Propyl 2-Ethylhexanoate ester | 2-Ethyl-1-butanol | 170 | 26.5 | 25.6 | 1.4 |
| 331 | 3-Ethylpentyl | 2-Ethylbutyloxy | Propyl 2-Ethylhexanoate ester | 2-Ethyl-1-butanol | 170 | 38.3 | 37.0 | 1.5 |
| 332 | 3-Butylheptyl | 2-Ethylbutyloxy | Propyl 2-Ethylhexanoate ester | 2-Ethyl-1-butanol | 170 | 37.0 | 36.0 | 1.2 |

*15) The trialkyl tin alkoxide production amount was calculated by the following mathematical formula (10).

[Mathematical Formula 26]

$$\text{Trialkyl tin alkoxide production amount} = T/(W_1^0 \times S_1^0) \times 100\% \quad (10)$$

[In the formula, "trialkyl tin alkoxide production amount" is the amount of trialkyl tin alkoxide produced [%] after continuous operation, T is the number of moles [mol] of trialkyl tin alkoxide produced after continuous operation, $W_1^0$ is the mass [kg] of the dialkyl tin dialkoxide composition introduced into the catalyst tank before continuous operation, and $S_1^0$ is the tin atom concentration (in the active component) [mol/kg] of the composition before continuous operation. The number of moles of trialkyl tin alkoxide T is calculated from the trialkyl tin alkoxide concentration determined by $^{119}$Sn-NMR spectral analysis of the composition collected after continuous operation and the mass of the dialkyl tin dialkoxide composition collected after continuous operation.]

Structural formula of dialkyl tin dialkoxide

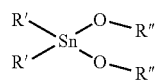

[Chemical Formula 59]

[R' represents a C1-15 alkyl group and R" represents a C1-8 alkyl group.]

Examples 333 to 351

The dialkyl tin dialkoxide compositions listed in Table 13, obtained by the same methods as Synthesis Examples 1, 4 and 7, were used for transesterification reaction with a continuous circulating reactor by the same method as Example 307. The flow rate of the dialkyl tin dialkoxide composition conveyed from the catalyst tank was adjusted so that the concentration of tin atoms in the reaction mixture in the tank reactor was 1.5 to 2.5 mol %, and transesterification reaction was carried out at the temperatures listed in Table 13, using the dialkyl tin dialkoxide as catalyst. Table 13 shows the reaction yields (initial yields) immediately after reaching a steady state and the reaction yields and trialkyl tin alkoxide production amounts (production amounts with respect to the number of moles of tin atoms (in the active component) introduced into the catalyst tank before continuous operation), after 15 days of continuous operation.

TABLE 13

| Example | Alkyl tin alkoxide R' (alkyl group) | OR" (alkoxy group) | Temperature [° C.] | Initial yield [mol %] | Yield [mol %] (after 15 days of continuous operation) | Trialkyl tin alkoxide production amount [mol %] *16) (after 15 days of continuous operation) |
|---|---|---|---|---|---|---|
| 333 | 3-Butylheptyl | 3-Methylbutyloxy | 170 | 33.1 | 32.2 | 1.2 |
| 334 | 3-Butylheptyl | Ethoxy | 150 | 32.4 | 31.2 | 1.6 |
| 335 | 3-Butylheptyl | N-Butoxy | 160 | 30.0 | 29.0 | 1.5 |
| 336 | 2-Butyloctyl | N-Pentoxy | 170 | 32.5 | 31.4 | 1.5 |
| 337 | 3-Ethylpentyl | 3-Methylbutyloxy | 170 | 33.8 | 32.5 | 1.7 |
| 338 | 3-Ethylpentyl | N-Pentoxy | 170 | 36.4 | 35.1 | 1.5 |
| 339 | Isopentyl | N-Pentoxy | 170 | 24.4 | 23.3 | 2.0 |
| 340 | Nonan-3-yl | N-Pentoxy | 170 | 15.4 | 14.1 | 3.7 |
| 341 | Isopentyl | N-Butoxy | 160 | 21.6 | 21.0 | 1.3 |
| 342 | 3-Ethylpentyl | Ethoxy | 150 | 33.1 | 32.0 | 1.5 |
| 343 | Pentan-3-yl | N-Butoxy | 160 | 15.0 | 13.9 | 3.3 |
| 344 | Pentan-3-yl | N-Pentoxy | 170 | 14.7 | 13.6 | 3.1 |
| 345 | 2-Butyloctyl | 3-Methylbutyloxy | 170 | 31.4 | 30.1 | 1.9 |
| 346 | Pentan-3-yl | 3-Methylbutyloxy | 170 | 14.9 | 13.8 | 3.1 |
| 347 | Pentan-3-yl | Ethoxy | 150 | 14.6 | 13.6 | 2.9 |
| 348 | Isopentyl | 3-Methylbutyloxy | 170 | 22.8 | 22.2 | 1.1 |
| 349 | 3-Ethylpentyl | N-Butoxy | 160 | 30.9 | 29.6 | 2.0 |
| 350 | Nonan-3-yl | 3-Methylbutyloxy | 170 | 15.2 | 14.4 | 2.6 |
| 351 | Nonan-3-yl | N-Butoxy | 160 | 15.2 | 14.1 | 3.1 |

*16) The trialkyl tin alkoxide production amount was calculated by the following mathematical formula (10).

[Mathematical Formula 27]

$$\text{Trialkyl tin alkoxide production amount} = T/(W_1^0 \times S_1^0) \times 100\% \quad (10)$$

[In the formula, "trialkyl tin alkoxide production amount" is the amount of trialkyl tin alkoxide produced [%] after continuous operation, T is the total number of moles of trialkyl tin alkoxide [mol] produced after continuous operation, $W_1^0$ is the mass [kg] of the composition introduced into the catalyst tank before continuous operation, and $S_1^0$ is the tin atom concentration (in the active component) [mol/kg] of the composition before continuous operation. The total number of moles of trialkyl tin alkoxide T is calculated from each trialkyl tin alkoxide concentration determined by $^{119}$Sn-NMR spectral analysis and the mass of the dialkyl tin dialkoxide composition collected after continuous operation.]

Structural formula of dialkyl tin dialkoxide

[Chemical Formula 60]

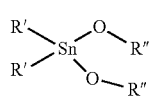

[R' represents a C1-15 alkyl group and R" represents a C1-8 alkyl group.]

Examples 352 to 374

The compositions listed in Table 14, obtained by the same methods as Synthesis Examples 2, 5 and 8, were used as catalysts for transesterification reaction with a continuous circulating reactor by the same method as Example 309. The flow rate of each tetraalkyldialkoxydistannoxane composition liquid conveyed from the catalyst tank was adjusted so that the concentration of tin atoms in the reaction mixture in the tube reactor was 1.5 to 2.5 mol %, and transesterification reaction was carried out at the temperatures listed in Table 14. Table 14 shows the reaction yields (initial yields) immediately after reaching a steady state and the reaction yields and trialkyl tin alkoxide production amounts (production amounts with respect to the number of moles of tin atoms (in the active component) introduced into the catalyst tank before continuous operation), after 15 days of continuous operation.

TABLE 14

| Example | Alkyl tin alkoxide R' (alkyl group) | OR" (alkoxy group) | Temperature [° C.] | Initial yield [mol %] | Yield [mol %] (after 15 days of continuous operation) | Trialkyl tin alkoxide production amount [mol %] *17) (after 15 days of continuous operation) |
|---|---|---|---|---|---|---|
| 352 | 3-Ethylpentyl | 3-Methylbutyloxy | 170 | 36.5 | 35.1 | 1.7 |
| 353 | Pentan-3-yl | Ethoxy | 160 | 16.6 | 15.4 | 3.2 |
| 354 | 3-Butylheptyl | Ethoxy | 160 | 34.8 | 33.8 | 1.3 |
| 355 | Nonan-3-yl | 3-Methylbutyloxy | 170 | 17.7 | 16.6 | 2.9 |

TABLE 14-continued

| | Alkyl tin alkoxide | | Temperature [°C.] | Initial yield [mol %] | Yield [mol %] (after 15 days of continuous operation) | Trialkyl tin alkoxide production amount [mol %] *17) (after 15 days of continuous operation) |
|---|---|---|---|---|---|---|
| Example | R' (alkyl group) | OR" (alkoxy group) | | | | |
| 356 | 2-Butyloctyl | 2-Methylpropyloxy | 160 | 35.7 | 34.4 | 1.6 |
| 357 | 3-Butylheptyl | 2-Methylpropyloxy | 160 | 37.1 | 35.8 | 1.7 |
| 358 | 2-Butyloctyl | Ethoxy | 160 | 33.3 | 31.9 | 1.9 |
| 359 | Nonan-3-yl | N-Butoxy | 160 | 17.6 | 16.3 | 3.1 |
| 360 | Pentan-3-yl | 3-Methylbutyloxy | 170 | 17.2 | 16.3 | 2.4 |
| 361 | 2-Butyloctyl | N-Butoxy | 160 | 34.0 | 32.6 | 1.8 |
| 362 | 3-Ethylpentyl | Ethoxy | 160 | 35.9 | 34.8 | 1.4 |
| 363 | 3-Ethylpentyl | 2-Methylpropyloxy | 160 | 39.2 | 38.1 | 1.3 |
| 364 | Nonan-3-yl | Ethoxy | 160 | 17.2 | 15.9 | 3.2 |
| 365 | Isopentyl | 2-Methylpropyloxy | 160 | 27.1 | 26.2 | 1.5 |
| 366 | Pentan-3-yl | N-Butoxy | 160 | 17.4 | 16.2 | 3.0 |
| 367 | Isopentyl | N-Butoxy | 160 | 25.4 | 24.4 | 1.7 |
| 368 | Nonan-3-yl | 2-Methylpropyloxy | 160 | 17.5 | 16.4 | 2.8 |
| 369 | 2-Butyloctyl | 3-Methylbutyloxy | 170 | 33.8 | 32.8 | 1.4 |
| 370 | 3-Ethylpentyl | N-Butoxy | 160 | 36.6 | 35.6 | 1.2 |
| 371 | Isopentyl | 3-Methylbutyloxy | 170 | 25.5 | 24.4 | 1.9 |
| 372 | 3-Butylheptyl | N-Butoxy | 160 | 35.5 | 34.3 | 1.5 |
| 373 | Pentan-3-yl | 2-Methylpropyloxy | 160 | 16.9 | 15.9 | 2.7 |
| 374 | 3-Butylheptyl | 3-Methylbutyloxy | 170 | 35.4 | 34.1 | 1.8 |

*17) The trialkyl tin alkoxide production amount was determined by mathematical formula (11).

[Mathematical Formula 28]

Trialkyl tin alkoxide production amount=$T/(W_2^0 \times S_2^0) \times 100\%$      (11)

[In the formula, "trialkyl tin alkoxide production amount" is the amount of trialkyl tin alkoxide produced [%] after continuous operation, T is the total number of moles of trialkyl tin alkoxide [mol] produced after continuous operation, $W_2^0$ is the mass [kg] of the tetraalkyldialkoxydistannoxane composition introduced into the catalyst tank before continuous operation, and $S_2^0$ is the tin atom concentration (in the active component) [mol/kg] of the composition before continuous operation. The total number of moles of trialkyl tin alkoxide T is calculated from each trialkyl tin alkoxide concentration determined by $^{119}$Sn-NMR spectral analysis and the mass of the tetraalkyldialkoxydistannoxane composition collected after continuous operation.]

Structural formula of
tetraalkyldialkoxydistannoxane

[Chemical Formula 61]

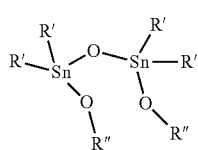

[R' represents a C1-15 alkyl group and R" represents a C1-8 alkyl group.]

Examples 375 to 396

Compositions comprising the dialkyl tin dialkoxides and tetraalkyldialkoxydistannoxanes listed in Table 15, produced by the same methods as in Synthesis Examples 1, 2, 4, 5, 7 and 8, were prepared and the compositions were used as catalysts for transesterification reaction in a continuous circulating reactor by the same method as Example 310. Each composition was prepared so that the molar ratio of tin atoms of the dialkyl tin dialkoxide and tetraalkyldialkoxydistannoxane with respect to the number of moles of tin atoms (in the active component) in the composition used for the transesterification reaction was 65:35, and was introduced into a catalyst tank. The flow rate of the composition conveyed from the catalyst tank was adjusted so that the concentration of tin atoms in the tank reactor was 1.5 to 2.0 mol %, and transesterification reaction was carried out at the temperatures listed in Table 15. Table 15 shows the reaction yields (initial yields) immediately after reaching a steady state and the reaction yields and trialkyl tin alkoxide production amounts (production amounts with respect to the number of moles of tin atoms (in the active component) introduced into the catalyst tank before continuous operation), after 15 days of continuous operation.

TABLE 15

| Example | Alkyl tin alkoxide R' (alkyl group) | OR" (alkoxy group) | Temperature [° C.] | Initial yield [mol %] | Yield [mol %] (after 15 days of continuous operation) | Trialkyl tin alkoxide production amount [mol %] *18) (after 15 days of continuous operation) |
|---|---|---|---|---|---|---|
| 375 | 3-Butylheptyl | 2-Methylpropyloxy | 170 | 43.2 | 42.1 | 1.2 |
| 376 | 3-Ethylpentyl | 2-Methylpropyloxy | 170 | 43.6 | 42.5 | 1.2 |
| 377 | Nonan-3-yl | 3-Methylbutyloxy | 170 | 18.0 | 17.0 | 2.5 |
| 378 | 2-methylbutyl | 2-Methylpropyloxy | 170 | 34.9 | 33.5 | 1.8 |
| 379 | 3-Butylheptyl | N-Butoxy | 160 | 39.1 | 37.8 | 1.6 |
| 380 | Pentan-3-yl | Ethoxy | 160 | 18.0 | 16.9 | 2.6 |
| 381 | Pentan-3-yl | 2-Methylpropyloxy | 170 | 17.2 | 16.0 | 3.0 |
| 382 | Nonan-3-yl | 2-Methylpropyloxy | 170 | 17.8 | 16.7 | 2.7 |
| 383 | 3-Butylheptyl | Ethoxy | 160 | 40.9 | 39.4 | 1.7 |
| 384 | Nonan-3-yl | N-Butoxy | 160 | 18.6 | 17.4 | 2.9 |
| 385 | 2-Butyloctyl | Ethoxy | 160 | 39.0 | 38.0 | 1.1 |
| 386 | Pentan-3-yl | 3-Methylbutyloxy | 170 | 17.6 | 16.4 | 3.1 |
| 387 | 2-Ethylbutyl | 3-Methylbutyloxy | 170 | 41.4 | 40.3 | 1.1 |
| 388 | Isopentyl | 3-Methylbutyloxy | 170 | 28.8 | 27.8 | 1.5 |
| 389 | 3-Ethylpentyl | N-Butoxy | 160 | 40.0 | 38.3 | 1.8 |
| 390 | Nonan-3-yl | Ethoxy | 160 | 18.2 | 17.1 | 2.8 |
| 391 | 3-Ethylpentyl | Ethoxy | 160 | 41.3 | 39.5 | 1.9 |
| 392 | Isopentyl | 2-Methylpropyloxy | 170 | 30.1 | 28.8 | 1.9 |
| 393 | Pentan-3-yl | N-Butoxy | 160 | 18.7 | 17.5 | 3.0 |
| 394 | 2-Butyloctyl | N-Butoxy | 160 | 36.9 | 35.7 | 1.5 |
| 395 | Isopentyl | N-Butoxy | 160 | 27.1 | 26.2 | 1.4 |
| 396 | 3-Ethylpentyl | 3-Methylbutyloxy | 170 | 41.9 | 40.2 | 1.8 |

*18) The trialkyl tin alkoxide production amount was determined by mathematical formula (12).

[Mathematical Formula 29]

Trialkyl tin alkoxide production amount = $T/(W_3^0 \times S_3^0) \times 100\%$ (12)

[In the formula, "trialkyl tin alkoxide production amount" is the amount of trialkyl tin alkoxide produced [%] after continuous operation, T is the total number of moles of trialkyl tin alkoxide [mol] produced after continuous operation, $W_3^0$ is the mass [kg] of the alkyl tin alkoxide composition introduced into the catalyst tank before continuous operation, and $S_3^0$ is the tin atom concentration (in the active component) [mol/kg] of the composition before continuous operation (calculated from the tetraalkyldialkoxydistannoxane concentration and dialkyl tin dialkoxide concentration in the composition). The total number of moles of trialkyl tin alkoxide T is calculated from each trialkyl tin alkoxide concentration determined by $^{119}$Sn-NMR spectral analysis and the mass of the alkyl tin alkoxide composition collected after continuous operation.]

Structural formulas of dialkyl tin dialkoxide and tetraalkyldialkoxydistannoxane in alkyl tin alkoxide composition

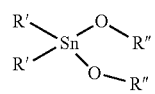

[Chemical Formula 62]

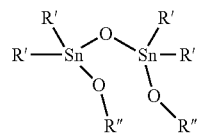

[Chemical Formula 63]

[R' represents a C1-15 alkyl group and R" represents a C1-8 alkyl group.]

Examples 397 to 416

The compositions comprising the dialkyl tin dialkoxides, tetraalkyldialkoxydistannoxanes and trialkyl tin alkoxides listed in Table 16, produced by the same methods as in Synthesis Examples 3 and 6, were used as catalysts for transesterification reaction in a continuous circulating reactor by the same method as Example 310. The tin atom concentration (in the active component) of the composition was calculated from the tetraalkyldialkoxydistannoxane concentration and dialkyl tin dialkoxide concentration of the composition. The flow rate of the composition conveyed from the catalyst tank was adjusted so that the concentration of tin atoms in the tank reactor was 1.5 to 2.0 mol %, and transesterification reaction was carried out at the temperatures listed in Table 16. Table 16 shows the reaction yields (initial yields) immediately after reaching a steady state and the reaction yields and trialkyl tin alkoxide production amounts (production amounts with respect to the number of moles of tin atoms (in the active component) introduced into the catalyst tank before continuous operation), after 15 days of continuous operation.

TABLE 16

| Example | Alkyl tin alkoxide R' (alkyl group) | OR" (alkoxy group) | Temperature [° C.] | Initial yield [mol %] | Yield [mol %] (after 15 days of continuous operation) | Trialkyl tin alkoxide production amount [mol %] *19) (after 15 days of continuous operation) |
|---|---|---|---|---|---|---|
| 397 | 3-Butylheptyl | 3-Methylbutyloxy | 170 | 44.2 | 42.7 | 1.6 |
| 398 | Isopentyl | 3-Methylbutyloxy | 170 | 30.6 | 29.6 | 1.4 |
| 399 | 2-Ethylbutyl | N-Butoxy | 160 | 41.4 | 39.8 | 1.7 |
| 400 | Nonan-3-yl | N-Pentoxy | 160 | 18.5 | 17.0 | 3.7 |
| 401 | 2-Butyloctyl | 3-Methylbutyloxy | 170 | 42.2 | 40.8 | 1.4 |
| 402 | Isopentyl | N-Butoxy | 160 | 28.8 | 27.8 | 1.4 |
| 403 | Pentan-3-yl | N-Butoxy | 160 | 19.4 | 18.0 | 3.3 |
| 404 | 2-methylbutyl | N-Butoxy | 160 | 33.5 | 32.5 | 1.3 |
| 405 | 2-Ethylbutyl | 3-Methylbutyloxy | 170 | 44.5 | 42.5 | 1.9 |
| 406 | Isopentyl | N-Pentoxy | 160 | 31.6 | 30.8 | 1.1 |
| 407 | Pentan-3-yl | 3-Methylbutyloxy | 170 | 17.6 | 16.5 | 2.7 |
| 408 | Nonan-3-yl | 3-Methylbutyloxy | 170 | 18.0 | 16.8 | 2.8 |
| 409 | 3-Butylheptyl | N-Pentoxy | 160 | 46.2 | 45.1 | 1.1 |
| 410 | 3-Ethylpentyl | N-Butoxy | 160 | 42.1 | 40.4 | 1.8 |
| 411 | Pentan-3-yl | N-Pentoxy | 160 | 18.1 | 16.7 | 3.6 |
| 412 | 2-Ethylbutyl | N-Pentoxy | 160 | 46.7 | 45.3 | 1.2 |
| 413 | Nonan-3-yl | N-Butoxy | 160 | 19.1 | 17.8 | 3.1 |
| 414 | 3-Ethylpentyl | 3-Methylbutyloxy | 170 | 45.2 | 43.9 | 1.3 |
| 415 | 3-Butylheptyl | N-Butoxy | 160 | 41.8 | 40.2 | 1.7 |
| 416 | 2-Butyloctyl | N-Pentoxy | 160 | 43.9 | 42.4 | 1.5 |

*19) The trialkyl tin alkoxide production amount was determined by mathematical formula (12).

[Mathematical Formula 30]

Trialkyl tin alkoxide production amount=$T/(W_3^0 \times S_3^0) \times 100\%$ (12)

[In the formula, "trialkyl tin alkoxide production amount" is the amount of trialkyl tin alkoxide produced [%] after continuous operation, T is the total number of moles of trialkyl tin alkoxide [mol] produced after continuous operation, $W_3^0$ is the mass [kg] of the composition introduced into the catalyst tank before continuous operation, and $S_3^0$ is the tin atom concentration (in the active component) [mol/kg] of the composition before continuous operation (calculated from the tetraalkyldialkoxydistannoxane concentration and dialkyl tin dialkoxide concentration in the composition). The total number of moles of trialkyl tin alkoxide T is calculated from each trialkyl tin alkoxide concentration determined by $^{119}$Sn-NMR spectral analysis and the mass of the alkyl tin alkoxide composition collected after continuous operation.]

Structural formulas of dialkyl tin dialkoxide, tetraalkyldialkoxydistannoxane and trialkyl tin alkoxide in alkyl tin alkoxide composition

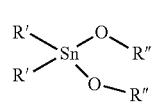

[Chemical Formula 64]

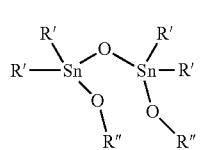

[Chemical Formula 65]

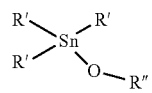

[Chemical Formula 66]

[R' represents a C1-15 alkyl group and R" represents a C1-8 alkyl group.]

Example 417

A continuous circulating reactor comprising a tank reactor and tower reactor as shown in FIG. 4 was used for carbonic acid ester synthesis. Approximately 30 kg of a 1,1,3,3-tetrakis(3-methylbutyl)-1,3-bis(3-methylbutoxy)distannoxane composition obtained by the method of Synthesis Example 5 (tin atom concentration (in the active component) of the composition: 2.76 mol/kg) was placed in a SUS316 catalyst tank 660, equipped with a heating jacket and a liquid conveyance pump, through a supply line 78. The catalyst tank 660 was heated with steam to maintain the flow property of the contents. The tank and pipes were also steam traced to maintain the flow property as well. A SUS316 tower reactor 620 with an inner diameter of 76 mm and an effective length of 4500 mm, equipped with 30 sieve trays, was heated and thermally insulated with a heater around the entire tower reactor to prevent radiated heat loss, the heater being set to about 150° C. A liquid conveyance pump and reboiler 622 were provided at the bottom of the tower reactor 620, and the reboiler 622 was heated with steam at 155° C. to 160° C.

The 1,1,3,3-tetrakis(3-methylbutyl)-1,3-bis(3-methylbutoxy)distannoxane composition was conveyed to the tower reactor 620 from the catalyst tank 660 through a transport line 74, an inline mixer 621 equipped with a heating jacket and a transport line 65 at 6.5 kg/hr, and the 3-methyl-1-butyl alcohol purified at the distillation column 610 was conveyed at 25 kg/hr through a transport line 63 and transport line 64. The fraction containing water and 3-methyl-1-butyl alcohol was conveyed from the top of the tower reactor 620 to a distillation column 610 (distillation column packed with MetalGauze CY filler, inner diameter: 83 mm, effective length: 3000 mm) through a transport line 66 at about 22 kg/hr, and the water was separated out. The water was collected from a collecting line 62 via a condenser 611. An alkyl tin alkoxide composition containing bis(3-methylbutyl)-bis(3-methylbutoxy)tin and 1,1,3,3-tetrakis(3-methylbutyl)-1,3-bis(3-methylbutoxy)-distannoxane was obtained from the bottom of the tower reactor, and as a result of analyzing the alkyl tin alkoxide composition sampled from a transport line 67, the bis(3-methylbutyl)-bis(3-methylbutoxy)tin content was found to be 89 mass %.

Step (1) (Obtaining Carbonic Acid Ester from Reaction Between Alkyl Tin Alkoxide Composition and Carbon Dioxide)

The alkyl tin alkoxide composition containing bis(3-methylbutyl)-bis(3-methylbutoxy)tin and 1,1,3,3-tetrakis(3-methylbutyl)-1,3-bis(3-methylbutoxy)distannoxane was conveyed to an autoclave 630 having a 15 L volume and equipped with a heating jacket and liquid conveyance pump, through the transport line 67, and reacted with carbon dioxide supplied through a supply line 68, at a temperature of 120° C. and a pressure of 4 MPa-G. The reaction mixture sampled from the autoclave 630 was transparent, and as a result of analyzing the reaction mixture, the bis(3-methylbutyl) carbonate yield was found to be 43% based on bis(3-methylbutyl)-bis(3-methylbutoxy)tin.

Step (2) (Separating Carbonic Acid Ester from Reaction Mixture to Obtain a Residual Solution)

A thin-film vaporizer 640 and thin-film vaporizer 650 equipped with a heating jacket and a liquid conveyance pump for conveying the high boiling point component were heated using steam at 150° C. The reaction mixture obtained from step (1) was conveyed through a transport line 71 to the thin-film vaporizer 640 set to a pressure of 26 kPaA, and first the excess carbon dioxide was separated out and collected from a purge line 70. The reaction mixture was conveyed through the transport line 71 to the thin-film vaporizer 650 that had been set to a pressure of 1.3 kPaA, the fraction containing bis(3-methylbutyl) carbonate was collected through a transport line 72, and the bis(3-methylbutyl) carbonate was further purified by a distillation column 670 (distillation column packed with MetalGauze CY filler, inner diameter: 83 mm, effective length: 2800 mm). Separately, the residual solution containing 1,1,3,3-tetrakis(3-methylbutyl)-1,3-bis(3-methylbutoxy)distannoxane was collected from a transport line 73 and conveyed to the catalyst tank 660.

Step (3) (Obtaining Alkyl Tin Alkoxide from Reaction Between Residual Solution and Alcohol)

The residual solution obtained from step (2) was again conveyed to the tower reactor 620 through the transport line 74, inline mixer 621 and transport line 65, and reacted with the 3-methyl-1-butyl alcohol conveyed through the transport line 63 and transport line 64. The fraction containing water and 3-methyl-1-butyl alcohol was conveyed from the top of the tower reactor 620 to a distillation column 610 through a transport line 66 at about 22 kg/hr, and the water was separated out. The water was collected from a collecting line 62 via a condenser 611. An alkyl tin alkoxide composition containing bis(3-methylbutyl)-bis(3-methylbutoxy)tin and 1,1,3,3-tetrakis(3-methylbutyl)-1,3-bis(3-methylbutoxy)distannoxane was obtained from the bottom of the tower reactor 620, and as a result of analyzing the alkyl tin alkoxide composition sampled from a transport line 67, the bis(3-methylbutyl)-bis(3-methylbutoxy)tin content was found to be 90 mass %.

When necessary, supply from the transport line 63 and transport line 65 to the tower reactor 620 was reduced or interrupted until the reactor interior reached a steady state. Steps (1), (2) and (3) above were carried out continuously, and after the reactor reached a steady state, the steps were further continued for 15 days. As a result of subsequently analyzing the reaction mixture sampled from the autoclave 630, the bis(3-methylbutyl) carbonate yield was found to be 42% based on bis(3-methylbutyl)-bis(3-methylbutoxy)tin. During the continuous operation period, bis(3-methylbutyl) carbonate was stably obtained from the collecting line 76 at about 1.2 kg/hr. The high boiling point component including the alkyl tin alkoxide composition in the continuous circulating reactor after continuous operation was separated using the thin-film vaporizer 640 and thin-film vaporizer 650, and collected in the catalyst tank 660.

Next, the alkyl tin alkoxide composition in the catalyst tank 660 was sampled from an extraction line 79, and as a result of $^{119}$Sn-NMR spectral analysis it was confirmed that bis(3-methylbutyl)-bis(3-methylbutoxy)tin, 1,1,3,3-tetrakis(3-methylbutyl)-1,3-bis(3-methylbutoxy)distannoxane and tris(3-methylbutyl)(3-methylbutoxy)tin were present after the continuous operation. Based on the analysis results, tris(3-methylbutyl)(3-methylbutoxy)tin was produced at approximately 0.37 mol after 15 days of continuous operation, an amount that was approximately 0.9 mol % with respect to the number of moles of tin atoms (in the active component) of the composition introduced into the catalyst tank before continuous operation.

Example 418

A continuous circulating reactor comprising a tank reactor and tower reactor as shown in FIG. 5 was used for carbonic acid ester synthesis. Approximately 35 kg of a 1,1,3,3-tetrakis(3-methylbutyl)-1,3-dibutoxydistannoxane composition obtained by the same method as Synthesis Example 2 (tin atom concentration (in the active component) of the composition: 2.88 mol/kg) was introduced into a SUS316 catalyst tank 770, equipped with a heating jacket and a liquid conveyance pump, through a supply line 107. The catalyst tank 770 was heated with steam to maintain the flow property of the contents. The tank and pipes were also steam traced to maintain the flow property as well.

The tank reactor 710 was a 10 L-volume reactor equipped with a heating jacket and liquid conveyance pump, and the 1,1,3,3-tetrakis(3-methylbutyl)-1,3-dibutoxydistannoxane composition was conveyed to the tank reactor 710 through the transport line 109, inline mixer 711 and transport line 110 at 6.5 kg/hr, and n-butyl alcohol purified at the distillation column 720 was conveyed at 25 kg/hr through a transport line 93, collecting tank 724, transport line 94, inline mixer 711 and transport line 110. The reaction mixture was conveyed from the bottom of the tank reactor 710 through a transport line 95 to a tower reactor 730 and further reacted while simultaneously distilling off the fraction containing water and n-butyl alcohol at the top of the tower reactor. The fraction was conveyed through the transport line 96 to a distillation column 720 (distillation column packed with MetalGauze CY filler, inner diameter: 83 mm, effective length: 3000 mm) at approximately 23 kg/hr, and the water and n-butyl alcohol were separated out. The water was collected from a collecting line 92 via a condenser 721. An alkyl tin alkoxide composition containing bis(3-methylbutyl)dibutoxytin and 1,1,3,3-tetrakis(3-methylbutyl)-1,3-dibutoxydistannoxane was obtained from the bottom of the tower reactor 730, and as a result of analyzing the alkyl tin alkoxide composition sampled from a transport line 97, the bis(3-methylbutyl)dibutoxytin content was found to be 83 mass %.

Step (1) (Obtaining Carbonic Acid Ester from Reaction Between Alkyl Tin Alkoxide Composition and Carbon Dioxide)

The alkyl tin alkoxide composition containing bis(3-methylbutyl)dibutoxytin and 1,1,3,3-tetrakis(3-methylbutyl)-1,3-dibutoxydistannoxane was conveyed to an autoclave 740 having a 15 L volume and equipped with a heating jacket and liquid conveyance pump, through the transport line 97, and reacted with carbon dioxide supplied through a supply line 98, at a temperature of 140° C. and a pressure of 4 MPa-G. The reaction mixture sampled from the autoclave 740 was transparent, and as a result of analyzing the reaction mixture, the obtained dibutyl carbonate yield was found to be 43% based on bis(3-methylbutyl)dibutoxytin.

Step (2) (Separating Carbonic Acid Ester from Reaction Mixture to Obtain a Residual Solution)

Thin-film vaporizers 750 and 760 equipped with a heating jacket and a liquid conveyance pump for conveying the high boiling point component were heated using steam at 140° C. The reaction mixture obtained from step (1) was conveyed through a transport line 99 to the thin-film vaporizer 750 set to a pressure of 26 kPaA, and first the excess carbon dioxide was separated out and collected from a purge line 100. The reaction mixture was conveyed through the transport line 101 to the thin-film vaporizer 760 that had been set to a pressure of 2.6 kPaA, the fraction containing dibutyl carbonate was collected through a transport line 102, and the dibutyl carbonate was further purified by a distillation column 780 (distillation column packed with MetalGauze CY filler, inner diameter: 83 mm, effective length: 2800 mm). Separately, the residual solution containing 1,1,3,3-tetrakis(3-methylbutyl)-1,3-dibutoxydistannoxane was collected from a transport line 103 and conveyed to the catalyst tank 770.

Step (3) (Obtaining Alkyl Tin Alkoxide from Reaction Between Residual Solution and Alcohol)

The residual solution obtained from step (2) was again conveyed to the tank reactor 710 through the transport line 109 at 6.5 kg/hr, and reacted with n-butyl alcohol being conveyed through the transport line 94, inline mixer 711 and transport line 110.

The reaction mixture was conveyed from the bottom of the tank reactor 710 through a transport line 95 to a tower reactor 730 and further reacted while simultaneously distilling off the fraction containing water and n-butyl alcohol at the top of the tower reactor. The fraction was conveyed to the distillation column 720 through the transport line 96 at approximately 23 kg/hr, and the water and n-butyl alcohol were separated. The water was collected from a collecting line 92 via a condenser 721. An alkyl tin alkoxide composition containing bis(3-methylbutyl)dibutoxy-tin and 1,1,3,3-tetrakis(3-methylbutyl)-1,3-dibutoxydistannoxane was obtained from the bottom of the tower reactor 730, and as a result of analyzing the alkyl tin alkoxide composition sampled from a transport line 97, the bis(3-methylbutyl)dibutoxy-tin content was found to be 82 mass %. When necessary, supply from the transport line 109 and transport line 94 to the tank reactor 710 was reduced or interrupted until the reactor interior reached a steady state. Steps (1), (2) and (3) above were carried out continuously, and after the reactor reached a steady state, the steps were further continued for 15 days. As a result of subsequently analyzing the reaction mixture sampled from the autoclave 740, the obtained dibutyl carbonate yield was found to be 42% based on bis(3-methylbutyl)dibutoxytin. Dibutyl carbonate was stably obtained from the collecting line 105 at approximately 1 kg/hr. The high boiling point component including the alkyl tin alkoxide composition in the continuous circulating reactor after continuous operation was separated using the thin-film vaporizer 750 and thin-film vaporizer 760, and collected in the catalyst tank 770. Next, the alkyl tin alkoxide composition in the catalyst tank 770 was sampled from an extraction line 108, and as a result of $^{119}$Sn-NMR spectral analysis it was confirmed that bis(3-methylbutyl)dibutoxy-tin, 1,1,3,3-tetrakis(3-methylbutyl)-1,3-dibutoxydistannoxane and tris(3-methylbutyl)butoxytin were present after the continuous operation. Based on the analysis results, tris(3-methylbutyl)butoxytin was produced at approximately 0.91 mol after 15 days of continuous operation, an amount that was approximately 0.9 mol % with respect to the number of moles of tin atoms (in the active component) of the composition introduced into the catalyst tank before continuous operation.

Examples 419 to 429

Carbonic acid ester synthesis was carried out with a continuous circulating reactor by the same method as Example 417. The tetraalkyldialkoxydistannoxanes listed in Table 17 were obtained by the same methods as in Synthesis Examples 2, 5 and 8, and approximately 30 kg of each was introduced into a catalyst tank. An alcohol with the same alkoxy group as the alkoxy group of the alkyl tin alkoxide was used for carbonic acid ester synthesis with an autoclave 630, under the temperature and pressure conditions listed in Table 17. Steps (1), (2) and (3) were continuously carried out for 15 days in the same manner as Example 417. Table 17 shows the carbonic acid ester initial yields immediately after reaching a steady state and the carbonic acid ester yields and trialkyl tin alkoxide production amounts (production amounts with respect to the number of moles of tin atoms (in the active component) of the composition introduced into the catalyst tank before continuous operation), after 15 days of continuous operation.

TABLE 17

| Example | Alkyl tin alkoxide R' (alkyl group) | Alkyl tin alkoxide R" (alkoxy group) | Temperature [° C.] | $CO_2$ pressure [MPa-G] | Carbonic acid ester initial yield [mol %] | Carbonic acid ester yield [mol %] (after 15 days of continuous operation) | Trialkyl tin alkoxide production amount [mol %] *20) (after 15 days of continuous operation) |
|---|---|---|---|---|---|---|---|
| 419 | 3-Butylnonyl | N-Butoxy | 125 | 4.0 | 40.6 | 40.2 | 0.8 |
| 420 | Isopentyl | N-Pentoxy | 110 | 4.5 | 40.9 | 40.2 | 0.8 |
| 421 | 3-Ethylheptyl | 2-Methylpropyloxy | 110 | 4.5 | 41.6 | 41.2 | 0.7 |
| 422 | 2-Butyloctyl | N-Pentoxy | 125 | 4.0 | 42.1 | 41.8 | 0.5 |
| 423 | Isopropyl | 2-Methylpropyloxy | 110 | 4.5 | 42.9 | 42.2 | 1.5 |
| 424 | 3-Ethylheptyl | N-Butoxy | 125 | 4.0 | 42.6 | 42.1 | 0.9 |
| 425 | Isopropyl | N-Butoxy | 125 | 4.0 | 44.8 | 44.0 | 1.7 |
| 426 | Nonan-3-yl | N-Pentoxy | 110 | 4.5 | 42.6 | 42.1 | 1.5 |
| 427 | 3-Butylnonyl | N-Pentoxy | 110 | 4.5 | 40.1 | 39.7 | 0.7 |
| 428 | 2-Ethylhexyl | 2-Methylpropyloxy | 110 | 4.5 | 40.6 | 40.3 | 0.5 |
| 429 | Nonan-3-yl | N-Pentoxy | 125 | 4.0 | 44.1 | 43.4 | 1.5 |

*20) The trialkyl tin alkoxide production amount was determined by mathematical formula (11).

[Mathematical Formula 31]

Trialkyl tin alkoxide production amount$=T/(W_2^0 \times S_2^0) \times 100\%$    (11)

[In the formula, "trialkyl tin alkoxide production amount" is the amount of trialkyl tin alkoxide produced [%] after continuous operation, T is the number of moles [mol] of trialkyl tin alkoxide produced after continuous operation, $W_2^0$ is the mass [kg] of the tetraalkyldialkoxydistannoxane composition introduced into the catalyst tank before continuous operation, and $S_2^0$ is the tin atom concentration (in the active component) [mol/kg] of the composition before continuous operation. The number of moles of trialkyl tin alkoxide T is calculated from the trialkyl tin alkoxide concentration determined by $^{119}$Sn-NMR spectral analysis and the mass of the composition collected after continuous operation.]

Structural formula of tetraalkyldialkoxydistannoxane

[Chemical Formula 67]

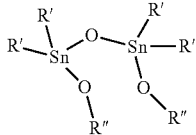

[R' represents a C1-15 alkyl group and R" represents a C1-8 alkyl group.]

Examples 430 to 440

Carbonic acid ester synthesis was carried out with a continuous circulating reactor by the same method as Example 418. The alkyl tin alkoxides listed in Table 18 were obtained by the same methods as Synthesis Examples 2, 5 and 8 and introduced into a catalyst tank. An alcohol with the same alkoxy group as the alkoxy group of the alkyl tin alkoxide was used for carbonic acid ester synthesis under the temperature and pressure conditions listed in Table 18, and steps (1), (2) and (3) were carried out continuously for 15 days in the same manner as Example 418. Table 18 shows the carbonic acid ester initial yields immediately after reaching a steady state and the carbonic acid ester yields and trialkyl tin alkoxide production amounts (production amounts with respect to the number of moles of tin atoms (in the active component) of the composition introduced into the catalyst tank before continuous operation), after 15 days of continuous operation.

TABLE 18

| Example | Alkyl tin alkoxide R' (alkyl group) | Alkyl tin alkoxide R" (alkoxy group) | Temperature [° C.] | $CO_2$ pressure [MPa-G] | Carbonic acid ester initial yield [mol %] | Carbonic acid ester yield [mol %] (after 15 days of continuous operation) | Trialkyl tin alkoxide production amount [mol %] *21) (after 15 days of continuous operation) |
|---|---|---|---|---|---|---|---|
| 430 | 3-Ethylheptyl | 2-Ethylbutyloxy | 105 | 4.5 | 40.1 | 39.5 | 1.3 |
| 431 | Isopropyl | 3-Methylbutyloxy | 120 | 4.0 | 44.3 | 43.3 | 1.8 |
| 432 | 3-Butylnonyl | 2-Ethylbutyloxy | 120 | 4.0 | 41.1 | 40.5 | 1.1 |
| 433 | Isopropyl | 2-Ethylbutyloxy | 105 | 4.5 | 37.8 | 37.0 | 2.1 |
| 434 | 3-Butylnonyl | 2-Ethylbutyloxy | 105 | 4.5 | 38.5 | 38.0 | 1.2 |
| 435 | 2-Butyloctyl | 2-Ethylbutyloxy | 105 | 4.5 | 40.2 | 39.7 | 0.8 |
| 436 | 3-Ethylheptyl | 3-Methylbutyloxy | 120 | 4.0 | 42.5 | 42.0 | 1.1 |
| 437 | Nonan-3-yl | 3-Methylbutyloxy | 120 | 4.0 | 44.2 | 43.3 | 1.9 |

TABLE 18-continued

| | Alkyl tin alkoxide | | Tempera-ture [° C.] | $CO_2$ pressure [MPa-G] | Carbonic acid ester initial yield [mol %] | Carbonic acid ester yield [mol %] (after 15 days of continuous operation) | Trialkyl tin alkoxide production amount [mol %] *21) (after 15 days of continuous operation) |
|---|---|---|---|---|---|---|---|
| Example | R' (alkyl group) | R" (alkoxy group) | | | | | |
| 438 | Nonan-3-yl | 2-Ethylbutyloxy | 105 | 4.5 | 37.4 | 36.6 | 2.0 |
| 439 | 2-Ethylhexyl | 3-Methylbutyloxy | 120 | 4.0 | 40.6 | 40.2 | 0.7 |
| 440 | Isopentyl | 3-Methylbutyloxy | 120 | 4.0 | 42.1 | 41.5 | 1.2 |

*21) The trialkyl tin alkoxide production amount was determined by mathematical formula (11).

[Mathematical Formula 32]

Trialkyl tin alkoxide production amount=$T/(W_2^0 \times S_2^0) \times 100\%$ (11)

[In the formula, "trialkyl tin alkoxide production amount" is the amount of trialkyl tin alkoxide produced [%] after continuous operation, T is the number of moles [mol] of trialkyl tin alkoxide produced after continuous operation, $W_2^0$ is the mass [kg] of the tetraalkyldialkoxydistannoxane composition introduced into the catalyst tank before continuous operation, and $S_2^0$ is the tin atom concentration (in the active component) [mol/kg] of the composition before continuous operation. The number of moles of trialkyl tin alkoxide T is calculated from the trialkyl tin alkoxide concentration determined by $^{119}$Sn-NMR spectral analysis and the mass of the composition collected after continuous operation.]

Structural formula of tetraalkyldialkoxydistannoxane

[Chemical Formula 68]

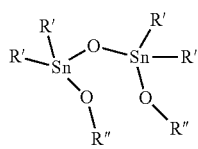

[R' represents a C1-15 alkyl group and R" represents a C1-8 alkyl group.]

Examples 441 to 467

Compositions comprising mixtures of the dialkyl tin dialkoxides, tetraalkyldialkoxydistannoxanes and trialkyl tin alkoxides with the structures listed in Table 19 were synthesized by the same methods as Synthesis Examples 3 and 6. The alkyl tin alkoxide compositions were used for carbonic acid ester synthesis with a continuous circulating reactor by the same method as Example 417. An alcohol with the same alkoxy group as the alkoxy group of the alkyl tin alkoxide was used for carbonic acid ester synthesis with an autoclave 630, under the temperature and pressure conditions listed in Table 19. Steps (1), (2) and (3) were continuously carried out for 15 days in the same manner as Example 417. The carbonic acid ester yields after continuous operation are shown in Table 19.

TABLE 19

| | Dialkyl tin alkoxide | | Initial concentration of trialkyl tin alkoxide [tin atom mol %] | Tempera-ture [° C.] | $CO_2$ pressure [MPa-G] | Carbonic acid ester yield [mol %] | Carbonic acid ester yield [mol %] (after 15 days of continuous operation) |
|---|---|---|---|---|---|---|---|
| Example | R' (alkyl group) | OR" (alkoxy group) | | | | | |
| 441 | Nonan-3-yl | N-Butoxy | 12 | 125 | 4.0 | 38.8 | 38.3 |
| 442 | Isobutyl | N-Butoxy | 13 | 125 | 4.0 | 36.8 | 36.5 |
| 443 | 3-Ethylheptyl | N-Butoxy | 11 | 125 | 4.0 | 37.9 | 37.5 |
| 444 | Nonan-3-yl | 3-Methylbutyloxy | 11 | 120 | 4.0 | 39.3 | 38.6 |
| 445 | Isobutyl | 3-Methylbutyloxy | 11 | 120 | 4.0 | 36.4 | 35.7 |
| 446 | 3-Ethylheptyl | 3-Methylbutyloxy | 12 | 120 | 4.0 | 37.4 | 37.0 |
| 447 | Nonan-3-yl | 2-Ethylbutyloxy | 11 | 105 | 4.5 | 33.2 | 32.6 |
| 448 | Isobutyl | 2-Ethylbutyloxy | 12 | 105 | 4.5 | 34.0 | 33.5 |
| 449 | 3-Ethylheptyl | 2-Ethylbutyloxy | 12 | 105 | 4.5 | 35.3 | 34.8 |
| 450 | Nonan-3-yl | N-Butoxy | 26 | 125 | 4.0 | 32.6 | 32.2 |
| 451 | Isobutyl | N-Butoxy | 25 | 125 | 4.0 | 30.7 | 30.4 |
| 452 | 3-Ethylheptyl | N-Butoxy | 25 | 125 | 4.0 | 31.9 | 31.6 |
| 453 | Nonan-3-yl | 3-Methylbutyloxy | 26 | 120 | 4.0 | 32.7 | 32.1 |
| 454 | Isobutyl | 3-Methylbutyloxy | 25 | 120 | 4.0 | 30.6 | 30.1 |
| 455 | 3-Ethylheptyl | 3-Methylbutyloxy | 25 | 120 | 4.0 | 31.9 | 31.5 |
| 456 | Nonan-3-yl | 2-Ethylbutyloxy | 25 | 105 | 4.5 | 28.0 | 27.5 |

TABLE 19-continued

| | Dialkyl tin alkoxide | | Initial concentration of trialkyl tin alkoxide | Tempera- | $CO_2$ | Carbonic acid ester | Carbonic acid ester yield [mol %] (after 15 days of |
|---|---|---|---|---|---|---|---|
| Example | R' (alkyl group) | OR" (alkoxy group) | [tin atom mol %] | ture [° C.] | pressure [MPa-G] | yield [mol %] | continuous operation) |
| 457 | Isobutyl | 2-Ethylbutyloxy | 26 | 105 | 4.5 | 28.6 | 28.2 |
| 458 | 3-Ethylheptyl | 2-Ethylbutyloxy | 26 | 105 | 4.5 | 29.7 | 29.3 |
| 459 | Nonan-3-yl | N-Butoxy | 44 | 125 | 4.0 | 24.7 | 24.4 |
| 460 | Isobutyl | N-Butoxy | 45 | 125 | 4.0 | 22.6 | 22.3 |
| 461 | 3-Ethylheptyl | N-Butoxy | 44 | 125 | 4.0 | 23.8 | 23.6 |
| 462 | Nonan-3-yl | 3-Methylbutyloxy | 45 | 120 | 4.0 | 24.3 | 23.9 |
| 463 | Isobutyl | 3-Methylbutyloxy | 46 | 120 | 4.0 | 21.9 | 21.7 |
| 464 | 3-Ethylheptyl | 3-Methylbutyloxy | 45 | 120 | 4.0 | 23.4 | 23.1 |
| 465 | Nonan-3-yl | 2-Ethylbutyloxy | 46 | 105 | 4.5 | 20.2 | 19.8 |
| 466 | Isobutyl | 2-Ethylbutyloxy | 45 | 105 | 4.5 | 21.3 | 21.0 |
| 467 | 3-Ethylheptyl | 2-Ethylbutyloxy | 45 | 105 | 4.5 | 22.1 | 21.8 |

Structural formulas of dialkyl tin dialkoxide, tetraalkyldialkoxydistannoxane and trialkyl tin alkoxide in alkyl tin alkoxide composition

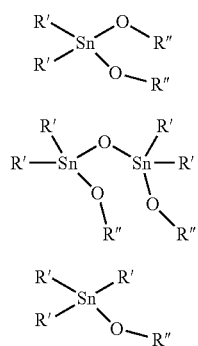

[Chemical Formula 69]

[Chemical Formula 70]

[Chemical Formula 71]

[R' represents a C1-15 alkyl group and R" represents a C1-8 alkyl group.]

Comparative Examples 1 to 8

Tetraalkyldialkoxydistannoxane compositions with the structures listed in Table 20 were synthesized by the same method as Synthesis Example 9. The compositions were then used by the same method as Example 3 for test operation in a continuous circulating reactor. Each composition was introduced into the catalyst tank of the continuous circulating reactor shown in FIG. 3, and circulating operation was carried out. Table 20 shows the percentage reductions in tin atom concentration in the compositions after circulating operation and production amounts of trialkyl tin alkoxide (production amounts with respect to tin atom concentrations of tetraalkyldialkoxydistannoxane compositions introduced into the catalyst tank before continuous operation).

TABLE 20

| | Alkyl tin alkoxide | | Continuous time [days] | Percentage reduction in tin atom concentration of tetraalkyldialkoxy-distannoxane composition solution [%] | Trialkyl tin alkoxide production amount [mol %] |
|---|---|---|---|---|---|
| Comparative Example | R' (alkyl group) | OR" (alkoxy group) | | | |
| 1 | Methyl | Ethoxy | 2 | 95 | 47 |
| 2 | Phenyl | Ethoxy | 3 | 82 | 41 |
| 3 | N-butyl | Ethoxy | 5 | 35 | 19 |
| 4 | N-Octyl | Ethoxy | 5 | 23 | 12 |
| 5 | Methyl | 2-Methylpropyloxy | 3 | 90 | 44 |
| 6 | Phenyl | 2-Methylpropyloxy | 3 | 76 | 39 |
| 7 | N-Butyl | 2-Methylpropyloxy | 5 | 30 | 15 |
| 8 | N-Octyl | 2-Methylpropyloxy | 5 | 21 | 10 |

Structural formula of
tetraalkyldialkoxydistannoxane

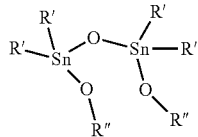

[Chemical Formula 72]

[R' represents a C1-8 alkyl or phenyl group, and R" represents a C1-8 alkyl group.]

Comparative Examples 9 to 16

Dialkyl tin dialkoxide compositions having the structures listed in Table 21 were synthesized by the same method as Synthesis Example 10. The dialkyl tin dialkoxide compositions were then used for test operation of a continuous circulating reactor by the same method as Example 5. Each dialkyl tin dialkoxide composition was introduced into the catalyst tank of the continuous circulating reactor shown in FIG. 5 for circulating operation. Table 21 shows the percentage reductions in tin atom concentrations in the compositions after circulating operation and the trialkyl tin alkoxide production amounts (production amounts with respect to tin atom concentrations of the dialkyl tin dialkoxide compositions introduced into the catalyst tank before continuous operation).

TABLE 21

| Comparative Example | Alkyl tin alkoxide | | Continuous time [days] | Percentage reduction in dialkyl tin dialkoxide concentration [%] | Trialkyl tin alkoxide production amount [mol %] |
|---|---|---|---|---|---|
| | R' (alkyl group) | OR" (alkoxy group) | | | |
| 9 | Methyl | Ethoxy | 4 | 78 | 41 |
| 10 | Phenyl | Ethoxy | 4 | 68 | 36 |
| 11 | N-butyl | Ethoxy | 5 | 27 | 14 |
| 12 | N-Octyl | Ethoxy | 5 | 17 | 8.8 |
| 13 | Methyl | 2-Methylpropyloxy | 4 | 68 | 37 |
| 14 | Phenyl | 2-Methylpropyloxy | 4 | 57 | 31 |
| 15 | N-Butyl | 2-Methylpropyloxy | 5 | 23 | 12 |
| 16 | N-Octyl | 2-Methylpropyloxy | 5 | 15 | 7.5 |

Structural formula of dialkyl tin dialkoxide

[Chemical Formula 73]

[R' represents a C1-8 alkyl or phenyl group, and R" represents a C1-8 alkyl group.]

Comparative Examples 17 to 24

Dialkyl tin dialkoxide compositions having the structures listed in Table 22 were synthesized by the same method as Synthesis Example 10. Each dialkyl tin dialkoxide composition was used for transesterification reaction by the same method as Example 306, with adjustment so that the tin atom concentration of the reaction mixture was approximately 1.5 to 2.5 mol %. Table 22 shows the initial yields and reaction yields after continuous operation for the transesterification reaction and the production amounts of trialkyl tin alkoxide (production amounts with respect to the number of moles of tin atoms of the dialkyl tin dialkoxide compositions introduced into the catalyst tank before continuous operation).

TABLE 22

| Comparative Example | Alkyl tin alkoxide | | Starting materials for transesterification reaction | | Temperature [° C.] | Initial yield [mol %] | Yield [mol %] (15 days of continuous operation) | Trialkyl tin alkoxide production amount [mol %] (after 15 days of continuous operation) |
|---|---|---|---|---|---|---|---|---|
| | R' (alkyl group) | OR" (alkoxy group) | Carboxylic acid ester | Alcohol | | | | |
| 17 | Methyl | Ethoxy | Methyl 2-Ethylhexanoate ester | Ethanol | 150 | 20 | 7 | 32 |
| 18 | Phenyl | Ethoxy | Methyl 2-Ethylhexanoate ester | Ethanol | 150 | 20 | 8 | 29 |

TABLE 22-continued

| Comparative Example | Alkyl tin alkoxide | | Starting materials for transesterification reaction | | Temperature [° C.] | Initial yield [mol %] | Yield [mol %] (15 days of continuous operation) | Trialkyl tin alkoxide production amount [mol %] (after 15 days of continuous operation) |
|---|---|---|---|---|---|---|---|---|
| | R' (alkyl group) | OR" (alkoxy group) | Carboxylic acid ester | Alcohol | | | | |
| 19 | N-Butyl | Ethoxy | Methyl 2-Ethylhexanoate ester | Ethanol | 150 | 17 | 13 | 11 |
| 20 | N-Octyl | Ethoxy | Methyl 2-Ethylhexanoate ester | Ethanol | 150 | 21 | 18 | 10 |
| 21 | Methyl | 2-Methylpropyloxy | Propyl 2-Ethylhexanoate ester | 2-Methyl-1-propanol | 160 | 18 | 8 | 28 |
| 22 | Phenyl | 2-Methylpropyloxy | Propyl 2-Ethylhexanoate ester | 2-Methyl-1-propanol | 160 | 14 | 7 | 23 |
| 23 | N-Butyl | 2-Methylpropyloxy | Propyl 2-Ethylhexanoate ester | 2-Methyl-1-propanol | 160 | 20 | 16 | 9 |
| 24 | N-Octyl | 2-Methylpropyloxy | Propyl 2-Ethylhexanoate ester | 2-Methyl-1-propanol | 160 | 19 | 16 | 9 |

Structural formula of dialkyl tin dialkoxide

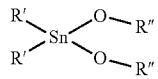

[Chemical Formula 74]

[R' represents a C1-8 alkyl or phenyl group, and R" represents a C1-8 alkyl group.]

Comparative Examples 25 to 32

Tetraalkyldialkoxydistannoxane compositions with the structures listed in Table 23 were synthesized by the same method as Synthesis Example 9. Each tetraalkyldialkoxydistannoxane composition was then used for transesterification reaction by the same method as Example 309, with adjustment so that the tin atom concentration in the reaction mixture was approximately 1.5 to 2.5 mol %. Table 23 shows the initial yields and reaction yields after continuous operation for the transesterification reaction, and the trialkyl tin alkoxide production amounts (the production amounts with respect to the number of moles of tin atoms of the tetraalkyldialkoxydistannoxane compositions introduced into the catalyst tank before continuous operation).

Structural formula of tetraalkyldialkoxydistannoxane

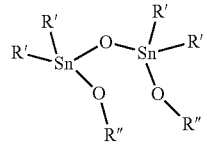

[Chemical Formula 75]

[R' represents a C1-8 alkyl or phenyl group, and R" represents a C1-8 alkyl group.]

Comparative Examples 33 to 41

Tetraalkyldialkoxydistannoxane compositions with the structures listed in Table 24 were synthesized by the same method as Synthesis Example 9. Each tetraalkyldialkoxydistannoxane composition was then used for carbonic acid ester synthesis by the same method as Example 417. Table 24 shows the carbonic acid ester initial yields and the carbonic acid ester yields after continuous operation, and the trialkyl tin alkoxide production amounts (the production amounts with respect to the number of moles of tin atoms of the tetraalkyldialkoxydistannoxane compositions introduced into the catalyst tank of the continuous circulating reactor).

TABLE 23

| Comparative Example | Alkyl tin alkoxide | | Temperature [° C.] | Initial yield [mol %] | Yield [mol %] (15 days of continuous operation) | Trialkyl tin alkoxide production amount [mol %] (after 15 days of continuous operation) |
|---|---|---|---|---|---|---|
| | R' (alkyl group) | OR" (alkoxy group) | | | | |
| 25 | Methyl | Ethoxy | 150 | 16 | 3 | 40 |
| 26 | Phenyl | Ethoxy | 150 | 19 | 6 | 33 |
| 27 | N-Butyl | Ethoxy | 150 | 18 | 13 | 14 |
| 28 | N-Octyl | Ethoxy | 150 | 14 | 12 | 10 |
| 29 | Methyl | 2-Methylpropyloxy | 160 | 20 | 5 | 37 |
| 30 | Phenyl | 2-Methylpropyloxy | 160 | 15 | 5 | 31 |
| 31 | N-Butyl | 2-Methylpropyloxy | 160 | 21 | 16 | 13 |
| 32 | N-Octyl | 2-Methylpropyloxy | 160 | 21 | 18 | 10 |

TABLE 24

| Comparative Example | Alkyl tin alkoxide | | Temperature [°C.] | CO$_2$ pressure [MPa-G] | Carbonic acid ester initial yield [mol %] | Carbonic acid ester yield [mol %] (after 15 days of continuous operation) | Trialkyl tin alkoxide production amount [mol %] (after 15 days of continuous operation) |
|---|---|---|---|---|---|---|---|
| | R' (alkyl group) | OR" (alkoxy group) | | | | | |
| 33 | Methyl | N-Butoxy | 120 | 4.5 | 47.6 | 35.5 | 13.6 |
| 34 | Phenyl | N-Butoxy | 120 | 4.5 | 32.8 | 25.6 | 12.0 |
| 35 | N-Butyl | N-Butoxy | 120 | 4.5 | 48.2 | 41.3 | 7.5 |
| 36 | N-Octyl | N-Butoxy | 120 | 4.5 | 48.4 | 42.7 | 6.3 |
| 37 | Methyl | 2-Methylpropyloxy | 120 | 4.5 | 47.3 | 34.7 | 13.8 |
| 38 | Phenyl | 2-Methylpropyloxy | 120 | 4.5 | 31.8 | 24.5 | 12.2 |
| 39 | N-Butyl | 2-Methylpropyloxy | 120 | 4.5 | 47.6 | 41.7 | 6.5 |
| 40 | N-Octyl | 2-Methylpropyloxy | 120 | 4.5 | 47.9 | 42.1 | 6.2 |
| 41 | N-Octyl | 2-Methylpropyloxy | 110 | 4.5 | 42.5 | 37.4 | 6.1 |

Structural formula of tetraalkyldialkoxydistannoxane

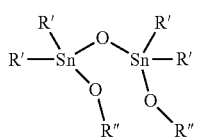

[Chemical Formula 76]

[R' represents a C1-8 alkyl or phenyl group, and R" represents a C1-8 alkyl group.]

Second Embodiment

A second embodiment of the invention, as a preferred embodiment, will now be described.

The alkyl tin compound of this embodiment is an alkyl tin compound for ester synthesis, wherein the cyclic group-substituted alkyl group is an alkyl group having a cyclic group selected from among alicyclic hydrocarbon groups and aromatic hydrocarbon groups bonded to at least one carbon atom among the first to third carbon atoms counting from the tin atom, and the valency of the tin atom is tetravalent. The alkyl tin compound functions as a catalyst during ester synthesis.

Synthesis reactions generally employ catalysts. They are used to more rapidly promote specific reactions. The catalysts themselves are unaltered before and after the reaction, or even if consumed they can be regenerated for repeated use in the reaction. Ideally, therefore, the catalyst is added initially and used perpetually and repeatedly in the reaction to produce a chemical product.

However, catalyst degradation and inactivation is an often encountered phenomenon, and in order to maintain the reaction rate, procedures are necessary for addition and replacement of fresh catalyst. With continued addition of catalyst, inactivated catalyst accumulates within the reaction system and replacement also results in removal and disposal of catalyst that still maintains its activity, together with the inactivated catalyst. The productivity is also impaired by carrying out the aforementioned procedure.

Inactivation of catalyst differs depending on the reaction and on the type (homogeneous system or non-homogeneous system) and structure of the catalyst, and therefore the method for dealing with it cannot be defined for all cases.

Among such synthesis reactions, the alkyl tin compound of this embodiment is a homogeneous catalyst for ester synthesis, the tin atom of the alkyl tin compound being tetravalent, and it is highly useful for industry. For the purpose of this embodiment, "ester synthesis reaction" refers to transesterification reaction, esterification reaction, carbonic acid ester synthesis reaction or carbamic acid ester synthesis reaction, and it is synthesis of a neutral ester of a carboxylic acid or carbamic acid, or transesterification reaction.

While very few examples exist of detailed research into the reactions of catalyst performance inactivation of alkyl tin compounds, the results of our research have shown that the alkyl group disproportionation reactions represented by chemical equations (8) and (9) occur very readily.

[Chemical Formula 77]

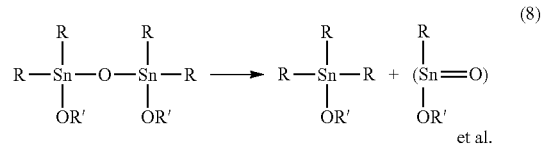
(8)
et al.

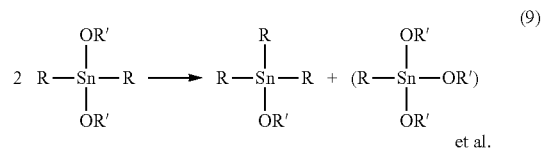
(9)
et al.

It was found that in these inactivation reactions, the number of alkyl groups bonding to the tin atom in the alkyl tin compound changes, such that the initial catalytic activity can no longer be obtained. While the reason for the reduction in catalytic activity occurring with inactivation reaction is not clearly understood, it is possible that, for example, the distannoxane-type alkyl tin compound represented in chemical equation (8) is structurally stabilized by adopting the ladder structure shown in formula (10) (or as has also been reported, forming a cyclic structure of two or more molecules when existing as a monomer), and the alkyl tin compound in equation (9) exhibits its catalytic action by forming a structure containing an aggregate such as the core structure shown in formula (11). It is presumed that when this disproportionation reaction takes place, such structures are difficult to form, or that the catalytic activity is altered by electron effects due to changes in the number of alkyl groups bonding to tin or by mutual effects between them.

[Chemical Formula 78]

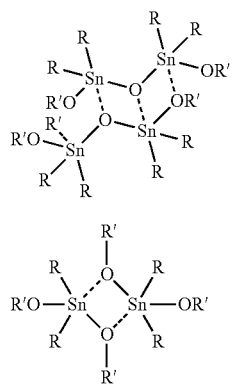

The invention has been completed in light of this situation, with specific cyclic group-substituted alkyl tin compounds that inhibit these disproportionation reactions and function as homogeneous catalysts in ester synthesis.

The compounds to be used for this embodiment will now be described.

The compound names used herein are in most cases names based on the rules of convention of Nomenclature (IUPAC Nomenclature of Organic Chemistry) as established by the IUPAC (The International Union of Pure and Applied Chemistry). The term "organic" refers to the group of compounds that are the subject matter of the Nomenclature according to the aforementioned rules of convention. This subject matter may be the subject matter described in the recommendations of 1993. However, "organic" compounds that are the subject matter of the aforementioned Nomenclature include organometallic compounds and metal complexes. For the embodiments described herein, "organic", "organic group" and/or "substituent", as well as other compounds used for the embodiments, are composed of atoms that do not include metal atoms and/or metalloids, unless otherwise specified. More preferably, "organic compound", "organic group" or "substituent" as used for the embodiment are composed of atoms selected from among H (hydrogen), C (carbon), N (nitrogen), O (oxygen), S (sulfur), Cl (chlorine), Br (bromine) and I (iodine).

The terms "aliphatic" and "aromatic" are also frequently used throughout the following explanation. According to IUPAC rules, organic compounds are classified as aliphatic compounds and aromatic compounds. Aliphatic compounds are defined as aliphatic compounds based on the IUPAC recommendations of 1995. The recommendations define aliphatic compounds as "acyclic or cyclic, saturated or unsaturated carbon compounds, excluding aromatic compounds". Also, the term "aliphatic compounds" used for the embodiments includes saturated aliphatic compounds and unsaturated aliphatic compounds, as well as straight-chain aliphatic compounds and cyclic aliphatic compounds, and it refers to "organic compounds", "organic groups" or "substituents" that are composed of atoms selected from among H (hydrogen), C (carbon), N (nitrogen), O (oxygen), S (sulfur), Si (silicon), and halogen atoms such as Cl (chlorine), Br (bromine) and I (iodine).

Also, when an aromatic group is bonded to an aliphatic group, as in an "aralkyl group", this is often referred to as an "aliphatic group substituted with an aromatic group", an "aromatic aliphatic group" or a "group comprising an aliphatic group to which an aromatic group is bonded". This is based on the reactivity in the embodiments, as the property relating to reaction of groups such as aralkyl groups is very similar to aliphatic reactivity instead of aromaticity. Furthermore, non-aromatic reactive groups that include aralkyl and alkyl groups are often referred to as "aliphatic groups optionally substituted with aromatic groups", "aromatic-substituted aliphatic groups" or "aromatic group-bonded aliphatic groups", and these are also included among "aliphatic groups".

When explaining a general formula for a compound used herein, the definition according to the rules of Nomenclature established by the IUPAC are used, but common names will often be used for the specific group names and exemplary compound names. Moreover, numbers of atoms and numbers of substituents are often mentioned herein, and these are all integers.

When the substituents or compounds mentioned herein have structural isomers, they include the structural isomers unless otherwise specified.

The alkyl tin compounds of the invention will be described first.

The alkyl tin compound according to one embodiment is a cyclic group-substituted alkyl tin compound, wherein the alkyl group is an alkyl group having a cyclic group selected from among alicyclic hydrocarbon groups and aromatic hydrocarbon groups bonded to at least one carbon atom among the first to third carbon atoms counting from the tin atom, and the valency of the tin atom is tetravalent. Although an effect may be exhibited even when the alkyl group contains a heteroatom (for example, oxygen), as in an ether bond, alkyl tin compounds substituted with cyclic groups selected from among saturated or unsaturated alicyclic hydrocarbon groups or aromatic hydrocarbon groups are preferred. Saturated cyclic hydrocarbon groups may be cycloalkyl groups.

As a result of diligent research on the problems of the prior art, it was found, surprisingly, that the placement of the carbon atom near the tin atom of the alkyl tin compound has a notable effect on formation of the inactivated form. It is unclear whether this effect is an electron effect or a steric effect, but it is presumed to be less than an effect of steric hindrance. Regardless of the manner of the effect, a notable effect is exhibited by alkyl groups substituted with specific cyclic groups. An effect was exhibited when using a compound in which carbon atoms near the tin in the alkyl tin compound (at least one of the first to third carbon atoms counting from the tin atom) were substituted with an alicyclic hydrocarbon group or an aromatic hydrocarbon group. On the other hand, in a structure wherein a cyclic group is directly bonded to the tin atom, the original catalytic action and reactivity are reduced. In order to obtain an effect of both preventing inactivation and maintaining activity, alkyl groups substituted with specific cyclic groups are preferred.

A cyclic group-substituted alkyl group is, for example, an alkyl tin compound wherein the carbon atom adjacent to the tin atom (the 1st carbon counting from the tin atom) is methylene (—CH$_2$—).

Specific examples where one alkyl group substituted with a cyclic group is bonded to a tin atom are shown in formulas (12) to (14) (where the tin atoms are tetravalent, and the other groups are omitted).

[Chemical Formula 79]

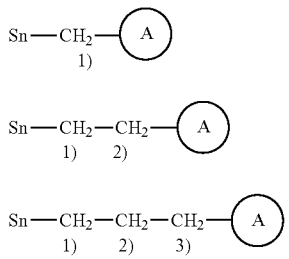

[In the formulas, ring A represents a C3-16 alicyclic hydrocarbon group or a C6-16 aromatic hydrocarbon group. The numerals 1), 2) and 3) represent the ordering of carbon atoms from the tin atom, being the primary, secondary and tertiary carbon atoms, respectively.]

Ring A represents a cyclic group which is a C3-16 alicyclic hydrocarbon group or C6-16 aromatic hydrocarbon group, ring A being further optionally substituted with a straight-chain or cyclic group. The cyclic group forming ring A is bonded to at least one carbon atom among the first to third carbon atoms from the tin atom, forming a cyclic group-substituted alkyl group.

Examples of alkyl groups substituted with such alicyclic hydrocarbon groups include cyclopropylmethyl, cyclobutylmethyl, cyclopentylmethyl, cyclohexylmethyl, 2-cyclopropylethyl, 2-cyclobutylethyl, 2-cyclopentylethyl, 2-cyclohexylethyl, 3-cyclopropylpropyl, 3-cyclobutylpropyl, 3-cyclopentylpropyl, 3-cyclohexylpropyl, 1-(2,3-dihydro-1H-inden-1-yl)methyl, 1-(2,3-dihydro-1H-inden-2-yl)methyl, 1-(1,2,3,4-tetrahydronaphthalen-1-yl)methyl, 1-(1,2,3,4-tetrahydronaphthalen-2-yl)methyl, 1-(1,2,3,4-tetrahydronaphthalen-3-yl)methyl, 2-(2,3-dihydro-1H-inden-1-yl)ethyl, 2-(2,3-dihydro-1H-inden-2-yl)ethyl, 2-(1,2,3,4-tetrahydronaphthalen-1-yl)ethyl, 2-(1,2,3,4-tetrahydronaphthalen-2-yl)ethyl, 2-(1,2,3,4-tetrahydronaphthalen-3-yl)ethyl, 2-(9,10-dimethyl-1,2,3,4-tetrahydroanthracen-1-yl)ethyl, 3-(2,3-dihydro-1H-inden-1-yl)propyl, 3-(2,3-dihydro-1H-inden-2-yl)propyl, 3-(1,2,3,4-tetrahydronaphthalen-1-yl)propyl, 3-(1,2,3,4-tetrahydronaphthalen-2-yl)propyl, 3-(1,2,3,4-tetrahydronaphthalen-3-yl)propyl and 3-(9,10-dimethyl-1,2,3,4-tetrahydroanthracen-1-yl)propyl. Examples of alkyl groups substituted with aromatic hydrocarbon groups include benzyl, (2-methylphenyl)methyl, (4-methylphenyl)methyl, (2,6-dimethylphenyl)methyl, (2,4,6-trimethylphenyl)methyl, (1-methylnaphthalen-2-yl)methyl, (1-methylanthracen-2-yl)methyl, 2-phenylethyl, 2-(2-methylphenyl)ethyl, 2-(4-methylphenyl)ethyl, 2-(2,6-dimethylphenyl)ethyl, 2-(2,4-dimethylphenyl)ethyl, 2-(2,4,6-trimethylphenyl)ethyl, 2-(1-methylnaphthalen-2-yl)ethyl, 2-(1-methylanthracen-2-yl)ethyl, 3-phenylpropyl, 3-(2-methylphenyl)propyl, 3-(4-methylphenyl)propyl, 3-(2,6-dimethylphenyl)propyl, 3-(2,4-dimethylphenyl)propyl, 3-(2,4,6-trimethylphenyl)propyl, 3-(1-methylnaphthalen-2-yl)propyl and 3-(1-methylanthracen-2-yl)propyl.

From the viewpoint of maintaining catalytic activity, among the cyclic group-substituted alkyl groups mentioned above there are more preferred, as cyclic group-substituted alkyl groups that can produce a greater effect, alkyl groups having cyclic groups selected from among alicyclic hydrocarbon groups and aromatic hydrocarbon groups bonded to the 1st or 2nd carbon atom counting from the tin atom.

As mentioned above, the degree of inactivation is higher when the alkyl tin compound is an alkyl tin alkoxide. Therefore, the effect of the invention is greater when the alkyl tin compound for this embodiment is an alkyl tin alkoxide. Also, the alkoxy group is more preferably C1-8 in consideration of catalytic action and reactivity.

Examples of preferred alkoxy groups include methyloxy, ethyloxy, propyloxy (all isomers), butyloxy (all isomers), pentyloxy (all isomers), hexyloxy (all isomers), heptyloxy (all isomers), and octyloxy (all isomers).

In consideration of regeneration of the cyclic group-substituted alkyl tin compound, more preferably the number of carbon atoms of the alkoxy group is 4 to 8, and the alcohol corresponding to the alkoxy group is an alcohol with a boiling point of 100° C. or higher at ordinary pressure.

Examples of such alkoxy groups include n-butyloxy, isobutyloxy, sec-butyloxy and C5-8 alkoxy groups.

For use at high temperature, branched alkoxy groups are preferred as alkoxy groups, from the viewpoint of obtaining an effect of further inhibiting disproportionation reaction of the alkyl groups. More preferably, it is a group in which a C1-3 alkyl group is substituted at the secondary or tertiary position (the position of the carbon in the alkoxy group, which is the position from the oxygen bonded to the tin atom). Examples of such alkyl groups include 2-methylpropyloxy, 2-methyl-butyloxy, 2-ethyl-butyloxy, 2-propyl-butyloxy, 2-methyl-pentyloxy, 2-ethyl-pentyloxy, 2-propyl-pentyloxy, 2-methyl-hexyloxy, 2-ethyl-hexyloxy, 3-methyl-butyloxy, 3-ethyl-butyloxy, 3-propyl-butyloxy, 3-methyl-pentyloxy, 3-ethyl-pentyloxy, 3-propyl-pentyloxy, 3-methyl-hexyloxy and 3-ethyl-hexyloxy.

In light of the above, the alkoxy group of the alkyl tin alkoxide is most preferably an alkoxy group selected from the group consisting of isobutyloxy and C5-8 alkoxy groups, and an alkoxy group in which a C1-3 alkyl group is substituted at the secondary or tertiary position (as the position of the carbon in the alkoxy group, which is the position from the oxygen bonded to the tin atom).

As alkyl tin compounds there are preferably used compositions that contain either or both a di(cyclic group-substituted alkyl) tin dialkoxide and/or tetra(cyclic group-substituted alkyl)dialkoxydistannoxane (hereunder referred to as "di(cyclic group-substituted alkyl) tin dialkoxide composition"), that is useful as a catalyst. The expression "active component" as used herein refers to, rather than alkyl tin compounds in general, alkyl tin compounds having two alkyl groups bonded to a tin atom, and specifically they include dialkyl tin alkoxides, tetraalkylalkoxydistannoxanes and/or dialkyl tin oxides. When the aforementioned composition is used, usually the molar ratio of tin atoms composing the di(cyclic group-substituted alkyl) tin dialkoxide and tetra(cyclic group-substituted alkyl)dialkoxydistannoxane in the composition is preferably in the range of 1:99 to 99:1 (or 1:49.5 to 99:0.5, represented as the molar ratio of di(cyclic group-substituted alkyl) tin dialkoxide molecules and tetra(cyclic group-substituted alkyl)dialkoxydistannoxane molecules), although this is not particularly restricted. When it is to be used at high temperature (for example, 100° C. or higher), a higher proportion of the more stable di(cyclic group-substituted alkyl) tin dialkoxide is preferred, with introduction into the reactor at a proportion of 99:1 to 50:50 (99:0.5 to 50:25 in terms of the molecular molar ratio).

The di(cyclic group-substituted alkyl) tin dialkoxide is preferably a compound represented by formula (1). The tetra(cyclic group-substituted alkyl)dialkoxydistannoxane is preferably a compound represented by formula (2).

[Chemical Formula 80]

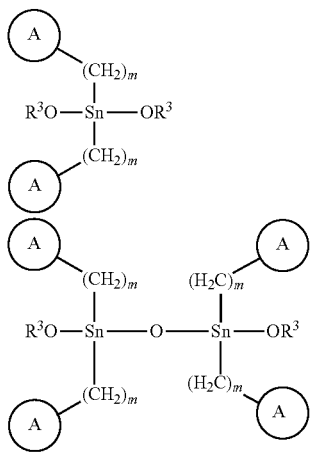

(1)

[Ring A represents a C3-16 alicyclic hydrocarbon group or a C6-16 aromatic hydrocarbon group, m is an integer of 1 to 3, and $R^3$ represents a C1-8 alkyl group.]

As used herein, the tetra(cyclic group-substituted alkyl) dialkoxydistannoxane structure is the structure represented by formula (2) as the canonical structure. However, as with the di(cyclic group-substituted alkyl) tin oxide described below, it may be present as the hydroxy structure represented by formula (4) below. Since the presence and content of hydroxy structures cannot be defined by analysis at the current time, the structures represented by formulas (2) and (4) mentioned herein are included among tetra(cyclic group-substituted alkyl)dialkoxydistannoxanes.

[Chemical Formula 81]

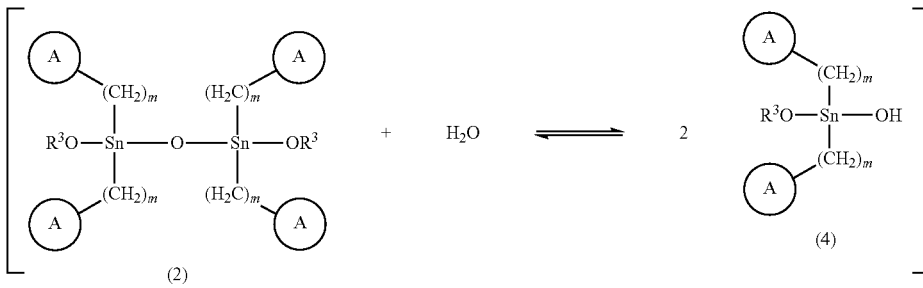

[In the formula, ring A, m and $R^3$ have the same definitions as above.]

According to one embodiment of the invention, the alkyl tin compound may be a tri(cyclic group-substituted alkyl) tin compound, or a composition containing a tri(cyclic group-substituted alkyl) tin compound. When the composition containing a di(cyclic group-substituted alkyl) tin dialkoxide and/or tetra(cyclic group-substituted alkyl)dialkoxydistannoxane further contains a tri(cyclic group-substituted alkyl) tin compound, the number of moles of tin atoms of the trialkyl tin compound with respect to the number of moles of tin atoms in the entire composition (the total number of moles of tin atoms of the di(cyclic group-substituted alkyl) tin dialkoxide, tetra(cyclic group-substituted alkyl)dialkoxydistannoxane and tri(cyclic group-substituted alkyl) tin compound in the composition), is preferably in the range of 1 to 50 mol %. The thermostability will sometimes be improved by including a tri(cyclic group-substituted alkyl) tin compound within this range. While the chemical reason for this is not completely understood, it is conjectured that the disproportionation equilibrium of alkyl groups may be shifted in the desired direction by heating. The catalytic activity and reactivity of tri(cyclic group-substituted alkyl) tin compounds is lower than that of di(cyclic group-substituted alkyl) tin dialkoxides and tetra(cyclic group-substituted alkyl)dialkoxydistannoxanes, and if the content of the tri(cyclic group-substituted alkyl) tin compound is greater than 50 mol % it may be necessary to increase the amount of composition to obtain desirable reaction results. The tri(cyclic group-substituted alkyl) tin compound content is more preferably 1 to 30 mol %.

Preferred examples of such tri(cyclic group-substituted alkyl) tin compounds include compounds represented by the following formula (3).

[Chemical Formula 82]

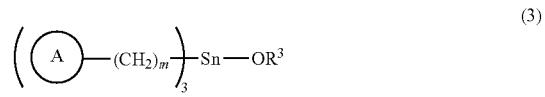

(3)

[Ring A represents a C3-16 alicyclic hydrocarbon group or a C6-16 aromatic hydrocarbon group, m is an integer of 1 to 3, and $R^3$ represents a C1-8 alkyl group.]

The alkyl tin alkoxide (di(cyclic group-substituted alkyl) tin dialkoxide and/or tetra(cyclic group-substituted alkyl) dialkoxydistannoxane and tri(cyclic group-substituted alkyl) tin alkoxide) can be obtained by known processes. Preferred starting materials include cyclic group-substituted alkyl tin carboxylates, cyclic group-substituted alkyl tin oxides, cyclic group-substituted alkyl tin oxide polymers and alkyl tin halides. Publicly known synthesis methods for these starting materials are preferably employed. The production conditions may modified for optimal performance (for example, Wilhelm P. Neumann et al., Justus Liebigs Annalen der Chemie, Vol. 663, pp 11-21 (1963), Egmond, J. C. van et al., Journal of Applied Chemistry (London), vol. 12, pp 17-27 (1962), Seyferth et al., Journal of Organic Chemistry, vol. 26, p 2934 (1961), Kerk, G. J. van der; Luijten et al., Journal of Applied Chemistry (London), vol. 7, pp 369-374 (1957), P. Fostein et al., Journal of Organometallic Chemistry, vol. 114, pp C7-C10 (1976)). Methods for producing alkyl tin alkoxides from starting materials may be any publicly known methods. The composition containing the alkyl tin alkoxide may include an alkyl tin oxide and/or alkyl tin oxide polymer for this purpose, but the alkyl tin carboxylate and halogenated (cyclic group-substituted alkyl) tin content is preferably as low as possible. For example, they are preferably used purified to no greater than 20 mol %, as expressed in mol % of tin atoms. A publicly known method is preferably used for purification. The method for producing an alkyl tin oxide or alkyl tin oxide polymer as a starting material is also preferably a known method.

In order to increase the analysis precision for production control, the cyclic group-substituted alkyl groups of the di(cyclic group-substituted alkyl) tin dialkoxide, tetra(cyclic group-substituted alkyl)dialkoxydistannoxane and tri(cyclic group-substituted alkyl) tin alkoxide are preferably the same group, and each of the alkoxy groups are also preferably the same alkoxy group.

The alkyl tin compound is preferably used as a homogeneous catalyst for ester synthesis, among other synthesis reactions. For the purpose of this disclosure, "ester synthesis reaction" refers to transesterification reaction, esterification reaction, carbonic acid ester synthesis reaction or carbamic acid ester synthesis reaction, and it is synthesis of a neutral ester of a carboxylic acid or carbamic acid, or transesterification reaction.

There are no particular restrictions on the reaction temperature, but the range is preferably 0° C. to 250° C. There are no restrictions on the use of reaction solvents, but preferred examples are hydroxyhydrocarbons such as alcohols and phenols; hydrocarbons; and ethers such as THF, and any solvents that do not notably impair the structure of the alkyl tin compound by oxidation reaction, reduction reaction or the like may be selected as appropriate. Undesirable secondary reactions often occur with strongly acidic solvents or strong alkali solvents, and preferably the reaction solvent and reaction temperature are selected in consideration of the appropriate secondary reaction rate.

Ester synthesis reaction is preferably conducted with the alkyl tin compound in a dissolved or molten state, and the temperature and solvent are preferably selected as appropriate for this purpose.

An inert gas may be used for the ester synthesis reaction. Examples of inert gases include nitrogen, argon and helium. Carbon dioxide may be used as it has no adverse effects. Oxygen, hydrogen, hydrogen sulfide, carbon monoxide and the like may be included in ranges that do not notably impair the structure of the cyclic group-substituted alkyl tin compound or the reaction results, and they are purified and controlled by known methods so that consistent, desired reaction results are obtained.

A method for producing a carbonic acid ester will now be described as a preferred method for the invention.

According to one embodiment, the alkyl tin compound is a catalyst for a process of producing a carbonic acid ester by reaction with carbon dioxide. The alkyl tin compound is preferably a cyclic group-substituted alkyl tin alkoxide.

The production method for this embodiment is a method for producing a carbonic acid ester using an alkyl tin alkoxide, wherein the alkyl tin alkoxide includes either or both a compound represented by formula (1) and/or a compound represented by formula (2), and the method for producing a carbonic acid ester includes the following steps (1) to (3).
Step (1): A step in which the cyclic group-substituted alkyl tin alkoxide and carbon dioxide are reacted to obtain a reaction mixture containing a carbonic acid ester.
Step (2): A step of separating the carbonic acid ester from the reaction mixture to obtain a residual solution.
Step (3): A step of reacting the residual solution with an alcohol and removing the water produced by the reaction, to obtain a cyclic group-substituted alkyl tin alkoxide, and recycling it to step (1).

[Chemical Formula 83]

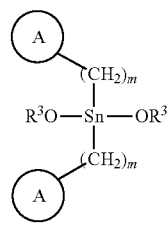

(1)

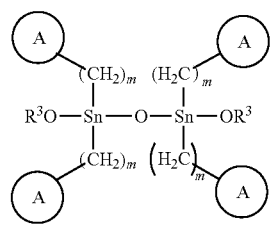

(2)

[Ring A represents a C3-16 alicyclic hydrocarbon group or a C6-16 aromatic hydrocarbon group, m is an integer of 1 to 3, and $R^3$ represents a C1-8 alkyl group.]

Examples for the di(cyclic group-substituted alkyl) tin dialkoxide and tetra(cyclic group-substituted alkyl)dialkoxydistannoxane to be used in the carbonic acid ester production method include the di(cyclic group-substituted alkyl) tin dialkoxides and tetra(cyclic group-substituted alkyl)dialkoxydistannoxanes mentioned above, it being preferred to use a composition containing either or both the di(cyclic group-substituted alkyl) tin dialkoxide and tetra (cyclic group-substituted alkyl)dialkoxydistannoxane. When a composition is used, the molar ratio of tin atoms composing the di(cyclic group-substituted alkyl) tin dialkoxide and tetra(cyclic group-substituted alkyl)dialkoxydistannoxane in the composition is preferably in the range of 1:99 to 99:1 (or 1:49.5 to 99:0.5, represented as the molar ratio of di(cyclic group-substituted alkyl) tin dialkoxide molecules and tetra(cyclic group-substituted alkyl)dialkoxydistannoxane molecules), although this is not particularly restricted. When it is to be used at high temperature (for example, 100° C. or higher), a higher proportion of the more stable di(cyclic group-substituted alkyl) tin dialkoxide is preferred, with introduction into the reactor so that the proportion is 99:1 to 50:50 (99:0.5 to 50:25 in terms of the molecular molar ratio).

In order to carry out step (3) in a desirable manner, in consideration of recycling of the alkyl tin compound, more preferably the alkoxy group of the alkyl tin alkoxide is a C4-8 alkoxy group, and the alcohol corresponding to the alkoxy group has a boiling point of 100° C. or higher at ordinary pressure.

Examples of such alkoxy groups include n-butyloxy, isobutyloxy, sec-butyloxy and C5-8 alkoxy groups.

In order to increase the analysis precision for production control, the cyclic group-substituted alkyl groups of the di(cyclic group-substituted alkyl) tin dialkoxide and tetra (cyclic group-substituted alkyl)dialkoxydistannoxane are preferably the same group, and each of the alkoxy groups are also preferably the same alkoxy group.

For the production method for this embodiment it is preferred to use a composition further containing a tri(cyclic group-substituted alkyl) tin compound as the alkyl tin compound. The thermostability will sometimes be improved if it contains a tri(cyclic group-substituted alkyl) tin compound in a range such that the number of moles of tin atoms in the tri(cyclic group-substituted alkyl) tin compound with respect to the number of moles of tin atoms in the composition is 1 to 50 mol %. While the chemical reason for this is not completely understood, it is conjectured that the disproportionation equilibrium of alkyl groups may be shifted in the desired direction by heating. The catalytic action and reactivity of the tri(cyclic group-substituted alkyl) tin compound are lower than the di(cyclic group-substituted alkyl) tin dialkoxide or tetra(cyclic group-substituted alkyl)dialkoxydistannoxane. If the tri(cyclic group-substituted alkyl) tin compound content is high it may be necessary to increase the amount of composition to obtain the desired reaction results, and therefore it is more preferred to use a composition containing the tri(cyclic group-substituted alkyl) tin compound in a range of 1 to 30 mol %.

Preferred examples of such tri(cyclic group-substituted alkyl) tin compounds include compounds represented by the following formula (3).

[Chemical Formula 84]

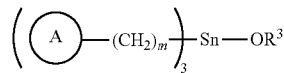

(3)

[Ring A represents a C3-16 alicyclic hydrocarbon group or a C6-16 aromatic hydrocarbon group, m is an integer of 1 to 3, and $R^3$ represents a C1-8 alkyl group.]

In order to increase the analysis precision for production control, the cyclic group-substituted alkyl groups of the di(cyclic group-substituted alkyl) tin dialkoxide, tetra(cyclic group-substituted alkyl)dialkoxydistannoxane and tri(cyclic group-substituted alkyl) tin alkoxide are preferably the same group, and each of the alkoxy groups are also preferably the same alkoxy group.

The alcohol used in step (3) will now be described.

The alcohol to be used in step (3) is preferably a C4-8 alcohol and an alcohol having a boiling point of 100° C. or higher at ordinary pressure, in consideration of recycling of the alkyl tin compound.

Examples of such alcohols include n-butyl alcohol, isobutyl alcohol, sec-butyl alcohol and C5-8 alkyl alcohols.

Through step (3), the alcohol is incorporated as the alkoxy group of the alkyl tin alkoxide. For use at high temperatures, the alcohol used in step (3) is preferably an alcohol having a C1-3 alkyl group bonded at the 2nd or 3rd carbon atom from the hydroxyl group, from the viewpoint of preventing alkyl group disproportionation reaction. Examples of such alcohols include 2-methyl-propyl alcohol, 2-methyl-butyl alcohol, 2-ethyl-butyl alcohol, 2-propyl-butyl alcohol, 2-methyl-pentyl alcohol, 2-ethyl-pentyl alcohol, 2-propyl-pentyl alcohol, 2-methyl-hexyl alcohol, 2-ethyl-hexyl alcohol, 3-methylbutyl alcohol, 3-ethyl-butyl alcohol, 3-propyl-butyl alcohol, 3-methyl-pentyl alcohol, 3-ethyl-pentyl alcohol, 3-propyl-pentyl alcohol, 3-methyl-hexyl alcohol and 3-ethyl-hexyl alcohol.

In order to increase analysis precision for production control and purity of the carbonic acid ester, the alkoxy groups of the di(cyclic group-substituted alkyl) tin dialkoxide, tetra(cyclic group-substituted alkyl)dialkoxydistannoxane and tri(cyclic group-substituted alkyl) tin alkoxide are preferably the same alkoxy group, and the alcohol used in step (3) is preferably the alcohol corresponding to the alkoxy group.

(Method for Producing Carbonic Acid Ester)

A method for producing carbonic acid esters using alkyl tin alkoxides will now be explained in detail.

Methods disclosed by the present inventors are preferably used (for example, International Patent Publication No. WO03/055840, International Patent Publication No. WO2004/014840, International Patent Publication No. WO2005/000783, International Patent Publication No. WO2005/111049 and International Patent Publication No. WO2007/114130).

(i) Alkyl Tin Alkoxide Synthesis Step (Continuous Operation Start-Up Step)

The alkyl tin alkoxide to be used for this embodiment may be an alkyl tin alkoxide obtained by a known method, as described above. The alkyl tin alkoxide can be obtained, for example, from an alkyl tin carboxylate, a cyclic group-substituted alkyl tin oxide, a cyclic group-substituted alkyl tin oxide polymer or a halogenated (cyclic group-substituted alkyl) tin compound. It is preferred to use the previously disclosed method for producing alkyl tin alkoxides (International Patent Publication No. WO2005/111049 and elsewhere). This step produces a cyclic group-substituted alkyl tin alkoxide preferably from a di(cyclic group-substituted alkyl) tin oxide and an alcohol. The alcohol used may be any of the aforementioned alcohols.

The di(cyclic group-substituted alkyl) tin oxide used in this process may be a compound represented by the following formula (15).

[Chemical Formula 85]

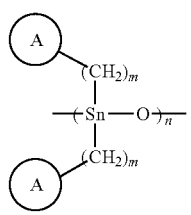

(15)

[Ring A represents a C3-16 alicyclic hydrocarbon group or a C6-16 aromatic hydrocarbon group, m is an integer of 1 to 3, and n is a positive integer.]

The structure of the di(cyclic group-substituted alkyl) tin oxide has not been fully elucidatable by current analysis methods. In this process, the di(cyclic group-substituted alkyl) tin oxide may be one having the monomer structure represented by formula (16) or the hydroxy structure represented by formula (17), instead of the polymer structure represented by formula (15). The hydroxy structure represented by formula (17) is not usually referred to as a di(cyclic group-substituted alkyl) tin oxide, but because it is difficult to confirm its presence and content by current methods of analysis, and the invention may be carried out under the conditions for this process with either structure, for the sake of convenience it will be described herein as having the same definition as a di(cyclic group-substituted alkyl) tin oxide.

[Chemical Formula 86]

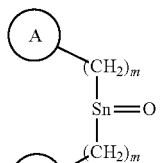
(16)

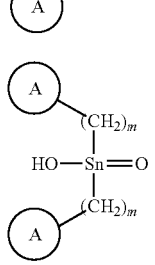
(17)

[In the formulas, ring A represents a C3-16 alicyclic hydrocarbon group or a C6-16 aromatic hydrocarbon group, and m represents an integer of 1-3.]

The alcohol and the di(cyclic group-substituted alkyl) tin oxide are used for dehydrating reaction, while removing the generated water out of the reaction system, to obtain a tetra(cyclic group-substituted alkyl)di(alkoxy)distannoxane and/or di(cyclic group-substituted alkyl) tin dialkoxide. During this time, the alcohol used is converted to an alkoxy group to form the alkyl tin alkoxide. The temperature for carrying out the reaction may be in the range of 80° C. to 180° C., for example, and from the viewpoint of easier distillation removal of the generated water out of the reaction system, it is more preferably in the range of 60° C. to 180° C., although this will depend on the reaction pressure, while from the viewpoint of increasing the reaction rate the reaction temperature is even more preferably a high temperature. On the other hand, since undesirable secondary reactions such as decomposition take place at high temperatures, thus lowering yields, the temperature is more preferably in the range of 80° C. to 160° C. The pressure in the reactor for the reaction is a pressure that allows the generated water to be removed out of the system, and although it will depend on the reaction temperature it may be between 20 and $1 \times 10^6$ Pa. The reaction time is not particularly restricted but will usually be 0.001 hour to 50 hours, preferably 0.01 hour to 10 hours and more preferably 0.1 hour to 2 hours. The reaction may be completed when the desired alkyl tin alkoxide has been obtained. Progress of the reaction can be confirmed by a method of measuring the amount of water removed out of the reaction system or a method of sampling the reaction mixture to measure the $^{119}$Sn-NMR spectrum. For production of an alkyl tin alkoxide in step (1), the reaction is completed upon confirming production of an alkyl tin alkoxide with a molar ratio in the range of 0:100 to 80:20 and preferably 1:99 to 70:30 for the tetra(cyclic group-substituted alkyl)dialkoxydistannoxane and di(cyclic group-substituted alkyl) tin dialkoxide in the cyclic group-substituted alkyl tin alkoxide obtained by the reaction. The used alcohol may continue to be used while copresent, or in some cases the alcohol may be distilled off and then used. It is preferred to remove the alcohol as much as possible since this will allow the reactor to be reduced in size for the other steps. The method of removal is preferably by a known distillation process, and the distiller used for distillation may be a known distilling apparatus. A thin-film distillation apparatus may be used as a preferred distilling apparatus, since it allows removal within a short period of time. There are no particular restrictions on the form of the reactor used, and a known type of tank or tower reactor may be used. The low-boiling-point reaction mixture containing water is gaseous and can be removed from the reactor by distillation, and the produced alkyl tin alkoxide or the high boiling point reaction mixture containing the alkyl tin alkoxide may be extracted as liquid from the bottom of the reactor. Examples of such a reactor include reactors comprising a stirring tank, a multistage stirring tank, a distillation column, a multistage distillation column, a multitube reactor, a continuous multistage distillation column, a packed tower, a thin-film evaporator, a reactor provided with an interior support, a forced circulation reactor, a falling film evaporator, a falling drop evaporator, a trickle phase reactor or a bubble tower, and known methods may be used that employ systems of these in combination. A method using a tower-type reactor is preferred from the viewpoint of efficiently shifting the equilibrium of the dehydrating reaction toward the alkyl tin alkoxide (product), or a method using a reactor with a large gas-liquid contact area is used so that the formed water rapidly migrates to the gas phase. This step may be carried out by a continuous method using a multitube reactor, multistage distillation column or a filler-packed tower, but when the di(cyclic group-substituted alkyl) tin oxide used is solid, it is more preferred to use a method of carrying out the reaction in a tank reactor and then increasing the di(cyclic group-substituted alkyl) tin dialkoxide content with a tower reactor. The materials of the reactor and line may be any publicly known materials that do not adversely affect the reaction, and since SUS304, SUS316, SUS316L and the like are inexpensive they are preferred for use. If necessary, there may be further included measuring devices such as a flowmeter and thermometer, and known processing equipment such as a reboiler, pump, condenser, heating means, cooling means and the like, while the heating means may be a known heating means such as steam or a heater, and the cooling means may be known cooling means such as natural cooling, cooling water or brine.

Step (1): A Step of Reacting an Alkyl Tin Alkoxide with Carbon Dioxide to Obtain a Reaction Mixture Containing a Carbonic Acid Ester.

In this step, the alkyl tin alkoxide is reacted with gaseous carbon dioxide to produce a carbonic acid ester. The step is preferably carried out using a previously disclosed method for producing carbonic acid esters (International Patent Publication No. WO03/055840, International Patent Publication No. WO04/014840 or elsewhere).

The alkyl tin alkoxide supplied to this step will sometimes be supplied from the cyclic group-substituted alkyl tin alkoxide synthesis step during start-up, or it will sometimes be supplied from the cyclic group-substituted alkyl tin alkoxide production step (3) during continuous production.

For this step, first the alkyl tin alkoxide and gaseous carbon dioxide are reacted to obtain a mixture comprising a carbon dioxide conjugate of the alkyl tin alkoxide.

During the chemical reaction, preferably either the alkyl tin alkoxide is heated to melting, or it is mixed with the solvent as a solution for reaction as a liquid. The pressure in the reactor for this reaction will depend on the reaction temperature, but it is preferably in the range from ordinary pressure to 1 MPa, and more preferably in the range of from ordinary pressure to 0.6 MPa. The reaction temperature will depend on the pressure of the reaction, but it is preferably −40° C. to 80° C., and in consideration of the flow property during transport, it is more preferably 0° C. to 80° C., and most preferably in the range of ordinary temperature (for example, 20° C.) to 80° C. The term "ordinary temperature" as used herein means the range of 1° C. to 30° C. The reaction time may be in a range from a few seconds to 100 hours, and is preferably from a few seconds to 10 hours in consideration of productivity. The reactor used may be a known tank reactor or tower reactor. Several different reactors may also be used combination. Since the reaction is between carbon dioxide (gas) and a solution containing alkyl tin alkoxide or alkyl tin alkoxide (liquid), for efficient reaction it is preferred to increase the gas-liquid contact surface area, in order to increase the contact area between the carbon dioxide and the alkyl tin alkoxide. The method for conducting reaction with increased gas-liquid contact surface area may take advantage of known observations, and preferred methods are those that involve increasing the stirring speed in an tank reactor or generating air bubbles in the liquid, or for a tower reactor, utilizing a packed tower or utilizing a tray tower. Examples of such tower reactors include tray tower systems using trays, such as a bubble-cap tray, porous plate tray, valve tray or counterflow tray; and packed tower systems packed with various types of packing agents such as Raschig rings, Lessing rings, pall rings, Berl saddles, Intalox saddles, Dixon packing, McMahon packing, Heli-Pak, Sulzer packing or Mellapak. The materials of the reactor and line may be any publicly known materials that do not adversely affect the reaction, and since SUS304, SUS316, SUS316L and the like are inexpensive they are preferred for use. If necessary, there may be further included measuring devices such as a flowmeter and thermometer, and known processing equipment such as a reboiler, pump, condenser, heating means, cooling means and the like, while the heating means may be a known heating means such as steam or a heater, and the cooling means may be known cooling means such as natural cooling, cooling water or brine. The reaction will usually be an exothermic reaction, and cooling may be accomplished by heat radiation from the reactor, for example. Heating may be performed when production of a carbonic acid ester is to be carried out simultaneously. Cooling or heating of the reactor may employ a publicly known method, such as a method using a jacket, or a method using an internal coil. The carbon dioxide and alkyl tin alkoxide supplied to the reactor may be supplied separately, or they may be combined before being supplied to the reactor. The carbon dioxide and alkyl tin alkoxide may also be supplied to the reactor from several different sections of the reactor. Completion of the reaction can be confirmed by $^{119}$Sn-NMR spectral analysis, for example. A step of obtaining a carbon dioxide conjugate of the alkyl tin alkoxide is not essential, and in some cases, depending on equipment operation and the like, the cyclic group-substituted alkyl tin alkoxide may be transported directly to the subsequent step to obtain a reaction mixture containing a carbonic acid ester.

The following method may be used to obtain a reaction mixture containing a carbonic acid ester from the carbon dioxide conjugate of the cyclic group-substituted alkyl tin alkoxide that is obtained.

The reaction conditions are preferably a high reaction temperature in the range of 40° C. to 200° C. to increase the reaction rate, but since undesirable secondary reactions such as decomposition may take place at high temperatures, potentially lowering the yield, the preferred range is 60° C. to 180° C., for a reaction time of 0.05 hour to 10 hours, and the reaction pressure is in the range of preferably ordinary pressure to 20 MPa and more preferably 2.0 MPa to 10 MPa. The reaction may be completed after the desired carbonic acid ester has been produced in the reactor. Progress of the reaction can be confirmed by sampling the reaction mixture in the reactor and analyzing the generated carbonic acid ester by $^1$H-NMR spectrum or gas chromatography. For example, the reaction may be completed after production of at least 10 mol % with respect to the number of moles of the carbon dioxide conjugate of the alkyl tin alkoxide and/or alkyl tin alkoxide in the carbon dioxide conjugate of the alkyl tin alkoxide and/or alkyl tin alkoxide, and if a higher carbonic acid ester yield is desired, the reaction may be continued to a reaction yield of 90% or greater and then terminated. The reactor used may be a known type of reactor, and is preferably a tower reactor or tank reactor. The materials of the reactor and line may be any publicly known materials that do not adversely affect the reaction, and since SUS304, SUS316, SUS316L and the like are inexpensive they are preferred for use. If necessary, there may be further included measuring devices such as a flowmeter and thermometer, and known processing equipment such as a reboiler, pump, condenser, heating means, cooling means and the like, while the heating means may be a known heating means such as steam or a heater, and the cooling means may be known cooling means such as natural cooling, cooling water or brine.

Step (2): A Step of Separating the Carbonic Acid Ester from the Reaction Mixture to Obtain a Residual Solution.

In this step, the carbonic acid ester is separated from the reaction mixture containing the carbonic acid ester obtained in step (1), and a residual solution is obtained. The separation process may employ any known method or apparatus, but is preferably distillation.

The reaction mixture transported from step (1) is subjected to a batch or semi-batch process or continuous distillation, to obtain a carbonic acid ester and a residual solution. The preferred distillation method is one in which the reaction mixture is supplied to a distiller and the carbonic acid ester is separated out of the system from the top of the distiller as a gas phase component, while the residual solution is removed from the bottom of the distiller as a liquid component. The temperature for this step will depend on the boiling point or pressure of the carbonic acid ester, but it may be carried out in a range from ordinary temperature (for example, 20° C.) to 200° C., and since the tin compound in the residual solution is sometimes degraded at high temperature, or the carbonic acid ester may decrease due to reverse reaction, the reaction is preferably carried out in a range from ordinary temperature (for example, 20° C.) to 150° C. The pressure in the reactor for the reaction will depend on the type of carbonic acid ester and the temperature at which it is carried out, but it will usually be conducted from ordinary pressure to reduced pressure conditions, and in consideration of productivity the pressure is preferably in the range of 100 Pa to 80 KPa and more preferably 100 Pa to 50 KPa. The reaction time may be in the range of 0.01 hour to 10 hours, but because the tin component in the reaction mixture may degrade during long periods at high temperature, or the carbonic acid ester may decrease due to reverse reaction, the time is preferably in the range of 0.01 hour to 0.5 hour and more preferably 0.01 hour to 0.3 hour. The distiller used may be a known one, and is preferably a tower distiller or a tank distiller, which may also be used in combination. A thin-film evaporator or thin-film distiller is even more preferred, and a thin-film evaporator or thin-film distiller equipped with a distillation column is most preferred. The materials of the distiller and line may be any publicly known materials that do not adversely affect the reaction, and since SUS304, SUS316, SUS316L and the like are inexpensive they are preferred for use. If necessary, there may be further included measuring devices such as a flowmeter and thermometer, and known processing equipment such as a reboiler, pump, condenser, heating means, cooling means and the like, while the heating means may be a known heating means such as steam or a heater, and the cooling means may be known cooling means such as natural cooling, cooling water or brine. In step (2), when unreacted carbon dioxide is present in the reaction mixture transported from step (1), or when carbon dioxide is incorporated into the alkyl tin alkoxide molecule, preferably the carbonic acid ester is separated after removal of the carbon dioxide from the reaction mixture. The method for removing the carbon dioxide may follow the method for separating the carbonic acid ester. It is preferably carried out at a lower temperature and at a higher pressure than for separation of the carbonic acid ester. The conditions are selected depending on the physical properties of the carbonic acid ester to be produced, as conditions having a low vapor pressure of the carbonic acid ester and allowing removal of carbon dioxide. The carbon dioxide that is removed is preferably recycled to step (1). For recycling, it is preferably returned after pressurization with a compressor or the like. When a compressor is used, inclusion of the cyclic group-substituted alkyl tin alkoxide can potentially clog the compressor or reactor, so it is therefore preferably separated out beforehand. In this case, separation may be carried out by a known method with a distillation column or the like.

Step (3): A Step of Reacting the Residual Solution with an Alcohol and Removing the Water Produced by the Reaction, to Obtain a Cyclic Group-Substituted Alkyl Tin Alkoxide, and Recycling it to Step (1).

This step is carried out after obtaining the residual solution in step 2, but it is similar to the alkyl tin alkoxide synthesis step described above. This step accomplishes dehydrating reaction of the residual solution and alcohol obtained in step (2) to regenerate the cyclic group-substituted alkyl tin alkoxide. The residual solution also contains the alkyl tin alkoxide, but in this step recycling (regeneration) is conducted to the ratio of the alkyl tin alkoxide for carrying out step (1). In other words, since in step (2) the carbonic acid ester is preferentially produced from the di(cyclic group-substituted alkyl tin alkoxide, increasing the proportion of tetra(cyclic group-substituted)alkyldialkoxydistannoxane, the purpose in this step is to regenerate alkyl tin alkoxide with an increased proportion of the di(cyclic group-substituted alkyl) tin dialkoxide.

The alcohol used may be any of the aforementioned alcohols. The dehydrating reaction conditions are also preferably the same as for the alkyl tin alkoxide synthesis step described above. The reaction may be completed when the desired cyclic group-substituted alkyl tin alkoxide has been obtained. Progress of the reaction can be confirmed by a method of measuring the amount of water removed out of the reaction system or a method of sampling the reaction mixture to measure the $^{119}$Sn-NMR spectrum. In order to produce the alkyl tin alkoxide of this embodiment in step (1), the reaction is completed upon confirming that the molar ratio of the tetra(cyclic group-substituted alkyl)dialkoxydistannoxane and di(cyclic group-substituted alkyl) tin dialkoxide in the alkyl tin alkoxide obtained by the previous reaction is in the range of 0:100 to 80:20 and more preferably 1:99 to 70:30. The alcohol may be used directly as a copresent component, or depending on the case the alcohol may be used after being distilled off. It is preferred to remove the alcohol in order to allow the reactor to be reduced in size for the other steps. The method of removal is preferably by a known distillation process, and the distiller used for distillation may be a known distilling apparatus. A thin-film distillation apparatus may be used as a preferred distilling apparatus, since it allows removal within a short period of time. Because a solid di(cyclic group-substituted alkyl) tin oxide is generally not used in this step, unlike the alkyl tin alkoxide synthesis step, there are no particular restrictions on the form of the reactor used for the dehydrating reaction, and any known tank or tower reactor may be used. The low-boiling-point reaction mixture containing water is gaseous and can be removed from the reactor by distillation, and the high boiling point reaction mixture containing the alkyl tin alkoxide may be extracted as liquid from the bottom of the reactor. Examples of such a reactor include reactors comprising a stirring tank, a multistage stirring tank, a distillation column, a multistage distillation column, a multitube reactor, a continuous multistage distillation column, a packed tower, a thin-film evaporator, a reactor provided with an interior support, a forced circulation reactor, a falling film evaporator, a falling drop evaporator, a trickle phase reactor or a bubble tower, and known methods may be used that employ systems of these in combination. A method using a tower-type reactor is preferred from the viewpoint of efficiently shifting the equilibrium of the dehydrating reaction toward the alkyl tin alkoxide, or a method using a reactor with a large gas-liquid contact area is used so that the formed water rapidly migrates to the gas phase. For this step it is especially preferred to employ a continuous method with a multitube reactor, a multistage distillation column or a packed tower packed with a filler. The materials of the distiller and line may be any publicly known materials that do not adversely affect the reaction, and since SUS304, SUS316, SUS316L and the like are inexpensive they are preferred for use. If necessary, there may be further included measuring devices such as a flowmeter and thermometer, and known processing equipment such as a reboiler, pump, condenser, heating means, cooling means and the like, while the heating means may be a known heating means such as steam or a heater, and the cooling means may be known cooling means such as natural cooling, cooling water or brine.

The above is an example of producing a carbonic acid ester using an alkyl tin alkoxide.

By using an alkyl tin compound for this embodiment, it is possible to notably improve accumulation of the inactivated forms of alkyl tin alkoxides that occurs during carbonic acid ester production processes in the prior art, and to produce carbonic acid esters at very high efficiency.

The carbonic acid ester obtained in this step can be suitably used as a polycarbonate starting material, isocyanate starting material or other chemical product starting material, or as a battery electrolyte for a lithium ion battery. Using this method it is possible to solve the problems of cost and waste in the production of carbonic acid esters. The invention is therefore of extreme industrial importance.

A second embodiment of the invention will now be explained in greater detail through examples and comparative examples, with the understanding that the invention is not limited to the examples.

The analysis methods applied in the examples and comparative examples will be described first.

<Analysis Methods>
1) NMR Spectral Analysis

Apparatus: JNM-A400 FT-NMR System by JEOL Corp.
(1) Preparation of $^1$H-NMR, $^{13}$C-NMR and $^{119}$Sn-NMR Spectral Analysis Samples After measuring out 0.3 g of liquid containing an alkyl tin alkoxide or alkyl tin alkoxide, there were added approximately 0.7 g of heavy chloroform (99.8% purity, Aldrich Co.) and 0.08 g of tetramethyltin (Wako Grade A, product of Wako Pure Chemical Industries) as an internal standard for $^{119}$Sn-NMR spectroscopy, and the uniformly mixed solution was used as a sample for NMR spectral analysis.
(2) Quantitative Analysis The alkyl tin alkoxide (di(cyclic group-substituted)alkyl tin dialkoxide, tetra(cyclic group-substituted)alkyldialkoxydistannoxane and/or tri(cyclic group-substituted)alkyl tin alkoxide) content was analyzed and a calibration curve was drawn based on an internal standard. Quantitative analysis was conducted for the analysis sample solution based on the resulting calibration curve.
2) Water Analysis Apparatus: CA-05 Micro Moisture Analyzer, product of Mitsubishi Chemical Corp.

An analysis sample was taken using a syringe and its mass measured, and was then directly injected into the moisture analyzer for quantitation of the moisture. The mass of the syringe was again measured and the difference used to calculate the weight of injected sample, to determine the moisture content in the sample.
3) Gas Chromatographic Analysis of Carbonic Acid Ester Compounds and Ester Compounds Apparatus: GC-2010 System by Shimadzu Corp.
(1) Preparation of Sample Solution for Analysis After weighing out 0.2 g of reaction mixture, approximately 1.5 g of dehydrated acetone (product of Wako Pure Chemical Industries, water content: ≤50 ppm) was added. After further adding approximately 0.05 g of dehydrated toluene (product of Wako Pure Chemical Industries, water content: ≤50 ppm) or diphenyl ether (special grade, product of Wako Pure Chemical Industries) as an internal standard, the mixture was used as a sample solution for gas chromatographic analysis.
(2) Gas Chromatographic Analysis Conditions Column: DB-1 (product of J&W Scientific)
Liquid phase: 100% dimethylpolysiloxane
Length: 30 m
Inner diameter: 0.25 mm
Film thickness: 1 μm
Column temperature: After holding at 50° C. for 5 minutes, the temperature was raised to 300° C. at a temperature-elevating rate of 10° C./min
Injection temperature: 300° C.
Detector temperature: 300° C.
Detector: FID
(3) Quantitative Analysis The ester compound or carbonic acid ester compound was analyzed and a calibration curve was drawn based on an internal standard. Quantitative analysis was conducted for the analysis sample solution based on the resulting calibration curve.
4) Analysis of Di(Cyclic Group-Substituted)Alkyl Tin Oxide Compounds Apparatus: Spectrum One/100 FT-IR system (ATR method), product of Perkin Elmer Placing approximately 5 mg of di(cyclic group-substituted)alkyl tin oxide on an ATR plate and applying pressure with a pressure arm, the IR spectrum was measured.

<Calculation of Tin Atom Concentration (in Active Component)>

The active component for this embodiment is an alkyl tin alkoxide that effectively functions in the reaction, and specifically it is a di(cyclic group-substituted)alkyl tin dialkoxide and/or tetra(cyclic group-substituted)alkyldialkoxydistannoxane. The tin atom concentration (in the active component) will now be defined for expressing the change in amount of active component.

The tin atom concentration (in the active component) of the di(cyclic group-substituted)alkyl tin dialkoxide was calculated by mathematical formula (1). For example, the tin atom concentration of the di(cyclic group-substituted)alkyl tin dialkoxide composition obtained by Synthesis Example 1 below was calculated by mathematical formula (1).

[Mathematical Formula 33]

$$\text{Tin atom concentration (in active component)} = C_1 \quad (1)$$

[In the formula, "tin atom concentration (in active component)" is the concentration [mol/kg] of tin atoms (in the active component) in the di(cyclic group-substituted)alkyl tin dialkoxide composition, and $C_1$: is the concentration [mol/kg] of di(cyclic group-substituted)alkyl tin dialkoxide in the di(cyclic group-substituted)alkyl tin dialkoxide composition. $C_1$ can be determined from $^{119}$Sn-NMR spectral analysis of the di(cyclic group-substituted)alkyl tin dialkoxide composition.]

The tin atom concentrations (in the active component) for the tetra(cyclic group-substituted)alkyldialkoxydistannoxane compositions were calculated by mathematical formula (2). For example, the tin atom concentration (in the active component) of the tetra(cyclic group-substituted)alkyldialkoxydistannoxane composition obtained by Synthesis Example 2 below was calculated by mathematical formula (2).

[Mathematical Formula 34]

$$\text{Tin atom concentration (in active component)} = 2 \cdot C_2 \quad (2)$$

[In the formula, "tin atom concentration (in active component)" is the concentration [mol/kg] of tin atoms (in the active component) in the tetra(cyclic group-substituted)alkyldialkoxydistannoxane composition, and $C_2$ is the concentration [mol/kg] of tetra(cyclic group-substituted)alkyldialkoxydistannoxane in the tetra(cyclic group-substituted)alkyldialkoxydistannoxane composition. $C_2$ can be determined from $^{119}$Sn-NMR spectral analysis of the tetra(cyclic group-substituted)alkyldialkoxydistannoxane composition.]

The concentration of tin atoms (in the active component) in the composition comprising a di(cyclic group-substituted)alkyl tin dialkoxide and/or tetra(cyclic group-substituted)alkyldialkoxydistannoxane or the composition further containing a tri(cyclic group-substituted)alkyl tin alkoxide, was calculated by mathematical formula (3).

[Mathematical Formula 35]

$$\text{Tin atom concentration (in active component)} = C_1 + 2 \cdot C_2 \quad (3)$$

[In the formula, "tin atom concentration (in active component)" is the concentration [mol/kg] of tin atoms of the di(cyclic group-substituted)alkyl tin dialkoxide and/or tetra(cyclic group-substituted)alkyldialkoxydistannoxane in the composition, $C_1$ is the concentration [mol/kg] of di(cyclic group-substituted)alkyl tin dialkoxide in the composition, and $C_2$ is the concentration [mol/kg] of tetra(cyclic group-substituted)alkyldialkoxydistannoxane in the composition. $C_1$ and $C_2$ can be determined by $^{119}$Sn-NMR spectral analysis of the composition.]

[Synthesis Example 1] Synthesis of di(cyclohexylmethyl)diethoxytin composition

Synthesis of di(cyclohexylmethyl)diacetoxytin

After placing 34.38 g (0.1 mol) of diphenyldichlorotin (99% purity, product of Wako Pure Chemical Industries) and 150 mL of cyclopentyl methyl ether (dehydration grade, product of Aldrich) in a 1 L-volume four-necked round bottom flask connected to a thermometer, a three-way cock and a Dimroth condenser, in a nitrogen box under a nitrogen atmosphere, a stirring bar was added and a magnetic stirrer was used for stirring at room temperature to form a homogeneous solution. Next, 400 mL of a 0.5 M tetrahydrofuran solution of cyclohexylmethylmagnesium bromide (product of Aldrich) was added to a 500 mL dropping funnel, and the dropping funnel was connected to a four-necked flask. The flask was removed from the nitrogen box and immersed in an ice bath while under a nitrogen gas atmosphere, and stirring was commenced. Dropping of the solution from the dropping funnel was then commenced, adjusting the dropping rate so that the temperature of the liquid mixture in the flask did not exceed 40° C. A white solid formed in the flask as dropping proceeded. Upon completion of the dropping, stirring of the mixture in the flask was continued for approximately 3 hours. The flask was then transferred to the nitrogen box, and a suction filter was used to filter the white solid under a nitrogen atmosphere. Distilling separation of diethyl ether and cyclopentyl methyl ether was performed from the collected filtrate. The high boiling point component after distilling separation was further subjected to distillation, and 45.5 g of di(cyclohexylmethyl)diphenyltin was obtained from the collected fraction.

The di(cyclohexylmethyl)diphenyltin was then introduced into a 300 mL-volume three-necked round bottom flask equipped with a thermometer, three-way cock and branch pipe connecting tube (the branch pipe connecting tube being connected to an apparatus having a Liebig condenser, reduced pressure connecting tube and two distillate collecting vessels linked together), and then 166.4 g (2.8 mol) of acetic acid (special grade, product of Wako Pure Chemical Industries) was added. The flask was immersed in an oil bath, and stirring and heating of the liquid mixture was initiated. The temperature of the oil bath was adjusted so that the temperature of the liquid mixture was approximately 100° C., and stirring and heating were continued for about 2 hours, after which the liquid mixture was sampled. Production of benzene in the mixture was confirmed as a result of gas chromatographic analysis. Production of benzene in the mixture was confirmed as a result of gas chromatographic analysis. The flask was then gradually reduced in pressure, and the excess acetic acid and benzene were separated by distillation. After distilling separation, di(cyclohexylmethyl)diacetoxytin was obtained from the high boiling point component.

Synthesis of di(cyclohexylmethyl)diethoxytin

The di(cyclohexylmethyl)diacetoxytin was introduced into a 300 mL-volume three-necked round bottom flask equipped with a thermometer, three-way cock and branch pipe connecting tube (the branch pipe connecting tube being connected to an apparatus having a Liebig condenser, reduced pressure connecting tube and two distillate collecting vessels linked together), under a nitrogen atmosphere, and then 295 g (2.5 mol) of diethyl carbonate (dehydration grade, product of Aldrich) was added. The flask was immersed in an oil bath, and stirring and heating of the liquid mixture was initiated. The temperature of the oil bath was adjusted so that the temperature of the liquid mixture was approximately 130° C., and stirring and heating were continued for about 8 hours, after which the liquid mixture was sampled. Production of ethyl acetate in the mixture was confirmed as a result of gas chromatographic analysis. The flask was then gradually reduced in pressure and the excess diethyl carbonate and ethyl acetate were separated out by distillation, after which 35.1 g of the high boiling point component (composition) containing di(cyclohexylmethyl) diethoxytin was collected. As a result of $^{119}$Sn-NMR spectral analysis, the amount of di(cyclohexylmethyl)diethoxytin in the composition was found to be 34.5 g. In other words, the di(cyclohexylmethyl)diethoxytin concentration in the composition was 2.44 mol/kg, and the tin atom concentration (in the active component) of the composition was 2.44 mol/kg.

[Synthesis Example 2] Synthesis of 1,1,3,3-tetra (cyclohexylmethyl)-1,3-diethoxydistannoxane composition After placing 20.2 g (0.05 mol) of the di(cyclohexylmethyl)diethoxytin obtained from Synthesis Example 1 in a 300 mL-volume four-necked round bottom flask equipped with a thermometer, three-way cock, dropping funnel and branch pipe connecting tube (the branch pipe connecting tube being connected to an apparatus having a Liebig condenser, reduced pressure connecting tube and two distillate collecting vessels linked together), 80 g of ethanol (dehydration grade, product of Wako Pure Chemical Industries) was added. Next, 85 g of ethanol and 0.45 g (0.025 mol) of ion-exchanged water were mixed in a 200 mL beaker, and upon forming a homogeneous solution it was placed in a dropping funnel. The flask was immersed in an oil bath, and stirring and heating was initiated. Dropping was initiated after adjusting the temperature of the oil bath so that the temperature of the liquid mixture was approximately 40° C. Upon completion of the dropping, the liquid mixture was kept at 40° C. and stirring was continued for 2 hours. The flask was then gradually reduced in pressure and the ethanol was distilled off, after which 18.6 g of the high boiling point component (composition) containing 1,1,3,3-tetra(cyclohexylmethyl)-1,3-diethoxydistannoxane was collected. The amount of 1,1,3,3-tetra(cyclohexylmethyl)-1,3-diethoxydistannoxane in the composition was determined by $^{119}$Sn-NMR spectral analysis to be 18.3 g. In other words, the 1,1,3,3-tetra(cyclohexylmethyl)-1,3-diethoxydistannoxane concentration in the composition was 1.34 mol/kg, and the tin atom concentration (in the active component) of the composition was 2.68 mol/kg.

[Synthesis Example 3] Synthesis of Tri(Cyclic group-substituted)alkyl tin alkoxide-containing composition After introducing 15 g of 1,1,3,3-tetra(cyclohexylmethyl)-1,3-diethoxydistannoxane produced by the method of Synthesis Example 2 into a 50 mL-volume three-necked flask equipped with a Dimroth condenser, silicon cap and thermometer connected with a three-way cock, using a gas-tight syringe (1050TLL, product of Hamilton), 10 g of di(cyclohexylmethyl)diethoxytin produced by the method of Synthesis Example 1 was then subsequently introduced, to prepare a cyclic group-substituted alkyl tin alkoxide composition comprising 1,1,3,3-tetra(cyclohexylmethyl)-1,3-diethoxydistannoxane and di(cyclohexylmethyl)diethoxytin. The flask was immersed in an oil bath that had been heated to 186° C. Upon stirring and heating for approximately 15 minutes, the liquid temperature of the cyclic group-substituted alkyl tin alkoxide composition in the flask had reached 180° C. Stirring and heating were continued while periodically sampling and $^{119}$Sn-NMR spectral analysis was performed, and upon confirming production of 0.0045 mol of tri(cyclohexylmethyl)ethoxytin in the composition, the heating was suspended. The post-heating component ratio was expressed as follows in terms of tin atoms. The tin atom concentration (in the active component) of the composition comprising di(cyclohexylmethyl)diethoxytin and 1,1,3,3-tetra(cyclohexylmethyl)-1,3-diethoxy-distannoxane before heating was 2.58 mol/kg as calculated by mathematical formula (3), and the concentration of tin atoms derived from the starting materials in the composition after heating (the concentration of tin atoms determined from the contents of the di(cyclohexylmethyl)diethoxytin and 1,1,3,3-tetra(cyclohexylmethyl)-1,3-diethoxydistannoxane) changed to 2.22 mol/kg (reduction of approximately 14% compared to before heating), while the concentration of tri(cyclohexylmethyl)ethoxytin was 0.18 mol/kg. In other words, the tri(cyclic group-substituted)alkyl tin alkoxide-containing composition that was obtained had approximately 7% modified to tri(cyclohexylmethyl)ethoxytin with respect to the tin atom concentration (in the active component) of the cyclic group-substituted alkyl tin alkoxide composition before heating.

[Synthesis Example 4] Synthesis of dibenzylbis(3-methylbutyloxy)tin composition

Synthesis of dibenzyldichlorotin

After introducing 17.81 g (0.15 mol) of metal tin powder (99.9% purity, product of Wako Pure Chemical Industries), 100 mL of toluene (dehydration grade, product of Wako Pure Chemical Industries) and 38.9 g (0.31 mol) of benzyl chloride (99.5% purity, product of Aldrich) into a 500 mL-volume four-necked round bottom flask connected to a thermometer, three-way cock and Dimroth condenser in a nitrogen box, a stirring bar was added. The flask was removed from the nitrogen box and immersed in an oil bath while kept under a nitrogen gas atmosphere, and stirring and heating of the liquid mixture was initiated. The temperature of the oil bath was adjusted to a state with the liquid mixture boiling and toluene in stable reflux, and stirring and heating were continued for about 3 hours.

The liquid mixture was then introduced into a 300 mL-volume three-necked round bottom flask equipped with a thermometer, three-way cock and branch pipe connecting tube (the branch pipe connecting tube being connected to an apparatus having a Liebig condenser, reduced pressure connecting tube and two distillate collecting vessels linked together). The flask was immersed in an oil bath, and stirring and heating of the liquid mixture was initiated. The temperature of the oil bath was adjusted so that the temperature of the liquid mixture was 100° C., and then the flask was gradually reduced in pressure and toluene was distilled off. Dibenzyldichlorotin composition was obtained from the high boiling point component after distilling separation. The dibenzyldichlorotin composition was recrystallized using ethyl acetate, and the dibenzyldichlorotin was purified. The amount of dibenzyldichlorotin collected was 33.5 g.

Synthesis of dibenzyltin oxide

After placing 33.0 g (0.089 mol) of the dibenzyldichlorotin and 50 mL of cyclopentyl methyl ether (dehydration grade, product of Aldrich) in a 500 mL-volume four-necked round bottom flask connected to a thermometer, a three-way cock and a Dimroth condenser, in a nitrogen box, a stirring bar was added and a magnetic stirrer was used for stirring at room temperature to form a homogeneous solution. Next, 180 mL of a 1M ethanol solution of potassium hydroxide (product of Wako Pure Chemical Industries) was placed in a 200 mL dropping funnel, and the dropping funnel was connected to the four-necked flask. The flask was removed from the nitrogen box and immersed in an ice bath while under a nitrogen gas atmosphere, and stirring was commenced. Dropping of the solution from the dropping funnel was then commenced, adjusting the dropping rate so that the temperature of the liquid mixture in the flask did not exceed 40° C. A white solid formed in the flask as dropping proceeded. Upon completion of the dropping, stirring of the mixture in the flask was continued for about 3 hours, and a suction filter was used in a nitrogen box for filtration of the white solid. The collected solid was rinsed 3 times with ion-exchanged water and two times with acetone, and then vacuum dried. The amount of dried solid was 24.5 g, and as a result of measuring the IR spectrum of the solid, it was found to have a dibenzyltin oxide content of approximately 98.7%.

Synthesis of dibenzylbis(3-methylbutyloxy)tin composition

Into a 1 L-volume round bottom flask there were introduced 25.4 g (0.08 mol) of dibenzyltin oxide and 881.5 g (10 mol) of 3-methyl-1-butyl alcohol (product of Aldrich). The flask containing the white slurry-like mixture was mounted on an evaporator connected to an oil bath with a temperature regulator, and a vacuum pump and vacuum controller. The oil bath temperature was set to 140° C., the flask was immersed in the oil bath, and rotation of the evaporator was commenced. After rotated stirring and heating for about 20 minutes at ordinary pressure with the purge valve of the evaporator left open, a distillate containing mainly 3-methyl-1-butyl alcohol began to be collected. This state was maintained for 5 hours, and then the flask was raised out of the oil bath. The reaction mixture was a transparent liquid. The total amount of the distillate was 620.5 g, and analysis of the distillate with a micro moisture analyzer revealed a moisture content of 1.48 g (0.08 mol). The temperature of the oil bath was then set to 120° C., the flask was again immersed in an oil bath and stirred while rotating for about 20 minutes at ordinary pressure, and then in order to remove the excess 3-methyl-1-butyl alcohol, the purge valve of the evaporator was closed and the vacuum pump and vacuum controller were used to gradually reduce the pressure in the system to 1.8 to 2.5 kPa. This state was maintained for 3 hours, and then the flask was raised out of the oil bath, the purge valve was slowly opened and dry nitrogen gas was introduced into the system to restore it to ordinary pressure. After distillation, 38.7 g of the high boiling point component (composition) containing dibenzylbis(3-methylbutyloxy)tin was collected. As a result of $^{119}$Sn-NMR spectral analysis of the composition, it was found to contain 38.1 g of dibenzylbis(3-methylbutyloxy)tin. In other words, the dibenzylbis (3-methylbutyloxy)tin concentration in the composition was 2.07 mol/kg, and the tin atom concentration (in the active component) of the composition was 2.07 mol/kg.

[Synthesis Example 5] Synthesis of 1,1,3,3-tetrabenzyl-1,3-bis(3-methylbutyloxy)-distannoxane composition After introducing 38.0 g (0.08 mol) of the dibenzylbis(3-methylbutyloxy)tin obtained from Synthesis Example 4 into a 300 mL-volume four-necked round bottom flask equipped with a thermometer, three-way cock, dropping funnel and branch pipe connecting tube (the branch pipe connecting tube being connected to an apparatus having a Liebig condenser, reduced pressure connecting tube and two distillate collecting vessels linked together), 100 g of isoamyl alcohol (special grade, product of Wako Pure Chemical Industries) that had been purified by distillation was added. Next, 100 g of isoamyl alcohol and 0.72 g (0.04 mol) of ion-exchanged water were mixed in a 200 mL beaker, and upon forming a homogeneous solution it was placed in a dropping funnel. The flask was immersed in an oil bath, and stirring and heating were initiated. Dropping was initiated after adjusting the temperature of the oil bath so that the temperature of the liquid mixture was approximately 45° C. Upon completion of the dropping, the liquid mixture was kept at 45° C. and stirring was continued for 2 hours. The flask was then gradually reduced in pressure, and distilling separation of the isoamyl alcohol was performed. After distillation, 31.8 g of the high boiling point component (composition) containing 1,1,3,3-tetrabenzyl-1,3-bis(3-methylbutyloxy)distannoxane was collected. As a result of $^{119}$Sn-NMR spectral analysis of the composition, it was found to contain 31.4 g of 1,1,3,3-tetrabenzyl-1,3-bis(3-methylbutyloxy)distannoxane. In other words, the 1,1,3,3-tetrabenzyl-1,3-bis(3-methylbutyloxy)distannoxane concentration in the composition was 1.25 mol/kg, and the tin atom concentration (in the active component) of the composition was 2.50 mol/kg.

[Synthesis Example 6] Synthesis of tri(cyclic group-substituted)alkyl tin alkoxide-containing composition A gas-tight syringe (1050TLL, product of Hamilton) was used to introduce 15 g of 1,1,3,3-tetrabenzyl-1,3-bis(3-methylbutyloxy)distannoxane produced by the method of Synthesis Example 2 into a 50 mL-volume three-necked flask equipped with a Dimroth condenser, silicon cap and thermometer connected with a three-way cock, and then 10 g of dibenzylbis(3-methylbutyloxy)tin produced by the method of Synthesis Example 1 was introduced in the same manner, to prepare a cyclic group-substituted alkyl tin alkoxide composition comprising 1,1,3,3-tetrabenzyl-1,3-bis(3-methylbutyloxy)distannoxane and dibenzylbis(3-methylbutyloxy)tin. The flask was immersed in an oil bath that had been heated to 186° C. Upon stirring and heating for approximately 15 minutes, the liquid temperature of the cyclic group-substituted alkyl tin alkoxide composition in the flask had reached 180° C. Stirring and heating were continued while periodically sampling and $^{119}$Sn-NMR spectral analysis was performed, and upon confirming production of 0.0041 mol of tribenzyl(3-methylbutyloxy)tin in the composition, the heating was suspended. The post-heating component ratio was expressed as follows in terms of tin atoms. The tin atom concentration (in the active component) of the composition comprising dibenzylbis(3-methylbutyloxy)tin and 1,1,3,3-tetrabenzyl-1,3-bis(3-methylbutyloxy)distannoxane before heating was 2.33 mol/kg, as calculated by mathematical formula (3), and the concentration of tin atoms derived from the starting material in the composition after heating (the concentration of tin atoms determined from the dibenzylbis(3-methylbutyloxy)tin and 1,1,3,3-tetrabenzyl-1,3-bis(3-methylbutyloxy)distannoxane contents) changed to 2.03 mol/kg (reduction of approximately 13% compared to before heating), while the concentration of tin atoms derived from tribenzyl (3-methylbutyloxy)tin was 0.16 mol/kg. In other words, the tri(cyclic group-substituted)alkyl tin alkoxide-containing composition that was obtained had approximately 7% modified to tribenzyl(3-methylbutyloxy)tin with respect to the tin atom concentration (in the active component) of the cyclic group-substituted alkyl tin alkoxide composition before heating.

[Synthesis Example 7] Synthesis of bis(2-phenylethyl)bis(3-methylbutyloxy)tin composition Synthesis of bis(2-phenylethyl)dichlorotin After introducing 17.81 g (0.15 mol) of metal tin powder (99.9% purity, product of Wako Pure Chemical Industries), 100 mL of toluene (dehydration grade, product of Wako Pure Chemical Industries) and 43.6 g (0.31 mol) of 2-chloroethylbenzene (99% purity, product of Aldrich) into a 500 mL-volume four-necked round bottom flask connected to a thermometer, three-way cock and Dimroth condenser in a nitrogen box, a stirring bar was added. The flask was removed from the nitrogen box and immersed in an oil bath while kept under a nitrogen gas atmosphere, and stirring and heating of the liquid mixture was initiated. The temperature of the oil bath was adjusted to a state with the liquid mixture boiling and toluene in stable reflux, and stirring and heating were continued for about 5 hours.

The liquid mixture was then introduced into a 300 mL-volume three-necked round bottom flask equipped with a thermometer, three-way cock, branch pipe connecting tube, Liebig condenser, reduced pressure connecting tube and two distillate collecting vessels. The flask was immersed in an oil bath, and stirring and heating of the liquid mixture were initiated. The temperature of the oil bath was adjusted so that the temperature of the liquid mixture was 100° C., and then the flask was gradually reduced in pressure and toluene was distilled off. After distillation, a bis(2-phenylethyl)dichlorotin composition was obtained from the high boiling point component. The bis(2-phenylethyl)dichlorotin composition was recrystallized using ethyl acetate to purify the bis(2-phenylethyl)dichlorotin. The amount of bis(2-phenylethyl)dichlorotin collected was 35.5 g.

Synthesis of bis(2-phenylethyl)tin oxide

After placing 34.5 g (0.086 mol) of the bis(2-phenylethyl)dichlorotin and 50 mL of cyclopentyl methyl ether (dehydration grade, product of Aldrich) in a 500 mL-volume four-necked round bottom flask connected to a thermometer, a three-way cock and a Dimroth condenser, in a nitrogen box, a stirring bar was added and a magnetic stirrer was used for stirring at room temperature to form a homogeneous solution. Next, 172 mL of a 1M ethanol solution of potassium hydroxide (product of Wako Pure Chemical Industries) was placed in a 200 mL dropping funnel, and the dropping funnel was connected to the four-necked flask. The flask was removed from the nitrogen box and immersed in an ice bath while under a nitrogen gas atmosphere, and stirring was commenced. Dropping of the solution from the dropping funnel was then commenced, adjusting the dropping rate so that the temperature of the liquid mixture in the flask did not exceed 40° C. A white solid formed in the flask as dropping proceeded. Upon completion of the dropping, stirring of the mixture in the flask was continued for about 3 hours, and a suction filter was used in a nitrogen box for filtration of the white solid. The collected solid was rinsed 3 times with ion-exchanged water and two times with acetone, and then vacuum dried. The amount of dried solid was 26.1 g, and as a result of measuring the IR spectrum of the solid, it was found to have a bis(2-phenylethyl)tin oxide content of approximately 25.8 g.

Synthesis of bis(2-phenylethyl)bis(3-methylbutyloxy)tin composition

Into a 1 L-volume round bottom flask there were introduced 24.1 g (0.07 mol) of bis(2-phenylethyl)tin oxide and 881.5 g (10 mol) of 3-methyl-1-butyl alcohol (product of Aldrich). The flask containing the white slurry-like mixture was mounted on an evaporator connected to an oil bath with a temperature regulator, and a vacuum pump and vacuum controller. The oil bath temperature was set to 140° C., the flask was immersed in the oil bath, and rotation of the evaporator was commenced. After rotated stirring and heating for about 20 minutes at ordinary pressure with the purge valve of the evaporator left open, a distillate containing mainly 3-methyl-1-butyl alcohol began to be collected. This state was maintained for 5 hours, and then the flask was raised out of the oil bath. The reaction mixture was a transparent liquid. The total amount of the obtained distillate was 630.5 g, and analysis of the distillate with a micro moisture analyzer revealed a moisture content of 1.27 g (0.07 mol). The temperature of the oil bath was then set to 120° C., the flask was again immersed in an oil bath and stirred while rotating for about 20 minutes at ordinary pressure, and then in order to remove the excess 3-methyl-1-butyl alcohol, the purge valve of the evaporator was closed and the vacuum pump and vacuum controller were used to gradually reduce the pressure in the system to 1.8 to 2.5 kPa. This state was maintained for 3 hours, and then the flask was raised out of the oil bath, the purge valve was slowly opened and dry nitrogen gas was introduced into the system to restore it to ordinary pressure. After distillation, 35.8 g of the high boiling point component (composition) containing bis (2-phenylethyl)bis(3-methylbutyloxy)tin was collected. As a result of $^{119}$Sn-NMR spectral analysis of the composition, it was found to contain 35.3 g of bis(2-phenylethyl)bis(3-methylbutyloxy)tin. In other words, the bis(2-phenylethyl) bis(3-methylbutyloxy)tin concentration in the composition was 1.96 mol/kg, and the tin atom concentration (in the active component) of the composition was 1.96 mol/kg.

[Synthesis Example 8] Synthesis of 1,1,3,3-tetrakis (2-phenylethyl)-1,3-bis(3-methylbutyloxy)distannoxane composition After introducing 30.2 g (0.06 mol) of the bis(2-phenylethyl)bis(3-methylbutyloxy)tin obtained from Synthesis Example 4 into a 300 mL-volume four-necked round bottom flask equipped with a thermometer, three-way cock, dropping funnel, branch pipe connecting tube, Liebig condenser, reduced pressure connecting tube and two distillate collecting vessels), 100 g of isoamyl alcohol (special grade, product of Wako Pure Chemical Industries) that had been purified by distillation was added. Next, 100 g of isoamyl alcohol and 0.54 g (0.03 mol) of ion-exchanged water were mixed in a 200 mL beaker, and upon forming a homogeneous solution it was placed in a dropping funnel. The flask was immersed in an oil bath, and stirring and heating were initiated. Dropping was initiated after adjusting the temperature of the oil bath so that the temperature of the liquid mixture was approximately 45° C. Upon completion of the dropping, the liquid mixture was kept at 45° C. and stirring was continued for 2 hours. The flask was then gradually reduced in pressure, and distilling separation of the isoamyl alcohol was performed. After distillation, 25.5 g of the high boiling point component (composition) containing 1,1,3,3-tetrakis(2-phenylethyl)-1,3-bis(3-methylbutyloxy)distannoxane was collected. As a result of $^{119}$Sn-NMR spectral analysis of the composition, the composition was found to contain 25.1 g of 1,1,3,3-tetrakis(2-phenylethyl)-1,3-bis(3-methylbutyloxy)distannoxane. In other words, the 1,1,3,3-tetrakis(2-phenylethyl)-1,3-bis(3-methylbutyloxy)distannoxane concentration in the composition was 1.16 mol/kg, and the tin atom concentration (in the active component) of the composition was 2.32 mol/kg.

[Synthesis Example 9] Synthesis of tri(cyclic group-substituted)alkyl tin alkoxide-containing composition A gas-tight syringe (1050TLL, product of Hamilton) was used to introduce 15 g of 1,1,3,3-tetrakis(2-phenylethyl)-1, 3-bis(3-methylbutyloxy)distannoxane produced by the method of Synthesis Example 2 into a 50 mL-volume three-necked flask equipped with a Dimroth condenser, silicon cap and thermometer connected with a three-way cock, and then 10 g of bis(2-phenylethyl)bis(3-methylbutyloxy)tin produced by the method of Synthesis Example 1 was introduced in the same manner, to prepare a cyclic group-substituted alkyl tin alkoxide composition comprising 1,1,3,3-tetrakis(2-phenylethyl)-1,3-bis(3-methylbutyloxy) distannoxane and bis(2-phenylethyl)bis(3-methylbutyloxy) tin. The flask was immersed in an oil bath that had been heated to 186° C. Upon stirring and heating for approximately 15 minutes, the liquid temperature of the cyclic group-substituted alkyl tin alkoxide composition in the flask had reached 180° C. Stirring and heating were continued while periodically sampling, $^{119}$Sn-NMR spectral analysis was performed, and upon confirming production of 0.0038 mol of tris(2-phenylethyl)(3-methylbutyloxy)tin in the composition, the heating was suspended. The post-heating component ratio was expressed as follows in terms of tin atoms. The tin atom concentration (in the active component) of the composition comprising bis(2-phenylethyl)bis(3-methylbutyloxy)tin and 1,1,3,3-tetrakis(2-phenylethyl)-1,3-bis(3-methylbutyloxy)distannoxane before heating was 2.18 mol/kg, as calculated by mathematical formula (3), and the concentration of tin atoms derived from the starting material in the composition after heating (the concentration of tin atoms determined from the bis(2-phenylethyl)bis(3-methylbutyloxy)tin and 1,1,3,3-tetrakis(2-phenylethyl)-1,3-bis(3-methylbutyloxy)distannoxane contents) changed to 1.87 mol/kg (reduction of approximately 14% compared to before heating), while the concentration of tin atoms derived from tris(2-phenylethyl)(3-methylbutyloxy)tin was 0.15 mol/kg. In other words, the tri(cyclic group-substituted) alkyl tin alkoxide-containing composition that was obtained had approximately 7% modified to tris(2-phenylethyl)(3-methylbutyloxy)tin with respect to the tin atom concentration (in the active component) of the cyclic group-substituted alkyl tin alkoxide composition before heating.

[Synthesis Example 10] Synthesis of 1,1,3,3-tetrabutyl-1,3-bis(2-ethylbutyloxy)distannoxane composition In a 2 L-volume three-necked flask equipped with a thermometer, a three-way cock, and a water measuring receptacle connected to a Dimroth condenser there were placed 199.8 g (0.80 mol) of dibutyltin oxide (product of Aldrich), 1045 g (8.0 mol) of 2-ethyl-1-butyl alcohol (product of Aldrich) and 500 g of toluene (for organic synthesis, product of Wako Pure Chemical Industries). The flask containing the white slurry-like mixture was immersed in an oil bath set to 130° C. After stirring and heating for about 30 minutes, the mixture began to boil and thus water and toluene began to be collected in the water measuring receptacle.

After maintaining this state for about 3 hours, approximately 7.2 mL of water was collected in the water measuring receptacle. The temperature of the oil bath was then lowered to 90° C., and once the mixture temperature fell, the water measuring receptacle was removed and the flask was connected to a branch pipe connecting tube, Liebig condenser, reduced pressure connecting tube and two distillate collecting vessels. The system interior was reduced to a pressure of 29 kPa and toluene was distilled from the flask, after which the system interior was reduced in pressure to distill off the excess 2-ethyl-1-butyl alcohol. After distillation, 300 g of the high boiling point component (composition) was collected from the flask. As a result of $^{119}$Sn-NMR spectral analysis of the composition, the composition was found to contain 295 g of 1,1,3,3-tetrabutyl-1,3-bis(2-ethylbutyloxy)distannoxane.

[Synthesis Example 11] Synthesis of dibutyl-bis(2-ethylbutyloxy)tin composition

In a 1 L-volume round bottom flask there were placed 20.1 g (0.081 mol) of dibutyltin oxide (product of Aldrich) and 835 g (8.2 mol) of 2-ethyl-1-butyl alcohol (product of Aldrich). The flask containing the white slurry-like mixture was mounted on an evaporator connected to an oil bath with a temperature regulator, and a vacuum pump and vacuum controller. The oil bath temperature was set to 150° C., the flask was immersed in the oil bath, and rotation of the evaporator was commenced. After rotated stirring and heating for about 20 minutes at ordinary pressure with the purge valve of the evaporator left open, the evaporator purge valve was closed and the system interior was gradually reduced in pressure using a vacuum pump and vacuum controller to 54 to 75 kPa. This state was maintained for 1.5 hours, and then the flask was raised out of the oil bath. The reaction mixture was a transparent liquid. The purge valve was gradually opened to introduce dry nitrogen gas into the system, restoring the pressure in the system to ordinary pressure. The distilled liquid amount was 99.2 g, and it was transparent and separated into 2 layers. Analysis of the distilled liquid with a micro moisture analyzer revealed a moisture content of 1.5 g (0.083 mol). The temperature of the oil bath was then lowered to 100° C., the flask was again immersed in an oil bath and stirred while rotating and stirred normally, for about 20 minutes at ordinary pressure, and then in order to remove the excess 2-ethyl-1-butyl alcohol, the purge valve of the evaporator was closed and the vacuum pump and vacuum controller were used to gradually reduce the pressure in the system to 1.8 to 2.5 kPa. This state was maintained for 3 hours, and then the flask was raised out of the oil bath and the purge valve was slowly opened to restore the system interior to ordinary pressure. After distillation, 36 g of the high boiling point component (composition) was collected from the flask. As a result of $^{119}$Sn-NMR spectral analysis of the composition, the dibutyl-bis(2-ethylbutoxy)tin content of the composition was found to be 35.5 g.

Example 1

FIG. 1 shows a continuous circulating reactor comprising a tank reactor, tube reactor and tower reactor for transesterification reaction. The tetra(cyclic group-substituted) alkyldialkoxydistannoxane composition was introduced into the continuous circulating reactor and circulated for test operation. Approximately 50 kg of a 1,1,3,3-tetrabenzyl-1,3-bis(3-methylbutyloxy)distannoxane composition produced by the method of Synthesis Example 5 (tin atom concentration (in the active component) of the composition: 2.49 mol/kg) was placed in a SUS316 catalyst tank 130, equipped with a heating jacket and a liquid conveyance pump, through a supply line 15. The composition was circulated in the catalyst tank 130 for about 10 hours. Next, using a chemical gear pump, the 1,1,3,3-tetrabenzyl-1,3-bis (3-methylbutyloxy)-distannoxane composition was conveyed from the catalyst tank 130 to a tank reactor 140 at 15 kg/hr, via a transport line 14, an inline mixer 141 equipped with a heating jacket, and a transport line 5. The tank reactor 140 was a 15 L-volume reactor, comprising a stirrer, heating jacket and liquid conveyance pump, and the heating jacket was heated with steam at about 155° C. The tube reactor 150 with an outer diameter of 200 mm and a length of 1000 mm also comprised a heating jacket, which was heated with steam at about 160° C. A SUS316 tower reactor 160 with an inner diameter of 75 mm and an effective length of 4500 mm, equipped with 30 sieve trays, was heated and thermally insulated with a heater around the entire tower reactor to prevent radiated heat loss, the heater being set to about 150° C. A liquid conveyance pump and reboiler 163 were provided at the bottom of the tower reactor 160, and the reboiler 163 was heated with steam at about 160° C. A thin-film vaporizer 170 with a heat transfer area of 0.1 m$^2$ was equipped with a heating jacket and a chemical gear pump for liquid conveyance of the high boiling point component, the heating jacket being heated with steam at 160° C. and the pressure of the thin-film vaporizer 170 being set to 115 kPaA. The tank and pipe were steam traced to maintain the flow property. The composition conveyed to the tank reactor 140 was then conveyed to the tube reactor 150 through a transport line 6, subsequently conveyed to the tower reactor 160 through a transport line 7, and then conveyed to the thin-film vaporizer 170 through a transport line 9, after which it was conveyed to the catalyst tank 130 through a transport line 11. The composition was thus continuously circulated through the tank reactor 140, tube reactor 150, tower reactor 160, thin-film vaporizer 170 and catalyst tank 130 via the transport line 14, inline mixer 141, transport line 5, transport line 6, transport line 7, transport line 9 and transport line 11, and this was continued for about 5 days. Next, the solution in the catalyst tank 130 was sampled from an extraction line 16, and as a result of $^{119}$Sn-NMR spectral analysis, 1,1,3,3-tetrabenzyl-1,3-bis(3-methylbutyloxy)distannoxane and tribenzyl-(3-methylbutyloxy)tin were confirmed to be present after the test operation. Upon calculating the concentration of tin atoms from the 1,1,3,3-tetrabenzyl-1,3-bis(3-methylbutyloxy)distannoxane concentration in the composition in the catalyst tank 130 after test operation determined by the analysis results, it was found to be 2.33 mol/kg, which was a 6.4% reduction compared to before start of the test operation. On the other hand, tribenzyl-(3-methylbutoxy)tin was produced at 3.9 mol, which was 3.1% of the number of moles of tin atoms (in the active component) of the composition placed in the catalyst tank before starting the test operation.

Example 2

FIG. 2 shows a continuous circulating reactor comprising a tube reactor for transesterification reaction and a tower reactor. The di(cyclic group-substituted)alkyl tin dialkoxide composition was placed in the continuous circulating reactor and circulated for test operation. After placing approximately 45 kg of a dibenzyl-bis(3-methylbutyloxy)tin composition produced by the method of Synthesis Example 4 (tin atom concentration (in the active component) of composition: 2.07 mol/kg) in a SUS316 catalyst tank 230 equipped with a heating jacket and a liquid conveyance pump, via a supply line 33, the composition was circulated in the catalyst tank 230 for about 10 hours. Next, using a chemical gear pump, the composition was conveyed from the catalyst tank 230 to a tube reactor 240 at 8.5 kg/hr, via a transport line 34, an inline mixer 241 equipped with a heating jacket, and a transport line 25. The tube reactor 240 with an outer diameter of 250 mm and a length of 1500 mm also comprised a heating jacket, which was heated with steam at about 140° C. A SUS316 tower reactor 250 with an inner diameter of 75 mm and an effective length of 4500 mm, equipped with 30 sieve trays, was heated and thermally insulated with a heater around the entire tower reactor to prevent radiated heat loss, the heater being set to about 150° C. At the bottom of the tower reactor 250 there were provided a liquid conveyance pump and reboiler 253, and the reboiler 253 was heated with steam at about 160° C. Also, a thin-film vaporizer 260 (heat transfer area: 0.1 m$^2$), equipped with a heating jacket and a chemical gear pump for liquid conveyance of the high boiling point component, was heated to 170° C., and the pressure was set to 115 kPaA. The tank and pipe were steam traced to maintain the flow property. The composition conveyed to the tube reactor 240 was then conveyed to the tower reactor 250 through a transport line 26, subsequently conveyed to the thin-film vaporizer 260 through a transport line 28, and then conveyed to the catalyst tank 230 through a transport line 30. The composition was thus continuously circulated through the tube reactor 240, tower reactor 250, thin-film vaporizer 260 and catalyst tank 230 via the transport line 34, inline mixer 241, transport line 25, transport line 26, transport line 28 and transport line 30, and this was continued for about 6 days. Next, the liquid in the catalyst tank 230 was sampled from an extraction line 35, and as a result of $^{119}$Sn-NMR spectral analysis it was confirmed that dibenzyl-bis(3-methylbutyloxy)tin and tribenzyl-(3-methylbutoxy)tin were present after the test operation. Upon calculating the concentration of tin atoms from the dibenzyl-bis(3-methylbutyloxy)tin concentration of the composition in the catalyst tank 230 after test operation, as determined by the analysis results, it was found to be 1.95 mol/kg, which was a reduction of 5.9% compared to before start of the test operation. On the other hand, tribenzyl-(3-methylbutoxy)tin was produced at 2.6 mol, which was 2.8% of the number of moles of tin atoms (in the active component) of the composition placed in the catalyst tank before starting the test operation.

Example 3

FIG. 3 shows a continuous circulating reactor comprising a tank reactor and tower reactor for transesterification reaction. The cyclic group-substituted alkyl tin alkoxide composition was placed in the continuous circulating reactor and circulated for test operation. Dibenzyl-bis(3-methylbutyloxy)tin and 1,1,3,3-tetrabenzyl-1,3-bis(3-methylbutyloxy) distannoxane produced by the methods of Synthesis Example 4 and Synthesis Example 5 were mixed to prepare a cyclic group-substituted alkyl tin alkoxide composition. It was prepared so that the molar ratio of tin atoms of the dibenzyl-bis(3-methylbutyloxy)tin and 1,1,3,3-tetrabenzyl-1,3-bis(3-methylbutyloxy)distannoxane with respect to the number of moles of tin atoms (in the active component) in the cyclic group-substituted alkyl tin alkoxide composition was 65:35. The tin atom concentration (in the active component) of the cyclic group-substituted alkyl tin alkoxide composition calculated by mathematical formula (3) was 2.22 mol/kg. Approximately 60 kg of the cyclic group-substituted alkyl tin alkoxide composition was introduced into a SUS316 catalyst tank 330 equipped with a heating jacket and liquid conveyance pump, through a supply line 53. The cyclic group-substituted alkyl tin alkoxide composition was first circulated in the catalyst tank 330 for about 10 hours. Next, using a chemical gear pump, the cyclic group-substituted alkyl tin alkoxide composition was conveyed from the catalyst tank 330 to a tank reactor 340 at 11 kg/hr, via a transport line 54, an inline mixer 341 and a transport line 45. The tank reactor 340 was a 15 L-volume reactor, comprising a stirrer, heating jacket and liquid conveyance pump, and the heating jacket was heated with steam at about 150° C. A SUS316 tower reactor 350 with an inner diameter of 76 mm and an effective length of 3500 mm, equipped with 25 sieve trays, was heated and thermally insulated with a heater around the entire tower reactor to prevent radiated heat loss, the heater being set to about 150° C. A liquid conveyance pump and reboiler 353 were provided at the bottom of the tower reactor 350, and the reboiler 353 was heated with steam at about 160° C. Also, a thin-film vaporizer 360 (heat transfer area: 0.1 m$^2$), equipped with a heating jacket and a liquid conveyance pump for conveyance of the high boiling point component, was heated to 165° C., and the pressure was set to 115 kPaA. The tank and pipe were steam traced to maintain the flow property. The cyclic group-substituted alkyl tin alkoxide composition conveyed to the tank reactor 340 was then conveyed to the tower reactor 350 through a transport line 46, subsequently conveyed to the thin-film vaporizer 360 through a transport line 48, and then conveyed to the catalyst tank 330 through a transport line 50. The cyclic group-substituted alkyl tin alkoxide composition was thus continuously circulated through the tank reactor 340, tower reactor 350, thin-film vaporizer 360 and catalyst tank 330 via the transport line 54, inline mixer 341, transport line 45, transport line 46, transport line 48 and transport line 50, and this was continued for about 5 days. Next, the solution in the catalyst tank 330 was sampled from an extraction line 55, and as a result of $^{119}$Sn-NMR spectral analysis, dibenzyl-bis(3-methylbutyloxy)tin, 1,1,3,3-tetrabenzyl-1,3-bis(3-methylbutyloxy)distannoxane and tribenzyl-(3-methylbutoxy)-tin were confirmed to be present after the test operation. Upon calculating the concentration of tin atoms of the composition after test operation, by determining the dibenzyl-bis(3-methylbutyloxy)tin concentration and 1,1,3,3-tetrabenzyl-1,3-bis(3-methylbutyloxy)distannoxane concentration in the catalyst tank 330 after test operation, based on the analysis results, it was found to be 2.09 mol/kg, which was a 5.8% reduction compared to before start of the test operation. On the other hand, tribenzyl-(3-methylbutoxy)tin was produced at 3.9 mol, which was 2.9% of the number of moles of tin atoms (in the active component) of the cyclic group-substituted alkyl tin alkoxide composition before starting the test operation.

Example 4

FIG. 4 shows a continuous circulating reactor for carbonic acid ester synthesis using a cyclic group-substituted alkyl tin alkoxide composition. The cyclic group-substituted alkyl tin alkoxide composition was placed in the continuous circulating reactor and circulated for test operation.

A tri(cyclic group-substituted)alkyl tin alkoxide-containing composition (cyclic group-substituted alkyl tin alkoxide composition comprising 1,1,3,3-tetrakis(2-phenylethyl)-1,3-bis(3-methylbutyloxy)distannoxane, bis(2-phenylethyl)bis(3-methylbutyloxy)tin and tris(2-phenylethyl)(3-methylbutyloxy)tin) was produced by the method of Synthesis Example 9. As a result of calculating the tin atom concentration (in the active component) of the composition from the 1,1,3,3-tetrakis(2-phenylethyl)-1,3-bis(3-methylbutyloxy)distannoxane concentration and bis(2-phenylethyl)bis(3-methylbutyloxy)tin concentration determined from the analysis results, it was found to be 1.91 mol/kg. The tris(2-phenylethyl)(3-methylbutyloxy)tin concentration was 0.13 mol/kg. Approximately 60 kg of the cyclic group-substituted alkyl tin alkoxide composition was introduced into a SUS316 catalyst tank 660 equipped with a heating jacket and liquid conveyance pump, through a supply line 78. The composition was first circulated in the catalyst tank 660 for about 10 hours. Next, using a chemical gear pump, the composition was conveyed from the catalyst tank 660 to a tower reactor 620 at 11 kg/hr, via a transport line 74, an inline mixer 621 equipped with a heating jacket, and a transport line 65. A SUS316 tower reactor 620 with an inner diameter of 76 mm and an effective length of 4500 mm, equipped with 30 sieve trays, was heated and thermally insulated with a heater around the entire tower reactor to prevent radiated heat loss, the heater being set to about 150° C. A liquid conveyance pump and reboiler 622 were provided at the bottom of the tower reactor 620, and the reboiler 622 was heated with steam at about 155° C. An autoclave 630 was used which was a 15 L-volume reactor, comprising a stirrer, heating jacket and liquid conveyance pump, and the heating jacket was heated with steam at about 150° C. A thin-film vaporizer 640 (heat transfer area: 0.1 m²) and a thin-film vaporizer 650 (heat transfer area: 0.2 m²) set to 115 kPaA pressure were equipped with a heating jacket and a liquid conveyance pump for conveyance of the high boiling point component, and steam at about 160° C. was used for heating. The tank and pipe were steam traced to maintain the flow property. The composition that had been conveyed to the tower reactor 620 was conveyed to the autoclave 630 through a transport line 67, and then conveyed to the thin-film vaporizer 640 through a transport line 69 and further conveyed to the thin-film vaporizer 650 through a transport line 71, after which it was conveyed to the catalyst tank 660 through a transport line 73. The composition was thus continuously circulated through the tower reactor 620, autoclave 630, thin-film vaporizer 640, thin-film vaporizer 650 and catalyst tank 660 via the transport line 74, inline mixer 621, transport line 65, transport line 67, transport line 69, transport line 71 and transport line 73, and this was continued for about 5 days. Next, the liquid in the catalyst tank 660 was sampled from an extraction line 79 and $^{119}$Sn-NMR spectral analysis was performed. Upon calculating the tin atom concentration (in the active component) in the composition from the 1,1,3,3-tetrakis(2-phenylethyl)-1,3-bis(3-methylbutyloxy)distannoxane concentration and bis(2-phenylethyl)bis(3-methylbutyloxy)tin concentration in the catalyst tank 660 after test operation, determined from the analysis results, it was found to be 1.79 mol/kg, which was a 6.2% reduction compared to before start of the test operation. On the other hand, the tris(2-phenylethyl)(3-methylbutyloxy)tin was produced at 3.4 mol, which was approximately 3% with respect to the number of moles of tin atoms (in the active component), calculated from the amount introduced into the catalyst tank before start of the test operation and the 1,1,3,3-tetrakis(2-phenylethyl)-1,3-bis(3-methylbutyloxy)distannoxane concentration and bis(2-phenylethyl)bis(3-methylbutyloxy)tin concentration in the composition.

Example 5

FIG. 5 shows a continuous circulating reactor for carbonic acid ester synthesis using a cyclic group-substituted alkyl tin alkoxide composition. The di(cyclic group-substituted)alkyl tin dialkoxide composition was placed in the continuous circulating reactor and circulated for test operation. Approximately 60 kg of a di(cyclohexylmethyl)diethoxytin composition obtained by the method as Synthesis Example 1 (tin atom concentration (in the active component) of the composition: 2.44 mol/kg) was introduced into a SUS316 catalyst tank 770 equipped with a heating jacket and liquid conveyance pump, via a supply line 107. The composition was first circulated in the catalyst tank 770 for about 12 hours. Next, the composition was conveyed from the catalyst tank 770 to a tank reactor 710 at 12 kg/hr, via a transport line 109, an inline mixer 711 equipped with a heating jacket, and a transport line 110. The tank reactor 710 was a 10 L-volume reactor, comprising a stirrer, heating jacket and liquid conveyance pump, and the heating jacket was heated with steam at about 150° C. A SUS316 tower reactor 730 with an inner diameter of 76 mm and an effective length of 3500 mm, equipped with 25 sieve trays, was heated and thermally insulated with a heater around the entire tower reactor to prevent radiated heat loss, the heater being set to about 150° C. A liquid conveyance pump and reboiler 733 were provided at the bottom of the tower reactor 730, and the reboiler 733 was heated with steam at about 160° C. An autoclave 740 was used which was a 15 L-volume reactor, comprising a stirrer, heating jacket and liquid conveyance pump, and the heating jacket was heated with steam at about 140° C. A thin-film vaporizer 750 (heat transfer area: 0.1 m²) and a thin-film vaporizer 760 (heat transfer area: 0.2 m²) set to 85 kPaA pressure were equipped with a heating jacket and a liquid conveyance pump for conveyance of the high boiling point component, and steam at 160° C. was used for heating. The composition conveyed to the tank reactor 710 was then conveyed to the tower reactor 730 through a transport line 95, subsequently conveyed to the autoclave 740 through a transport line 97, then conveyed to the thin-film vaporizer 750 through a transport line 99 and further conveyed to the thin-film vaporizer 760 through a transport line 101, after which it was conveyed to the catalyst tank 770 through a transport line 103. The composition was thus continuously circulated through the tank reactor 710, tower reactor 730, autoclave 740, thin-film vaporizer 750, thin-film vaporizer 760 and catalyst tank 770 via the transport line 109, inline mixer 711, transport line 110, transport line 95, transport line 97, transport line 99, transport line 101 and transport line 103, and this was continued for about 5 days. Next, the solution in the catalyst tank 770 was sampled from an extraction line 108, and as a result of $^{119}$Sn-NMR spectral analysis, di(cyclohexylmethyl)diethoxytin and tri(cyclohexylmethyl)ethoxytin were confirmed to be present after test operation. Upon calculating the tin atom concentration (in the active component) in the composition from the di(cyclohexylmethyl)diethoxytin concentration of the composition in the catalyst tank after test operation, as determined by the analysis results, it was found to be 2.32 mol/kg, which was a reduction of 5.1% compared to before start of the test operation. On the other hand, tris(cyclohexylmethyl)ethoxytin was produced at 3.7 mol, which was 2.5% of the number of moles of tin atoms (in the active component) of the composition before starting the test operation.

Examples 6 to 38

The tetra(cyclic group-substituted)alkyldialkoxydistannoxane compositions listed in Table 25 were produced by the same methods as in Synthesis Examples 2, 5 and 8, and test operation of the continuous circulating reactor was conducted by the same method as Example 1, confirming modification reaction during heated circulation. Of these tetra(cyclic group-substituted)alkyldialkoxydistannoxane compositions, some have a low flow property at the environmental temperature at the start of the reaction (about 15° C. to 35° C.), in which case tetralin (product of Wako Pure Chemical Industries), diphenyl ether (product of Wako Pure Chemical Industries) or undecane (product of Wako Pure Chemical Industries) was added as a diluent to prepare a liquid mixture with a diluent concentration of 10 to 35 mass %, and this was introduced into the catalyst tank and test operation (circulating operation) was conducted using a continuous circulating reactor as shown in FIG. 1 in the same manner as Example 1. The mass of the composition charged into the catalyst tank was about 50 kg, similar to Example 1, whether or not a diluent was used. The tetra (cyclic group-substituted)alkyldialkoxydistannoxane concentration in the composition was determined by $^{119}$Sn-NMR spectral analysis, and the tin atom concentration (in the active component) of the composition before circulating operation was calculated. A sampling solution was taken from the catalyst tank after circulating operation and subjected to $^{119}$Sn-NMR spectral analysis. The tin atom concentration (in the active component) of the composition was calculated from the tetra(cyclic group-substituted)alkyldialkoxydistannoxane concentration after test operation as determined from the analysis results, and the percentage reduction from before the start of test operation was calculated. The number of moles of tri(cyclic group-substituted) alkyl tin alkoxide was also determined from the analysis results, and the amount produced with respect to the number of moles of tin atoms (in the active component) of the composition before the start of test operation was calculated. The percentage reductions in the tin atom concentration (in the active component) of the compositions and the tri(cyclic group-substituted)alkyl tin alkoxide production amounts are shown in Table 25.

TABLE 25

| | Tetraalkyldialkoxydistannoxane | | Continuous operation time [days] | Percentage reduction in tin atom concentration (in active component) [%] *1) | Trialkyl tin alkoxide production amount [%] *2) |
| --- | --- | --- | --- | --- | --- |
| Example | R' (alkyl group) | OR'' (alkoxy group) | | | |
| 6 | Cyclohexylmethyl | 3-Methylbutyloxy | 5 | 5.6 | 2.8 |
| 7 | 2-Cyclohexylethyl | 3-Methylbutyloxy | 5 | 6.7 | 3.4 |
| 8 | Cyclopentylmethyl | Ethoxy | 5 | 5.3 | 2.6 |
| 9 | 3-Cyclopentylpropyl | 3-Methylbutyloxy | 5 | 7.0 | 3.5 |
| 10 | Phenethyl | 2-Methylpropyloxy | 4 | 6.8 | 3.4 |
| 11 | Benzyl | 2-Ethylbutyloxy | 6 | 6.3 | 3.2 |
| 12 | 2-Cyclohexylethyl | Ethoxy | 4 | 6.8 | 3.3 |
| 13 | 2-Cyclohexylethyl | 2-Ethylbutyloxy | 5 | 6.7 | 3.4 |
| 14 | 3-Phenylpropyl | 2-Ethylbutyloxy | 6 | 7.0 | 3.5 |
| 15 | Cyclohexylmethyl | N-Butoxy | 4 | 5.4 | 2.7 |
| 16 | Cyclohexylmethyl | 2-Ethylbutyloxy | 6 | 5.3 | 2.7 |
| 17 | Phenethyl | 2-Ethylbutyloxy | 5 | 6.7 | 3.3 |
| 18 | Cyclohexylmethyl | Ethoxy | 5 | 5.5 | 2.7 |
| 19 | 3-Cyclopentylpropyl | N-Butoxy | 5 | 7.1 | 3.5 |
| 20 | 3-Phenylpropyl | 2-Methylpropyloxy | 5 | 7.0 | 3.5 |
| 21 | Cyclohexylmethyl | 2-Methylpropyloxy | 5 | 5.3 | 2.7 |
| 22 | Benzyl | N-Butoxy | 4 | 6.6 | 3.3 |
| 23 | Cyclopentylmethyl | 2-Ethylbutyloxy | 5 | 5.2 | 2.6 |
| 24 | Phenethyl | N-Butoxy | 5 | 6.9 | 3.5 |
| 25 | 3-Phenylpropyl | 3-Methylbutyloxy | 6 | 7.3 | 3.6 |
| 26 | 3-Phenylpropyl | N-Butoxy | 5 | 7.1 | 3.5 |

TABLE 25-continued

| | Tetraalkyldialkoxydistannoxane | | Continuous operation time [days] | Percentage reduction in tin atom concentration (in active component) [%] *1) | Trialkyl tin alkoxide production amount [%] *2) |
|---|---|---|---|---|---|
| Example | R' (alkyl group) | OR" (alkoxy group) | | | |
| 27 | Cyclopentylmethyl | 2-Methylpropyloxy | 5 | 5.2 | 2.6 |
| 28 | Cyclopentylmethyl | 3-Methylbutyloxy | 5 | 5.3 | 2.6 |
| 29 | 3-Phenylpropyl | Ethoxy | 5 | 7.2 | 3.6 |
| 30 | 3-Cyclopentylpropyl | 2-Ethylbutyloxy | 5 | 6.9 | 3.5 |
| 31 | Phenethyl | Ethoxy | 4 | 6.9 | 3.4 |
| 32 | Benzyl | Ethoxy | 5 | 6.5 | 3.2 |
| 33 | 2-Cyclohexylethyl | 2-Methylpropyloxy | 5 | 6.7 | 3.4 |
| 34 | 3-Cyclopentylpropyl | 2-Methylpropyloxy | 5 | 6.9 | 3.4 |
| 35 | Benzyl | 2-Methylpropyloxy | 5 | 6.3 | 3.1 |
| 36 | Phenethyl | 3-Methylbutyloxy | 5 | 6.9 | 3.5 |
| 37 | Cyclopentylmethyl | N-Butoxy | 4 | 5.3 | 2.7 |
| 38 | 3-Cyclopentylpropyl | Ethoxy | 4 | 7.1 | 3.5 |

*1) The percentage reduction in the tin atom concentrations (in the active component) for the tetra(cyclic group-substituted) alkyldialkoxydistannoxane compositions were calculated by mathematical formula (4).
*2) The amount of tri(cyclic group-substituted)alkyl tin alkoxide production was calculated by mathematical formula (5).

[Mathematical Formula 36]

Percentage reduction in tin atom concentration (in active component)$=(S_2^0-S_2')/S_2^0 \times 100\%$ (4)

[In the formula, "percentage reduction in tin atom concentration (in active component)" is the percentage reduction [%] in the tin atom concentration (in the active component) of the composition after circulating operation, $S_2^0$ is the tin atom concentration (in the active component) [mol/kg] of the composition before circulating operation, and $S_2'$ is the tin atom concentration (in the active component) [mol/kg] of the composition after circulating operation. $S_2^0$ and $S_2'$ were calculated from the tetra(cyclic group-substituted)alkyl-dialkoxydistannoxane concentration of the composition, as determined by $^{119}$Sn-NMR spectral analysis.]

[Mathematical Formula 37]

Tri(cyclic group-substituted)alkyl tin alkoxide production amount$=T/(W_2^0 \times S_2^0) \times 100\%$ (5)

[In the formula, "tri(cyclic group-substituted)alkyl tin alkoxide production amount" is the amount of tri(cyclic group-substituted)alkyl tin alkoxide produced [%] after circulating operation, T is the number of moles [mol] of tri(cyclic group-substituted)alkyl tin alkoxide produced after circulating operation, $W_2^0$ is the mass [kg] of the composition introduced into the catalyst tank before circulating operation, and $S_2^0$ is the tin atom concentration (in the active component) [mol/kg] of the composition before circulating operation.

Structural formula of tetra(cyclic group-substituted)alkyldialkoxydistannoxane

[Chemical Formula 87]

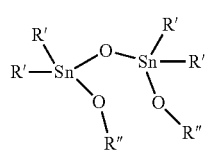

[R' represents a C3-16 alicyclic hydrocarbon group or C6-16 aromatic hydrocarbon group, and R" represents a C1-8 alkyl group.]

Examples 39 to 71

The di(cyclic group-substituted)alkyl tin dialkoxide compositions listed in Table 26 were produced by the same methods as in Synthesis Examples 1, 4 and 7, and test operation of the continuous circulating reactor was conducted by the same method as Example 2, confirming modification reaction during heated circulation. Approximately 45 kg of the composition was introduced into the catalyst tank, and test operation (circulating operation) of the composition was conducted in the same manner as Example 2, using a continuous circulating reactor as shown in FIG. 2. A sampling solution was taken from the catalyst tank after circulating operation and subjected to $^{119}$Sn-NMR spectral analysis. The tin atom concentration (in the active component) of the composition was calculated from the di(cyclic group-substituted)alkyl tin dialkoxide concentration of the composition after test operation as determined from the analysis results, and the percentage reduction from before the start of test operation was calculated. The number of moles of tri(cyclic group-substituted)alkyl tin alkoxide was also determined from the analysis results, and the amount produced with respect to the number of moles of tin atoms (in the active component) of the composition before the start of test operation was calculated. The percentage reductions in the tin atom concentration (in the active component) of the compositions and the tri(cyclic group-substituted)alkyl tin alkoxide production amounts are shown in Table 26.

TABLE 26

| Example | Dialkyl tin dialkoxide R' (alkyl group) | OR" (alkoxy group) | Continuous operation time [days] | Percentage reduction in tin atom concentration (in active component) [%] *3) | Trialkyl tin alkoxide production amount [%] *4) |
|---|---|---|---|---|---|
| 39 | 3-Phenylpropyl | Ethoxy | 4 | 6.6 | 6.7 |
| 40 | Cyclohexylmethyl | N-Butoxy | 5 | 5.1 | 5.0 |
| 41 | Phenethyl | N-Butoxy | 5 | 6.4 | 6.3 |
| 42 | Cyclohexylethyl | 2-Ethylbutyloxy | 5 | 6.2 | 6.2 |
| 43 | Benzyl | Ethoxy | 5 | 5.9 | 6.0 |
| 44 | Cyclohexylmethyl | 3-Methylbutyloxy | 5 | 5.1 | 5.1 |
| 45 | 3-Cyclopentylpropyl | 2-Ethylbutyloxy | 4 | 6.5 | 6.5 |
| 46 | 3-Phenylpropyl | 2-Methylpropyloxy | 4 | 6.4 | 6.5 |
| 47 | 3-Phenylpropyl | 2-Ethylbutyloxy | 4 | 6.6 | 6.6 |
| 48 | Cyclopentylmethyl | 3-Methylbutyloxy | 5 | 4.9 | 4.8 |
| 49 | Phenethyl | 2-Methylpropyloxy | 5 | 6.2 | 6.2 |
| 50 | Cyclohexylmethyl | 2-Methylpropyloxy | 4 | 4.9 | 4.9 |
| 51 | Cyclopentylmethyl | N-Butoxy | 5 | 4.8 | 4.8 |
| 52 | Phenethyl | 3-Methylbutyloxy | 5 | 6.3 | 6.3 |
| 53 | 3-Cyclopentylpropyl | N-Butoxy | 4 | 6.5 | 6.5 |
| 54 | Benzyl | 2-Ethylbutyloxy | 4 | 6.0 | 5.9 |
| 55 | Cyclopentylmethyl | Ethoxy | 5 | 4.9 | 5.0 |
| 56 | Cyclohexylethyl | N-Butoxy | 5 | 6.3 | 6.3 |
| 57 | Cyclohexylethyl | 2-Methylpropyloxy | 5 | 6.2 | 6.3 |
| 58 | Phenethyl | 2-Ethylbutyloxy | 4 | 6.4 | 6.3 |
| 59 | Benzyl | N-Butoxy | 5 | 6.0 | 6.0 |
| 60 | Cyclopentylmethyl | 2-Methylpropyloxy | 4 | 4.7 | 4.8 |
| 61 | Cyclohexylethyl | 3-Methylbutyloxy | 5 | 6.2 | 6.2 |
| 62 | Cyclopentylmethyl | 2-Ethylbutyloxy | 5 | 4.9 | 4.8 |
| 63 | 3-Phenylpropyl | 3-Methylbutyloxy | 5 | 6.7 | 6.7 |
| 64 | Cyclohexylmethyl | 2-Ethylbutyloxy | 5 | 5.1 | 5.2 |
| 65 | Phenethyl | Ethoxy | 4 | 6.4 | 6.3 |
| 66 | 3-Cyclopentylpropyl | Ethoxy | 4 | 6.5 | 6.6 |
| 67 | 3-Cyclopentylpropyl | 2-Methylpropyloxy | 4 | 6.4 | 6.5 |
| 68 | Cyclohexylethyl | Ethoxy | 5 | 6.3 | 6.1 |
| 69 | Benzyl | 2-Methylpropyloxy | 5 | 5.7 | 5.8 |
| 70 | 3-Cyclopentylpropyl | 3-Methylbutyloxy | 4 | 6.5 | 6.6 |
| 71 | 3-Phenylpropyl | N-Butoxy | 4 | 6.6 | 6.5 |

*3) The percentage reduction in the tin atom concentration (in the active component) of the di(cyclic group-substituted) alkyl tin dialkoxide composition was determined by the following mathematical formula (6).
*4) The amount of tri(cyclic group-substituted)alkyl tin alkoxide production was calculated by mathematical formula (7).

[Mathematical Formula 38]

Percentage reduction in tin atom concentration (in active component)=$(S_1^0-S_1^t)/S_1^0 \times 100\%$     (6)

[In the formula, "percentage reduction in tin atom concentration" is the percentage reduction [%] in the tin atom concentration (in the active component) of the composition after circulating operation, $S_1^0$ is the tin atom concentration (in the active component) [mol/kg] of the composition before circulating operation, and $S_1^t$ is the tin atom concentration (in the active component) [mol/kg] of the composition after circulating operation. $S_1^0$ and $S_1^t$ were calculated from the di(cyclic group-substituted)alkyl tin dialkoxide concentration of the composition, as determined by $^{119}$Sn-NMR spectral analysis.]

[Mathematical Formula 39]

Tri(cyclic group-substituted)alkyl tin alkoxide production amount=$T/(W_1^0 \times S_1^0) \times 100\%$     (7)

[In the formula, "tri(cyclic group-substituted)alkyl tin alkoxide production amount" is the amount of tri(cyclic group-substituted)alkyl tin alkoxide produced [%] after circulating operation, T is the number of moles [mol] of tri(cyclic group-substituted)alkyl tin alkoxide produced after circulating operation, $W_1^0$ is the mass [kg] of the composition introduced into the catalyst tank before circulating operation, and $S_1^0$ is the tin atom concentration (in the active component) [mol/kg] of the composition before circulating operation.

Structural formula of di(cyclic group-substituted)alkyl tin dialkoxide

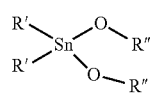

[Chemical Formula 88]

[R' represents a C3-16 alicyclic hydrocarbon group or C6-16 aromatic hydrocarbon group, and R" represents a C1-8 alkyl group.]

Examples 72 to 105

Cyclic group-substituted alkyl tin alkoxide compositions comprising the di(cyclic group-substituted)alkyl tin dialkoxides and tetra(cyclic group-substituted)alkyldialkoxydistannoxanes listed in Table 27 produced by the same method as in Synthesis Examples 1, 2, 4, 5, 7 and 8 were prepared, and test operation of the continuous circulating reactor was conducted by the same method as Example 3, confirming modification reaction during heated circulation. The compositions were prepared so that the molar ratios of tin atoms of the di(cyclic group-substituted)alkyl tin dialkoxides and tetra(cyclic group-substituted)alkyldialkoxydistannoxanes with respect to the number of moles of tin atoms (in the active component)s of the cyclic group-substituted alkyl tin alkoxide compositions comprising the di(cyclic group-substituted)alkyl tin dialkoxides and tetra(cyclic group-substituted)alkyldialkoxydistannoxanes with the structures listed in Table 27 were 65:35, and approximately 60 kg was introduced into the catalyst tank. The tin atom concentration (in the active component) of each composition was determined by mathematical formula (3). Test operation (circulating operation) of the composition was conducted in the same manner as Example 3, using a continuous circulating reactor as shown in FIG. 3. A sampling solution was taken from the catalyst tank after circulating operation and subjected to $^{119}$Sn-NMR spectral analysis. The concentration of tin atoms in the composition was calculated from the tetra(cyclic group-substituted)alkyldialkoxydistannoxane concentration and di(cyclic group-substituted)alkyl tin dialkoxide concentration of the composition after test operation as determined from the analysis results, and the percentage reduction from before the start of test operation was calculated. The number of moles of tri(cyclic group-substituted)alkyl tin alkoxide produced after test operation was also determined from the analysis results, and the amount produced with respect to the number of moles of tin atoms (in the active component) of the composition before the start of test operation was calculated. The percentage reductions in the tin atom concentration (in the active component) of the compositions and the tri(cyclic group-substituted)alkyl tin alkoxide production amounts are shown in Table 27.

TABLE 27

| Example | Alkyl tin alkoxide | | Continuous operation time [days] | Percentage reduction in tin atom concentration (in active component) [%] *5) | Trialkyl tin alkoxide production amount [%] *6) |
|---|---|---|---|---|---|
| | R' (alkyl group) | OR" (alkoxy group) | | | |
| 72 | Phenethyl | 3-Methylbutyloxy | 6 | 6.3 | 6.3 |
| 73 | Cyclohexylmethyl | 3-Methylbutyloxy | 5 | 4.9 | 5.0 |
| 74 | Cyclohexylethyl | Ethoxy | 5 | 6.2 | 6.2 |
| 75 | Cyclohexylethyl | 2-Methylpropyloxy | 5 | 6.0 | 5.8 |
| 76 | 3-Phenylpropyl | 3-Methylbutyloxy | 5 | 6.4 | 6.5 |
| 77 | Phenethyl | 2-Methylpropyloxy | 5 | 6.0 | 6.1 |
| 78 | 3-Phenylpropyl | 2-Methylpropyloxy | 6 | 6.3 | 6.2 |
| 79 | 3-Cyclopentylpropyl | 2-Ethylbutyloxy | 5 | 6.3 | 6.3 |
| 80 | Phenethyl | N-Butoxy | 4 | 6.3 | 6.1 |
| 81 | 3-Cyclopentylpropyl | 2-Methylpropyloxy | 5 | 6.2 | 6.3 |
| 82 | 3-Cyclopentylpropyl | 3-Methylbutyloxy | 5 | 6.3 | 6.3 |
| 83 | Benzyl | 2-Ethylbutyloxy | 6 | 5.8 | 5.8 |
| 84 | Cyclohexylethyl | 2-Ethylbutyloxy | 6 | 6.0 | 6.1 |
| 85 | 3-Cyclopentylpropyl | N-Butoxy | 5 | 6.3 | 6.2 |
| 86 | Cyclohexylmethyl | N-Butoxy | 5 | 5.0 | 4.9 |
| 87 | 3-Cyclopentylpropyl | Ethoxy | 4 | 6.4 | 6.3 |
| 88 | Cyclohexylethyl | N-Butoxy | 5 | 6.2 | 6.2 |
| 89 | Cyclopentylmethyl | Ethoxy | 5 | 4.8 | 4.7 |
| 90 | Cyclopentylmethyl | N-Butoxy | 5 | 4.7 | 4.8 |
| 91 | Cyclohexylmethyl | 2-Methylpropyloxy | 6 | 4.7 | 4.8 |
| 92 | Phenethyl | Ethoxy | 5 | 6.3 | 6.4 |
| 93 | Benzyl | Ethoxy | 5 | 5.8 | 5.9 |
| 94 | Benzyl | N-Butoxy | 4 | 5.9 | 6.0 |
| 95 | Benzyl | 2-Methylpropyloxy | 6 | 5.5 | 5.6 |
| 96 | Cyclohexylmethyl | 2-Ethylbutyloxy | 5 | 5.0 | 4.9 |
| 97 | Phenethyl | 2-Ethylbutyloxy | 5 | 6.2 | 6.1 |
| 98 | 3-Phenylpropyl | Ethoxy | 4 | 6.5 | 6.5 |
| 99 | Cyclohexylmethyl | Ethoxy | 4 | 5.0 | 4.9 |
| 100 | 3-Phenylpropyl | N-Butoxy | 4 | 6.4 | 6.4 |
| 101 | 3-Phenylpropyl | 2-Ethylbutyloxy | 5 | 6.5 | 6.5 |
| 102 | Cyclopentylmethyl | 3-Methylbutyloxy | 6 | 4.7 | 4.7 |
| 103 | Cyclohexylethyl | 3-Methylbutyloxy | 5 | 6.2 | 6.1 |
| 104 | Cyclopentylmethyl | 2-Ethylbutyloxy | 6 | 4.7 | 4.7 |
| 105 | Cyclopentylmethyl | 2-Methylpropyloxy | 6 | 4.6 | 4.6 |

*5) The percentage reduction in the tin atom concentration (in the active component) of the cyclic group-substituted alkyl tin alkoxide composition was determined by the following mathematical formula (8).
*6) The amount of tri(cyclic group-substituted)alkyl tin alkoxide production was calculated by mathematical formula (9).

[Mathematical Formula 40]

Percentage reduction of tin atom concentration (in active component)=$(S_3^0-S_3^t)/S_3^0 \times 100\%$ (8)

[In the formula, "percentage reduction of tin atom concentration (in active component)" is the percentage reduction [%] of the tin atom concentration (in the active component) of the composition after circulating operation, $S_3^0$ is the tin atom concentration (in the active component) [mol/kg] of the composition before circulating operation, and $S_3^t$ is the tin atom concentration (in the active component) [mol/kg] of the composition after circulating operation. $S_3^0$ and $S_3^t$ were calculated from the tetra(cyclic group-substituted)alkyldialkoxydistannoxane concentration and di(cyclic group-substituted)alkyl tin dialkoxide concentration of the composition, as determined by $^{119}$Sn-NMR spectral analysis.]

Tri(cyclic group-substituted)alkyl tin alkoxide production amount=$T/(W_3^0 \times S_3^0) \times 100\%$     [Mathematical Formula 41]

[In the formula, "tri(cyclic group-substituted)alkyl tin alkoxide production amount" is the amount of tri(cyclic group-substituted)alkyl tin alkoxide produced [%] after circulating operation, T is the number of moles [mol] of tri(cyclic group-substituted)alkyl tin alkoxide produced after circulating operation, $W_3^0$ is the mass [kg] of the cyclic group-substituted alkyl tin alkoxide composition introduced into the catalyst tank before circulating operation, and $S_3^0$ is the tin atom concentration (in the active component) [mol/kg] of the composition before circulating operation.

Structural formulas of tetra(cyclic group-substituted)alkyldialkoxydistannoxane and di(cyclic group-substituted)alkyl tin dialkoxide in cyclic group-substituted alkyl tin alkoxide composition

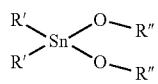

[Chemical Formula 89]

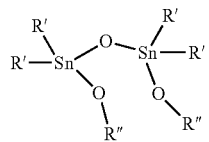

[Chemical Formula 90]

[R' represents a C3-16 alicyclic hydrocarbon group or C6-16 aromatic hydrocarbon group, and R" represents a C1-8 alkyl group.]

Examples 106 to 139

Cyclic group-substituted alkyl tin alkoxide compositions comprising the di(cyclic group-substituted)alkyl tin dialkoxides, tetra(cyclic group-substituted)alkyldialkoxydistannoxanes and tri(cyclic group-substituted)alkyl tin alkoxides listed in Table 28 produced by the same method as in Synthesis Examples 3, 6 and 9 were used, and test operation (circulating operation) of the continuous circulating reactor shown in FIG. 4 was conducted by the same method as Example 4, confirming modification reaction during heated circulation. Approximately 60 kg of each of the cyclic group-substituted alkyl tin alkoxide compositions comprising the di(cyclic group-substituted)alkyl tin dialkoxides, tetra(cyclic group-substituted)alkyldialkoxydistannoxanes and tri(cyclic group-substituted)alkyl tin alkoxides listed in Table 28, produced by the same method as in Synthesis Examples 3, 6 and 9, was introduced into the catalyst tank and circulated in the continuous circulating reactor. A sampling solution was taken from the catalyst tank after circulating operation and subjected to $^{119}$Sn-NMR spectral analysis. The tin atom concentration (in the active component) of the composition was calculated from the tetra(cyclic group-substituted)alkyldialkoxydistannoxane concentration and di(cyclic group-substituted)alkyl tin dialkoxide concentration of the composition after test operation as determined from the analysis results, and the percentage reduction from before the start of test operation was calculated. The number of moles of tri(cyclic group-substituted)alkyl tin alkoxide was also determined from the analysis results, and the amount produced with respect to number of moles of tin atoms (in the active component) of the composition before the start of test operation was calculated. The percentage reductions in the tin atom concentration (in the active component) of the compositions and the tri(cyclic group-substituted)alkyl tin alkoxide production amounts are shown in Table 28.

TABLE 28

| | Alkyl tin alkoxide | | Continuous operation time | Percentage reduction in tin atom concentration (in active component) | Trialkyl tin alkoxide production amount |
|---|---|---|---|---|---|
| Example | R' (alkyl group) | OR" (alkoxy group) | [days] | [%] *7 | [%] *8 |
| 106 | Cyclohexylmethyl | 2-Methylpropyloxy | 5 | 4.6 | 4.7 |
| 107 | 3-Phenylpropyl | 2-Methylpropyloxy | 5 | 6.2 | 6.0 |
| 108 | Cyclopentylmethyl | 3-Methylbutyloxy | 6 | 4.5 | 4.4 |
| 109 | Cyclohexylmethyl | 3-Methylbutyloxy | 6 | 4.8 | 4.6 |
| 110 | Cyclopentylmethyl | 2-Ethylbutyloxy | 6 | 4.6 | 4.6 |
| 111 | Cyclohexylmethyl | Ethoxy | 5 | 4.9 | 4.8 |
| 112 | 3-Phenylpropyl | 3-Methylbutyloxy | 6 | 6.3 | 6.1 |
| 113 | Phenethyl | 2-Ethylbutyloxy | 5 | 6.0 | 6.1 |
| 114 | Cyclohexylethyl | N-Butoxy | 5 | 6.1 | 6.2 |
| 115 | Cyclopentylmethyl | 2-Methylpropyloxy | 6 | 4.4 | 4.5 |
| 116 | Cyclopentylmethyl | N-Butoxy | 6 | 4.6 | 4.6 |
| 117 | 3-Cyclopentylpropyl | 3-Methylbutyloxy | 5 | 6.1 | 6.2 |
| 118 | Phenethyl | Ethoxy | 6 | 6.1 | 6.2 |
| 119 | Benzyl | N-Butoxy | 5 | 5.7 | 5.6 |
| 120 | Cyclohexylethyl | 2-Methylpropyloxy | 5 | 5.8 | 6.0 |
| 121 | Cyclopentylmethyl | Ethoxy | 6 | 4.7 | 4.8 |
| 122 | 3-Phenylpropyl | Ethoxy | 6 | 6.3 | 6.2 |
| 123 | Cyclohexylmethyl | N-Butoxy | 5 | 4.8 | 4.8 |
| 124 | Benzyl | 2-Ethylbutyloxy | 5 | 5.7 | 5.7 |
| 125 | 3-Cyclopentylpropyl | 2-Ethylbutyloxy | 5 | 6.1 | 6.1 |
| 126 | Cyclohexylethyl | Ethoxy | 6 | 6.1 | 6.2 |
| 127 | Benzyl | 2-Methylpropyloxy | 5 | 5.5 | 5.5 |
| 128 | Phenethyl | N-Butoxy | 5 | 6.1 | 6.0 |
| 129 | Cyclohexylmethyl | 2-Ethylbutyloxy | 6 | 4.9 | 4.9 |

TABLE 28-continued

| | Alkyl tin alkoxide | | Continuous operation time [days] | Percentage reduction in tin atom concentration (in active component) [%] *7) | Trialkyl tin alkoxide production amount [%] *8) |
|---|---|---|---|---|---|
| Example | R' (alkyl group) | OR" (alkoxy group) | | | |
| 130 | Benzyl | Ethoxy | 5 | 5.7 | 5.7 |
| 131 | 3-Cyclopentylpropyl | Ethoxy | 5 | 6.2 | 6.2 |
| 132 | 3-Cyclopentylpropyl | 2-Methylpropyloxy | 6 | 6.1 | 6.0 |
| 133 | 3-Phenylpropyl | N-Butoxy | 5 | 6.3 | 6.4 |
| 134 | Cyclohexylethyl | 3-Methylbutyloxy | 6 | 6.0 | 6.1 |
| 135 | 3-Cyclopentylpropyl | N-Butoxy | 5 | 6.3 | 6.4 |
| 136 | Benzyl | 3-Methylbutyloxy | 5 | 5.9 | 5.9 |
| 137 | Cyclohexylethyl | 2-Ethylbutyloxy | 5 | 5.9 | 6.0 |
| 138 | 3-Phenylpropyl | 2-Ethylbutyloxy | 6 | 6.2 | 6.2 |
| 139 | Phenethyl | 2-Methylpropyloxy | 6 | 6.0 | 5.9 |

*7) The percentage reduction in the tin atom concentration (in the active component) of the cyclic group-substituted alkyl tin alkoxide composition was determined by the following mathematical formula (8).
*8) The amount of tri(cyclic group-substituted)alkyl tin alkoxide production was calculated by mathematical formula (9).

[Mathematical Formula 42]

$$\text{Percentage reduction of tin atom concentration (in active component)} = (S_3^0 - S_3^t)/S_3^0 \times 100\% \quad (8)$$

[In the formula, "percentage reduction of tin atom concentration (in active component)" is the percentage reduction [%] of the tin atom concentration (in the active component) of the composition after circulating operation, $S_3^0$ is the tin atom concentration (in the active component) [mol/kg] of the composition before circulating operation, and $S_3^t$ is the tin atom concentration (in the active component) [mol/kg] of the composition after circulating operation. $S_3^0$ and $S_3^t$ were calculated from the tetra(cyclic group-substituted)alkyl-dialkoxydistannoxane concentration and di(cyclic group-substituted)alkyl tin dialkoxide concentration of the composition, as determined by $^{119}$Sn-NMR spectral analysis.]

[Mathematical Formula 43]

$$\text{Tri(cyclic group-substituted)alkyl tin alkoxide production amount} = T/(W_3^0 \times S_3^0) \times 100\% \quad (9)$$

[In the formula, "tri(cyclic group-substituted)alkyl tin alkoxide production amount" is the amount of tri(cyclic group-substituted)alkyl tin alkoxide produced [%] after circulating operation, T is the number of moles [mol] of tri(cyclic group-substituted)alkyl tin alkoxide produced after circulating operation, $W_3^0$ is the mass [kg] of the cyclic group-substituted alkyl tin alkoxide composition introduced into the catalyst tank before circulating operation, and $S_3^0$ is the tin atom concentration (in the active component) [mol/kg] of the composition before circulating operation.

Structural formulas of tetra(cyclic group-substituted)alkyldialkoxydistannoxane and di(cyclic group-substituted)alkyl tin dialkoxide in cyclic group-substituted alkyl tin alkoxide composition

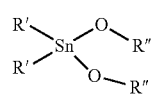

[Chemical Formula 91]

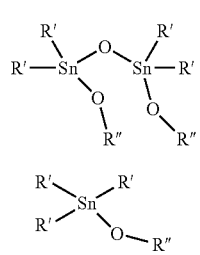

[Chemical Formula 92]

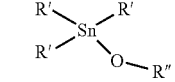

[Chemical Formula 93]

[R' represents a C3-16 alicyclic hydrocarbon group or C6-16 aromatic hydrocarbon group, and R" represents a C1-8 alkyl group.]

Examples 140 to 187

Di(cyclic group-substituted)alkyl tin dialkoxides and tetraalkyl dialkoxydistannoxanes having the structures listed in Table 29 were produced by the same methods as Synthesis Examples 1, 2, 4, 5, 7 and 8, and cyclic group-substituted alkyl tin alkoxide compositions comprising the di(cyclic group-substituted)alkyl tin dialkoxides and tetraalkyl-dialkoxydistannoxanes were prepared. Cyclic group-substituted alkyl tin alkoxide compositions comprising di(cyclic group-substituted)alkyl tin dialkoxides and tetraalkyl dialkoxydistannoxanes were prepared so that the molar ratios of tin atoms of the di(cyclic group-substituted)alkyl tin dialkoxides and tetraalkyl dialkoxydistannoxanes with respect to the number of moles of tin atoms (in the active component) of the compositions were 5:95 to 50:50. The compositions were used by the same method as Example 5 for test operation (circulating operation) in a continuous circulating reactor as shown in FIG. 5, confirming modification reaction during heated circulation. Approximately 60 kg of each composition was introduced into the catalyst tank and circulated in a continuous circulating reactor as shown in FIG. 5 by the same method. Each composition was sampled from the catalyst tank after circulating operation and subjected to $^{119}$Sn-NMR spectral analysis. The tin atom concentration (in the active component) of the composition was calculated from the tetra(cyclic group-substituted)alkyldialkoxydistannoxane concentration and di(cyclic group-substituted)alkyl tin dialkoxide concentration of the composition after test operation as determined from the analysis results, and the percentage reduction from before the start of test operation was calculated. The number of moles of tri(cyclic group-substituted)alkyl tin alkoxide was also determined from the analysis results, and the amount produced with respect to number of moles of tin atoms (in the active component) of the composition before the start of test operation was calculated. The percentage reductions in the tin atom concentration (in the active component) of the compositions and the trialkyl tin alkoxide production amounts are shown in Table 29.

[Mathematical Formula 44]

Percentage reduction of tin atom concentration (in active component)=$(S_3^0-S_3^t)/S_3^0\times100\%$ (8)

[In the formula, "percentage reduction of tin atom concentration (in active component)" is the percentage reduction [%] of the tin atom concentration (in the active component) of the composition after circulating operation, $S_3^0$ is the tin atom concentration (in the active component) [mol/kg] of the composition before circulating operation, and $S_3^t$ is the tin atom concentration (in the active component) [mol/kg] of

TABLE 29

| Example | Alkyl tin alkoxide composition | | Molar ratio of tin atoms of dialkyl tin dialkoxide and tetraalkyldialkoxy-distannoxane | Continuous operation time [days] | Percentage reduction in tin atom concentration (in active component) [%] *9) | Trialkyl tin alkoxide production amount [%] *10) |
|---|---|---|---|---|---|---|
| | R' (alkyl group) | OR" (alkoxy group) | | | | |
| 140 | Cyclopentylmethyl | N-Butoxy | 5:95 | 6 | 5.2 | 5.1 |
| 141 | 2-Cyclohexylethyl | N-Butoxy | 5:95 | 5 | 6.5 | 6.5 |
| 142 | 3-Cyclopentylpropyl | N-Butoxy | 5:95 | 5 | 6.9 | 7.0 |
| 143 | Benzyl | N-Butoxy | 5:95 | 5 | 6.4 | 6.4 |
| 144 | Phenethyl | N-Butoxy | 5:95 | 6 | 6.8 | 6.6 |
| 145 | 3-Phenylpropyl | N-Butoxy | 5:95 | 6 | 7.0 | 6.9 |
| 146 | Cyclopentylmethyl | 2-Ethylbutyloxy | 5:95 | 5 | 5.1 | 4.9 |
| 147 | 2-Cyclohexylethyl | 2-Ethylbutyloxy | 5:95 | 6 | 6.6 | 6.5 |
| 148 | 3-Cyclopentylpropyl | 2-Ethylbutyloxy | 5:95 | 6 | 6.8 | 6.9 |
| 149 | Benzyl | 2-Ethylbutyloxy | 5:95 | 6 | 6.2 | 6.1 |
| 150 | Phenethyl | 2-Ethylbutyloxy | 5:95 | 6 | 6.6 | 6.6 |
| 151 | 3-Phenylpropyl | 2-Ethylbutyloxy | 5:95 | 5 | 6.8 | 7.0 |
| 152 | Cyclopentylmethyl | N-Butoxy | 15:85 | 6 | 5.1 | 5.1 |
| 153 | 2-Cyclohexylethyl | N-Butoxy | 15:85 | 6 | 6.4 | 6.2 |
| 154 | 3-Cyclopentylpropyl | N-Butoxy | 15:85 | 5 | 6.8 | 6.9 |
| 155 | Benzyl | N-Butoxy | 15:85 | 5 | 6.3 | 6.4 |
| 156 | Phenethyl | N-Butoxy | 15:85 | 5 | 6.7 | 6.7 |
| 157 | 3-Phenylpropyl | N-Butoxy | 15:85 | 5 | 6.8 | 6.9 |
| 158 | Cyclopentylmethyl | 2-Ethylbutyloxy | 15:85 | 6 | 5.0 | 4.9 |
| 159 | 2-Cyclohexylethyl | 2-Ethylbutyloxy | 15:85 | 6 | 6.4 | 6.3 |
| 160 | 3-Cyclopentylpropyl | 2-Ethylbutyloxy | 15:85 | 5 | 6.6 | 6.4 |
| 161 | Benzyl | 2-Ethylbutyloxy | 15:85 | 6 | 6.0 | 6.0 |
| 162 | Phenethyl | 2-Ethylbutyloxy | 15:85 | 6 | 6.4 | 6.3 |
| 163 | 3-Phenylpropyl | 2-Ethylbutyloxy | 15:85 | 5 | 6.7 | 6.6 |
| 164 | Cyclopentylmethyl | N-Butoxy | 35:65 | 5 | 5.1 | 5.0 |
| 165 | 2-Cyclohexylethyl | N-Butoxy | 35:65 | 6 | 6.3 | 6.3 |
| 166 | 3-Cyclopentylpropyl | N-Butoxy | 35:65 | 5 | 6.7 | 6.6 |
| 167 | Benzyl | N-Butoxy | 35:65 | 5 | 6.2 | 6.1 |
| 168 | Phenethyl | N-Butoxy | 35:65 | 5 | 6.6 | 6.4 |
| 169 | 3-Phenylpropyl | N-Butoxy | 35:65 | 6 | 6.7 | 6.6 |
| 170 | Cyclopentylmethyl | 2-Ethylbutyloxy | 35:65 | 6 | 4.9 | 5.0 |
| 171 | 2-Cyclohexylethyl | 2-Ethylbutyloxy | 35:65 | 6 | 6.3 | 6.2 |
| 172 | 3-Cyclopentylpropyl | 2-Ethylbutyloxy | 35:65 | 6 | 6.4 | 6.4 |
| 173 | Benzyl | 2-Ethylbutyloxy | 35:65 | 6 | 5.9 | 5.8 |
| 174 | Phenethyl | 2-Ethylbutyloxy | 35:65 | 5 | 6.3 | 6.3 |
| 175 | 3-Phenylpropyl | 2-Ethylbutyloxy | 35:65 | 5 | 6.6 | 6.4 |
| 176 | Cyclopentylmethyl | N-Butoxy | 50:50 | 5 | 4.8 | 4.8 |
| 177 | 2-Cyclohexylethyl | N-Butoxy | 50:50 | 5 | 6.1 | 6.2 |
| 178 | 3-Cyclopentylpropyl | N-Butoxy | 50:50 | 6 | 6.4 | 6.6 |
| 179 | Benzyl | N-Butoxy | 50:50 | 6 | 6.0 | 5.9 |
| 180 | Phenethyl | N-Butoxy | 50:50 | 5 | 6.3 | 6.3 |
| 181 | 3-Phenylpropyl | N-Butoxy | 50:50 | 6 | 6.4 | 6.2 |
| 182 | Cyclopentylmethyl | 2-Ethylbutyloxy | 50:50 | 6 | 4.7 | 4.6 |
| 183 | 2-Cyclohexylethyl | 2-Ethylbutyloxy | 50:50 | 5 | 6.0 | 6.2 |
| 184 | 3-Cyclopentylpropyl | 2-Ethylbutyloxy | 50:50 | 5 | 6.2 | 6.2 |
| 185 | Benzyl | 2-Ethylbutyloxy | 50:50 | 6 | 5.6 | 5.6 |
| 186 | Phenethyl | 2-Ethylbutyloxy | 50:50 | 6 | 6.0 | 6.1 |
| 187 | 3-Phenylpropyl | 2-Ethylbutyloxy | 50:50 | 6 | 6.3 | 6.2 |

*9) The percentage reduction in the tin atom concentration (in the active component) of the cyclic group-substituted alkyl tin alkoxide composition was determined by the following mathematical formula (8).
*10) The amount of tri(cyclic group-substituted)alkyl tin alkoxide production was calculated by mathematical formula (9).

the composition after circulating operation. $S_3^0$ and $S_3^t$ were calculated from the tetra(cyclic group-substituted)alkyldialkoxydistannoxane concentration and di(cyclic group-substituted)alkyl tin dialkoxide concentration of the composition, as determined by $^{119}$Sn-NMR spectral analysis.]

[Mathematical Formula 45]

Tri(cyclic group-substituted)alkyl tin alkoxide production amount=$T/(W_3^0 \times S_3^0) \times 100\%$  (9)

[In the formula, "tri(cyclic group-substituted)alkyl tin alkoxide production amount" is the amount of tri(cyclic group-substituted)alkyl tin alkoxide produced [%] after circulating operation, T is the number of moles [mol] of tri(cyclic group-substituted)alkyl tin alkoxide produced after circulating operation, $W_3^0$ is the mass [kg] of the cyclic group-substituted alkyl tin alkoxide composition introduced into the catalyst tank before circulating operation, and $S_3^0$ is the tin atom concentration (in the active component) [mol/kg] of the composition before circulating operation.

Structural formulas of tetra(cyclic group-substituted)alkyldialkoxydistannoxane and di(cyclic group-substituted)alkyl tin dialkoxide in cyclic group-substituted alkyl tin alkoxide composition

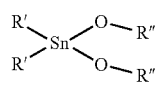

[Chemical Formula 94]

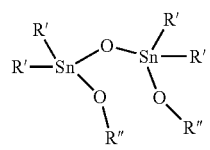

[Chemical Formula 95]

[R' represents a C3-16 alicyclic hydrocarbon group or C6-16 aromatic hydrocarbon group, and R" represents a C1-8 alkyl group.]

Examples 188 to 229

Di(cyclic group-substituted)alkyl tin dialkoxides and tetraalkyl dialkoxydistannoxanes having the structures listed in Table 30 were produced by the same methods as Synthesis Examples 1, 2, 4, 5, 7 and 8, and cyclic group-substituted alkyl tin alkoxide compositions comprising the di(cyclic group-substituted)alkyl tin dialkoxides and tetra(cyclic group-substituted)alkyldialkoxydistannoxanes were prepared. The compositions were prepared so that the molar ratios of tin atoms of the di(cyclic group-substituted)alkyl tin dialkoxides and tetra(cyclic group-substituted)alkyldialkoxydistannoxanes with respect to the number of moles of tin atoms (in the active component) were 65:35. Trialkyl tin alkoxides having the structures listed in Table 30 were then added to the cyclic group-substituted alkyl tin alkoxide compositions, to prepare cyclic group-substituted alkyl tin alkoxide compositions containing trialkyl tin alkoxides. The compositions were prepared so that the number of moles of tin atoms in the trialkyl tin alkoxides with respect to the number of moles of tin atoms of the cyclic group-substituted alkyl tin alkoxide compositions containing the trialkyl tin alkoxides were 11 to 13 mol %.

The compositions were used by the same method as Example 5 for test operation (circulating operation) in a continuous circulating reactor as shown in FIG. 5, confirming modification reaction during heated circulation. Approximately 60 kg of each composition was introduced into the catalyst tank and circulated in a continuous circulating reactor as shown in FIG. 5 by the same method. Each composition was sampled from the catalyst tank after circulating operation and subjected to $^{119}$Sn-NMR spectral analysis. The concentration of tin atoms in the composition was calculated from the tetra(cyclic group-substituted)alkyldialkoxydistannoxane concentration and di(cyclic group-substituted)alkyl tin dialkoxide concentration of the composition after test operation as determined from the analysis results, and the percentage reduction from before the start of test operation was calculated. The number of moles of tri(cyclic group-substituted)alkyl tin alkoxide was also determined from the analysis results, and the amount produced with respect to number of moles of tin atoms (in the active component) of the composition before the start of test operation was calculated. The percentage reductions in the tin atom concentration (in the active component) of the compositions and the tri(cyclic group-substituted)alkyl tin alkoxide production amounts are shown in Table 30.

TABLE 30

| | Alkyl tin alkoxide composition | | | Trialkyl tin alkoxide Concentration [tin atom mol %] | Continuous operation time [days] | Percentage reduction in tin atom concentration (in active component) [%] *11) | Trialkyl tin alkoxide production amount [%] *12) |
|---|---|---|---|---|---|---|---|
| Example | R' (alkyl group) | OR" (alkoxy group) | R'" (alkyl group) | | | | |
| 188 | Cyclopentylmethyl | 3-Methylbutyloxy | N-Octyl | 12 | 5 | 4.5 | 4.6 |
| 189 | 2-Cyclohexylethyl | 3-Methylbutyloxy | N-Octyl | 11 | 5 | 5.9 | 6.1 |
| 190 | 3-Cyclopentylpropyl | 3-Methylbutyloxy | N-Octyl | 12 | 4 | 6.0 | 5.8 |
| 191 | Benzyl | 3-Methylbutyloxy | N-Octyl | 13 | 4 | 5.8 | 5.9 |
| 192 | Phenethyl | 3-Methylbutyloxy | N-Octyl | 12 | 5 | 6.1 | 6.3 |
| 193 | 3-Phenylpropyl | 3-Methylbutyloxy | N-Octyl | 11 | 5 | 6.2 | 6.0 |
| 194 | Cyclopentylmethyl | 3-Methylbutyloxy | Cyclopentylmethyl | 11 | 5 | 4.2 | 4.2 |
| 195 | 2-Cyclohexylethyl | 3-Methylbutyloxy | Cyclopentylmethyl | 12 | 5 | 5.4 | 5.2 |
| 196 | 3-Cyclopentylpropyl | 3-Methylbutyloxy | Cyclopentylmethyl | 11 | 4 | 5.5 | 5.2 |
| 197 | Benzyl | 3-Methylbutyloxy | Cyclopentylmethyl | 12 | 5 | 5.4 | 5.4 |
| 198 | Phenethyl | 3-Methylbutyloxy | Cyclopentylmethyl | 12 | 4 | 5.6 | 5.5 |
| 199 | 3-Phenylpropyl | 3-Methylbutyloxy | Cyclopentylmethyl | 12 | 5 | 5.7 | 5.7 |
| 200 | Cyclopentylmethyl | 3-Methylbutyloxy | Benzyl | 12 | 4 | 4.1 | 4.2 |
| 201 | 2-Cyclohexylethyl | 3-Methylbutyloxy | Benzyl | 13 | 5 | 5.5 | 5.5 |
| 202 | 3-Cyclopentylpropyl | 3-Methylbutyloxy | Benzyl | 11 | 5 | 5.5 | 5.4 |
| 203 | Benzyl | 3-Methylbutyloxy | Benzyl | 12 | 5 | 5.3 | 5.3 |

TABLE 30-continued

| | Alkyl tin alkoxide composition | | | Trialkyl tin alkoxide Concentration | Continuous operation | Percentage reduction in tin atom concentration | Trialkyl tin alkoxide |
|---|---|---|---|---|---|---|---|
| Example | R' (alkyl group) | OR" (alkoxy group) | R''' (alkyl group) | [tin atom mol %] | time [days] | (in active component) [%] *11) | production amount [%] *12) |
| 204 | Phenethyl | 3-Methylbutyloxy | Benzyl | 12 | 5 | 5.6 | 5.7 |
| 205 | 3-Phenylpropyl | 3-Methylbutyloxy | Benzyl | 12 | 5 | 5.7 | 5.6 |
| 206 | Cyclopentylmethyl | 3-Methylbutyloxy | 2-Cyclohexylethyl | 12 | 5 | 4.2 | 4.1 |
| 207 | 2-Cyclohexylethyl | 3-Methylbutyloxy | 2-Cyclohexylethyl | 11 | 5 | 5.5 | 5.5 |
| 208 | 3-Cyclopentylpropyl | 3-Methylbutyloxy | 2-Cyclohexylethyl | 12 | 4 | 5.5 | 5.4 |
| 209 | Benzyl | 3-Methylbutyloxy | 2-Cyclohexylethyl | 12 | 5 | 5.4 | 5.4 |
| 210 | Phenethyl | 3-Methylbutyloxy | 2-Cyclohexylethyl | 11 | 5 | 5.7 | 5.7 |
| 211 | 3-Phenylpropyl | 3-Methylbutyloxy | 2-Cyclohexylethyl | 11 | 4 | 5.7 | 5.8 |
| 212 | Cyclopentylmethyl | 3-Methylbutyloxy | Phenethyl | 12 | 5 | 4.1 | 4.1 |
| 213 | 2-Cyclohexylethyl | 3-Methylbutyloxy | Phenethyl | 12 | 4 | 5.4 | 5.3 |
| 214 | 3-Cyclopentylpropyl | 3-Methylbutyloxy | Phenethyl | 11 | 4 | 5.6 | 5.7 |
| 215 | Benzyl | 3-Methylbutyloxy | Phenethyl | 13 | 4 | 5.3 | 5.2 |
| 216 | Phenethyl | 3-Methylbutyloxy | Phenethyl | 12 | 5 | 5.6 | 5.8 |
| 217 | 3-Phenylpropyl | 3-Methylbutyloxy | Phenethyl | 12 | 5 | 5.7 | 5.6 |
| 218 | Cyclopentylmethyl | 3-Methylbutyloxy | 3-Cyclopentylpropyl | 12 | 5 | 4.1 | 4.2 |
| 219 | 2-Cyclohexylethyl | 3-Methylbutyloxy | 3-Cyclopentylpropyl | 11 | 5 | 5.4 | 5.5 |
| 220 | 3-Cyclopentylpropyl | 3-Methylbutyloxy | 3-Cyclopentylpropyl | 12 | 4 | 5.6 | 5.5 |
| 221 | Benzyl | 3-Methylbutyloxy | 3-Cyclopentylpropyl | 12 | 4 | 5.3 | 5.3 |
| 222 | Phenethyl | 3-Methylbutyloxy | 3-Cyclopentylpropyl | 12 | 5 | 5.6 | 5.7 |
| 223 | 3-Phenylpropyl | 3-Methylbutyloxy | 3-Cyclopentylpropyl | 11 | 4 | 5.7 | 5.6 |
| 224 | Cyclopentylmethyl | 3-Methylbutyloxy | 3-Phenylpropyl | 12 | 4 | 4.1 | 4.2 |
| 225 | 2-Cyclohexylethyl | 3-Methylbutyloxy | 3-Phenylpropyl | 12 | 5 | 5.5 | 5.6 |
| 226 | 3-Cyclopentylpropyl | 3-Methylbutyloxy | 3-Phenylpropyl | 11 | 4 | 5.6 | 5.7 |
| 227 | Benzyl | 3-Methylbutyloxy | 3-Phenylpropyl | 11 | 5 | 5.3 | 5.3 |
| 228 | Phenethyl | 3-Methylbutyloxy | 3-Phenylpropyl | 12 | 4 | 5.6 | 5.4 |
| 229 | 3-Phenylpropyl | 3-Methylbutyloxy | 3-Phenylpropyl | 12 | 5 | 5.8 | 6.0 |

*11) The percentage reduction in the tin atom concentration (in the active component) of the cyclic group-substituted alkyl tin alkoxide composition was determined by the following mathematical formula (8).
*12) The amount of tri(cyclic group-substituted)alkyl tin alkoxide production was calculated by mathematical formula (9).

[Mathematical Formula 46]

$$\text{Percentage reduction of tin atom concentration (in active component)} = (S_3^0 - S_3^t)/S_3^0 \times 100\% \quad (8)$$

[In the formula, "percentage reduction of tin atom concentration (in active component)" is the percentage reduction [%] of the tin atom concentration (in the active component) of the composition after circulating operation, $S_3^0$ is the tin atom concentration (in the active component) [mol/kg] of the composition before circulating operation, and $S_3^t$ is the tin atom concentration (in the active component) [mol/kg] of the composition after circulating operation. $S_3^0$ and $S_3^t$ were calculated from the tetra(cyclic group-substituted)alkyl-dialkoxydistannoxane concentration and di(cyclic group-substituted)alkyl tin dialkoxide concentration of the composition, as determined by $^{119}$Sn-NMR spectral analysis.]

[Mathematical Formula 47]

$$\text{Tri(cyclic group-substituted)alkyl tin alkoxide production amount} = T/(W_3^0 \times S_3^0) \times 100\% \quad (9)$$

[In the formula, "tri(cyclic group-substituted)alkyl tin alkoxide production amount" is the amount of tri(cyclic group-substituted)alkyl tin alkoxide produced [%] after circulating operation, T is the number of moles [mol] of tri(cyclic group-substituted)alkyl tin alkoxide produced after circulating operation, $W_3^0$ is the mass [kg] of the cyclic group-substituted alkyl tin alkoxide composition introduced into the catalyst tank before circulating operation, and $S_3^0$ is the tin atom concentration (in the active component) [mol/kg] of the composition before circulating operation.

Structural formulas of tetra(cyclic group-substituted)alkyldialkoxydistannoxane, di(cyclic group-substituted)alkyl tin dialkoxide and tri(cyclic group-substituted)alkyl tin alkoxide in cyclic group-substituted alkyl tin alkoxide composition

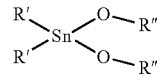

[Chemical Formula 96]

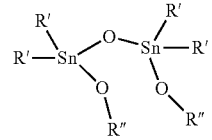

[Chemical Formula 97]

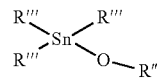

[Chemical Formula 98]

[R' represents a C3-16 alicyclic hydrocarbon group or C6-16 aromatic hydrocarbon group, and R" represents a C1-8 alkyl group.]

Examples 230 to 265

Cyclic group-substituted alkyl tin alkoxide compositions comprising the di(cyclic group-substituted)alkyl tin dialkoxides, tetraalkyl dialkoxydistannoxanes and tri(cyclic group-substituted)alkyl tin alkoxides having the structures listed in Table 31 were produced by the same methods as Synthesis Examples 3, 6 and 9. Next, using cyclic group-substituted alkyl tin alkoxide compositions comprising di(cyclic group-substituted)alkyl tin dialkoxides, tetraalkyl dialkoxydistannoxanes and tri(cyclic group-substituted)alkyl tin alkoxides were used according to the same method as in Example 1, and test operation (circulating operation) of the continuous circulating reactor shown in FIG. 1 was conducted, confirming modification reaction during heated circulation. Approximately 50 kg of each composition was introduced into the catalyst tank and circulated in a continuous circulating reactor as shown in FIG. 1 by the same method. Each composition was sampled from the catalyst tank after circulating operation and subjected to $^{119}$Sn-NMR spectral analysis. The concentration of tin atoms in the composition was calculated from the tetra(cyclic group-substituted)alkyldialkoxydistannoxane concentration and di(cyclic group-substituted)alkyl tin dialkoxide concentration of the composition after test operation as determined from the analysis results, and the percentage reduction from before the start of test operation was calculated. The number of moles of tri(cyclic group-substituted)alkyl tin alkoxide was also determined from the analysis results, and the amount produced with respect to number of moles of tin atoms (in the active component) of the composition before the start of test operation was calculated. The percentage reductions in the tin atom concentration (in the active component) of the compositions and the tri(cyclic group-substituted)alkyl tin alkoxide production amounts are shown in Table 31.

TABLE 31

| | Alkyl tin alkoxide composition | | Trialkyl tin alkoxide | | Continuous operation time [days] | Percentage reduction in tin atom concentration (in active component) [%] *13) | Trialkyl tin alkoxide production amount [%] *14) |
|---|---|---|---|---|---|---|---|
| Example | R' (alkyl group) | OR" (alkoxy group) | R'" (alkyl group) | Concentration [tin atom mol %] | | | |
| 230 | Cyclopentylmethyl | N-Butoxy | Cyclopentylmethyl | 12 | 5 | 4.4 | 4.4 |
| 231 | Cyclohexylethyl | N-Butoxy | Cyclohexylethyl | 11 | 5 | 5.9 | 6.0 |
| 232 | 3-Cyclopentylpropyl | N-Butoxy | 3-Cyclopentylpropyl | 12 | 4 | 6.1 | 6.2 |
| 233 | Benzyl | N-Butoxy | Benzyl | 12 | 5 | 5.5 | 5.3 |
| 234 | Phenethyl | N-Butoxy | Phenethyl | 12 | 4 | 5.9 | 5.9 |
| 235 | 3-Phenylpropyl | N-Butoxy | 3-Phenylpropyl | 12 | 4 | 6.1 | 6.1 |
| 236 | Cyclopentylmethyl | N-Butoxy | Cyclopentylmethyl | 24 | 4 | 4.3 | 4.3 |
| 237 | Cyclohexylethyl | N-Butoxy | Cyclohexylethyl | 25 | 4 | 5.7 | 5.6 |
| 238 | 3-Cyclopentylpropyl | N-Butoxy | 3-Cyclopentylpropyl | 25 | 4 | 5.8 | 5.7 |
| 239 | Benzyl | N-Butoxy | Benzyl | 25 | 5 | 5.3 | 5.2 |
| 240 | Phenethyl | N-Butoxy | Phenethyl | 25 | 4 | 5.7 | 5.6 |
| 241 | 3-Phenylpropyl | N-Butoxy | 3-Phenylpropyl | 25 | 5 | 5.8 | 5.8 |
| 242 | Cyclopentylmethyl | N-Butoxy | Cyclopentylmethyl | 45 | 5 | 4.1 | 4.1 |
| 243 | Cyclohexylethyl | N-Butoxy | Cyclohexylethyl | 46 | 4 | 5.5 | 5.3 |
| 244 | 3-Cyclopentylpropyl | N-Butoxy | 3-Cyclopentylpropyl | 45 | 5 | 5.6 | 5.4 |
| 245 | Benzyl | N-Butoxy | Benzyl | 45 | 4 | 5.1 | 5.1 |
| 246 | Phenethyl | N-Butoxy | Phenethyl | 45 | 5 | 5.4 | 5.4 |
| 247 | 3-Phenylpropyl | N-Butoxy | 3-Phenylpropyl | 45 | 4 | 5.6 | 5.5 |
| 248 | Cyclopentylmethyl | 2-Ethylbutyloxy | Cyclopentylmethyl | 12 | 5 | 4.4 | 4.5 |
| 249 | Cyclohexylethyl | 2-Ethylbutyloxy | Cyclohexylethyl | 12 | 5 | 5.6 | 5.6 |
| 250 | 3-Cyclopentylpropyl | 2-Ethylbutyloxy | 3-Cyclopentylpropyl | 12 | 4 | 5.9 | 6.0 |
| 251 | Benzyl | 2-Ethylbutyloxy | Benzyl | 11 | 5 | 5.5 | 5.4 |
| 252 | Phenethyl | 2-Ethylbutyloxy | Phenethyl | 11 | 4 | 5.7 | 5.7 |
| 253 | 3-Phenylpropyl | 2-Ethylbutyloxy | 3-Phenylpropyl | 12 | 5 | 6.0 | 5.8 |
| 254 | Cyclopentylmethyl | 2-Ethylbutyloxy | Cyclopentylmethyl | 25 | 5 | 4.2 | 4.2 |
| 255 | Cyclohexylethyl | 2-Ethylbutyloxy | Cyclohexylethyl | 24 | 4 | 5.4 | 5.2 |
| 256 | 3-Cyclopentylpropyl | 2-Ethylbutyloxy | 3-Cyclopentylpropyl | 24 | 4 | 5.6 | 5.4 |
| 257 | Benzyl | 2-Ethylbutyloxy | Benzyl | 25 | 5 | 5.3 | 5.3 |
| 258 | Phenethyl | 2-Ethylbutyloxy | Phenethyl | 24 | 5 | 5.4 | 5.4 |
| 259 | 3-Phenylpropyl | 2-Ethylbutyloxy | 3-Phenylpropyl | 25 | 4 | 5.9 | 6.0 |
| 260 | Cyclopentylmethyl | 2-Ethylbutyloxy | Cyclopentylmethyl | 46 | 4 | 4.1 | 4.0 |
| 261 | Cyclohexylethyl | 2-Ethylbutyloxy | Cyclohexylethyl | 46 | 4 | 5.1 | 5.0 |
| 262 | 3-Cyclopentylpropyl | 2-Ethylbutyloxy | 3-Cyclopentylpropyl | 45 | 4 | 5.3 | 5.2 |
| 263 | Benzyl | 2-Ethylbutyloxy | Benzyl | 45 | 4 | 5.1 | 5.0 |
| 264 | Phenethyl | 2-Ethylbutyloxy | Phenethyl | 45 | 5 | 5.2 | 5.3 |
| 265 | 3-Phenylpropyl | 2-Ethylbutyloxy | 3-Phenylpropyl | 46 | 5 | 5.5 | 5.6 |

*7) The percentage reduction in the tin atom concentration (in the active component) of the cyclic group-substituted alkyl tin alkoxide composition was determined by the following mathematical formula (8).
*8) The amount of tri(cyclic group-substituted)alkyl tin alkoxide production was calculated by mathematical formula (9).

[Mathematical Formula 48]

Percentage reduction of tin atom concentration (in active component)=$(S_3^0-S_3')/S_3^0 \times 100\%$  (8)

[In the formula, "percentage reduction of tin atom concentration (in active component)" is the percentage reduction [%] of the tin atom concentration (in the active component) of the composition after circulating operation, $S_3^0$ is the tin atom concentration (in the active component) [mol/kg] of the composition before circulating operation, and $S_3'$ is the tin atom concentration (in the active component) [mol/kg] of the composition after circulating operation. $S_3^0$ and $S_3'$ were calculated from the tetra(cyclic group-substituted)alkyldialkoxydistannoxane concentration and di(cyclic group-substituted)alkyl tin dialkoxide concentration of the composition, as determined by $^{119}$Sn-NMR spectral analysis.]

[Mathematical Formula 49]

Tri(cyclic group-substituted)alkyl tin alkoxide production amount=$T/(W_3^0 \times S_3^0) \times 100\%$  (9)

[In the formula, "tri(cyclic group-substituted)alkyl tin alkoxide production amount" is the amount of tri(cyclic group-substituted)alkyl tin alkoxide produced [%] after circulating operation, T is the number of moles [mol] of tri(cyclic group-substituted)alkyl tin alkoxide produced after circulating operation, $W_3^0$ is the mass [kg] of the cyclic group-substituted alkyl tin alkoxide composition introduced into the catalyst tank before circulating operation, and $S_3^0$ is the tin atom concentration (in the active component) [mol/kg] of the composition before circulating operation.

Structural formulas of tetra(cyclic group-substituted)alkyldialkoxydistannoxane, di(cyclic group-substituted)alkyl tin dialkoxide and tri(cyclic group-substituted)alkyl tin alkoxide in cyclic group-substituted alkyl tin alkoxide composition

[Chemical Formula 99]

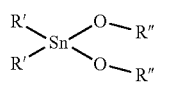

[Chemical Formula 100]

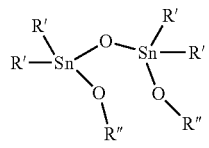

[Chemical Formula 101]

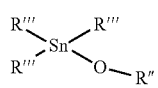

[R' represents a C3-16 alicyclic hydrocarbon group or C6-16 aromatic hydrocarbon group, and R" represents a C1-8 alkyl group.]

Example 266

A continuous circulating reactor comprising a tank reactor, a tube reactor and a tower reactor such as shown in FIG. 1 was used for transesterification reaction. Approximately 20 kg of a di(cyclohexylmethyl)-bis(3-methylbutoxy)tin composition produced by the same method as Synthesis Example 1 (tin atom concentration (in the active component) of composition: 2.02 mol/kg) was introduced into a SUS316 catalyst tank 130 equipped with a heating jacket and a liquid conveyance pump, via a supply line 15. Next, n-propyl 2-ethylhexanoate ester (product of Wako Pure Chemical Industries) was introduced into a starting material tank 110 via a supply line 1, and 3-methyl-1-butyl alcohol (product of Kuraray Co., Ltd.) was introduced into a starting material tank 120 via a supply line 2. The tank and pipe were steam traced to maintain the flow property. To the tank reactor 140 there were conveyed n-propyl 2-ethylhexanoate ester at a flow rate of about 10 kg/hr via a transport line 3, inline mixer 141 and transport line 5, and 3-methyl-1-butyl alcohol at a flow rate of about 12 kg/hr via a transport line 4, inline mixer 141 and transport line 5. The composition was conveyed from the catalyst tank 130 to the tank reactor 140 at 1.6 kg/hr, via a transport line 14, an inline mixer 141 equipped with a heating jacket, and a transport line 5. At the inline mixer 141, the di(cyclohexylmethyl)-bis(3-methylbutoxy) tin composition, n-propyl 2-ethylhexanoate ester and 3-methyl-1-butyl alcohol were mixed and heated. The concentration of tin atoms in the mixture in the tank reactor was 1.8 mol %. The tank reactor 140 was a 15 L-volume reactor, comprising a stirrer, heating jacket and liquid conveyance pump, and the heating jacket was heated with steam to control the mixture in the reactor to about 160° C. The tube reactor 150 with an outer diameter of 200 mm and a length of 1000 mm also comprised a heating jacket, which was heated with steam at about 160° C. The n-propyl 2-ethylhexanoate ester and 3-methyl-1-butyl alcohol that had been conveyed to the tank reactor 140 were subjected to transesterification reaction using a di(cyclohexylmethyl)-bis(3-methylbutoxy)tin composition as the catalyst, and then it was conveyed to a tube reactor 150 via a transport line 6 for reaction and further conveyed to a tower reactor 160 via a transport line 7 for reaction.

A SUS316 tower reactor 160 with an inner diameter of 75 mm and an effective length of 4500 mm, equipped with 30 sieve trays, was heated and thermally insulated with a heater around the entire tower reactor to prevent radiated heat loss, the heater being set to about 160° C. A liquid conveyance pump and reboiler 163 were provided at the bottom of the tower reactor 160, and the reboiler 163 was heated with steam at about 165° C. As further transesterification reaction proceeded in the tower reactor 160, the n-propanol and 3-methyl-1-butyl alcohol produced by the reaction were separated off by distillation, and the fraction composed mainly of n-propanol was collected from a collecting line 8. The mixture containing the 3-methylbutyl 2-ethylhexanoate ester reaction product was conveyed from the tower reactor 160 through a transport line 9 to a thin-film vaporizer 170 set to a temperature of 180° C. and a pressure of about 40 kPaA, and then the low-boiling-point component including 3-methylbutyl 2-ethylhexanoate ester was conveyed through a transport line 10 to a distillation column 180 (column packed with MetalGauze CY filler, inner diameter: 83 mm, effective length: 2800 mm), and purified. Separately, the high boiling point component including the di(cyclohexylmethyl)-bis(3-methylbutoxy)tin composition was conveyed to the catalyst tank 130 through a transport line 11, and then circulated to a continuous circulating reactor through the transport line 14, inline mixer 141 and transport line 5. When necessary, supply from the starting material tank and catalyst tank to the tank reactor was reduced or interrupted until the system interior reached a steady state. Operation was continued, and after the system interior reached a steady state, the mixture was sampled from the bottom of the tower reactor 160 and subjected to quantitative analysis by gas chromatography, and the yield of 3-methylbutyl 2-ethylhexanoate ester was found to be 18.8% based on n-propyl 2-ethylhexanoate ester groups. This state was continued for about 15 days, after which the mixture was again sampled from the bottom of the tower reactor 160 and subjected to quantitative analysis by gas chromatography, and the yield of 3-methylbutyl 2-ethylhexanoate ester was found to be 18.3%. It was possible to stably obtain 3-methylbutyl 2-ethylhexanoate ester at about 1.9 kg/hr from the collecting line 13 during continuous operation. The high boiling point component containing the di(cyclohexylmethyl)-bis(3-methylbutoxy)tin composition in the continuous circulating reactor after continuous operation was separated using the thin-film vaporizer 170, and collected in a catalyst tank 130, and the mass was measured. A sample was taken from the catalyst tank 130 through an extraction line 16, and as a result of $^{119}$Sn-NMR spectral analysis it was confirmed that di(cyclohexylmethyl)-bis(3-methylbutoxy)tin and tri(cyclohexylmethyl)(3-methylbutoxy)tin were present after continuous operation. Based on the analysis results, tri(cyclohexylmethyl)(3-methylbutoxy)tin was produced at approximately 0.34 mol after 15 days of continuous operation, an amount that was approximately 0.7% with respect to the number of moles of tin atoms (in the active component) of the composition introduced into the catalyst tank 130 before the start of continuous operation.

Example 267

A continuous circulating reactor comprising a tank reactor, a tube reactor and a tower reactor such as shown in FIG. 1 was used for transesterification reaction. Approximately 20 kg of a di(cyclohexylmethyl)-bis(3-methylbutoxy)tin composition produced by the same method as Synthesis Example 1 (tin atom concentration (in the active component) of composition: 2.26 mol/kg) was introduced into a SUS316 catalyst tank 130 equipped with a heating jacket and a liquid conveyance pump, via a supply line 15. The 3-methylbutyl 2-ethylhexanoate ester obtained from Example 306 was then introduced into a starting material tank 110 through a supply line 1, and ethyl 2-methylpropanoate ester (product of Aldrich) was introduced into a starting material tank 120 through a supply line 2. The tank and pipe were steam traced to maintain the flow property. The 3-methylbutyl 2-ethylhexanoate ester was conveyed at a flow rate of about 12 kg/hr through a transport line 3, inline mixer 141 and transport line 5, and the ethyl 2-methylpropanoate ester was conveyed to a tank reactor 140 at a flow rate of about 10 kg/hr through a transport line 4, inline mixer 141 and transport line 5. Separately, the catalyst tank 130 was heated by steam to maintain the flow property of the contents, and the di(cyclohexylmethyl)-bis(3-methylbutoxy)tin composition in this state was conveyed at 1.3 kg/hr through a transport line 14, an inline mixer 141 equipped with a heating jacket, and the transport line 5. At the inline mixer 141, the di(cyclohexylmethyl)-bis(3-methylbutoxy)tin composition, 3-methylbutyl 2-ethylhexanoate ester and ethyl 2-methylpropanoate ester were mixed and heated. The concentration of tin atoms in the mixture in the tank reactor 140 was 1.9 mol %. The tank reactor 140 was a 15 L-volume reactor, comprising a stirrer, heating jacket and liquid conveyance pump, and the heating jacket was heated with steam to control the mixture in the reactor to about 160° C. The tube reactor 150 also comprised a heating jacket, which was heated with steam at about 160° C. The 3-methylbutyl 2-ethylhexanoate ester and ethyl 2-methylpropanoate ester that had been conveyed to the tank reactor 140 were subjected to transesterification reaction using a di(cyclohexylmethyl)-bis(3-methylbutoxy)tin composition as the catalyst, and then it was conveyed to the tube reactor 150 via a transport line 6 for reaction and subsequently conveyed to a tower reactor 160 via a transport line 7 for reaction.

A SUS316 tower reactor 160 with an inner diameter of 75 mm and an effective length of 4500 mm, equipped with 30 sieve trays, was heated and thermally insulated with a heater around the entire tower reactor to prevent radiated heat loss, the heater being set to about 160° C. A liquid conveyance pump and reboiler 163 were provided at the bottom of the tower reactor 160, and the reboiler 163 was heated with steam at about 165° C. As further transesterification reaction proceeded in the tower reactor 160, the 3-methylbutyl 2-ethylpropanoate ester generated by the reaction and the unreacted ethyl 2-methylpropanoate ester were separated out by distillation, and the fraction containing the ethyl 2-methylpropanoate ester and 3-methylbutyl 2-methylpropanoate ester was collected from a collecting line 8.

The mixture containing the ethyl 2-ethylhexanoate ester reaction product and unreacted 3-methylbutyl 2-ethylhexanoate ester was conveyed from the tower reactor 160 through a transport line 9 to a thin-film vaporizer 170 set to a temperature of 180° C. and a pressure of about 30 kPaA, and then the low-boiling-point component including ethyl 2-ethylhexanoate ester and 3-methylbutyl 2-ethylhexanoate ester was conveyed through a transport line 11 to a distillation column 180 (column packed with MetalGauze CY filler, inner diameter: 83 mm, effective length: 2800 mm), and purified. Separately, the high boiling point component including the di(cyclohexylmethyl)-bis(3-methylbutoxy)tin composition was conveyed to the catalyst tank 130 through a transport line 11, and then circulated to a continuous circulating reactor through the transport line 14, inline mixer 141 and transport line 5. When necessary, supply from the starting material tank and catalyst tank to the tank reactor was reduced or interrupted until the system interior reached a steady state. Operation was continued, and after the system interior reached a steady state, the mixture was sampled from the bottom of the tower reactor 160 and subjected to quantitative analysis by gas chromatography, and the yield of ethyl 2-ethylhexanoate ester was found to be 31.1% (based on 3-methylbutyl 2-ethylhexanoate ester groups). This state was continued for about 15 days, after which the mixture was again sampled from the bottom of the tower reactor 160 and subjected to quantitative analysis by gas chromatography, and the yield of ethyl 2-ethylhexanoate ester was found to be 30.5%. It was possible to stably obtain ethyl 2-ethylhexanoate ester in the collected fraction at about 2.6 kg/hr from the collecting line 12 during continuous operation. The high boiling point component containing the di(cyclohexylmethyl)-bis(3-methylbutoxy)tin composition in the continuous circulating reactor after continuous operation was separated using the thin-film vaporizer 170, and collected in a catalyst tank 130, and the mass was measured. A sample was taken from the catalyst tank 130 through an extraction line 16, and as a result of $^{119}$Sn-NMR spectral analysis it was confirmed that di(cyclohexylmethyl)-bis(3-methylbutoxy)tin, di(cyclohexylmethyl)diethoxytin, tri(cyclohexylmethyl)(3-methylbutoxy)tin and tri(cyclohexylmethyl)ethoxytin were present after continuous operation. Based on the analysis results, tri(cyclohexylmethyl)(3-methylbutoxy)tin and tri(cyclohexylmethyl)ethoxytin were produced at a total of 0.36 mol after 15 days of continuous operation, an amount that was approximately 0.9% with respect to the number of moles of tin atoms (in the active component) of the composition introduced into the catalyst tank 130 before the start of continuous operation.

Example 268

A continuous circulating reactor comprising a tank reactor, a tube reactor and a tower reactor such as shown in FIG. 1 was used for transesterification reaction. Approximately 20 kg of a 1,1,3,3-tetra(cyclohexylmethyl)-1,3-diethoxydistannoxane composition produced by the same method as Synthesis Example 2 (tin atom concentration (in the active component) of the composition: 2.68 mol/kg) was introduced into a SUS316 catalyst tank 130, equipped with a heating jacket and a liquid conveyance pump, through a supply line 15. The 3-methylbutyl 2-ethylhexanoate ester was then introduced into a starting material tank 110 through a supply line 1, and ethyl 2-methylpropanoate ester (product of Aldrich) was introduced into a starting material tank 120 through a supply line 2. The tank and pipe were steam traced to maintain the flow property. The 3-methylbutyl 2-ethylhexanoate ester was conveyed at a flow rate of about 12 kg/hr through a transport line 3, inline mixer 141 and transport line 5, and the ethyl 2-methylpropanoate ester was conveyed to a tank reactor 140 at a flow rate of about 10 kg/hr through a transport line 4, inline mixer 141 and transport line 5. Also, the catalyst tank 130 was heated by steam to maintain the flow property of the contents, and the composition in this state was conveyed at 0.9 kg/hr through a transport line 14, an inline mixer 141 equipped with a heating jacket, and the transport line 5. At the inline mixer 141, the composition, 3-methylbutyl 2-ethylhexanoate ester and ethyl 2-methylpropanoate ester were mixed and heated. The concentration of tin atoms in the mixture in the tank reactor 140 was 1.8 mol %. The tank reactor 140 was a 15 L-volume reactor, comprising a stirrer, heating jacket and liquid conveyance pump, and the heating jacket was heated with steam to control the mixture in the reactor to about 160° C. The tube reactor 150 also comprised a heating jacket, which was heated with steam at about 160° C. The 3-methylbutyl 2-ethylhexanoate ester and ethyl 2-methylpropanoate ester conveyed to the tank reactor 140 were subjected to transesterification reaction using 1,1,3,3-tetra(cyclohexylmethyl)-1,3-diethoxydistannoxane as the catalyst, and then conveyed to the tube reactor 150 through a transport line 6 for reaction, and further conveyed to a tower reactor 160 through a transport line 7 for reaction. A SUS316 tower reactor 160 with an inner diameter of 75 mm and an effective length of 4500 mm, equipped with 30 sieve trays, was heated and thermally insulated with a heater around the entire tower reactor to prevent radiated heat loss, the heater being set to about 160° C. A liquid conveyance pump and reboiler 163 were provided at the bottom of the tower reactor 160, and the reboiler 163 was heated with steam at about 165° C. As further transesterification reaction proceeded in the tower reactor 160, the 3-methylbutyl 2-methylpropanoate ester generated by the reaction and the unreacted ethyl 2-methylpropanoate ester were separated out by distillation, and the fraction containing the ethyl 2-methylpropanoate ester and 3-methylbutyl 2-methylpropanoate ester was collected from a collecting line 8. The mixture containing the ethyl 2-ethylhexanoate ester reaction product and unreacted 3-methylbutyl 2-ethylhexanoate ester was conveyed from the tower reactor 160 through a transport line 9 to a thin-film vaporizer 170 set to a temperature of 180° C. and a pressure of about 30 kPaA, and then the low-boiling-point component including ethyl 2-ethylhexanoate ester and 3-methylbutyl 2-ethylhexanoate ester was conveyed through a transport line 10 to a distillation column 180 (column packed with MetalGauze CY filler, inner diameter: 83 mm, effective length: 2800 mm), and purified. Separately, the high boiling point component including the 1,1,3,3-tetra(cyclohexylmethyl)-1,3-diethoxydistannoxane composition was conveyed to the catalyst tank 130 through a transport line 11, and then circulated to the continuous circulating reactor through the transport line 14, inline mixer 141 and transport line 5. When necessary, supply from the starting material tank and catalyst tank to the tank reactor was reduced or interrupted until the system interior reached a steady state. Operation was continued, and after the system interior reached a steady state, the mixture was sampled from the bottom of the tower reactor 160 and subjected to quantitative analysis by gas chromatography, and the yield of ethyl 2-ethylhexanoate ester was found to be 27.5% (based on 3-methylbutyl 2-ethylhexanoate ester groups). This state was continued for about 15 days, after which the mixture was again sampled from the bottom of the tower reactor 160 and subjected to quantitative analysis by gas chromatography, and the yield of ethyl 2-ethylhexanoate ester was found to be 26.9%. It was possible to stably obtain ethyl 2-ethylhexanoate ester in the collected fraction at about 2.3 kg/hr from the collecting line 12 during continuous operation. The high boiling point component including the 1,1,3,3-tetra(cyclohexylmethyl)-1,3-diethoxydistannoxane composition in the continuous circulating reactor after continuous operation was separated using a thin-film vaporizer 170 and collected in the catalyst tank 130, and the mass was measured. A sample was taken from the extraction line 16 of the catalyst tank 130, and as a result of $^{119}$Sn-NMR spectral analysis the catalyst tank 130 was found to contain 1,1,3,3-tetra(cyclohexylmethyl)-1,3-bis(3-methylbutoxy)distannoxane, 1,1,3,3-tetra(cyclohexylmethyl)-1,3-diethoxydistannoxane, tri(cyclohexylmethyl)(3-methylbutoxy)tin and tri(cyclohexylmethyl)ethoxytin. Based on the analysis results, tri(cyclohexylmethyl)(3-methylbutoxy)tin and tri(cyclohexylmethyl)ethoxytin were produced at a total of 0.59 mol after 15 days of continuous operation, an amount that was approximately 1.1% with respect to the number of moles of tin atoms (in the active component) introduced into the catalyst tank 130 before the start of continuous operation.

Example 269

A continuous circulating reactor comprising a tube reactor and a tower reactor such as shown in FIG. 2 was used for transesterification reaction. Approximately 20 kg of a 1,1,3,3-tetra(cyclohexylmethyl)-1,3-bis(3-methylbutyloxy)distannoxane composition produced by the same method as Synthesis Example 2 (tin atom concentration (in the active component) of the composition: 2.41 mol/kg) was introduced into a SUS316 catalyst tank 230, equipped with a heating jacket and a liquid conveyance pump, through a supply line 33. The 3-methylbutyl 2-ethylhexanoate ester was then introduced into a starting material tank 210 through a supply line 21, and ethyl 2-methylpropanoate ester was introduced into a starting material tank 220 through a supply line 22. The tank and pipe were steam traced to maintain the flow property. The 3-methylbutyl 2-ethylhexanoate ester was conveyed through a transport line 23, inline mixer 241 and transport line 25 at a flow rate of about 12 kg/hr, and the ethyl 2-methylpropanoate ester was conveyed to a tube reactor 240 equipped with a heating jacket, through a transport line 24, inline mixer 241 and transport line 25 at a flow rate of about 10 kg/hr. Also, the catalyst tank 230 was heated by steam to maintain the flow property of the contents, and the composition in this state was conveyed at 1.0 kg/hr through a transport line 34, an inline mixer 241 and the transport line 25. At the inline mixer 241, the composition, 3-methylbutyl 2-ethylhexanoate ester and ethyl 2-methylpropanoate ester were mixed and heated. The 3-methylbutyl 2-ethylhexanoate ester and ethyl 2-methylpropanoate ester that had been conveyed to the tube reactor 240 were subjected to transesterification reaction using 1,1,3,3-tetra(cyclohexylmethyl)-1,3-bis(3-methylbutyloxy)distannoxane as the catalyst, and were conveyed to the tower reactor 250 through a transport line 26 for further reaction. The SUS316 tower reactor 250 with an inner diameter of 130 mm and an effective length of 4500 mm, equipped with 30 sieve trays, was provided with a heater, reboiler 253 and liquid conveyance pump, and the reactor interior was controlled to approximately 160° C. with the heater and reboiler 253. At the top of the tower reactor 250, the fraction containing the 3-methylbutyl 2-methylpropanoate ester produced by the transesterification reaction and the unreacted ethyl 2-methylpropanoate ester was condensed with a condenser 251, and collected by a collecting line 27 via a condensate tank 252. The mixture containing the ethyl 2-ethylhexanoate ester reaction product and unreacted 3-methylbutyl 2-ethylhexanoate ester was conveyed from the bottom of the tower reactor 250 through a transport line 28 to a thin-film vaporizer 260 set to a temperature of 180° C. and a pressure of about 30 kPaA, and then the low-boiling-point component including ethyl 2-ethylhexanoate ester and the unreacted 3-methylbutyl 2-ethylhexanoate ester was conveyed through a transport line 29 to a distillation column 270 (column packed with MetalGauze CY filler, inner diameter: 83 mm, effective length: 2800 mm), and purified. Separately, the high boiling point component including the 1,1,3,3-tetra(cyclohexylmethyl)-1,3-bis(3-methylbutyloxy)distannoxane composition was conveyed to the catalyst tank 230 through a transport line 30, and then circulated to the continuous circulating reactor through the transport line 34, inline mixer 241 and transport line 25. When necessary, supply from the starting material tank and catalyst tank to the tube reactor was reduced or interrupted until the system interior reached a steady state. Operation was continued, and after the system interior reached a steady state, the mixture was sampled from the bottom of the tower reactor 250 and subjected to quantitative analysis by gas chromatography, and the yield of ethyl 2-ethylhexanoate ester was found to be 27.1% based on 3-methylbutyl 2-ethylhexanoate ester groups. This state was continued for about 15 days, after which the mixture was again sampled from the bottom of the tower reactor 250 and subjected to quantitative analysis by gas chromatography, and the yield of ethyl 2-ethylhexanoate ester was found to be 26.5%.

It was possible to stably obtain ethyl 2-ethylhexanoate ester in the collected fraction at about 2.6 kg/hr from the collecting line 31 during continuous operation. The high boiling point component including the 1,1,3,3-tetra(cyclohexylmethyl)-1,3-bis(3-methylbutyloxy)distannoxane composition in the continuous circulating reactor after continuous operation was separated using a thin-film vaporizer 260 and collected in the catalyst tank 230, and the mass was measured. A sample was taken from the extraction line 35 of the catalyst tank 230, and as a result of $^{119}$Sn-NMR spectral analysis the catalyst tank was found to contain 1,1,3,3-tetra(cyclohexylmethyl)-1,3-bis(3-methylbutyloxy)distannoxane 1,1,3,3-tetra(cyclohexylmethyl)-1,3-diethoxy-distannoxane, tri(cyclohexylmethyl)(3-methylbutoxy)tin and tri(cyclohexylmethyl)ethoxytin. Based on the analysis results, tri(cyclohexylmethyl)(3-methylbutoxy)tin and tri(cyclohexylmethyl)ethoxytin were produced at a total of 0.58 mol after 15 days of continuous operation, an amount that was approximately 1.2% with respect to the number of moles of tin atoms (in the active component) introduced into the catalyst tank 230 before the start of continuous operation.

Example 270

A continuous circulating reactor comprising a tank reactor and a tower reactor such as shown in FIG. 3 was used for transesterification reaction. Di(cyclohexylmethyl)-bis(3-methylbutoxy)tin and 1,1,3,3-tetra(cyclohexylmethyl)-1,3-bis(3-methylbutoxy)distannoxane produced by the same method as Synthesis Example 1 and Synthesis Example 2 were mixed to prepare a cyclic group-substituted alkyl tin alkoxide composition. The composition was prepared so that the molar ratio of tin atoms of the di(cyclohexylmethyl)-bis(3-methylbutoxy)tin and 1,1,3,3-tetra(cyclohexylmethyl)-1,3-bis(3-methylbutoxy)distannoxane with respect to the number of moles of tin atoms (in the active component) in the composition was 65:35. The tin atom concentration (in the active component) of the composition was 2.31 mol/kg, as determined from the di(cyclohexylmethyl)-bis(3-methylbutoxy)tin concentration and 1,1,3,3-tetra(cyclohexylmethyl)-1,3-bis(3-methylbutoxy)distannoxane concentration of the composition. Approximately 20 kg of the composition was introduced into a SUS316 catalyst tank 330 equipped with a heating jacket and liquid conveyance pump, through a supply line 53. The 3-methylbutyl 2-ethylhexanoate ester was then introduced into a starting material tank 310 through a supply line 41, and ethyl 2-methylpropanoate ester was introduced into a starting material tank 320 through a supply line 42. The tank and pipe were steam traced to maintain the flow property. The 3-methylbutyl 2-ethylhexanoate ester was conveyed at a flow rate of about 12 kg/hr through a transport line 43, inline mixer 341 and transport line 45, and the ethyl 2-methylpropanoate ester was conveyed to a tank reactor 340 at a flow rate of about 10 kg/hr through a transport line 44, inline mixer 341 and transport line 45. Also, the catalyst tank 330 was heated by steam to maintain the flow property of the contents, and the composition in this state was conveyed at 1.3 kg/hr through a transport line 54, an inline mixer 341 equipped with a heating jacket, and the transport line 45. At the inline mixer 341, the cyclic group-substituted alkyl tin alkoxide composition comprising bis(3-methylbutyl)diethoxytin and tetrakis(3-methylbutyl)diethoxydistannoxane was mixed with 3-methylbutyl 2-ethylhexanoate ester and ethyl 2-methylpropanoate ester, and the mixture was heated. The tank reactor 340 was a 15 L-volume reactor, comprising a stirrer, heating jacket and liquid conveyance pump, and the heating jacket was heated with steam to control the mixture in the reactor to about 160° C. The 3-methylbutyl 2-ethylhexanoate ester and ethyl 2-methylpropanoate ester that had been conveyed to the tank reactor 340 were subjected to transesterification reaction using the composition as the catalyst, and then it was conveyed to the tower reactor 350 via a transport line 46 for reaction. The SUS316 tower reactor 350 with an inner diameter of 130 mm and an effective length of 4500 mm, equipped with 25 sieve trays, was provided with a heater, reboiler 353 and liquid conveyance pump, and the reactor interior was controlled to approximately 160° C. with the heater and reboiler 353. At the top of the tower reactor 350, the fraction containing the 3-methylbutyl 2-methylpropanoate ester produced by the transesterification reaction and the unreacted ethyl 2-methylpropanoate ester was condensed with a condenser 351, and collected from a collecting line 47 via a condensate tank 352. The mixture containing the ethyl 2-ethylhexanoate ester reaction product and unreacted 3-methylbutyl 2-ethylhexanoate ester was conveyed from the bottom of the tower reactor 350 through a transport line 48 to a thin-film vaporizer 360 set to a temperature of 180° C. and a pressure of about 30 kPaA, and then the low-boiling-point component including ethyl 2-ethylhexanoate ester and 3-methylbutyl 2-ethylhexanoate ester was conveyed through a transport line 49 to a distillation column 370 (column packed with MetalGauze CY filler, inner diameter: 83 mm, effective length: 2800 mm), and purified. Separately, the high boiling point component including the composition was conveyed to the catalyst tank 330 through a transport line 50, and then circulated to the continuous circulating reactor through the transport line 54, inline mixer 341 and transport line 45. When necessary, supply from the starting material tank and catalyst tank to the tank reactor was reduced or interrupted until the system interior reached a steady state. Operation was continued, and after the system interior reached a steady state, the mixture was sampled from the bottom of the tower reactor 350 and subjected to quantitative analysis by gas chromatography, and the yield of ethyl 2-ethylhexanoate ester was found to be 30.5% based on 3-methylbutyl 2-ethylhexanoate ester groups. This state was continued for about 15 days, after which the mixture was again sampled from the bottom of the tower reactor 350 and subjected to quantitative analysis by gas chromatography, and the yield of 2-methylpropyl 2-ethylhexanoate ester was found to be 29.7%.

It was possible to stably obtain ethyl 2-ethylhexanoate ester in the collected fraction at about 2.6 kg/hr from the collecting line 51 during continuous operation. The high boiling point component including the composition in the continuous circulating reactor after continuous operation was separated using the thin-film vaporizer 360 and collected in the catalyst tank 330, and the mass was measured. A sample was taken from the extraction line 55 of the catalyst tank 330, and as a result of $^{119}$Sn-NMR spectral analysis the catalyst tank 330 was found to contain di(cyclohexylmethyl)-bis(3-methylbutoxy)tin, di(cyclohexylmethyl)diethoxytin, 1,1,3,3-tetra(cyclohexylmethyl)-1,3-bis(3-methylbutoxy)distannoxane, 1,1,3,3-tetra(cyclohexylmethyl)-1,3-diethoxydistannoxane, tri(cyclohexylmethyl)(3-methylbutoxy)tin and tri(cyclohexylmethyl)ethoxytin. Based on the analysis results, tri(cyclohexylmethyl)(3-methylbutoxy)tin and tri(cyclohexylmethyl)ethoxytin were produced at a total of 0.46 mol after 15 days of continuous operation, an amount that was approximately 1% with respect to the number of moles of tin atoms (in the active component) of the composition introduced into the catalyst tank 330 before the start of continuous operation.

Examples 271 to 304

The di(cyclic group-substituted)alkyl tin dialkoxide compositions listed in Table 32, obtained by the same methods as Synthesis Examples 1, 4 and 7, were used for transesterification reaction with a continuous circulating reactor by the same method as Example 269. The carboxylic acid esters and alcohols used as starting materials for transesterification reaction, listed in Table 32, were each introduced into a starting material tank and conveyed to a tank reactor, and transesterification reaction was carried out with a di(cyclic group-substituted)alkyl tin dialkoxide as the catalyst. The flow rate of the composition conveyed from the catalyst tank was adjusted so that the concentration of tin atoms in the reaction mixture in the tank reactor was 1.5 to 2.5 mol %, and transesterification reaction was carried out at the temperatures listed in Table 32. Table 32 shows the reaction yields (initial yields) immediately after reaching a steady state and the reaction yields and tri(cyclic group-substituted) alkyl tin alkoxide production amounts (production amounts with respect to the number of moles of tin atoms (in the active component) introduced into the catalyst tank before continuous operation), after 15 days of continuous operation.

TABLE 32

| | Dialkyl tin dialkoxide | | Starting materials for transesterification reaction | | Temperature | Initial yield | Yield [mol %] (after 15 days of continuous | Trialkyl tin alkoxide concentration [mol %] (after 15 days of continuous |
|---|---|---|---|---|---|---|---|---|
| Example | R' (alkyl group) | OR" (alkoxy group) | Carboxylic acid ester | Alcohol | [° C.] | [mol %] | operation) | operation) *15) |
| 271 | Cyclopentylmethyl | Ethoxy | Methyl 2-ethylhexanoate | Ethanol | 150 | 33.3 | 32.3 | 1.4 |
| 272 | Cyclohexylethyl | Ethoxy | Methyl 2-ethylhexanoate | Ethanol | 150 | 23.9 | 23.1 | 1.6 |
| 273 | 3-Cyclopentylpropyl | Ethoxy | Methyl 2-ethylhexanoate | Ethanol | 150 | 23.4 | 22.4 | 2.2 |
| 274 | Benzyl | Ethoxy | Methyl 2-ethylhexanoate | Ethanol | 150 | 25.6 | 24.9 | 1.4 |
| 275 | Phenethyl | Ethoxy | Methyl 2-ethylhexanoate | Ethanol | 150 | 23.4 | 22.3 | 2.5 |
| 276 | 3-Phenylpropyl | Ethoxy | Methyl 2-ethylhexanoate | Ethanol | 150 | 23.1 | 22.5 | 1.4 |
| 277 | Cyclopentylmethyl | N-Butoxy | Methyl 2-ethylhexanoate | Ethanol | 150 | 33.0 | 31.8 | 1.9 |
| 278 | Cyclohexylmethyl | N-Butoxy | Methyl 2-ethylhexanoate | Ethanol | 150 | 31.3 | 30.6 | 1.2 |
| 279 | Cyclohexylethyl | N-Butoxy | Methyl 2-ethylhexanoate | Ethanol | 150 | 23.7 | 23.1 | 1.3 |
| 280 | 3-Cyclopentylpropyl | N-Butoxy | Methyl 2-ethylhexanoate | Ethanol | 150 | 22.5 | 22.2 | 0.7 |
| 281 | Benzyl | N-Butoxy | Methyl 2-ethylhexanoate | Ethanol | 150 | 25.2 | 24.2 | 2.2 |
| 282 | Phenethyl | N-Butoxy | Methyl 2-ethylhexanoate | Ethanol | 150 | 22.9 | 22.3 | 1.5 |
| 283 | 3-Phenylpropyl | N-Butoxy | Methyl 2-ethylhexanoate | Ethanol | 150 | 22.7 | 21.8 | 2.1 |
| 284 | Cyclopentylmethyl | 2-Methylpropyloxy | Propyl 2-ethylhexanoate | 2-Methyl-1-propanol | 160 | 32.9 | 31.8 | 1.7 |
| 285 | Cyclohexylmethyl | 2-Methylpropyloxy | Propyl 2-ethylhexanoate | 2-Methyl-1-propanol | 160 | 31.9 | 30.5 | 2.3 |
| 286 | Cyclohexylethyl | 2-Methylpropyloxy | Propyl 2-ethylhexanoate | 2-Methyl-1-propanol | 160 | 23.5 | 23.1 | 0.9 |
| 287 | 3-Cyclopentylpropyl | 2-Methylpropyloxy | Propyl 2-ethylhexanoate | 2-Methyl-1-propanol | 160 | 22.9 | 21.9 | 2.4 |
| 288 | Benzyl | 2-Methylpropyloxy | Propyl 2-ethylhexanoate | 2-Methyl-1-propanol | 160 | 25.4 | 24.8 | 1.2 |

TABLE 32-continued

| Example | Dialkyl tin dialkoxide R' (alkyl group) | OR" (alkoxy group) | Starting materials for transesterification reaction Carboxylic acid ester | Alcohol | Temperature [° C.] | Initial yield [mol %] | Yield [mol %] (after 15 days of continuous operation) | Trialkyl tin alkoxide concentration [mol %] (after 15 days of continuous operation) *15) |
|---|---|---|---|---|---|---|---|---|
| 289 | Phenethyl | 2-Methylpropyloxy | Propyl 2-ethylhexanoate | 2-Methyl-1-propanol | 160 | 22.7 | 22.1 | 1.4 |
| 290 | 3-Phenylpropyl | 2-Methylpropyloxy | Propyl 2-ethylhexanoate | 2-Methyl-1-propanol | 160 | 22.8 | 22.1 | 1.7 |
| 291 | Cyclopentylmethyl | 3-Methylbutyloxy | Propyl 2-ethylhexanoate | 3-methyl-1-butanol | 160 | 32.8 | 31.2 | 2.4 |
| 292 | Cyclohexylmethyl | 3-Methylbutyloxy | Propyl 2-ethylhexanoate | 3-methyl-1-butanol | 160 | 31.7 | 30.6 | 1.8 |
| 293 | Cyclohexylethyl | 3-Methylbutyloxy | Propyl 2-ethylhexanoate | 3-methyl-1-butanol | 160 | 23.4 | 22.5 | 2.2 |
| 294 | 3-Cyclopentylpropyl | 3-Methylbutyloxy | Propyl 2-ethylhexanoate | 3-methyl-1-butanol | 160 | 23.1 | 22.3 | 1.9 |
| 295 | Benzyl | 3-Methylbutyloxy | Propyl 2-ethylhexanoate | 3-methyl-1-butanol | 160 | 25.2 | 24.5 | 1.5 |
| 296 | Phenethyl | 3-Methylbutyloxy | Propyl 2-ethylhexanoate | 3-methyl-1-butanol | 160 | 22.8 | 22.1 | 1.7 |
| 297 | 3-Phenylpropyl | 3-Methylbutyloxy | Propyl 2-ethylhexanoate | 3-methyl-1-butanol | 160 | 22.8 | 21.9 | 2.1 |
| 298 | Cyclopentylmethyl | 2-Ethylbutyloxy | Propyl 2-ethylhexanoate | 3-methyl-1-butanol | 160 | 32.7 | 31.6 | 1.9 |
| 299 | Cyclohexylmethyl | 2-Ethylbutyloxy | Propyl 2-ethylhexanoate | 3-methyl-1-butanol | 160 | 31.8 | 30.4 | 2.4 |
| 300 | Cyclohexylethyl | 2-Ethylbutyloxy | Propyl 2-ethylhexanoate | 3-methyl-1-butanol | 160 | 23.5 | 22.8 | 1.7 |
| 301 | 3-Cyclopentylpropyl | 2-Ethylbutyloxy | Propyl 2-ethylhexanoate | 3-methyl-1-butanol | 160 | 22.9 | 22.4 | 1.1 |
| 302 | Benzyl | 2-Ethylbutyloxy | Propyl 2-ethylhexanoate | 3-methyl-1-butanol | 160 | 25.4 | 24.1 | 2.8 |
| 303 | Phenethyl | 2-Ethylbutyloxy | Propyl 2-ethylhexanoate | 3-methyl-1-butanol | 160 | 22.9 | 22.1 | 1.7 |
| 304 | 3-Phenylpropyl | 2-Ethylbutyloxy | Propyl 2-ethylhexanoate | 3-methyl-1-butanol | 160 | 22.8 | 22.5 | 0.6 |

*15) The amount of tri(cyclic group-substituted)alkyl tin alkoxide production was calculated by mathematical formula (10).

[Mathematical Formula 50]

Tri(cyclic group-substituted)alkyl tin alkoxide production amount = $T/(W_1^0 \times S_1^0) \times 100\%$     (10)

[In the formula, "tri(cyclic group-substituted)alkyl tin alkoxide production amount" is the amount of tri(cyclic group-substituted)alkyl tin alkoxide produced [%] after continuous operation, T is the number of moles [mol] of tri(cyclic group-substituted)alkyl tin alkoxide produced after continuous operation, $W_1^0$ is the mass [kg] of the di(cyclic group-substituted)alkyl tin dialkoxide composition introduced into the catalyst tank before continuous operation, and $S_1^0$ is the tin atom concentration (in the active component) [mol/kg] of the composition before continuous operation. The number of moles of tri(cyclic group-substituted)alkyl tin alkoxide T is calculated from the tri(cyclic group-substituted)alkyl tin alkoxide concentration determined by $^{119}$Sn-NMR spectral analysis of the composition collected after continuous operation, and the mass of the di(cyclic group-substituted)alkyl tin dialkoxide composition collected after continuous operation.]

Structural formula of di(cyclic group-substituted)alkyl tin dialkoxide

[Chemical Formula 102]

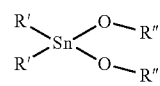

[R' represents a C3-16 alicyclic hydrocarbon group or C6-16 aromatic hydrocarbon group, and R" represents a C1-8 alkyl group.]

Examples 305 to 331

The di(cyclic group-substituted)alkyl tin dialkoxide compositions listed in Table 33, obtained by the same methods as Synthesis Examples 1, 4 and 7, were used for transesterification reaction with a continuous circulating reactor by the same method as Example 267. The flow rate of the composition conveyed from the catalyst tank was adjusted so that the concentration of tin atoms in the reaction mixture in the tank reactor was 1.5 to 2.5 mol %, and transesterification reaction was carried out at the temperatures listed in Table 33, using the composition as the catalyst. Table 33 shows the reaction yields (initial yields) immediately after reaching a steady state and the reaction yields and tri(cyclic group-substituted)alkyl tin alkoxide production amounts (production amounts with respect to the number of moles of tin atoms (in the active component) introduced into the catalyst tank before continuous operation), after 15 days of continuous operation.

Structural formula of di(cyclic group-substituted)alkyl tin dialkoxide

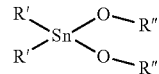

[Chemical Formula 103]

TABLE 33

| | Dialkyl tin dialkoxide | | Temperature | Initial yield | Yield [mol %] (after 15 days of | Trialkyl tin alkoxide production amount [%] (after 15 days of |
|---|---|---|---|---|---|---|
| Example | R' (alkyl group) | OR" (alkoxy group) | [° C.] | [mol %] | continuous operation) | continuous operation) *16) |
| 305 | Cyclopentylmethyl | Ethoxy | 160 | 30.3 | 29.5 | 1.5 |
| 306 | Cyclohexylethyl | Ethoxy | 160 | 21.8 | 21.1 | 1.6 |
| 307 | 3-Cyclopentylpropyl | Ethoxy | 160 | 21.3 | 20.5 | 2.1 |
| 308 | Benzyl | Ethoxy | 160 | 23.3 | 22.7 | 1.4 |
| 309 | Phenethyl | Ethoxy | 160 | 21.3 | 20.3 | 2.5 |
| 310 | 3-Phenylpropyl | Ethoxy | 160 | 21.0 | 20.5 | 1.4 |
| 311 | Cyclopentylmethyl | N-Butoxy | 160 | 30.1 | 29.0 | 1.9 |
| 312 | Cyclohexylmethyl | N-Butoxy | 160 | 28.5 | 27.9 | 1.1 |
| 313 | Cyclohexylethyl | N-Butoxy | 160 | 21.6 | 21.1 | 1.3 |
| 314 | 3-Cyclopentylpropyl | N-Butoxy | 160 | 20.5 | 20.3 | 0.6 |
| 315 | Benzyl | N-Butoxy | 160 | 23.0 | 22.0 | 2.2 |
| 316 | Phenethyl | N-Butoxy | 160 | 20.9 | 20.3 | 1.5 |
| 317 | 3-Phenylpropyl | N-Butoxy | 160 | 20.7 | 19.9 | 2.1 |
| 318 | Cyclopentylmethyl | 2-Methylpropyloxy | 170 | 30.0 | 29.0 | 1.7 |
| 319 | Cyclohexylmethyl | 2-Methylpropyloxy | 170 | 29.1 | 27.8 | 2.3 |
| 320 | Cyclohexylethyl | 2-Methylpropyloxy | 170 | 21.4 | 21.0 | 0.9 |
| 321 | 3-Cyclopentylpropyl | 2-Methylpropyloxy | 170 | 20.9 | 20.0 | 2.3 |
| 322 | Benzyl | 2-Methylpropyloxy | 170 | 23.2 | 22.6 | 1.2 |
| 323 | Phenethyl | 2-Methylpropyloxy | 170 | 20.7 | 20.2 | 1.5 |
| 324 | 3-Phenylpropyl | 2-Methylpropyloxy | 170 | 20.8 | 20.2 | 1.7 |
| 325 | Cyclopentylmethyl | 3-Methylbutyloxy | 170 | 29.8 | 28.5 | 2.4 |
| 326 | Cyclohexylmethyl | 3-Methylbutyloxy | 170 | 28.9 | 27.9 | 1.8 |
| 327 | Cyclohexylethyl | 3-Methylbutyloxy | 170 | 21.4 | 20.5 | 2.2 |
| 328 | 3-Cyclopentylpropyl | 3-Methylbutyloxy | 170 | 21.0 | 20.3 | 2.0 |
| 329 | Benzyl | 3-Methylbutyloxy | 170 | 23.0 | 22.3 | 1.5 |
| 330 | Phenethyl | 3-Methylbutyloxy | 170 | 20.8 | 20.2 | 1.8 |
| 331 | 3-Phenylpropyl | 3-Methylbutyloxy | 170 | 20.8 | 20.0 | 2.0 |

*16) The amount of tri(cyclic group-substituted)alkyl tin alkoxide production was calculated by mathematical formula (10).

[Mathematical Formula 51]

Tri(cyclic group-substituted)alkyl tin alkoxide production amount $= T/(W_1^0 \times S_1^0) \times 100\%$ (10)

[In the formula, "tri(cyclic group-substituted)alkyl tin alkoxide production amount" is the amount of tri(cyclic group-substituted)alkyl tin alkoxide produced [%] after continuous operation, T is the number of moles [mol] of tri(cyclic group-substituted)alkyl tin alkoxide produced after continuous operation, $W_1^0$ is the mass [kg] of the di(cyclic group-substituted)alkyl tin dialkoxide composition introduced into the catalyst tank before continuous operation, and $S_1^0$ is the tin atom concentration (in the active component) [mol/kg] of the composition before continuous operation. The number of moles of tri(cyclic group-substituted)alkyl tin alkoxide T is calculated from the tri(cyclic group-substituted)alkyl tin alkoxide concentration determined by $^{119}$Sn-NMR spectral analysis of the composition collected after continuous operation, and the mass of the di(cyclic group-substituted)alkyl tin dialkoxide composition collected after continuous operation.]

[R' represents a C3-16 alicyclic hydrocarbon group or C6-16 aromatic hydrocarbon group, and R" represents a C1-8 alkyl group.]

Examples 332 to 359

The tetra(cyclic group-substituted)alkyldialkoxydistannoxane compositions listed in Table 34, obtained by the same methods as Synthesis Examples 2, 5 and 8, were used as catalysts for transesterification reaction with a continuous circulating reactor by the same method as Example 270. The flow rate of the composition conveyed from the catalyst tank was adjusted so that the concentration of tin atoms in the reaction mixture in the tube reactor was 1.5 to 2.5 mol %, and transesterification reaction was carried out at the temperatures listed in Table 34. Table 34 shows the reaction yields (initial yields) immediately after reaching a steady state and the reaction yields and tri(cyclic group-substituted) alkyl tin alkoxide production amounts (production amounts with respect to the number of moles of tin atoms (in the active component) introduced into the catalyst tank before continuous operation), after 15 days of continuous operation.

TABLE 34

| Example | Tetraalkyldialkoxydistannoxane R' (alkyl group) | OR" (alkoxy group) | Temperature [° C.] | Initial yield [mol %] | Yield [mol %] (after 15 days of continuous operation) | Trialkyl tin alkoxide production amount [%] (after 15 days of continuous operation) *17) |
|---|---|---|---|---|---|---|
| 332 | Cyclopentylmethyl | Ethoxy | 160 | 27.3 | 26.1 | 2.3 |
| 334 | Cyclohexylethyl | Ethoxy | 160 | 19.5 | 18.5 | 2.7 |
| 335 | 3-Cyclopentylpropyl | Ethoxy | 160 | 19.0 | 18.5 | 1.4 |
| 336 | Benzyl | Ethoxy | 160 | 21.0 | 19.9 | 2.9 |
| 337 | Phenethyl | Ethoxy | 160 | 19.0 | 18.5 | 1.4 |
| 338 | 3-Phenylpropyl | Ethoxy | 160 | 18.9 | 18.4 | 1.7 |
| 339 | Cyclopentylmethyl | N-Butoxy | 170 | 27.1 | 26.2 | 2.0 |
| 340 | Cyclohexylmethyl | N-Butoxy | 170 | 25.7 | 25.3 | 0.7 |
| 341 | Cyclohexylethyl | N-Butoxy | 170 | 19.4 | 18.8 | 1.6 |
| 342 | 3-Cyclopentylpropyl | N-Butoxy | 170 | 18.6 | 18.2 | 1.1 |
| 343 | Benzyl | N-Butoxy | 170 | 20.8 | 20.1 | 1.6 |
| 344 | Phenethyl | N-Butoxy | 170 | 18.6 | 18.0 | 1.6 |
| 345 | 3-Phenylpropyl | N-Butoxy | 170 | 18.5 | 18.1 | 1.2 |
| 346 | Cyclopentylmethyl | 2-Methylpropyloxy | 170 | 26.8 | 26.3 | 1.0 |
| 347 | Cyclohexylmethyl | 2-Methylpropyloxy | 170 | 25.9 | 25.0 | 2.0 |
| 348 | Cyclohexylethyl | 2-Methylpropyloxy | 170 | 19.3 | 18.6 | 2.1 |
| 349 | 3-Cyclopentylpropyl | 2-Methylpropyloxy | 170 | 18.6 | 17.9 | 2.2 |
| 350 | Benzyl | 2-Methylpropyloxy | 170 | 20.8 | 19.8 | 2.5 |
| 351 | Phenethyl | 2-Methylpropyloxy | 170 | 18.6 | 18.1 | 1.4 |
| 352 | 3-Phenylpropyl | 2-Methylpropyloxy | 170 | 18.8 | 18.2 | 1.8 |
| 353 | Cyclopentylmethyl | 3-Methylbutyloxy | 170 | 26.8 | 26.1 | 1.3 |
| 354 | Cyclohexylmethyl | 3-Methylbutyloxy | 170 | 25.7 | 24.8 | 2.0 |
| 355 | Cyclohexylethyl | 3-Methylbutyloxy | 170 | 19.0 | 18.7 | 0.9 |
| 356 | 3-Cyclopentylpropyl | 3-Methylbutyloxy | 170 | 18.7 | 18.3 | 1.3 |
| 357 | Benzyl | 3-Methylbutyloxy | 170 | 20.6 | 20.4 | 0.5 |
| 358 | Phenethyl | 3-Methylbutyloxy | 170 | 18.7 | 18.3 | 1.3 |
| 359 | 3-Phenylpropyl | 3-Methylbutyloxy | 170 | 18.7 | 18.1 | 1.7 |

*17) The amount of tri(cyclic group-substituted)alkyl tin alkoxide production was calculated by mathematical formula (11).

[Mathematical Formula 52]

Tri(cyclic group-substituted)alkyl tin alkoxide production amount=$T/(W_2^0 \times S_2^0) \times 100\%$ (11)

[In the formula, "tri(cyclic group-substituted)alkyl tin alkoxide production amount" is the amount of tri(cyclic group-substituted)alkyl tin alkoxide produced [%] after continuous operation, T is the total number of moles of tri(cyclic group-substituted)alkyl tin alkoxide [mol] produced after continuous operation, $W_2^0$ is the mass [kg] of the tetra(cyclic group-substituted)alkyldialkoxydistannoxane composition introduced into the catalyst tank before continuous operation, and $S_2^0$ is the tin atom concentration (in the active component) [mol/kg] of the composition before continuous operation. The total number of moles of tri(cyclic group-substituted)alkyl tin alkoxide T is calculated from each tri(cyclic group-substituted)alkyl tin alkoxide concentration determined by $^{119}$Sn-NMR spectral analysis and the mass of the tetra(cyclic group-substituted)alkyldialkoxydistannoxane composition collected after continuous operation.]

Structural formula of tetra(cyclic group-substituted)alkyldialkoxydistannoxane

[Chemical Formula 104]

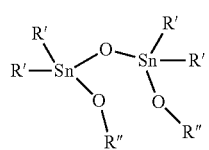

[R' represents a C3-16 alicyclic hydrocarbon group or C6-16 aromatic hydrocarbon group, and R" represents a C1-8 alkyl group.]

Examples 360 to 387

Cyclic group-substituted alkyl tin alkoxide compositions comprising the di(cyclic group-substituted)alkyl tin dialkoxides and tetra(cyclic group-substituted)alkyldialkoxydistannoxanes listed in Table 35, produced by the same method as in Synthesis Examples 1, 2, 4, 5, 7 and 8, were prepared and used as catalysts for transesterification reaction with the continuous circulating reactor by the same method as Example 270. The compositions were prepared so that the molar ratios of tin atoms of the di(cyclic group-substituted)alkyl tin dialkoxides and tetra(cyclic group-substituted)alkyldialkoxydistannoxanes with respect to the number of moles of tin atoms (in the active component)s of compositions used for transesterification reaction (the tin atoms derived from the di(cyclic group-substituted)alkyl tin dialkoxides and tetra(cyclic group-substituted)alkyldialkoxydistannoxanes) were 65:35, and were introduced into the catalyst tank. The flow rate of the composition conveyed from the catalyst tank was adjusted so that the concentration of tin atoms in the tank reactor was 1.5 to 2.0 mol %, and transesterification reaction was carried out at the temperatures listed in Table 35. Table 35 shows the reaction yields (initial yields) immediately after reaching a steady state and the reaction yields and tri(cyclic group-substituted)alkyl tin alkoxide production amounts (production amounts with respect to the number of moles of tin atoms (in the active component) introduced into the catalyst tank before continuous operation), after 15 days of continuous operation.

TABLE 35

| Example | Alkyl tin alkoxide composition R' (alkyl group) | OR" (alkoxy group) | Temperature [° C.] | Initial yield [mol %] | Yield [mol %] (after 15 days of continuous operation) | Trialkyl tin alkoxide production amount [%] (after 15 days of continuous operation) *18) |
|---|---|---|---|---|---|---|
| 360 | Cyclopentylmethyl | Ethoxy | 160 | 29.8 | 29.0 | 1.4 |
| 362 | Cyclohexylethyl | Ethoxy | 160 | 21.2 | 20.8 | 1.1 |
| 363 | 3-Cyclopentylpropyl | Ethoxy | 160 | 20.9 | 20.1 | 2.0 |
| 364 | Benzyl | Ethoxy | 160 | 22.7 | 22.2 | 1.2 |
| 365 | Phenethyl | Ethoxy | 160 | 20.9 | 20.4 | 1.2 |
| 366 | 3-Phenylpropyl | Ethoxy | 160 | 20.7 | 20.1 | 1.4 |
| 367 | Cyclopentylmethyl | N-Butoxy | 160 | 29.5 | 28.2 | 2.4 |
| 368 | Cyclohexylmethyl | N-Butoxy | 160 | 29.0 | 27.1 | 3.6 |
| 369 | Cyclohexylethyl | N-Butoxy | 160 | 21.4 | 20.6 | 1.9 |
| 370 | 3-Cyclopentylpropyl | N-Butoxy | 160 | 21.0 | 19.4 | 4.1 |
| 371 | Benzyl | N-Butoxy | 160 | 22.9 | 22.2 | 1.5 |
| 372 | Phenethyl | N-Butoxy | 160 | 20.9 | 19.7 | 3.2 |
| 373 | 3-Phenylpropyl | N-Butoxy | 160 | 20.7 | 19.6 | 2.8 |
| 374 | Cyclopentylmethyl | 2-Methylpropyloxy | 170 | 29.5 | 28.1 | 2.4 |
| 375 | Cyclohexylmethyl | 2-Methylpropyloxy | 170 | 28.5 | 28.0 | 0.9 |
| 376 | Cyclohexylethyl | 2-Methylpropyloxy | 170 | 21.2 | 20.1 | 2.8 |
| 377 | 3-Cyclopentylpropyl | 2-Methylpropyloxy | 170 | 20.1 | 19.7 | 1.0 |
| 378 | Benzyl | 2-Methylpropyloxy | 170 | 22.6 | 22.3 | 0.8 |
| 379 | Phenethyl | 2-Methylpropyloxy | 170 | 20.5 | 19.4 | 2.8 |
| 380 | 3-Phenylpropyl | 2-Methylpropyloxy | 170 | 20.3 | 19.5 | 2.1 |
| 381 | Cyclopentylmethyl | 3-Methylbutyloxy | 170 | 29.3 | 28.6 | 1.3 |
| 382 | Cyclohexylmethyl | 3-Methylbutyloxy | 170 | 28.7 | 27.5 | 2.2 |
| 383 | Cyclohexylethyl | 3-Methylbutyloxy | 170 | 21.1 | 20.5 | 1.4 |
| 384 | 3-Cyclopentylpropyl | 3-Methylbutyloxy | 170 | 20.3 | 19.7 | 1.7 |
| 385 | Benzyl | 3-Methylbutyloxy | 170 | 22.6 | 21.7 | 2.1 |
| 386 | Phenethyl | 3-Methylbutyloxy | 170 | 20.3 | 19.8 | 1.2 |
| 387 | 3-Phenylpropyl | 3-Methylbutyloxy | 170 | 20.3 | 19.9 | 1.0 |

*18) The amount of tri(cyclic group-substituted)alkyl tin alkoxide production was calculated by mathematical formula (12).

[Mathematical Formula 53]

Tri(cyclic group-substituted)alkyl tin alkoxide production amount $= T/(W_3^0 \times S_3^0) \times 100\%$ (12)

[In the formula, "tri(cyclic group-substituted)alkyl tin alkoxide production amount" is the amount of tri(cyclic group-substituted)alkyl tin alkoxide produced [%] after continuous operation, T is the total number of moles [mol] of tri(cyclic group-substituted)alkyl tin alkoxide produced after continuous operation, $W_3^0$ is the mass [kg] of the cyclic group-substituted alkyl tin alkoxide composition introduced into the catalyst tank before continuous operation, and $S_3^0$ is the tin atom concentration (in the active component) [mol/kg] of the composition before continuous operation (calculated from the tetra(cyclic group-substituted)alkyldialkoxydistannoxane concentration and di(cyclic group-substituted)alkyl tin dialkoxide concentration of the composition). The total number of moles of tri(cyclic group-substituted)alkyl tin alkoxide T is calculated from each tri(cyclic group-substituted)alkyl tin alkoxide concentration determined by $^{119}$Sn-NMR spectral analysis, and the mass of the cyclic group-substituted alkyl tin alkoxide composition collected after continuous operation.]

Structural formulas of di(cyclic group-substituted)alkyl tin dialkoxide and tetra(cyclic group-substituted)alkyldialkoxydistannoxane in cyclic group-substituted alkyl tin alkoxide composition

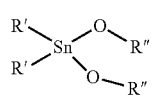

[Chemical Formula 105]

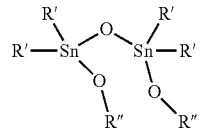

[Chemical Formula 106]

[R' represents a C3-16 alicyclic hydrocarbon group or C6-16 aromatic hydrocarbon group, and R" represents a C1-8 alkyl group.]

Examples 388 to 415

Cyclic group-substituted alkyl tin alkoxide compositions comprising the di(cyclic group-substituted)alkyl tin dialkoxides, tetra(cyclic group-substituted)alkyldialkoxydistannoxanes and tri(cyclic group-substituted)alkyl tin alkoxides listed in Table 36 obtained by the same method as in Synthesis Examples 3, 6 and 9 were used as catalysts for transesterification reaction with the continuous circulating reactor by the same method as Example 269. The tin atom concentration (in the active component) of each composition was calculated from the di(cyclic group-substituted)alkyl tin dialkoxide concentration and tetra(cyclic group-substituted) alkyldialkoxydistannoxane concentration of the composition. The flow rate of the composition conveyed from the catalyst tank was adjusted so that the concentration of tin atoms in the tank reactor was 1.5 to 2.0 mol %, and transesterification reaction was carried out at the temperatures listed in Table 36. Table 36 shows the reaction yields (initial yields) immediately after reaching a steady state and the reaction yields and tri(cyclic group-substituted)alkyl tin alkoxide production amounts (production amounts with respect to the number of moles of tin atoms (in the active component) introduced into the catalyst tank before continuous operation), after 15 days of continuous operation.

TABLE 36

| Example | Alkyl tin alkoxide composition R' (alkyl group) | OR" (alkoxy group) | Temperature [° C.] | Yield [mol %] | Yield [mol %] (after 15 days of continuous operation) | Trialkyl tin alkoxide production amount [%] (after 15 days of continuous operation) *19) |
|---|---|---|---|---|---|---|
| 388 | Cyclopentylmethyl | Ethoxy | 170 | 26.3 | 25.6 | 1.5 |
| 389 | Cyclohexylmethyl | Ethoxy | 170 | 25.2 | 24.9 | 0.8 |
| 390 | Cyclohexylethyl | Ethoxy | 170 | 18.7 | 18.3 | 1.2 |
| 391 | 3-Cyclopentylpropyl | Ethoxy | 170 | 18.2 | 17.7 | 1.4 |
| 392 | Benzyl | Ethoxy | 170 | 20.2 | 19.7 | 1.5 |
| 393 | Phenethyl | Ethoxy | 170 | 18.1 | 17.7 | 1.2 |
| 394 | 3-Phenylpropyl | Ethoxy | 170 | 18.3 | 17.5 | 2.4 |
| 395 | Cyclopentylmethyl | N-Butoxy | 170 | 26.4 | 25.2 | 2.4 |
| 396 | Cyclohexylmethyl | N-Butoxy | 170 | 25.4 | 24.9 | 1.0 |
| 397 | Cyclohexylethyl | N-Butoxy | 170 | 18.7 | 18.4 | 0.8 |
| 398 | 3-Cyclopentylpropyl | N-Butoxy | 170 | 18.2 | 17.5 | 2.0 |
| 399 | Benzyl | N-Butoxy | 170 | 20.1 | 19.7 | 1.1 |
| 400 | Phenethyl | N-Butoxy | 170 | 18.2 | 17.6 | 1.5 |
| 401 | 3-Phenylpropyl | N-Butoxy | 170 | 18.1 | 17.8 | 1.1 |
| 402 | Cyclopentylmethyl | 2-Methylpropyloxy | 170 | 26.7 | 26.4 | 0.7 |
| 403 | Cyclohexylmethyl | 2-Methylpropyloxy | 170 | 26.6 | 24.6 | 4.1 |
| 404 | Cyclohexylethyl | 2-Methylpropyloxy | 170 | 19.5 | 18.6 | 2.3 |
| 405 | 3-Cyclopentylpropyl | 2-Methylpropyloxy | 170 | 19.1 | 18.1 | 2.8 |
| 406 | Benzyl | 2-Methylpropyloxy | 170 | 20.9 | 20.3 | 1.7 |
| 407 | Phenethyl | 2-Methylpropyloxy | 170 | 19.0 | 18.3 | 2.0 |
| 408 | 3-Phenylpropyl | 2-Methylpropyloxy | 170 | 18.8 | 18.1 | 1.9 |
| 409 | Cyclopentylmethyl | 3-Methylbutyloxy | 170 | 26.7 | 25.4 | 2.6 |
| 410 | Cyclohexylmethyl | 3-Methylbutyloxy | 170 | 26.0 | 25.4 | 1.1 |
| 411 | Cyclohexylethyl | 3-Methylbutyloxy | 170 | 19.2 | 18.4 | 2.4 |
| 412 | 3-Cyclopentylpropyl | 3-Methylbutyloxy | 170 | 18.4 | 18.0 | 1.1 |
| 413 | Benzyl | 3-Methylbutyloxy | 170 | 20.7 | 19.6 | 2.9 |
| 414 | Phenethyl | 3-Methylbutyloxy | 170 | 18.8 | 18.0 | 2.2 |
| 415 | 3-Phenylpropyl | 3-Methylbutyloxy | 170 | 18.5 | 17.9 | 1.8 |

*19) The amount of tri(cyclic group-substituted)alkyl tin alkoxide production was calculated by mathematical formula (12).

[Mathematical Formula 54]

$$\text{Tri(cyclic group-substituted)alkyl tin alkoxide production amount} = T/(W_3^0 S_3^0) \times 100\% \qquad (12)$$

[In the formula, "tri(cyclic group-substituted)alkyl tin alkoxide production amount" is the amount of tri(cyclic group-substituted)alkyl tin alkoxide produced [%] after continuous operation, T is the total number of moles [mol] of tri(cyclic group-substituted)alkyl tin alkoxide produced after continuous operation, $W_3^0$ is the mass [kg] of the cyclic group-substituted alkyl tin alkoxide composition introduced into the catalyst tank before continuous operation, and $S_3^0$ is the tin atom concentration (in the active component) [mol/kg] of the composition before continuous operation (calculated from the tetra(cyclic group-substituted)alkyldialkoxydistannoxane concentration and di(cyclic group-substituted)alkyl tin dialkoxide concentration of the composition). The total number of moles of tri(cyclic group-substituted)alkyl tin alkoxide T is calculated from each tri(cyclic group-substituted)alkyl tin alkoxide concentration determined by $^{119}$Sn-NMR spectral analysis, and the mass of the cyclic group-substituted alkyl tin alkoxide composition collected after continuous operation.]

Structural formulas of di(cyclic group-substituted)alkyl tin dialkoxide, tetra(cyclic group-substituted)alkyldialkoxydistannoxane and tri(cyclic group-substituted)alkyl tin alkoxide in cyclic group-substituted alkyl tin alkoxide composition

[Chemical Formula 107]

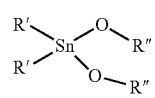

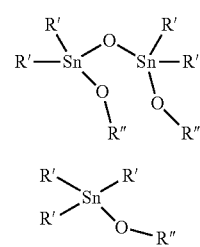

[Chemical Formula 108]

[Chemical Formula 109]

[R' represents a C3-16 alicyclic hydrocarbon group or C6-16 aromatic hydrocarbon group, and R" represents a C1-8 alkyl group.]

Example 416

A continuous circulating reactor comprising a tank reactor and tower reactor as shown in FIG. 4 was used for carbonic acid ester synthesis. Approximately 30 kg of a 1,1,3,3-tetrabenzyl-1,3-bis(3-methylbutyloxy)distannoxane composition obtained by the method of Synthesis Example 5 (tin atom concentration (in the active component) of the composition: 2.49 mol/kg) was introduced into a SUS316 catalyst tank 660, equipped with a heating jacket and a liquid conveyance pump, through a supply line 78. The catalyst tank 660 was heated with steam to maintain the flow property of the contents. The tank and pipes were also steam traced to maintain the flow property as well. A SUS316 tower reactor 620 with an inner diameter of 76 mm and an effective length of 4500 mm, equipped with 30 sieve trays, was heated and thermally insulated with a heater to prevent radiated heat loss, the heater being set to about 150° C. A liquid conveyance pump and reboiler 622 were provided at the bottom of the tower reactor 620, and the reboiler 622 was heated with steam at 155° C. to 160° C.

The composition was conveyed to the tower reactor 620 from the catalyst tank 660 through a transport line 74, an inline mixer 621 equipped with a heating jacket and a transport line 65 at 6.5 kg/hr, and the 3-methyl-1-butyl alcohol purified at the distillation column 610 was conveyed at 25 kg/hr through a transport line 63 and transport line 64. The fraction containing water and 3-methyl-1-butyl alcohol was conveyed from the top of the tower reactor 620 to a distillation column 610 (distillation column packed with MetalGauze CY filler, inner diameter: 83 mm, effective length: 3000 mm) through a transport line 66 at about 22 kg/hr, and the water was separated out. The water was collected from a collecting line 62 via a condenser 611. A cyclic group-substituted alkyl tin alkoxide composition containing dibenzyl-bis(3-methylbutoxy)tin and 1,1,3,3-tetrabenzyl-1,3-bis(3-methylbutyloxy)distannoxane was obtained from the bottom of the tower reactor, and as a result of analyzing the composition sampled from the transport line 67, the dibenzyl-bis(3-methylbutoxy)tin content was found to be 78 mass %.

Step (1) (Obtaining Carbonic Acid Ester from Reaction Between Cyclic Group-Substituted Alkyl Tin Alkoxide Composition and Carbon Dioxide)

The cyclic group-substituted alkyl tin alkoxide composition containing dibenzyl-bis(3-methylbutoxy)tin and 1,1,3,3-tetrabenzyl-1,3-bis(3-methylbutyloxy)distannoxane was conveyed to an autoclave 630 having a 15 L volume and equipped with a heating jacket and liquid conveyance pump, through the transport line 67, and reacted with carbon dioxide supplied through a supply line 68, at a temperature of 120° C. and a pressure of 4 MPa-G. The reaction mixture sampled from the autoclave 630 was transparent, and as a result of analyzing the reaction mixture, the bis(3-methylbutyl) carbonate yield was found to be 37% based on dibenzyl-bis(3-methylbutoxy)tin.

Step (2) (Separating Carbonic Acid Ester from Reaction Mixture to Obtain Residual Solution)

A thin-film vaporizer 640 and thin-film vaporizer 650 equipped with a heating jacket and a liquid conveyance pump for conveying the high boiling point component were heated using steam at 150° C. The reaction mixture obtained from step (1) was conveyed through a transport line 71 to the thin-film vaporizer 640 set to a pressure of 26 kPaA, and first the excess carbon dioxide was separated out and collected from a purge line 70. The reaction mixture was conveyed through the transport line 71 to the thin-film vaporizer 650 that had been set to a pressure of 1.3 kPaA, the fraction containing bis(3-methylbutyl) carbonate was collected through a transport line 72, and the bis(3-methylbutyl) carbonate was further purified by a distillation column 670 (distillation column packed with MetalGauze CY filler, inner diameter: 83 mm, effective length: 2800 mm). Separately, a residual solution containing 1,1,3,3-tetrabenzyl-1,3-bis(3-methylbutyloxy)distannoxane was collected from the transport line 73 and conveyed to the catalyst tank 660.

Step (3) (Obtaining Cyclic Group-Substituted Alkyl Tin Alkoxide from Reaction Between Residual Solution and Alcohol)

The residual solution obtained from step (2) was again conveyed to the tower reactor 620 through the transport line 74, inline mixer 621 and transport line 65, and reacted with the 3-methyl-1-butyl alcohol conveyed through the transport line 63 and transport line 64. The fraction containing water and 3-methyl-1-butyl alcohol was conveyed from the top of the tower reactor 620 to a distillation column 610 through a transport line 66 at about 22 kg/hr, and the water was separated out. The water was collected from a collecting line 62 via a condenser 611. A cyclic group-substituted alkyl tin alkoxide composition containing dibenzyl-bis(3-methylbutoxy)tin and 1,1,3,3-tetrabenzyl-1,3-bis(3-methylbutyloxy) distannoxane was obtained from the bottom of the tower reactor 620, and as a result of analyzing the composition sampled from the transport line 67, the dibenzyl-bis(3-methylbutoxy)tin content was found to be 77 mass %.

When necessary, supply from the transport line 63 and transport line 65 to the tower reactor 620 was reduced or interrupted until the system interior reached a steady state. Steps (1), (2) and (3) above were carried out continuously, and after the system reached a steady state, the steps were further continued for 15 days. As a result of subsequently analyzing the reaction mixture sampled from the autoclave 630, the bis(3-methylbutyl) carbonate yield was found to be 37% based on dibenzyl-bis(3-methylbutoxy)tin. During the continuous operation period, bis(3-methylbutyl) carbonate was stably obtained from the collecting line 76 at about 0.9 kg/hr. The high boiling point component including the cyclic group-substituted alkyl tin alkoxide composition in the continuous circulating reactor after continuous operation was separated using the thin-film vaporizer 640 and thin-film vaporizer 650, and collected in the catalyst tank 660.

Next, the composition in the catalyst tank 660 was sampled from an extraction line 79, and as a result of $^{119}$Sn-NMR spectral analysis, dibenzyl-bis(3-methylbutoxy)tin, 1,1,3,3-tetrabenzyl-1,3-bis(3-methylbutyloxy)distannoxane and tribenzyl-(3-methylbutoxy)tin were found to be present after continuous operation. Based on the analysis results, tribenzyl-(3-methylbutoxy)tin was produced at approximately 0.75 mol after 15 days of continuous operation, an amount that was approximately 1.0% with respect to the number of moles of tin atoms (in the active component) of the composition introduced into the catalyst tank before continuous operation.

Example 417

A continuous circulating reactor comprising a tank reactor and tower reactor as shown in FIG. 5 was used for carbonic acid ester synthesis. Approximately 35 kg of a 1,1,3,3-tetra(cyclohexylmethyl)-1,3-bis(3-methylbutoxy)distannoxane composition obtained by the same method as Synthesis Example 2 (tin atom concentration (in the active component) of the composition: 2.41 mol/kg) was introduced into a SUS316 catalyst tank 770, equipped with a heating jacket and a liquid conveyance pump, through a supply line 107. The catalyst tank 770 was heated with steam to maintain the flow property of the contents. The tank and pipes were also steam traced to maintain the flow property as well.

The tank reactor 710 was a 10 L-volume reactor equipped with a heating jacket and liquid conveyance pump, the composition was conveyed to the tank reactor 710 through the transport line 109, inline mixer 711 and transport line 110 at 6.7 kg/hr, and 3-methyl-1-butyl alcohol purified at the distillation column 720 was conveyed at 28 kg/hr through a transport line 93, collecting tank 724, transport line 94, inline mixer 711 and transport line 110. The reaction mixture was conveyed from the bottom of the tank reactor 710 through a transport line 95 to a tower reactor 730 and further reacted while simultaneously distilling off the fraction containing water and 3-methyl-1-butyl alcohol at the top of the tower reactor. The fraction was conveyed through the transport line 96 to a distillation column 720 (distillation column packed with MetalGauze CY filler, inner diameter: 83 mm, effective length: 3000 mm) at approximately 26 kg/hr, and the water and 3-methyl-1-butyl alcohol were separated out. The water was collected from a collecting line 92 via a condenser 721. A cyclic group-substituted alkyl tin alkoxide composition containing di(cyclohexylmethyl)-bis(3-methylbutoxy)tin and 1,1,3,3-tetra(cyclohexylmethyl)-1,3-bis(3-methylbutoxy)distannoxane was obtained from the bottom of the tower reactor 730, and as a result of analyzing the composition sampled from the transport line 97, the di(cyclohexylmethyl)-bis(3-methylbutoxy)tin content was found to be approximately 80 mass %.

Step (1) (Obtaining Carbonic Acid Ester from Reaction Between Cyclic Group-Substituted Alkyl Tin Alkoxide Composition and Carbon Dioxide)

The cyclic group-substituted alkyl tin alkoxide composition containing di(cyclohexylmethyl)-bis(3-methylbutoxy)tin and 1,1,3,3-tetra(cyclohexylmethyl)-1,3-bis(3-methylbutoxy)distannoxane was conveyed to an autoclave 740, having a 15 L volume and equipped with a heating jacket and liquid conveyance pump, through the transport line 97, and reacted with carbon dioxide supplied through a supply line 98, at a temperature of 140° C. and a pressure of 4 MPa-G. The reaction mixture sampled from the autoclave 740 was transparent, and as a result of analyzing the reaction mixture, the bis(3-methylbutyl) carbonate yield was found to be 41% based on di(cyclohexylmethyl)-bis(3-methylbutoxy)tin.

Step (2) (Separating Carbonic Acid Ester from Reaction Mixture to Obtain Residual Solution)

Thin-film vaporizers 750 and 760 equipped with a heating jacket and a liquid conveyance pump for conveying the high boiling point component were heated using steam at 140° C. The reaction mixture obtained from step (1) was conveyed through a transport line 99 to the thin-film vaporizer 750 set to a pressure of 26 kPaA, and first the excess carbon dioxide was separated out and collected from a purge line 100. The reaction mixture was conveyed through the transport line 101 to the thin-film vaporizer 760 that had been set to a pressure of 2.6 kPaA, the fraction containing dibutyl carbonate was collected through a transport line 102, and the dibutyl carbonate was further purified by a distillation column 780 (distillation column packed with MetalGauze CY filler, inner diameter: 83 mm, effective length: 2800 mm). Separately, the residual solution containing 1,1,3,3-tetra(cyclohexylmethyl)-1,3-bis(3-methylbutoxy)distannoxane was collected from a transport line 103 and conveyed to the catalyst tank 770.

Step (3) (Obtaining Cyclic Group-Substituted Alkyl Tin Alkoxide from Reaction Between Residual Solution and Alcohol)

The residual solution obtained from step (2) was again conveyed to the tank reactor 710 through the transport line 109 at 6.5 kg/hr, and reacted with n-butyl alcohol being conveyed through the transport line 94, inline mixer 711 and transport line 110.

The reaction mixture was conveyed from the bottom of the tank reactor 710 through a transport line 95 to a tower reactor 730 and further reacted while simultaneously distilling off the fraction containing water and n-butyl alcohol at the top of the tower reactor. The fraction was conveyed to the distillation column 720 through the transport line 96 at approximately 28 kg/hr, and the water and n-butyl alcohol were separated. The water was collected from a collecting line 92 via a condenser 721. A cyclic group-substituted alkyl tin alkoxide composition containing di(cyclohexylmethyl)-bis(3-methylbutoxy)tin and 1,1,3,3-tetra(cyclohexylmethyl)-1,3-bis(3-methylbutoxy)distannoxane was obtained from the bottom of the tower reactor 730, and as a result of analyzing the composition sampled from the transport line 97, the di(cyclohexylmethyl)-bis(3-methylbutoxy)tin content was found to be approximately 80 mass %.

When necessary, supply from the transport line 109 and transport line 94 to the tank reactor 710 was reduced or interrupted until the system interior reached a steady state. Steps (1), (2) and (3) above were carried out continuously, and after the system reached a steady state, the steps were further continued for 15 days. When the reaction mixture sampled from the autoclave 740 was then analyzed, the bis(3-methylbutyl) carbonate yield was found to be 41% based on di(cyclohexylmethyl)-bis(3-methylbutoxy)tin. Also, bis(3-methylbutyl) carbonate was stably obtained from the collecting line 105 at about 0.9 kg/hr. The high boiling point component including the cyclic group-substituted alkyl tin alkoxide composition in the continuous circulating reactor after continuous operation was separated using the thin-film vaporizer 750 and thin-film vaporizer 760, and collected in the catalyst tank 770. Next, the alkyl tin alkoxide composition in the catalyst tank 770 was sampled from an extraction line 108, and as a result of $^{119}$Sn-NMR spectral analysis it was confirmed that di(cyclohexylmethyl)-bis(3-methylbutoxy)tin, 1,1,3,3-tetra(cyclohexylmethyl)-1,3-bis(3-methylbutoxy)distannoxane and tri(cyclohexylmethyl)-(3-methylbutoxy)tin were present after the continuous operation. Based on the analysis results, tri(cyclohexylmethyl)-(3-methylbutoxy)tin was produced at approximately 0.87 mol after 15 days of continuous operation, an amount that was approximately 1.2% with respect to the number of moles of tin atoms (in the active component) of the composition introduced into the catalyst tank before continuous operation.

Examples 418 to 431

Carbonic acid ester synthesis was carried out with a continuous circulating reactor by the same method as Example 416. The tetra(cyclic group-substituted)alkyl-dialkoxydistannoxane compositions listed in Table 37 were obtained by the same methods as in Synthesis Examples 2, 5 and 8, and approximately 30 kg of each was introduced into a catalyst tank. An alcohol with the same alkoxy group as the alkoxy group of the tetra(cyclic group-substituted)

alkyldialkoxydistannoxane was used for carbonic acid ester synthesis with an autoclave 630, under the temperature and pressure conditions listed in Table 37. Steps (1), (2) and (3) were continuously carried out for 15 days in the same manner as Example 416. Table 37 shows the carbonic acid ester initial yields immediately after reaching a steady state and the carbonic acid ester yields and tri(cyclic group-substituted)alkyl tin alkoxide production amounts (production amounts with respect to the number of moles of tin atoms (in the active component) of the composition introduced into the catalyst tank before continuous operation), after 15 days of continuous operation.

Structural formula of tetra(cyclic group-substituted)alkyldialkoxydistannoxane

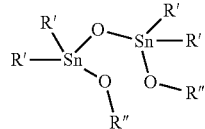

[Chemical Formula 110]

TABLE 37

| | | | | | Carbonic acid ester yield [mol %] (after 15 days of continuous operation) | Trialkyl tin alkoxide production amount [%] (after 15 days of continuous operation) *20) |
|---|---|---|---|---|---|---|
| | Tetraalkyldialkoxydistannoxane | | Temperature [° C.] | $CO_2$ pressure [MPa-G] | Carbonic acid ester initial yield [mol %] | |
| Example | R' (alkyl group) | OR" (alkoxy group) | | | | |
| 418 | Cyclopentylmethyl | N-Butoxy | 125 | 4 | 40.3 | 39.6 | 0.7 |
| 419 | Cyclohexylmethyl | N-Butoxy | 125 | 4 | 41.7 | 40.5 | 0.8 |
| 420 | Cyclohexylethyl | N-Butoxy | 125 | 4 | 42.6 | 41.6 | 0.9 |
| 421 | 3-Cyclopentylpropyl | N-Butoxy | 125 | 4 | 42.7 | 41.5 | 1.1 |
| 422 | Benzyl | N-Butoxy | 125 | 4 | 41.7 | 41.1 | 0.9 |
| 423 | Phenethyl | N-Butoxy | 125 | 4 | 40.1 | 39.1 | 1.0 |
| 424 | 3-Phenylpropyl | N-Butoxy | 125 | 4 | 39.9 | 39.0 | 1.2 |
| 425 | Cyclopentylmethyl | 2-Methylpropyloxy | 110 | 4.5 | 39.3 | 38.7 | 0.5 |
| 426 | Cyclohexylmethyl | 2-Methylpropyloxy | 110 | 4.5 | 40.0 | 39.0 | 0.5 |
| 427 | Cyclohexylethyl | 2-Methylpropyloxy | 110 | 4.5 | 40.8 | 40.0 | 0.6 |
| 428 | 3-Cyclopentylpropyl | 2-Methylpropyloxy | 110 | 4.5 | 40.7 | 40.2 | 0.8 |
| 429 | Benzyl | 2-Methylpropyloxy | 110 | 4.5 | 40.1 | 39.2 | 0.6 |
| 430 | Phenethyl | 2-Methylpropyloxy | 110 | 4.5 | 40.8 | 40.0 | 0.7 |
| 431 | 3-Phenylpropyl | 2-Methylpropyloxy | 110 | 4.5 | 41.0 | 40.2 | 0.8 |

*20) The amount of tri(cyclic group-substituted)alkyl tin alkoxide production was calculated by mathematical formula (11).

[Mathematical Formula 55]

$$\text{Tri(cyclic group-substituted)alkyl tin alkoxide production amount} = T/(W_2^0 \times S_2^0) \times 100\% \quad (11)$$

[In the formula, "tri(cyclic group-substituted)alkyl tin alkoxide production amount" is the amount of tri(cyclic group-substituted)alkyl tin alkoxide produced [%] after continuous operation, T is the number of moles of tri(cyclic group-substituted)alkyl tin alkoxide [mol] produced after continuous operation, $W_2^0$ is the mass [kg] of the tetra(cyclic group-substituted)alkyldialkoxydistannoxane composition introduced into the catalyst tank before continuous operation, and $S_2^0$ is the tin atom concentration (in the active component) [mol/kg] of the composition before continuous operation. The number of moles of tri(cyclic group-substituted)alkyl tin alkoxide T is calculated from the tri(cyclic group-substituted)alkyl tin alkoxide concentration determined by $^{119}$Sn-NMR spectral analysis and the mass of the composition collected after continuous operation.]

[R' represents a C3-16 alicyclic hydrocarbon group or C6-16 aromatic hydrocarbon group, and R" represents a C1-8 alkyl group.]

Examples 432 to 443

Carbonic acid ester synthesis was carried out with a continuous circulating reactor by the same method as Example 417. The tetra(cyclic group-substituted)alkyl-dialkoxydistannoxane compositions listed in Table 38 were obtained by the same methods as in Synthesis Examples 2, 5 and 8, and approximately 35 kg of each was introduced into a catalyst tank. An alcohol with the same alkoxy group as the alkoxy group of the tetra(cyclic group-substituted) alkyldialkoxydistannoxane composition was used for carbonic acid ester synthesis, and steps (1), (2) and (3) were carried out continuously for 15 days in the same manner as Example 417. Table 38 shows the carbonic acid ester initial yields immediately after reaching a steady state and the carbonic acid ester yields and tri(cyclic group-substituted) alkyl tin alkoxide production amounts (production amounts with respect to the number of moles of tin atoms (in the active component) of the composition introduced into the catalyst tank before continuous operation), after 15 days of continuous operation.

TABLE 38

| Example | Tetraalkyldialkoxydistannoxane R' (alkyl group) | OR" (alkoxy group) | Temperature [° C.] | $CO_2$ pressure [MPa-G] | Carbonic acid ester initial yield [mol %] | Carbonic acid ester yield [mol %] (after 15 days of continuous operation) | Trialkyl tin alkoxide production amount [%] (after 15 days of continuous operation) *21) |
|---|---|---|---|---|---|---|---|
| 432 | Cyclopentylmethyl | 3-Methylbutyloxy | 120 | 4 | 40.1 | 39.0 | 0.7 |
| 433 | Cyclohexylethyl | 3-Methylbutyloxy | 120 | 4 | 41.7 | 40.7 | 0.9 |
| 434 | 3-Cyclopentylpropyl | 3-Methylbutyloxy | 120 | 4 | 41.4 | 40.6 | 1.1 |
| 435 | Phenethyl | 3-Methylbutyloxy | 120 | 4 | 42.1 | 41.1 | 1.0 |
| 436 | 3-Phenylpropyl | 3-Methylbutyloxy | 120 | 4 | 40.6 | 39.6 | 1.1 |
| 437 | Cyclopentylmethyl | 2-Ethylbutyloxy | 105 | 4.5 | 38.6 | 37.6 | 0.7 |
| 438 | Cyclohexylmethyl | 2-Ethylbutyloxy | 105 | 4.5 | 37.8 | 37.3 | 0.7 |
| 439 | Cyclohexylethyl | 2-Ethylbutyloxy | 105 | 4.5 | 39.8 | 38.6 | 0.9 |
| 440 | 3-Cyclopentylpropyl | 2-Ethylbutyloxy | 105 | 4.5 | 39.6 | 38.8 | 1.0 |
| 441 | Benzyl | 2-Ethylbutyloxy | 105 | 4.5 | 38.4 | 37.6 | 0.9 |
| 442 | Phenethyl | 2-Ethylbutyloxy | 105 | 4.5 | 38.8 | 37.6 | 1.0 |
| 443 | 3-Phenylpropyl | 2-Ethylbutyloxy | 105 | 4.5 | 39.7 | 38.8 | 1.2 |

*21) The amount of tri(cyclic group-substituted)alkyl tin alkoxide production was calculated by mathematical formula (11).

[Mathematical Formula 56]

Tri(cyclic group-substituted)alkyl tin alkoxide production amount $=T/(W_2^0 \times S_2^0) \times 100\%$ (11)

[In the formula, "tri(cyclic group-substituted)alkyl tin alkoxide production amount" is the amount of tri(cyclic group-substituted)alkyl tin alkoxide produced [%] after continuous operation, T is the number of moles of tri(cyclic group-substituted)alkyl tin alkoxide [mol] produced after continuous operation, $W_2^0$ is the mass [kg] of the tetra(cyclic group-substituted)alkyldialkoxydistannoxane composition introduced into the catalyst tank before continuous operation, and $S_2^0$ is the tin atom concentration (in the active component) [mol/kg] of the composition before continuous operation. The number of moles of tri(cyclic group-substituted)alkyl tin alkoxide T is calculated from the tri(cyclic group-substituted)alkyl tin alkoxide concentration determined by $^{119}$Sn-NMR spectral analysis and the mass of the composition collected after continuous operation.]

Structural formula of tetra(cyclic group-substituted)alkyldialkoxydistannoxane

[Chemical Formula 111]

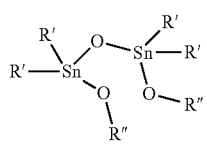

[R' represents a C3-16 alicyclic hydrocarbon group or C6-16 aromatic hydrocarbon group, and R" represents a C1-8 alkyl group.]

Comparative Examples 1 to 8

Tetraalkyldialkoxydistannoxane compositions with the structures listed in Table 39 were synthesized by the same method as Synthesis Example 10. The tetraalkyldialkoxydistannoxane compositions were then used for test operation in a continuous circulating reactor by the same method as Example 3. The tetraalkyldialkoxydistannoxane composition was placed in the catalyst tank of the continuous circulating reactor shown in FIG. 3 and circulating operation was conducted. Table 39 shows the percentage reductions in tin atom concentration of the compositions after circulating operation and production amounts of tri(cyclic group-substituted)alkyl tin alkoxide (production amounts with respect to tin atom concentrations of tetraalkyldialkoxydistannoxane compositions introduced into the catalyst tank before continuous operation).

TABLE 39

| Comparative Example | Alkyl tin alkoxide R' (alkyl group) | OR" (alkoxy group) | Continuous time [days] | Percentage reduction in tin atom concentration of tetraalkyldialkoxydistannoxane composition [%] | Trialkyl tin alkoxide production amount [mol %] |
|---|---|---|---|---|---|
| 1 | Methyl | Ethoxy | 2 | 95 | 47 |
| 2 | Phenyl | Ethoxy | 3 | 82 | 41 |
| 3 | N-Butyl | Ethoxy | 5 | 35 | 19 |
| 4 | N-Octyl | Ethoxy | 5 | 23 | 12 |
| 5 | Methyl | 2-Methylpropyloxy | 3 | 90 | 44 |
| 6 | Phenyl | 2-Methylpropyloxy | 3 | 76 | 39 |

TABLE 39-continued

| Comparative Example | Alkyl tin alkoxide R' (alkyl group) | OR" (alkoxy group) | Continuous time [days] | Percentage reduction in tin atom concentration of tetraalkyldialkoxydistannoxane composition [%] | Trialkyl tin alkoxide production amount [mol %] |
|---|---|---|---|---|---|
| 7 | N-Butyl | 2-Methylpropyloxy | 5 | 30 | 15 |
| 8 | N-Octyl | 2-Methylpropyloxy | 5 | 21 | 10 |

Structural formula of tetraalkyldialkoxydistannoxane

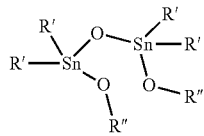

[Chemical Formula 112]

[R' represents a C1-8 alkyl or phenyl group, and R" represents a C1-8 alkyl group.]

Comparative Examples 9 to 16

Di(cyclic group-substituted)alkyl tin dialkoxide compositions having the structures listed in Table 40 were synthesized by the same method as Synthesis Example 11. The di(cyclic group-substituted)alkyl tin dialkoxide compositions were then used for test operation of a continuous circulating reactor by the same method as Example 2. Each di(cyclic group-substituted)alkyl tin dialkoxide composition was introduced into the catalyst tank of the continuous circulating reactor shown in FIG. 2 for circulating operation. Table 40 shows the percentage reductions in tin atom concentrations in the compositions after circulating operation and the tri(cyclic group-substituted)alkyl tin alkoxide amounts (production amounts with respect to tin atom concentrations of the di(cyclic group-substituted)alkyl tin dialkoxide compositions introduced into the catalyst tank before continuous operation).

Structural formula of di(cyclic group-substituted)alkyl tin dialkoxide

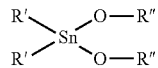

[Chemical Formula 113]

[R' represents a C1-8 alkyl or phenyl group, and R" represents a C1-8 alkyl group.]

Comparative Examples 17 to 24

Di(cyclic group-substituted)alkyl tin dialkoxide compositions having the structures listed in Table 41 were synthesized by the same method as Synthesis Example 11. Each di(cyclic group-substituted)alkyl tin dialkoxide composition was used for transesterification reaction by the same method as Example 266, with adjustment so that the tin atom concentration of the reaction mixture was approximately 1.5 to 2.5 mol %. Table 41 shows the initial yields and reaction yields after continuous operation for the transesterification reaction and the production amounts of tri(cyclic group-substituted)alkyl tin alkoxide (production amounts with respect to the number of moles of tin atoms of the di(cyclic group-substituted)alkyl tin dialkoxide compositions introduced into the catalyst tank before continuous operation).

TABLE 40

| Comparative Example | Alkyl tin alkoxide R' (alkyl group) | OR" (alkoxy group) | Continuous time [days] | Percentage reduction in dialkyl tin dialkoxide concentration [%] | Trialkyl tin alkoxide production amount [mol %] |
|---|---|---|---|---|---|
| 9 | Methyl | Ethoxy | 4 | 78 | 41 |
| 10 | Phenyl | Ethoxy | 4 | 68 | 36 |
| 11 | N-Butyl | Ethoxy | 5 | 27 | 14 |
| 12 | N-Octyl | Ethoxy | 5 | 17 | 8.8 |
| 13 | Methyl | 2-Methylpropyloxy | 4 | 68 | 37 |
| 14 | Phenyl | 2-Methylpropyloxy | 4 | 57 | 31 |
| 15 | N-Butyl | 2-Methylpropyloxy | 5 | 23 | 12 |
| 16 | N-Octyl | 2-Methylpropyloxy | 5 | 15 | 7.5 |

TABLE 41

| Comparative Example | Alkyl tin alkoxide R' (alkyl group) | Alkyl tin alkoxide OR" (alkoxy group) | Starting materials for transesterification reaction Carboxylic acid ester | Starting materials for transesterification reaction Alcohol | Temperature [° C.] | Initial yield [mol %] | Yield [mol %] (15 days of continuous operation) | Trialkyl tin alkoxide production amount [mol %] (after 15 days of continuous operation) |
|---|---|---|---|---|---|---|---|---|
| 17 | Methyl | Ethoxy | Methyl 2-Ethylhexanoate ester | Ethanol | 150 | 20 | 7 | 32 |
| 18 | Phenyl | Ethoxy | Methyl 2-Ethylhexanoate ester | Ethanol | 150 | 20 | 8 | 29 |
| 19 | N-Butyl | Ethoxy | Methyl 2-Ethylhexanoate ester | Ethanol | 150 | 17 | 13 | 11 |
| 20 | N-Octyl | Ethoxy | Methyl 2-Ethylhexanoate ester | Ethanol | 150 | 21 | 18 | 10 |
| 21 | Methyl | 2-Methylpropyloxy | Propyl 2-Ethylhexanoate ester | 2-Methyl-1-propanol | 160 | 18 | 8 | 28 |
| 22 | Phenyl | 2-Methylpropyloxy | Propyl 2-Ethylhexanoate ester | 2-Methyl-1-propanol | 160 | 14 | 7 | 23 |
| 23 | N-Butyl | 2-Methylpropyloxy | Propyl 2-Ethylhexanoate ester | 2-Methyl-1-propanol | 160 | 20 | 16 | 9 |
| 24 | N-Octyl | 2-Methylpropyloxy | Propyl 2-Ethylhexanoate ester | 2-Methyl-1-propanol | 160 | 19 | 16 | 9 |

Structural formula of di(cyclic group-substituted)alkyl tin dialkoxide

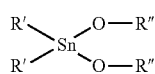

[Chemical Formula 114]

[R' represents a C1-8 alkyl or phenyl group, and R" represents a C1-8 alkyl group.]

Comparative Examples 25 to 32

Tetraalkyldialkoxydistannoxane compositions with the structures listed in Table 42 were synthesized by the same method as Synthesis Example 10. Each tetraalkyldialkoxydistannoxane composition was then used for transesterification reaction by the same method as Example 269, with adjustment so that the tin atom concentration in the reaction mixture was approximately 1.5 to 2.5 mol %. Table 42 shows the initial yields and reaction yields after continuous operation for the transesterification reaction, and the tri(cyclic group-substituted)alkyl tin alkoxide production amounts (the production amounts with respect to the number of moles of tin atoms of the tetraalkyldialkoxydistannoxane compositions introduced into the catalyst tank before continuous operation).

TABLE 42

| Comparative Example | Alkyl tin alkoxide R' (alkyl group) | Alkyl tin alkoxide OR" (alkoxy group) | Temperature [° C.] | Initial yield [mol %] | Yield [mol %] (15 days of continuous operation) | Trialkyl tin alkoxide production amount [mol %] (after 15 days of continuous operation) |
|---|---|---|---|---|---|---|
| 25 | Methyl | Ethoxy | 150 | 16 | 3 | 40 |
| 26 | Phenyl | Ethoxy | 150 | 19 | 6 | 33 |
| 27 | N-Butyl | Ethoxy | 150 | 18 | 13 | 14 |
| 28 | N-Octyl | Ethoxy | 150 | 14 | 12 | 10 |
| 29 | Methyl | 2-Methylpropyloxy | 160 | 20 | 5 | 37 |
| 30 | Phenyl | 2-Methylpropyloxy | 160 | 15 | 5 | 31 |

TABLE 42-continued

| Comparative Example | Alkyl tin alkoxide R' (alkyl group) | OR" (alkoxy group) | Temperature [° C.] | Initial yield [mol %] | Yield [mol %] (15 days of continuous operation) | Trialkyl tin alkoxide production amount [mol %] (after 15 days of continuous operation) |
|---|---|---|---|---|---|---|
| 31 | N-Butyl | 2-Methylpropyloxy | 160 | 21 | 16 | 13 |
| 32 | N-Octyl | 2-Methylpropyloxy | 160 | 21 | 18 | 10 |

Structural formula of tetraalkyldialkoxydistannoxane

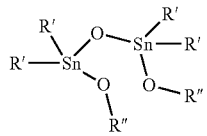

[Chemical Formula 115]

[R' represents a C1-8 alkyl or phenyl group, and R" represents a C1-8 alkyl group.]

Structural formula of tetraalkyldialkoxydistannoxane

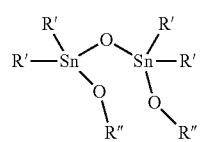

[Chemical Formula 116]

[R' represents a C1-8 alkyl or phenyl group, and R" represents a C1-8 alkyl group.]

Comparative Examples 33 to 40

Tetraalkyldialkoxydistannoxane compositions with the structures listed in Table 43 were synthesized by the same method as Synthesis Example 10. Each tetraalkyldialkoxydistannoxane composition was then used for carbonic acid ester synthesis by the same method as Example 416. Table 43 shows the carbonic acid ester initial yields and the carbonic acid ester yields after continuous operation, and the tri(cyclic group-substituted)alkyl tin alkoxide production amounts (the production amounts with respect to the number of moles of tin atoms of the tetraalkyldialkoxydistannoxane compositions introduced into the catalyst tank of the continuous circulating reactor).

REFERENCE SIGNS LIST 110, 120: Starting material tanks, 130: catalyst tank, 140: tank reactor, 150: tube reactor, 160: tower reactor, 170: thin-film vaporizer, 180: distillation column, 141: inline mixer, 161, 181: condensers, 162, 182: condensate tanks, 163, 183: reboilers, 1, 2, 15: supply lines, 3, 4, 5, 6, 7, 9, 10, 11, 14: transport lines, 8, 12, 13: collecting lines, 16: extraction line.

210, 220: Starting material tanks, 230: catalyst tank, 240: tube reactor, 250: tower reactor, 260: thin-film vaporizer, 270: distillation column, 241: inline mixer, 251, 271: condensers, 252, 272: condensate tanks, 253, 273: reboilers, 21, 22, 33: supply lines, 23, 24, 25, 26, 28, 29, 30, 34: transport lines, 27, 31, 32: collecting lines, 35: extraction line.

310, 320: Starting material tanks, 330: catalyst tank, 340: tank reactor, 350: tower reactor, 360: thin-film vaporizer,

TABLE 43

| Comparative Example | Alkyl tin alkoxide R' (alkyl group) | OR" (alkoxy group) | Temperature [° C.] | $CO_2$ pressure [MPa-G] | Carbonic acid ester initial yield [mol %] | Carbonic acid ester yield [mol %] (after 15 days of continuous operation) | Trialkyl tin alkoxide production amount [mol %] (after 15 days of continuous operation) |
|---|---|---|---|---|---|---|---|
| 33 | Methyl | N-Butoxy | 120 | 4.5 | 47.6 | 35.5 | 13.6 |
| 34 | Phenyl | N-Butoxy | 120 | 4.5 | 32.8 | 25.6 | 12.0 |
| 35 | N-Butyl | N-Butoxy | 120 | 4.5 | 48.2 | 41.3 | 7.5 |
| 36 | N-Octyl | N-Butoxy | 120 | 4.5 | 48.4 | 42.7 | 6.3 |
| 37 | Methyl | 2-Methylpropyloxy | 120 | 4.5 | 47.3 | 34.7 | 13.8 |
| 38 | Phenyl | 2-Methylpropyloxy | 120 | 4.5 | 31.8 | 24.5 | 12.2 |
| 39 | N-Butyl | 2-Methylpropyloxy | 120 | 4.5 | 47.6 | 41.7 | 6.5 |
| 40 | N-Octyl | 2-Methylpropyloxy | 120 | 4.5 | 47.9 | 42.1 | 6.2 |

370: distillation column, 341: inline mixer, 351, 371: condensers, 352, 372: condensate tanks, 353, 373: reboilers, 41, 42, 53: supply lines, 43, 44, 45, 46, 48, 49, 50, 54: transport lines, 47, 51, 52: collecting lines, 55: extraction line.

610, 670: Distillation columns, 620: tower reactor, 630: autoclave, 640, 650: thin-film vaporizers, 660: catalyst tank, 621: inline mixer, 611, 671, 673: condensers, 612, 672: condensate tanks, 613, 622, 674: reboilers, 614: collecting tank, 61, 68, 78: supply lines, 63, 64, 65, 66, 67, 69, 71, 72, 73, 74: transport lines, 62, 75, 76, 77: collecting lines, 70: purge line, 79: extraction line.

710: Tank reactor, 720, 780: distillation columns, 730: tower reactor, 740: autoclave, 750, 760: thin-film vaporizers, 770: catalyst tank, 711: inline mixer, 721, 731, 781, 783: condensers, 722, 732, 782: condensate tanks, 723, 733, 784: reboilers, 724: collecting tank, 91, 98, 107: supply lines, 93, 94, 95, 96, 97, 99, 101, 102, 103, 109, 110: transport lines, 92, 104, 105, 106: collecting lines, 100: purge line, 108: extraction line.

The invention claimed is:

1. An alkyl tin compound having an alkyl group bonded to a tin atom and a C2-8 alkoxy group bonded to the tin atom,
    wherein the alkyl group is a C5-18 branched alkyl or cyclic group-substituted alkyl group,
    the C5-C18 branched alkyl group being an alkyl group branched at at least one carbon atom of the first to third carbon atoms counting from the tin atom, and
    the cyclic group-substituted alkyl group being an alkyl group having a cyclic group bonded at at least one carbon atom of the first to third carbon atoms counting from the tin atom.

2. The alkyl tin compound according to claim 1, which is an alkyl tin compound having one to three branched alkyl groups bonded to one tin atom,
    the valency of the tin atom being tetravalent.

3. The alkyl tin compound according to claim 2,
    wherein a C2-8 alkoxy group is further bonded to the tin atom.

4. The alkyl tin compound according to claim 2, which is a dialkyl tin alkoxide or a tetraalkyldialkoxydistannoxane.

5. The alkyl tin compound according to claim 4, which is a compound represented by formula (1) or a compound represented by formula (2);

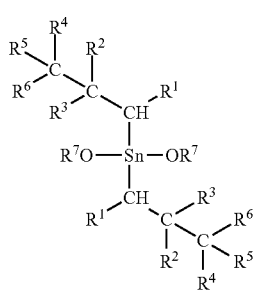

(1)

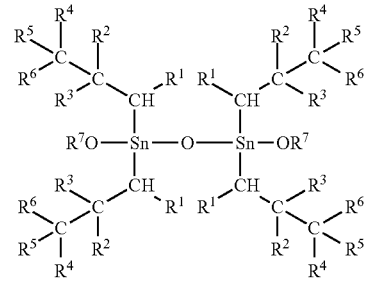

(2)

wherein (i) $R^1$, $R^2$, $R^3$, $R^4$, $R^5$ and $R^6$ each independently represent hydrogen or a C1-15 alkyl group, and $R^7$ represents a C2-8 alkyl group, (ii-1) at least one of $R^1$, $R^2$ and $R^3$ is an alkyl group, or (ii-2) all of $R^1$, $R^2$ and $R^3$ are hydrogens, and at least two of $R^4$, $R^5$ and $R^6$ are alkyl groups, and (iii) the total number of carbon atoms of $R^1$, $R^2$, $R^3$, $R^4$, $R^5$ and $R^6$ is 2-15.

6. The alkyl tin compound according to claim 2, which is a trialkyl tin compound.

7. The alkyl tin compound according to claim 6, which is a compound represented by formula (3);

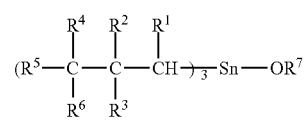

(3)

wherein (i) $R^1$, $R^2$, $R^3$, $R^4$, $R^5$ and $R^6$ each independently represent hydrogen or a C1-15 alkyl group, and $R^7$ represents a C2-8 alkyl group, (ii-1) at least one of $R^1$, $R^2$ and $R^3$ is an alkyl group, or (ii-2) all of $R^1$, $R^2$ and $R^3$ are hydrogens, and at least two of $R^4$, $R^5$ and $R^6$ are alkyl groups, and (iii) the total number of carbon atoms of $R^1$, $R^2$, $R^3$, $R^4$, $R^5$ and $R^6$ is 2-15.

8. The alkyl tin compound according to claim 3, wherein the alkoxy group is an alkoxy group selected from among n-butyloxy, isobutyloxy, sec-butyloxy and C5-8 alkoxy groups.

9. The alkyl tin compound according to claim 3, wherein the alkoxy group is a branched alkoxy group.

10. The alkyl tin compound according to claim 3, which is an alkyl tin alkoxide obtained from an alkyl tin carboxylate, alkyl tin oxide, alkyl tin oxide polymer or alkyl tin halide.

11. The alkyl tin compound according to claim 2,
    which is an alkyl tin alkoxide having a C5-18 branched alkyl group and a C4-8 branched alkoxy group, and
    which is a compound represented by formula (1) or a compound represented by formula (2);

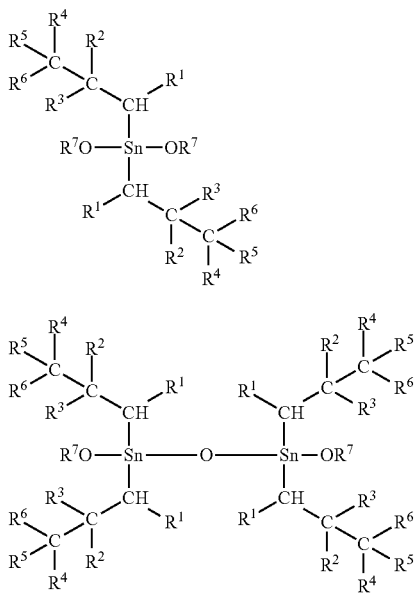

(1)

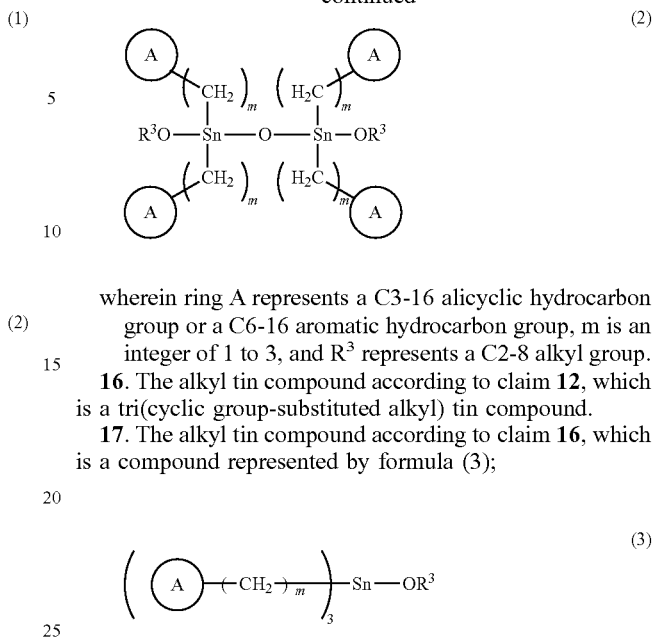

(2)

wherein ring A represents a C3-16 alicyclic hydrocarbon group or a C6-16 aromatic hydrocarbon group, m is an integer of 1 to 3, and $R^3$ represents a C2-8 alkyl group.

16. The alkyl tin compound according to claim 12, which is a tri(cyclic group-substituted alkyl) tin compound.

17. The alkyl tin compound according to claim 16, which is a compound represented by formula (3);

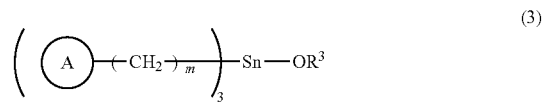

(3)

wherein ring A represents a C3-16 alicyclic hydrocarbon group or a C6-16 aromatic hydrocarbon group, m is an integer of 1 to 3, and $R^3$ represents a C2-8 alkyl group.

18. The alkyl tin compound according to claim 13, wherein
the alkoxy group is a C4-8 alkoxy group, and
the alcohol corresponding to the alkoxy group is an alcohol having a boiling point of 100° C. or higher at ordinary pressure.

19. The alkyl tin compound according to claim 18, wherein the alcohol forms an azeotropic mixture with water.

20. The alkyl tin compound according to claim 13, wherein the alkoxy group is a branched alkoxy group.

21. The alkyl tin compound according to claim 13, which is an alkyl tin alkoxide obtained from a cyclic group-substituted alkyl tin carboxylate, a cyclic group-substituted alkyl tin oxide, a cyclic group-substituted alkyl tin oxide polymer or a halogenated (cyclic group-substituted alkyl) tin compound.

22. A composition comprising an alkyl tin compound according to claim 1.

23. The composition according to claim 22, wherein the alkyl tin compound comprises:
a dialkyl tin alkoxide and a trialkyl tin compound;
a tetraalkyldialkoxydistannoxane and a trialkyl tin compound;
a di(cyclic group-substituted alkyl) tin dialkoxide and a tri(cyclic group-substituted alkyl) tin compound; or
a tetra(cyclic group-substituted alkyl)dialkoxydistannoxane and a tri(cyclic group-substituted alkyl) tin compound.

24. A catalyst for a process for producing a carbonic acid ester from carbon dioxide and an alcohol,
the catalyst comprising an alkyl tin compound according to claim 1.

25. A method for producing a carbonic acid ester using an alkyl tin compound according to claim 1, the method comprising steps (1) to (3);
Step (1): A step of reacting the alkyl tin compound with carbon dioxide to obtain a reaction mixture containing a carbonic acid ester;

wherein (i) $R^1$, $R^2$, $R^3$, $R^4$, $R^5$ and $R^6$ each independently represent hydrogen or a C1-15 alkyl group, and $R^7$ represents a C4-8 branched alkyl group,
(ii-1) at least one of $R^1$, $R^2$ and $R^3$ is an alkyl group, or
(ii-2) all of $R^1$, $R^2$ and $R^3$ are hydrogens, and at least two of $R^4$, $R^5$ and $R^6$ are alkyl groups, and
(iii) the total number of carbon atoms of $R^1$, $R^2$, $R^3$, $R^4$, $R^5$ and $R^6$ is 2-15.

12. The alkyl tin compound according to claim 1,
which is an alkyl tin compound having a cyclic group-substituted alkyl group bonded to a tin atom,
the cyclic group-substituted alkyl group being an alkyl group having a cyclic group selected from among alicyclic hydrocarbon groups and aromatic hydrocarbon groups bonded to at least one carbon atom among the first to third carbon atoms counting from the tin atom, and
the valency of the tin atom being tetravalent.

13. The alkyl tin compound according to claim 12, wherein
the alkyl tin compound further has a C2-8 alkoxy group, and
the cyclic group is a C4-18 cyclic group.

14. The alkyl tin compound according to claim 12, which is a di(cyclic group-substituted alkyl) tin dialkoxide or a tetra(cyclic group-substituted alkyl)dialkoxydistannoxane.

15. The alkyl tin compound according to claim 14, which is a compound represented by the following formula (1) or a compound represented by formula (2):

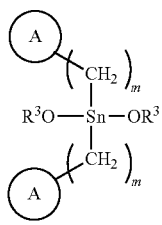

(1)

Step (2): A step of separating the carbonic acid ester from the reaction mixture to obtain a residual solution;

Step (3): A step of reacting the residual solution with an alcohol and removing the water produced by the reaction, to obtain an alkyl tin alkoxide, and recycling it to step (1).

26. The method according to claim 25, wherein the alkyl tin compound includes either or both a compound represented by formula (1) and/or a compound represented by formula (2);

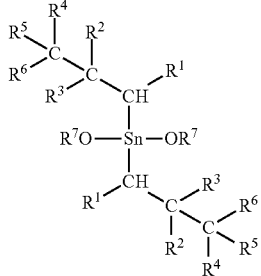

(1)

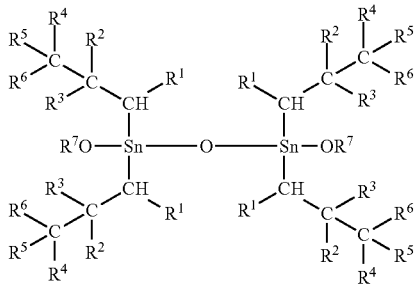

(2)

wherein (i) $R^1$, $R^2$, $R^3$, $R^4$, $R^5$ and $R^6$ each independently represent hydrogen or a C1-15 alkyl group, and $R^7$ represents a C2-8 alkyl group, (ii-1) at least one of $R^1$, $R^2$ and $R^3$ is an alkyl group, or (ii-2) all of $R^1$, $R^2$ and $R^3$ are hydrogens, and at least two of $R^4$, $R^5$ and $R^6$ are alkyl groups, and (iii) the total number of carbon atoms of $R^1$, $R^2$, $R^3$, $R^4$, $R^5$ and $R^6$ is 2-15.

27. The method according to claim 26, wherein the alkyl tin compound further includes a compound represented by formula (3);

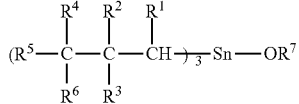

(3)

wherein (i) $R^1$, $R^2$, $R^3$, $R^4$, $R^5$ and $R^6$ each independently represent hydrogen or a C1-15 alkyl group, and $R^7$ represents a C2-8 alkyl group, (ii-1) at least one of $R^1$, $R^2$ and $R^3$ is an alkyl group, or (ii-2) all of $R^1$, $R^2$ and $R^3$ are hydrogens, and at least two of $R^4$, $R^5$ and $R^6$ are alkyl groups, and (iii) the total number of carbon atoms of $R^1$, $R^2$, $R^3$, $R^4$, $R^5$ and $R^6$ is 2-15.

28. The method according to claim 26, wherein the alkoxy group of the alkyl tin compound is selected from among n-butyloxy, isobutyloxy, sec-butyloxy and C5-8 alkoxy groups.

29. The method according to claim 26, wherein the alcohol is an alcohol selected from among n-butyl alcohol, isobutyl alcohol, sec-butyl alcohol and C5-8 alkyl alcohols.

30. The method according to claim 26, wherein the alkoxy group of the alkyl tin compound is a branched alkoxy group, and the alcohol is the branched alcohol corresponding to the branched alkoxy group.

31. The method according to claim 25, wherein the alkyl tin compound includes either or both a compound represented by formula (1) and/or a compound represented by formula (2);

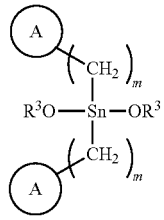

(1)

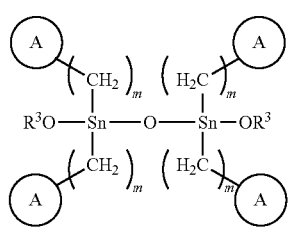

(2)

wherein ring A represents a C3-16 alicyclic hydrocarbon group or a C6-16 aromatic hydrocarbon group, m is an integer of 1 to 3, and $R^3$ represents a C2-8 alkyl group.

32. The method according to claim 31, wherein the alkyl tin compound further includes a compound represented by formula (3);

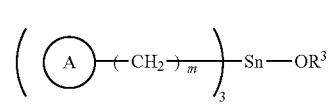

(3)

wherein ring A represents a C3-16 alicyclic hydrocarbon group or a C6-16 aromatic hydrocarbon group, m is an integer of 1 to 3, and $R^3$ represents a C2-8 alkyl group.

33. The method according to claim 31, wherein the alkoxy groups of the compound represented by formula (1) and the compound represented by formula (2) are C4-8 alkoxy groups, the alcohols corresponding to the alkoxy groups are alcohols with boiling points of 100° C. or higher at ordinary pressure, and the alcohol used in step (3) is the alcohol corresponding to the alkoxy group.

34. The method according to claim 31, wherein the alcohol is a C4-8 alcohol with a boiling point of 100° C. or higher at ordinary pressure.

35. The method according to claim 31, wherein the alcohol is an alcohol selected from among n-butyl alcohol, isobutyl alcohol, sec-butyl alcohol and C5-8 alkyl alcohols.

36. The method according to claim 31, wherein
the alkoxy group of the alkyl tin compound is a branched alkoxy group, and
the alcohol is a branched alcohol.

* * * * *